United States Patent
Lan et al.

(10) Patent No.: US 9,879,008 B2
(45) Date of Patent: Jan. 30, 2018

(54) 2,3,4,6-TETRA-SUBSTITUTED BENZENE-1,5-DIAMINE DERIVATIVES, PREPARATION METHOD THEREFOR AND MEDICINAL USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Jiong Lan, Shanghai (CN); Yunzhou Jin, Shanghai (CN); Fusheng Zhou, Shanghai (CN); Qi He, Shanghai (CN); Xiangyu He, Shanghai (CN); Qiang Lv, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 15/303,475

(22) PCT Filed: Apr. 13, 2015

(86) PCT No.: PCT/CN2015/076451
§ 371 (c)(1),
(2) Date: Nov. 15, 2016

(87) PCT Pub. No.: WO2015/158233
PCT Pub. Date: Oct. 22, 2015

(65) Prior Publication Data
US 2017/0057957 A1 Mar. 2, 2017

(30) Foreign Application Priority Data
Apr. 14, 2014 (CN) .......................... 2014 1 0148176

(51) Int. Cl.
| C07D 239/02 | (2006.01) |
| C07D 239/24 | (2006.01) |
| C07D 401/12 | (2006.01) |
| C07D 401/14 | (2006.01) |
| C07D 403/12 | (2006.01) |
| A61K 31/16 | (2006.01) |
| A61K 31/505 | (2006.01) |
| A61K 31/506 | (2006.01) |
| A61K 31/55 | (2006.01) |
| C07D 471/04 | (2006.01) |
| C07C 211/51 | (2006.01) |
| C07C 211/54 | (2006.01) |
| A61K 45/06 | (2006.01) |

(52) U.S. Cl.
CPC ............ *C07D 471/04* (2013.01); *A61K 31/16* (2013.01); *A61K 31/505* (2013.01); *A61K 31/506* (2013.01); *A61K 31/55* (2013.01); *A61K 45/06* (2013.01); *C07C 211/51* (2013.01); *C07C 211/54* (2013.01); *C07D 239/02* (2013.01); *C07D 401/12* (2013.01); *C07D 401/14* (2013.01); *C07D 403/12* (2013.01)

(58) Field of Classification Search
CPC .. C07D 239/02; C07D 239/24; C07D 401/12; C07D 401/14; C07D 403/12; A61K 31/16; A61K 31/505; A61K 31/506; A61K 31/55
See application file for complete search history.

(56) References Cited

U.S. PATENT DOCUMENTS

| 2010/0249092 A1 | 9/2010 | Singh et al. |
| 2013/0072469 A1 | 3/2013 | Singh et al. |
| 2015/0246040 A1 | 9/2015 | Lee et al. |

FOREIGN PATENT DOCUMENTS

| CN | 102083800 A | 6/2011 |
| CN | 102740847 A | 10/2012 |
| CN | 103269704 A | 8/2013 |
| WO | 2011/140338 A1 | 11/2011 |

OTHER PUBLICATIONS

International Search Report dated Jul. 17, 2015 corresponding to International Patent Application No. PCT/CN2015/076451, filed on Apr. 13, 2015, 3 pages.

*Primary Examiner* — Sahar Javanmard
(74) *Attorney, Agent, or Firm* — Mintz Levin Cohn Ferris Glovsky and Popeo PC

(57) ABSTRACT

The present invention relates to 2,3,4,6-tetra-substituted benzene-1,5-diamine derivatives, a preparation method therefor and a medicinal use thereof. Specifically, disclosed are compounds of formula (I) or pharmaceutically acceptable salts, stereoisomers, solvates or prodrugs, preparation method therefor and application thereof. Definition of each group in the formula can be found in the specification for details.

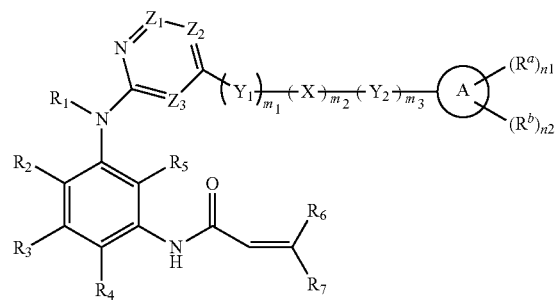

10 Claims, No Drawings

2,3,4,6-TETRA-SUBSTITUTED BENZENE-1,5-DIAMINE DERIVATIVES, PREPARATION METHOD THEREFOR AND MEDICINAL USE THEREOF

TECHNICAL FIELD

The present invention relates to the field of medical technology, and particularly to 2,3,4,6-tetra-substituted benzene-1,5-diamine derivatives, preparation method therefor and their use as EGFR tyrosine kinase inhibitors, and pharmaceutical compositions and medicinal compositions prepared therefrom.

BACKGROUND

Lung cancer is a cancer having the highest incidence in the world. In China, the incidence of lung cancer ranks first among all cancers, and the incidence and mortality rate of the lung cancer are also the highest in all diseases in China. In the lung cancer patients in China, 30% of patients have EGFR mutations, over 90% of which are L858R and exon 19 deletion mutation, and these patients are more sensitive to EGFR inhibitors. The marketed first-generation of EGFR inhibitors, such as erlotinib, gefitinib have good effects in these patients, and the tumors in more than 60% of patients will shrink, thereby significantly prolonging the progression-free survival of patients. However, most of patients acquire resistance in 6-12 months so that the first generation of EGFR inhibitors will be no longer effective, and currently no drugs are available for these patients. EGFR T790M mutation is clinically detected in 50% of patients who are resistant to the first-generation of EGFR inhibitors. In T790M mutant cell line H1975, the first-generation of EGFR inhibitors, such as gefitinib and erlotinib, are more than 3 uM, which means almost no activity.

The therapeutic effect of the second generation of irreversible pan-EGFR inhibitors (Afatinib (BIBW2992)) which are currently launched is significantly better than that of the first-generation of EGFR inhibitors in lung cancer patients with EGFR mutations. However, the second-generation of inhibitors also have strong inhibitory activity on wild-type EGFR, and the inhibitory activity on wild-type EGFR are significantly higher than that on resistant T790M mutation. Side effects, such as skin rashes, are severe in some patients. The effect of the second-generation of inhibitors in drug resistant patients is poor, and only a small portion of patients resistant to the first generation of EGFR inhibitors response to these drugs.

In order to improve the inhibitory activity on resistant T790M mutation and reduce the inhibitory activity on wild-type EGFR, it is greatly significant to develop the third generation of selective inhibitors for EGFR mutants with higher activity, better selectivity, and lower toxicity.

SUMMARY OF INVENTION

The object of the present invention is to provide 2,3,4,6-tetra-substituted benzene-1,5-diamine derivatives as new EGFR tyrosine kinase inhibitors with higher EGFR T790M selective inhibitory.

In the first aspect of the present invention, a compound of formula (I), or a pharmaceutically acceptable salt, a solvate, a stereoisomer or a prodrug thereof is provided;

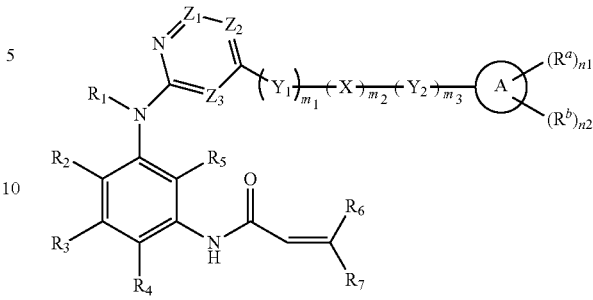

wherein, each of $Z_1$, $Z_2$, $Z_3$ is independently $CR_{10}$ or N; $R_{10}$ is a hydrogen, hydroxy, CN, $NO_2$, halogen (preferably F or Cl), $-NR_{11}R_{12}$, $C_{1-10}$ alkyl (preferably $C_{1-6}$ alkyl, more preferably $C_{1-3}$ alkyl), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), $C_{1-10}$ alkoxy (preferably $C_{1-6}$ alkoxy, more preferably $C_{1-3}$ alkoxy), $-CHO$, $-COC_{1-10}$ alkyl (preferably $-COC_{1-6}$ alkyl, more preferably $-COC_{1-3}$ alkyl), $-COC_{6-10}$ aryl (preferably $-COC_6$ aryl, such as $-CO$-phenyl), $C_{6-10}$ aryl (preferably $C_6$ aryl, such as phenyl), $-CONR_{11}R_{12}$, $-C(O)OC_{1-10}$ alkyl (preferably $-C(O)OC_{1-6}$ alkyl, more preferably $-C(O)OC_{1-3}$ alkyl), $-OC(O)C_{1-10}$ alkyl (preferably $-OC(O)C_{1-6}$ alkyl, more preferably $-OC(O)C_{1-3}$ alkyl), $-SO_2C_{1-10}$ alkyl (preferably $-SO_2C_{1-6}$ alkyl, more preferably $-SO_2C_{1-3}$ alkyl), $-SO_2C_{6-10}$ aryl (preferably $-SO_2C_6$ aryl, such as $-SO_2$-phenyl) or t-butyloxycarbonyl, wherein, each of alkyl, cycloalkyl, alkenyl, alkynyl, aryl, alkoxy is unsubstituted or substituted with 1-3 substituents selected from the group consisting of halogen (preferably F or Cl), nitro, $C_{6-10}$ aryl (preferably phenyl), $C_{1-10}$ alkyl (preferably $C_{1-6}$ alkyl, more preferably $C_{1-3}$ alkyl), $C_{1-10}$ alkoxy (preferably $C_{1-6}$ alkoxy, more preferably $C_{1-3}$ alkoxy), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), $-CONR_{11}R_{12}$, $-C(O)OC_{1-10}$ alkyl (preferably $-C(O)OC_{1-6}$ alkyl, more preferably $-C(O)OC_{1-3}$ alkyl), $-CHO$, $-OC(O)C_{1-10}$ alkyl (preferably $-OC(O)C_{1-6}$ alkyl, more preferably $-OC(O)C_{1-3}$ alkyl), $-SO_2C_{1-10}$ alkyl (preferably $-SO_2C_{1-6}$ alkyl, more preferably $-SO_2C_{1-3}$ alkyl), $-SO_2C_{6-10}$ aryl (preferably $-SO_2C_6$ aryl, such as $-SO_2$-phenyl), $-COC_{6-10}$ aryl (preferably $-COC_6$ aryl, such as $-CO$-phenyl);

each of $Y_1$ and $Y_2$ is independently divalent $C_{1-3}$ hydrocarbyl, or the methylidene ($-CH_2-$) in $Y_1$ or $Y_2$ is replaced with $-C(R^yR^x)-$, $-NR^yC(O)-$, cyclopropylidene, $-C(O)NR^y-$, $-N(R^y)SO_2-$, $-SO_2N(R^y)-$, $-S-$, $-S(O)-$, $-SO_2-$, $-OC(O)-$, $-C(O)O-$, $-O-$, $-N(R^y)-$ or $-C(O)-$; wherein, each of $R^y$ and $R^x$ is independently a hydrogen, halogen (preferably F or Cl), hydroxy, CN, $NO_2$, $C_{1-10}$ alkyl (preferably $C_{1-6}$ alkyl, more preferably $C_{1-3}$ alkyl), $C_{1-10}$ alkoxy (preferably $C_{1-6}$ alkoxy, more preferably $C_{1-3}$ alkoxy), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), $C_{6-10}$ aryl (preferably phenyl);

X is $NR^z$, O or S; $R^z$ is a hydrogen, $C_{1-10}$ alkyl (preferably $C_{1-6}$ alkyl, more preferably $C_{1-3}$ alkyl), halogenated $C_{1-10}$ alkyl (preferably halogenated $C_{1-6}$ alkyl, more preferably halogenated $C_{1-3}$ alkyl) or $C_{3-8}$ cycloalkyl (preferably $C_{3-6}$ cycloalkyl);

each of $m_1$ and $m_3$ is independently 0, 1 or 2; $m_2$ is 0 or 1; and $m_1$, $m_2$ and $m_3$ are not 0 simultaneously;

Ring A is $C_{6-10}$ aryl(such as phenyl), 3 to 7 membered saturated or partially unsaturated monocyclic ring, 8 to 10 membered saturated or partially unsaturated bicyclic ring, 3 to 7 membered saturated or partially unsaturated heterocyclic monoring having 1 to 3 heteroatoms independently selected from N, O and S, 8 to 10 membered saturated or partially unsaturated heterocyclic biring having 1 to 5 heteroatoms independently selected from N, O and S, 5 to 6 membered monocyclic heteroaryl having 1 to 3 heteroatoms independently selected from N, O and S, or 8 to 10 membered bicyclic heteroaryl having 1 to 5 heteroatoms independently selected from N, O and S;

each of $R^a$ and $R^b$ is independently a hydrogen, hydroxy, CN, $NO_2$, halogen (preferably F or Cl), $-NR_{11}R_{12}$, $C_{1-10}$ alkyl (preferably $C_{1-6}$ alkyl, more preferably $C_{1-3}$ alkyl), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), $C_{1-10}$ alkoxy (preferably $C_{1-6}$ alkoxy, more preferably $C_{1-3}$ alkoxy), —CHO, —$COC_{1-10}$ alkyl (preferably —$COC_{1-6}$ alkyl, more preferably —$COC_{1-3}$ alkyl), —$COC_{6-10}$ aryl (preferably —$COC_6$ aryl, such as —CO-phenyl), $C_{6-10}$ aryl (preferably $C_6$ aryl, such as phenyl), —$CONR_{11}R_{12}$, —$C(O)OC_{1-10}$ alkyl (preferably —$C(O)OC_{1-6}$ alkyl, more preferably —$C(O)OC_{1-3}$ alkyl), —$OC(O)C_{1-10}$ alkyl (preferably —$OC(O)C_{1-6}$ alkyl, more preferably —$OC(O)C_{1-3}$ alkyl), —$SO_2C_{1-10}$ alkyl (preferably —$SO_2C_{1-6}$ alkyl, more preferably —$SO_2C_{1-3}$ alkyl), —$SO_2C_{6-10}$ aryl (preferably —$SO_2C_6$ aryl, such as —$SO_2$-phenyl), —$S(O)C_{1-10}$ alkyl (preferably —$S(O)C_{1-6}$ alkyl, more preferably —$S(O)C_{1-3}$ alkyl), —$S(O)C_{6-10}$ aryl (preferably —$S(O)C_6$ aryl, such as —S(O)-phenyl), t-butyloxycarbonyl, —$NHC_{1-10}$ alkyl (preferably —$NHC_{1-6}$ alkyl, more preferably —$NHC_{1-3}$ alkyl), —$NC(O)C_{1-10}$ alkyl (preferably —$NC(O)C_{1-6}$ alkyl, more preferably —$NC(O)C_{1-3}$ alkyl), —$NSO_2C_{1-10}$ alkyl (preferably —$NSO_2C_{1-6}$ alkyl, more preferably —$NSO_2C_{1-3}$ alkyl); wherein the alkyl, cycloalkyl, alkenyl, alkynyl, and alkoxy may be unsubstituted or optionally substituted with 1-3 substituents selected from the group consisting of halogen (preferably F or Cl), hydroxy, $NO_2$, $C_{6-10}$ aryl (preferably phenyl), $C_{1-10}$ alkyl (preferably $C_{1-6}$ alkyl, more preferably $C_{1-3}$ alkyl), $C_{1-10}$ alkoxy (preferably $C_{1-6}$ alkoxy, more preferably $C_{1-3}$ alkoxy), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), —$CONR_{11}R_{12}$, —$C(O)OC_{1-10}$ alkyl (preferably —$C(O)OC_{1-6}$ alkyl, more preferably —$C(O)OC_{1-3}$ alkyl), —CHO, —$OC(O)C_{1-10}$ alkyl (preferably —$OC(O)C_{1-6}$ alkyl, more preferably —$OC(O)C_{1-3}$ alkyl), —$SO_2C_{1-10}$ alkyl (preferably —$SO_2C_{1-6}$ alkyl, more preferably —$SO_2C_{1-3}$ alkyl), —$SO_2C_{6-10}$ aryl (preferably —$SO_2C_6$ aryl, such as —$SO_2$-phenyl), —$COC_{6-10}$ aryl (preferably —$COC_6$ aryl, such as —CO-phenyl);

or each of $R^a$ and $R^b$ is independently 5 to 6 membered monocyclic heteroaryl having 1 to 4 heteroatoms independently selected from N, O and S, 8 to 10 membered bicyclic heteroaryl having 1 to 5 heteroatoms independently selected from N, O and S (preferably 9 to 10 membered bicyclic heteroaryl); wherein, the 5 to 6 membered monocyclic heteroaryl or 8 to 10 membered bicyclic heteroaryl may be unsubstituted or substituted with 1-5 substituents selected from the group consisting of halogen (preferably F or Cl), hydroxy, CN, $NO_2$, $C_{1-10}$ alkyl (preferably $C_{1-6}$ alkyl, more preferably $C_{1-3}$ alkyl), halogenated $C_{1-10}$ alkyl (preferably halogenated $C_{1-6}$ alkyl, more preferably halogenated $C_{1-3}$ alkyl), $C_{1-10}$ alkoxy (preferably $C_{1-6}$ alkoxy, more preferably $C_{1-3}$ alkoxy), halogenated $C_{1-10}$ alkoxy (preferably halogenated $C_{1-6}$ alkoxy, more preferably halogenated $C_{1-3}$ alkoxy), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), —$CONR_{11}R_{12}$, —$C(O)OC_{1-10}$ alkyl (preferably —$C(O)OC_{1-6}$ alkyl, more preferably —$C(O)OC_{1-3}$ alkyl), —CHO, —$OC(O)C_{1-10}$ alkyl (preferably —$OC(O)C_{1-6}$ alkyl, more preferably —$OC(O)C_{1-3}$ alkyl), —$SO_2C_{1-10}$ alkyl (preferably —$SO_2C_{1-6}$ alkyl, more preferably —$SO_2C_{1-3}$ alkyl), —$SO_2C_{6-10}$ aryl (preferably —$SO_2C_6$ aryl, such as —$SO_2$-phenyl), —$COC_{6-10}$ aryl (preferably —$COC_6$ aryl, such as —CO-phenyl);

each of $n_1$ and $n_2$ is independently 0, 1, 2, 3, 4, 5 or 6;

$R_1$ is a hydrogen or $C_{1-10}$ alkyl (preferably $C_{1-6}$ alkyl, more preferably $C_{1-3}$ alkyl);

each of $R_2$, $R_3$, and $R_5$ is independently a hydrogen, halogen (preferably F or Cl), $C_{1-10}$ alkyl (preferably $C_{1-6}$ alkyl, more preferably $C_{1-3}$ alkyl) or $C_{1-10}$ alkoxy (preferably $C_{1-6}$ alkoxy, more preferably $C_{1-3}$ alkoxy);

$R_4$ is a hydrogen, hydroxy, —$OC_{1-10}$ alkyl, CN, $NO_2$, halogen, $C_{3-8}$ cycloalkyl, $C_{3-8}$ cycloalkoxy, $C_{2-10}$ alkenyl, $C_{2-10}$ alkynyl, —CHO, —$COC_{1-10}$ alkyl, —$COC_{6-10}$ aryl, $C_{6-10}$ aryl, —$CONR_{11}R_{12}$, —$C(O)OC_{1-10}$ alkyl, —$OC(O)C_{1-10}$ alkyl, —$SO_2C_{1-10}$ alkyl, —$SO_2C_{6-10}$ aryl, t-butyloxycarbonyl, —$NHC_{1-10}$ alkyl, —$N(C_{1-10}$ alkyl$)_2$, —$N(C_{1-10}$ alkyl$)(C_{3-8}$ cycloalkyl), —$NC(O)C_{1-10}$ alkyl, —$NSO_2C_{1-10}$ alkyl, or 3 to 7 membered saturated or partially unsaturated heterocyclic monoring having 1 or 2 nitrogen atoms and 0 to 3 oxygen or sulfur atoms (preferably 5 to 6 membered saturated or partially unsaturated heterocyclic monoring); wherein, each of alkyl, cycloalkyl, alkenyl, alkynyl, aryl, and 3 to 7 membered saturated or partially unsaturated heterocyclic monoring is unsubstituted or substituted with 1-3 substituents selected from the group consisting of halogen (preferably F or Cl), $NO_2$, CN, hydroxy, —$CH_2NR_{11}R_{12}$, —$NR_{11}R_{12}$, $C_{1-10}$ alkyl (preferably $C_{1-6}$ alkyl, more preferably $C_{1-3}$ alkyl), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), $C_{1-10}$ alkoxy (preferably $C_{1-6}$ alkoxy, more preferably $C_{1-3}$ alkoxy), —CHO, —$COC_{1-10}$ alkyl (preferably —$COC_{1-6}$ alkyl, more preferably —$COC_{1-3}$ alkyl), —$COC_{6-10}$ aryl (preferably —$COC_6$ aryl, such as —CO-phenyl), $C_{6-10}$ aryl (preferably $C_6$ aryl, such as phenyl), —$CONR_{11}R_{12}$, —$C(O)OC_{1-10}$ alkyl (preferably —$C(O)OC_{1-6}$ alkyl, more preferably —$C(O)OC_{1-3}$ alkyl), —$OC(O)C_{1-10}$ alkyl (preferably —$OC(O)C_{1-6}$ alkyl, more preferably —$OC(O)C_{1-3}$ alkyl), —$SO_2C_{1-10}$ alkyl (preferably —$SO_2C_{1-6}$ alkyl, more preferably —$SO_2C_{1-3}$ alkyl), —$SO_2C_{6-10}$ aryl (preferably —$SO_2C_6$ aryl, such as —$SO_2$-phenyl), t-butyloxycarbonyl, —$NHC_{1-10}$ alkyl (preferably —$NHC_{1-6}$ alkyl, more preferably —$NHC_{1-3}$ alkyl), —$NC(O)C_{1-10}$ alkyl (preferably —$NC(O)C_{1-6}$ alkyl, more preferably —$NC(O)C_{1-3}$ alkyl), —$NSO_2C_{1-10}$ alkyl (preferably —NSO₂C₁₋₆ alkyl, more preferably —NSO₂C₁₋₃ alkyl), morpholinyl, tetrahydro-pyrrolyl, piperazinyl, and methyl piperazinyl;

each of $R_6$ and $R_7$ is independently a hydrogen or —CH₂NR₁₃R₁₄; wherein, each of $R_{13}$ and $R_{14}$ is independently a hydrogen or methyl; or $R_{13}$ and $R_{14}$ together with the conjoint nitrogen form a 5-6 membered saturated N-containing heterocyclic ring;

wherein, each of $R_{11}$ and $R_{12}$ is independently a hydrogen, $C_{1-10}$ alkyl (more preferably $C_{1-6}$ alkyl, most preferably $C_{1-3}$ alkyl), $C_{1-10}$ alkoxy (more preferably $C_{1-6}$ alkoxy, most preferably $C_{1-3}$ alkoxy), $C_{3-8}$ cycloalkyl (more preferably $C_{3-6}$ cycloalkyl), $C_{3-8}$ cycloalkoxy (more preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), or $C_{6-10}$ aryl (preferably phenyl); or $R_{11}$ and $R_{12}$ together with the conjoint nitrogen form 3-6 membered saturated N-containing heterocyclic ring.

In another preferred embodiment, in the compound of formula (I), ring A is 3 to 7 membered saturated or partially unsaturated monocyclic ring, 8 to 10 membered saturated or partially unsaturated bicyclic ring, 3 to 7 membered saturated or partially unsaturated heterocyclic monoring having 1 to 3 heteroatoms independently selected from N, O and S, 8 to 10 membered saturated or partially unsaturated heterocyclic biring having 1 to 5 heteroatoms independently selected from N, O and S.

In another preferred embodiment, when ring A is monocyclic ring, bicyclic ring, heterocyclic monoring or heterocyclic biring, it is selected from the group consisting of 3 to 7 membered saturated or partially unsaturated monocyclic ring; 8 to 10 membered saturated or partially unsaturated bicyclic ring; 3 to 7 membered saturated or partially unsaturated heterocyclic monoring having 1 or 2 nitrogen atoms; 8 to 10 membered saturated or partially unsaturated heterocyclic biring having 1, 2 or 3 nitrogen atoms; 3 to 7 membered saturated or partially unsaturated heterocyclic monoring having 1 or 2 O or S atoms; 8 to 10 membered saturated or partially unsaturated heterocyclic biring having 1, 2 or 3 O or S atoms; 3 to 7 membered saturated or partially unsaturated heterocyclic monoring having 1 nitrogen atom and 1 oxygen or sulfur atom; 8 to 10 membered saturated or partially unsaturated heterocyclic biring having 1 or 2 nitrogen atoms and 1 oxygen or sulfur atom; 3 to 7 membered saturated or partially unsaturated heterocyclic monoring having 1 sulfur atom and 1 oxygen atom; or 8 to 10 membered saturated or partially unsaturated heterocyclic biring having 1 sulfur atom and 1 oxygen atom.

In another preferred embodiment, when ring A is 5 to 6 membered monocyclic heteroaryl ring or 8 to 10 membered bicyclic heteroaryl ring, it is selected from the group consisting of

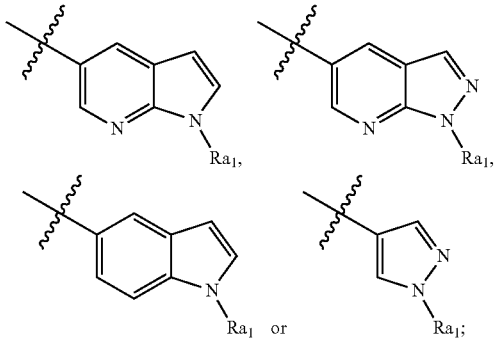

wherein, $R_{a1}$ is a hydrogen, methyl or ethyl.

In another preferred embodiment, the compound of formula (I) is a compound of formula (II):

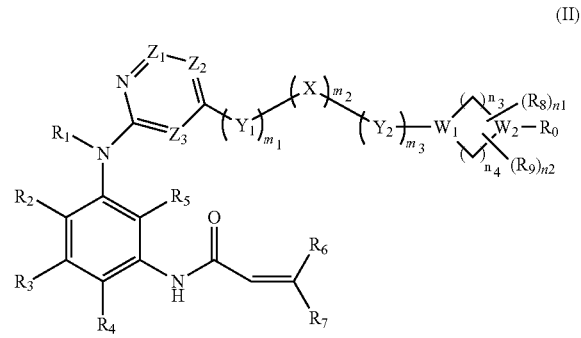

(II)

wherein, each of $n_3$ and $n_4$ is independently 0, 1, 2 or 3, and $n_3$ and $n_4$ are not 0 simultaneously;

$W_1$ is N or $CR_{15}$; $W_2$ is N, O, S or $CR_{15}$; $R_{15}$ is a hydrogen, hydroxy, CN, NO₂, halogen (preferably F or Cl), —NR₁₁R₁₂, $C_{1-10}$ alkyl (preferably $C_{1-6}$ alkyl, more preferably $C_{1-3}$ alkyl), $C_{3-8}$ cycloalkyl (preferably $C_{3-6}$ cycloalkyl), $C_{3-8}$ cycloalkoxy (preferably $C_{3-6}$ cycloalkoxy), $C_{2-10}$ alkenyl (preferably $C_{2-6}$ alkenyl, more preferably $C_{2-4}$ alkenyl), $C_{2-10}$ alkynyl (preferably $C_{2-6}$ alkynyl, more preferably $C_{2-4}$ alkynyl), $C_{1-10}$ alkoxy (preferably $C_{1-6}$ alkoxy, more preferably $C_{1-3}$ alkoxy), $C_{6-10}$ aryl (preferably $C_6$ aryl, such as phenyl); and when $W_2$ is O or S, $R_0$ does not exist;

$R_8$, $R_9$, and $R_0$ are defined as that of $R^a$ or $R^b$ as described above;

$Z_1$, $Z_2$, $Z_3$, $R_1$, $R_2$, $R_3$, $R_4$, $R_5$, $R_6$, $R_7$, $R_{11}$, $R_{12}$, $Y_1$, $Y_2$, X, $m_1$, $m_2$, $m_3$, $n_1$ and $n_2$ are defined as above.

In another preferred embodiment, in the compound of formula (I), each of $Y_1$ and $Y_2$ is independently divalent $C_{1-3}$ hydrocarbyl, and the methylidene in $Y_1$ or $Y_2$ are not replaced.

In another preferred embodiment, the compound of formula (I) is a compound of formula (VII-1), formula (VII-2), formula (VII-3), formula (VII-4), formula (VII-5), formula (VII-6), formula (VII-7), formula (VII-8), formula (VII-9), or formula (VII-10):

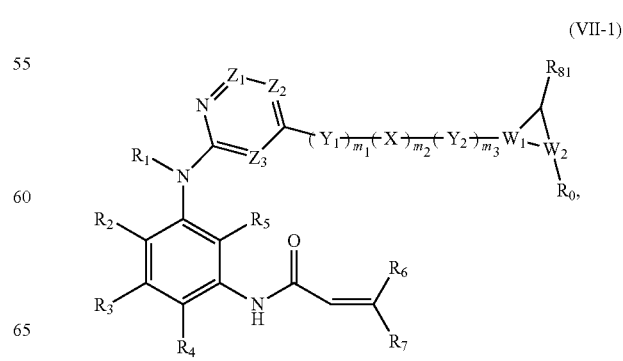

(VII-1)

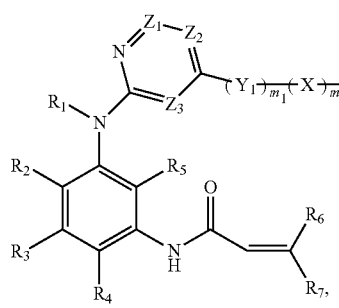
(VII-2)
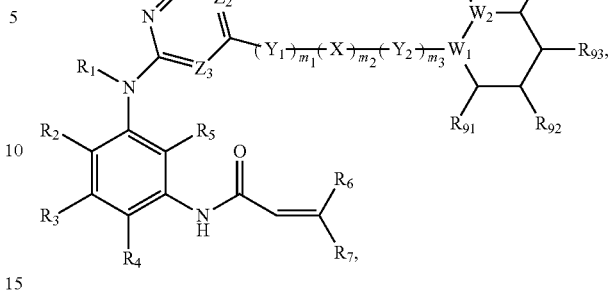
(VII-6)
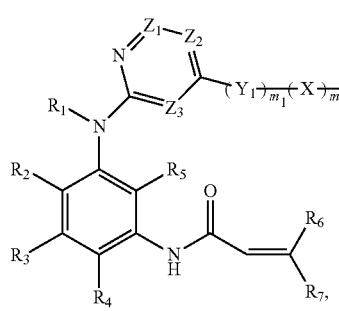
(VII-3)
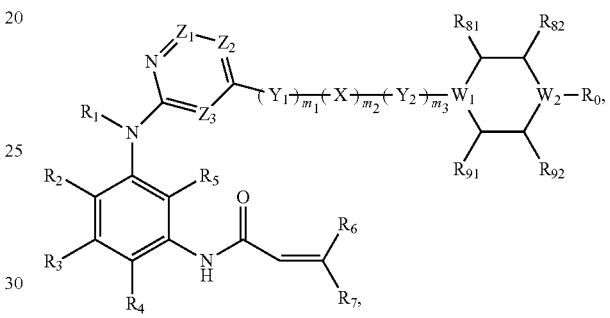
(VII-7)
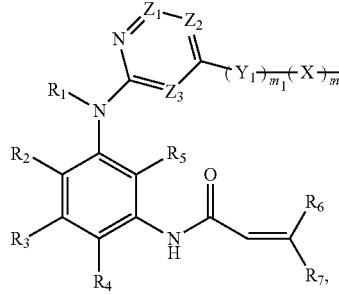
(VII-4)
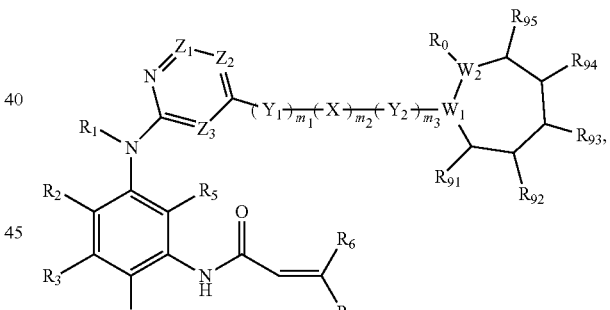
(VII-8)
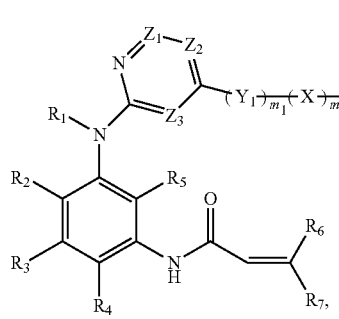
(VII-5)
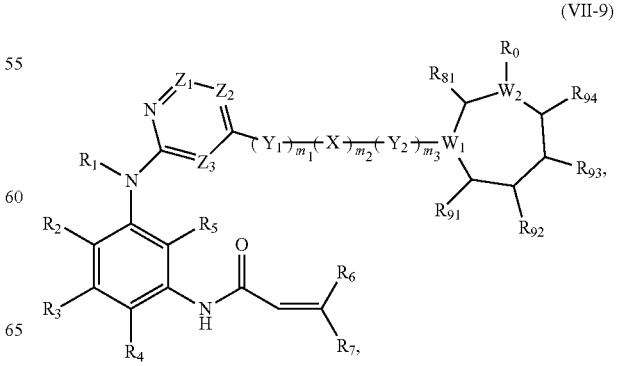
(VII-9)

-continued (VII-10)

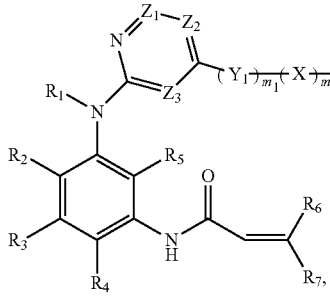

wherein, $Z_1$, $Z_2$, $Z_3$, $R_1$, $R_2$, $R_3$, $R_4$, $R_5$, $R_6$, $R_7$, $Y_1$, $Y_2$, X, $m_1$, $m_2$, $m_3$, $W_1$, $W_2$, and $R_0$ are defined as above; $R_{91}$, $R_{92}$, $R_{93}$, $R_{94}$, $R_{95}$, $R_{81}$, $R_{82}$, and $R_{83}$ are defined as that of $R_8$ or $R_9$.

In another preferred embodiment, in the compound of formula (I), $W_1$ is CH or N; $W_2$ is N, O, S or CH.

In another preferred embodiment, in the compound of formula (I), $W_1$ is CH or N; $W_2$ is N or CH.

In another preferred embodiment, in the compound of formula (I), $W_1$ is CH; and $W_2$ is N, O, S or CH.

In another preferred embodiment, in the compound of formula (I), $W_1$ is CH; and $W_2$ is N.

In another preferred embodiment, the compound of formula (I) is a compound of formula (III):

(III)

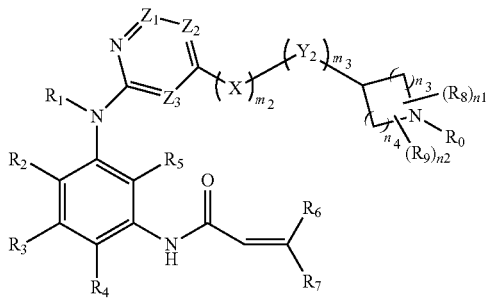

wherein, $Z_1$, $Z_2$, $Z_3$, $R_1$, $R_2$, $R_3$, $R_4$, $R_5$, $R_6$, $R_7$, $R_8$, $R_9$, $Y_2$, X, $m_2$, $m_3$, $n_1$, $n_2$, $n_3$, $n_4$, and $R_0$ are defined as above.

In another preferred embodiment, the compound of formula (I) is a compound of formula (IV):

(IV)

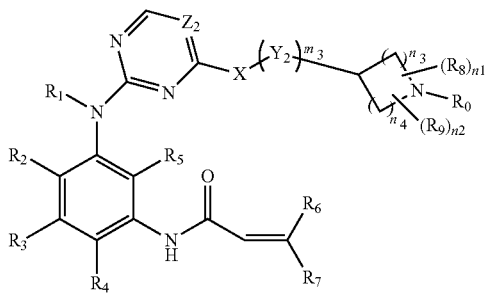

wherein, $Z_2$, $R_1$, $R_2$, $R_3$, $R_4$, $R_5$, $R_6$, $R_7$, $R_8$, $R_9$, $Y_2$, X, $m_3$, $n_1$, $n_2$, $n_3$, $n_4$, and $R_0$ are defined as above.

In another preferred embodiment, the compound of formula (I) is a compound of formula (V):

(V)

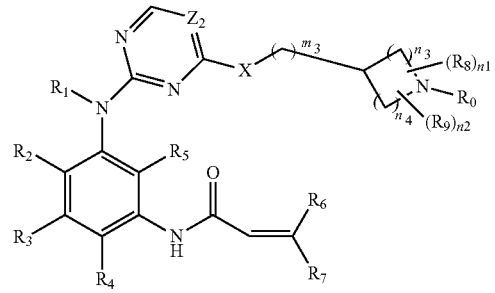

wherein, $Z_2$, $R_1$, $R_2$, $R_3$, $R_4$, $R_5$, $R_6$, $R_7$, $R_8$, $R_9$, X, $m_3$, $n_1$, $n_2$, $n_3$, $n_4$, and $R_0$ are defined as above.

In another preferred embodiment, the compound of formula (I) is a compound of formula (VI):

(VI)

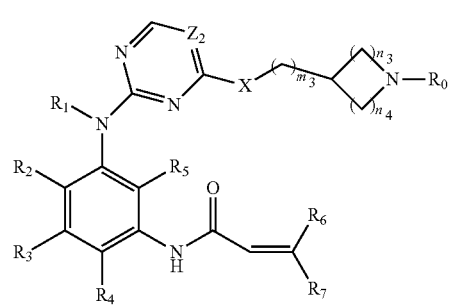

wherein, $Z_2$, $R_1$, $R_2$, $R_3$, $R_4$, $R_5$, $R_6$, $R_7$, X, $m_3$, $n_3$, $n_4$, and $R_0$ are defined as above.

In another preferred embodiment, $Z_2$ is $CR_{10}$ or N; $R_{10}$ is a hydrogen, hydroxy, CN, $NO_2$, fluorine, chlorine, —$NR_{11}R_{12}$, $C_{1-3}$ alkyl, $C_{3-6}$ cycloalkyl, $C_{3-6}$ cycloalkoxy, $C_{1-3}$ alkoxy, —CHO, —$COC_{1-3}$ alkyl, —CO-phenyl, phenyl, —$CONR_{11}R_{12}$, —$C(O)OC_{1-3}$ alkyl, —$OC(O)C_{1-3}$ alkyl, —$SO_2C_{1-3}$ alkyl, —$SO_2$-phenyl or t-butyloxycarbonyl; wherein, each of alkyl, cycloalkyl, phenyl, and alkoxy is unsubstituted or substituted with 1-3 substituents selected from the group consisting of fluorine, chlorine, nitro, phenyl, $C_{1-3}$ alkyl, $C_{1-3}$ alkoxy, $C_{3-6}$ cycloalkyl, $C_{3-6}$ cycloalkoxy, —$CONR_{11}R_{12}$, —$C(O)OC_{1-3}$ alkyl, —CHO, —$OC(O)C_{1-3}$ alkyl, —$SO_2C_{1-3}$ alkyl, —$SO_2$-phenyl, and —CO-phenyl.

In another preferred embodiment, $Z_2$ is $CR_{10}$, $R_{10}$ is a hydrogen, hydroxy, $NO_2$, fluorine, chlorine, —$NH_2$, —$N(CH_3)_2$, $C_{1-3}$ alkyl, cyclopropyl, cyclopropyloxy, $C_{1-3}$ alkoxy, —CHO, —$COCH_3$, —CO-phenyl, phenyl, —$CONH_2$, —$CON(CH_3)_2$, —$C(O)OCH_3$, —$OC(O)CH_3$, —$SO_2CH_3$, —$SO_2$-phenyl or t-butyloxycarbonyl; wherein each of alkyl, cyclopropyl, alkoxy and phenyl is unsubstituted or substituted with 1-3 substituents selected from the group consisting of fluorine, chlorine, nitro, phenyl, methyl, methoxy, cyclopropyl, cyclopropyloxy, —$CONH_2$, —$CON(CH_3)_2$, —$C(O)OCH_3$, —CHO, —$OC(O)CH_3$, —$SO_2CH_3$, —$SO_2$-phenyl, and —CO-phenyl.

In another preferred embodiment, $Z_2$ is $CR_{10}$, $R_{10}$ is hydroxy, $NO_2$, fluorine, chlorine, —$NH_2$, —$N(CH_3)_2$, trifluoromethyl, methoxy, —CHO, —COCH$_3$, —CONH$_2$, —C(O)OCH$_3$ or —OC(O)CH$_3$.

In another preferred embodiment, R$_0$ is a hydrogen, hydroxy, C$_{1-3}$ alkyl, C$_{3-6}$ cycloalkyl, —CHO, —COC$_{1-3}$ alkyl, —CO-phenyl, phenyl, —CONR$_{11}$R$_{12}$, —C(O)OC$_{1-3}$ alkyl, —SO$_2$C$_{1-3}$ alkyl, —SO$_2$-phenyl, —S(O)C$_{1-3}$ alkyl, —S(O)-phenyl, or t-butyloxycarbonyl; wherein each of alkyl, cycloalkyl, and phenyl is unsubstituted or substituted with 1-3 substituents selected from the group consisting of fluorine, chlorine, hydroxy, NO$_2$, phenyl, C$_{1-3}$ alkyl, C$_{1-3}$ alkoxy, C$_{3-6}$ cycloalkyl, C$_{3-6}$ cycloalkoxy, C$_{2-4}$ alkenyl, C$_{2-4}$ alkynyl, —CONR$_{11}$R$_{12}$, —C(O)OC$_{1-3}$ alkyl, —CHO, —OC(O)C$_{1-3}$ alkyl, —SO$_2$C$_{1-3}$ alkyl, —SO$_2$-phenyl, and —CO-phenyl; or R$_0$ is 5 to 6 membered monocyclic heteroaryl having 1 to 4 heteroatoms independently selected from N, O and S, or is

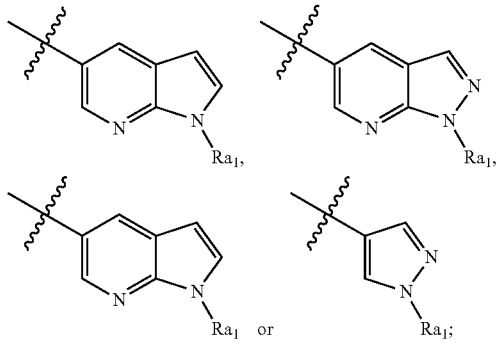

wherein, R$_{a1}$ is a hydrogen, methyl or ethyl.

In another preferred embodiment, R$_0$ is a hydrogen, hydroxy, C$_{1-3}$ alkyl, cyclopropyl, —CHO, —COC$_{1-3}$ alkyl (preferably —COCH$_3$), —CO-phenyl, phenyl, —CONH$_2$, —CON(CH$_3$)$_2$, —C(O)OCH$_3$, —SO$_2$C$_{1-3}$ alkyl (preferably —SO$_2$CH$_3$), —SO$_2$-phenyl, —S(O)C$_{1-3}$ alkyl (preferably —S(O)CH$_3$), —S(O)-phenyl, or t-butyloxycarbonyl; wherein, each of alkyl and phenyl is unsubstituted or substituted with 1-3 (preferably 1) substituent selected from the group consisting of fluorine, chlorine, hydroxy, NO$_2$, phenyl, methyl, methoxy, cyclopropyl, cyclopropyloxy, —CONH$_2$, —CON(CH$_3$)$_2$, —C(O)OCH$_3$, —CHO, —OC(O)CH$_3$, —SO$_2$CH$_3$, —SO$_2$-phenyl, —CO-phenyl; or R$_0$ is selected from: pyridyl,

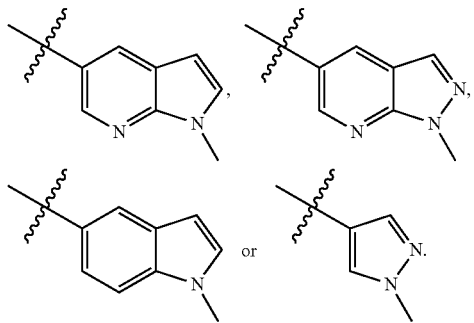

In another preferred embodiment, R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, or t-butyloxycarbonyl; wherein each of alkyl and phenyl is unsubstituted or substituted with 1-3 (preferably 1) substituents selected from the group consisting of fluorine, chlorine, methyl;

In another preferred embodiment, R$_0$ is C$_{1-3}$ alkyl, —COC$_{1-3}$ alkyl (preferably —COCH$_3$), or —SO$_2$C$_{1-3}$ alkyl (preferably —SO$_2$CH$_3$); wherein, the alkyl is unsubstituted or substituted with 1 substituent selected from the group consisting of fluorine and chlorine.

In another preferred embodiment, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$).

In another preferred embodiment, m$_3$ is 0 or 1.

In another preferred embodiment, n$_3$ is 1, 2 or 3; n$_4$ is 1 or 2.

In another preferred embodiment, n$_3$ is 1; n$_4$ is 1.

In another preferred embodiment, X is NH, N(C$_{1-3}$ alkyl), O or S.

In another preferred embodiment, in the compound of formula (VI), (i) Z$_2$ is CR$_{10}$, R$_{10}$ is trifluoromethyl, fluorine or chlorine; m$_3$ is 0; n$_3$ is 1; n$_4$ is 1;

X is NH, O or S;

R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, or t-butyloxycarbonyl; wherein each of alkyl and phenyl is unsubstituted or substituted with 1-3 (preferably 1) substituents selected from the group consisting of fluorine, chlorine and methyl; (preferably, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$))

R$_1$ is a hydrogen; R$_2$ is methoxy; each of R$_3$, R$_5$, R$_6$ and R$_7$ is independently a hydrogen;

R$_4$ is

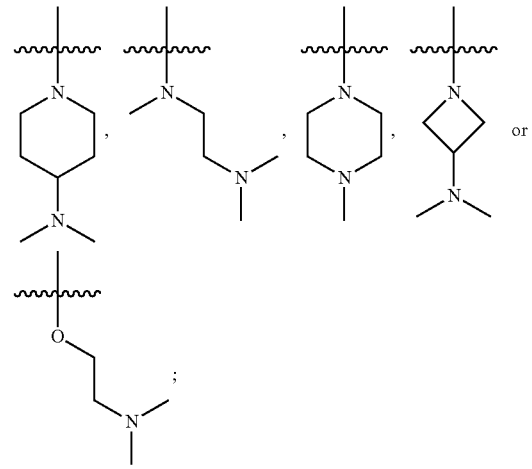

or (ii) Z$_2$ is CR$_{10}$, R$_{10}$ is trifluoromethyl, fluorine or chlorine; m$_3$ is 0; n$_3$ is 3; n$_4$ is 2;

X is O;

R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, and t-butyloxycarbonyl; wherein each of alkyl and phenyl is unsubstituted or substituted with 1-3 (preferably 1) substituents selected from the group consisting of fluorine, chlorine and methyl; (preferably, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$));

R$_1$ is a hydrogen; R$_2$ is methoxy; each of R$_3$, R$_5$, R$_6$ and R$_7$ is independently a hydrogen;

R$_4$ is

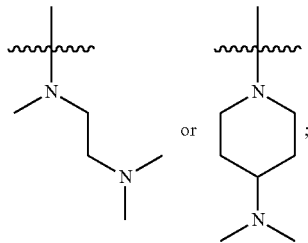

or (iii) Z$_2$ is CR$_{10}$, R$_{10}$ is trifluoromethyl, fluorine or chlorine;

m$_3$ is 0; n$_3$ is 2; n$_4$ is 2;

X is NH or O;

R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, or t-butyloxycarbonyl; wherein each of alkyl and phenyl is unsubstituted or substituted with 1-3 (preferably 1) substituents selected from the group consisting of fluorine, chlorine and methyl; (preferably, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$));

R$_1$ is a hydrogen; R$_2$ is methoxy; each of R$_3$, R$_5$, R$_6$ and R$_7$ is independently a hydrogen;

R$_4$ is

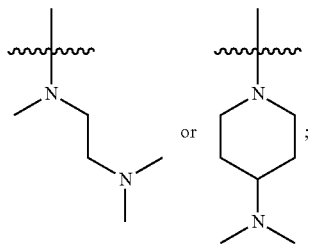

or (iv) Z$_2$ is CR$_{10}$, R$_{10}$ is trifluoromethyl, fluorine or chlorine;

m$_3$ is 0; n$_3$ is 1; n$_4$ is 2;

X is O;

R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, or t-butyloxycarbonyl; wherein each of alkyl and phenyl is unsubstituted or substituted with 1-3 (preferably 1) substituents selected from the group consisting of fluorine, chlorine and methyl; (preferably, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$));

R$_1$ is a hydrogen; R$_2$ is methoxy; each of R$_3$, R$_5$, R$_6$ and R$_7$ is independently a hydrogen;

R$_4$ is

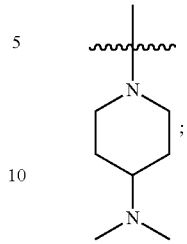

or (v) Z$_2$ is CR$_{10}$, R$_{10}$ is trifluoromethyl, fluorine or chlorine;

m$_3$ is 0; n$_3$ is 3; n$_4$ is 1;

X is NH or O;

R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, or t-butyloxycarbonyl; wherein each of alkyl and phenyl is unsubstituted or substituted with 1-3 (preferably 1) substituents selected from the group consisting of fluorine, chlorine and methyl; (preferably, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$));

R$_1$ is a hydrogen; R$_2$ is methoxy; each of R$_3$, R$_5$, R$_6$ and R$_7$ is independently a hydrogen;

R$_4$ is

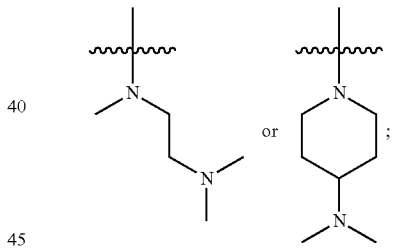

or (vi) Z$_2$ is CR$_{10}$, R$_{10}$ is trifluoromethyl, fluorine or chlorine;

m$_3$ is 1; n$_3$ is 1; n$_4$ is 1;

X is O;

R$_0$ is a hydrogen, C$_{1-3}$ alkyl, —COC$_{1-3}$ alkyl (preferably —COCH$_3$), —CO-phenyl, —SO$_2$C$_{1-3}$ alkyl (preferably —SO$_2$CH$_3$), —SO$_2$-phenyl, or t-butyloxycarbonyl; wherein each of alkyl and phenyl is unsubstituted or substituted with 1-3 (preferably 1) substituents selected from the group consisting of fluorine, chlorine and methyl; (preferably, R$_0$ is C$_{1-3}$ alkyl substituted by one fluorine (preferably fluoroethyl), —COC$_{1-3}$ alkyl (preferably —COCH$_3$) or —SO$_2$C$_{1-3}$ alkyl (preferably —SO$_2$CH$_3$));

R$_1$ is a hydrogen; R$_2$ is methoxy; each of R$_3$, R$_5$, R$_6$ and R$_7$ is independently a hydrogen;

$R_4$ is

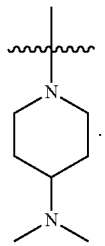 [SMILES: *N1CCC(N(C)C)CC1]

In another preferred embodiment, in the compound of formula (VI), (i) X is NH, $m_3$ is 0; $n_3$ is 1; $n_4$ is 1;
$Z_2$ is $CR_{10}$, $R_{10}$ is fluorine, chlorine or trifluoromethyl;
$R_0$ is —$COC_{1-3}$ alkyl (preferably —$COCH_3$) or —$SO_2C_{1-3}$ alkyl (preferably —$SO_2CH_3$);
$R_1$ is a hydrogen; $R_2$ is methoxy; each of $R_3$, $R_5$, $R_6$ and $R_7$ is independently a hydrogen;
$R_4$ is

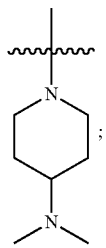

or (ii) X is O, $m_3$ is 0 or 1; $n_3$ is 1, 2 or 3; $n_4$ is 1 or 2;
$Z_2$ is $CR_{10}$, $R_{10}$ is fluorine, chlorine or trifluoromethyl;
$R_1$ is a hydrogen; $R_2$ is methoxy; each of $R_3$, $R_5$, $R_6$ and $R_7$ is independently a hydrogen;
$R_0$ is —$COC_{1-3}$ alkyl (preferably —$COCH_3$), —$SO_2C_{1-3}$ alkyl (preferably —$SO_2CH_3$) or $C_{1-3}$ alkyl substituted by one fluorine (preferably fluoroethyl);
$R_4$ is selected from the group consisting of

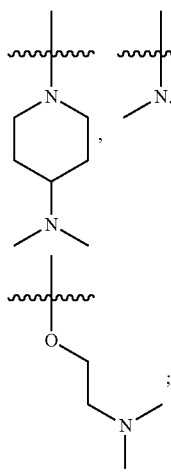

(iii) X is S, $m_3$ is 0; $n_3$ is 1; $n_4$ is 1;
$Z_2$ is $CR_{10}$, $R_{10}$ is fluorine, chlorine or trifluoromethyl;
$R_1$ is a hydrogen; $R_2$ is methoxy; each of $R_3$, $R_5$, $R_6$ and $R_7$ is independently a hydrogen;
$R_0$ is —$COC_{1-3}$ alkyl (preferably —$COCH_3$), or —$SO_2C_{1-3}$ alkyl (preferably —$SO_2CH_3$);

$R_4$ is

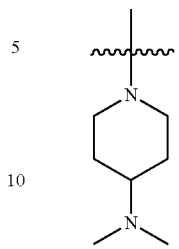

In another preferred embodiment, in the compound of formula (I), each of $R_3$ and $R_5$ is independently a hydrogen or $C_{1-10}$ alkyl (preferably $C_{1-6}$ alkyl, more preferably $C_{1-3}$ alkyl).

In another preferred embodiment, in the compound of formula (I), $R_1$ is a hydrogen.

In another preferred embodiment, in the compound of formula (I), $R_2$ is $C_{1-10}$ alkoxy (preferably $C_{1-6}$ alkoxy, more preferably $C_{1-3}$ alkoxy, most preferably methoxy).

In another preferred embodiment, in the compound of formula (I), $R_4$ is a hydrogen, —$OC_{1-10}$ alkyl, —$N(C_{1-10}$ alkyl$)_2$, —$N(C_{1-10}$ alkyl$)(C_{3-8}$ cycloalkyl), 3 to 7 membered saturated or partially unsaturated heterocyclic monoring having 1 or 2 nitrogen atoms and 0, 1, 2 or 3 O or S atoms; wherein each of alkyl, cycloalkyl, and 3 to 7 membered saturated or partially unsaturated heterocyclic monoring may be optionally substituted by 1-3 substituents selected from the group consisting of halogen, $NO_2$, CN, hydroxy, —$CH_2NR_{11}R_{12}$, —$NR_{11}R_{12}$, $C_{1-6}$ alkyl, $C_{3-8}$ cycloalkyl, $C_{3-8}$ cycloalkoxy, $C_{2-6}$ alkenyl, $C_{2-6}$ alkynyl, $C_{1-6}$ alkoxy, —CHO, —$COC_{1-6}$ alkyl, —$COC_6$ aryl, $C_6$ aryl, —$CONR_{11}R_{12}$, —$C(O)OC_{1-6}$ alkyl, —$OC(O)C_{1-6}$ alkyl, —$SO_2C_{1-6}$ alkyl, —$SO_2C_6$ aryl, t-butyloxycarbonyl, —$NHC_{1-6}$ alkyl, —$NC(O)C_{1-6}$ alkyl, —$NSO_2C_{1-6}$ alkyl, morpholinyl, tetrahydro-pyrrolyl, piperazinyl, and methylpiperazinyl.

In another preferred embodiment, in the compound of formula (I), $R_4$ is a hydrogen, or selected from the group consisting of

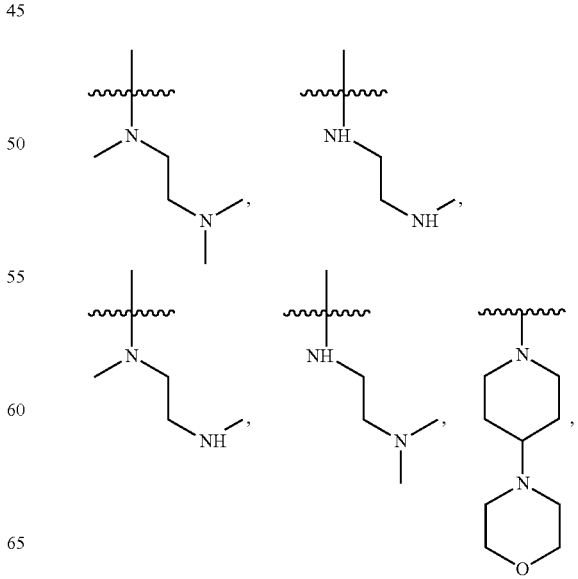

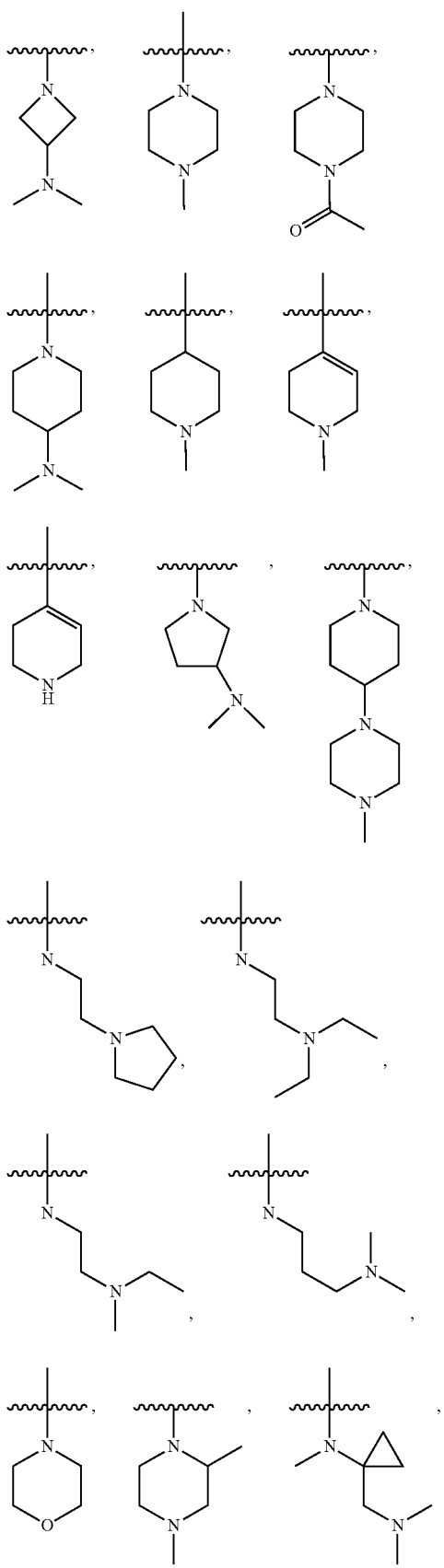

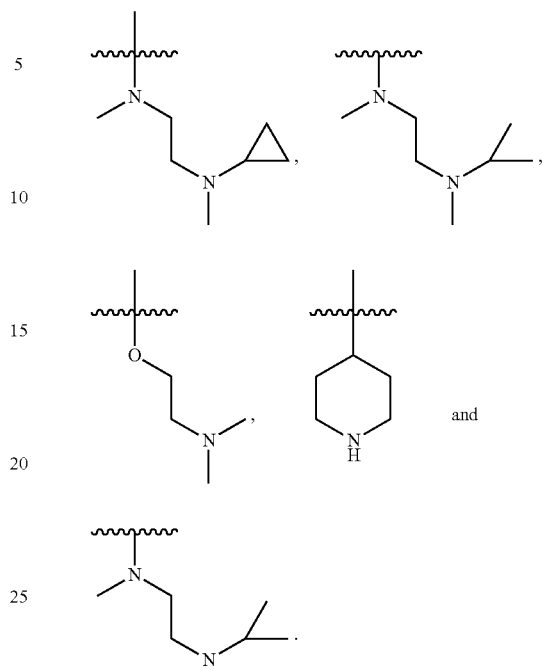

In another preferred embodiment, $R_4$ is a group selected from the group consisting of:

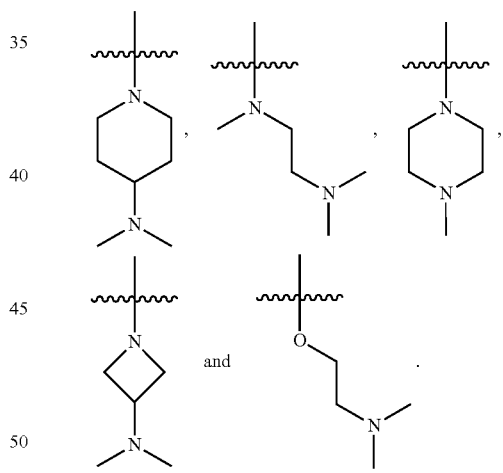

In another preferred embodiment, in the compound of formula (I), each of $R_6$ and $R_7$ is independently a hydrogen.

In another preferred embodiment, in the compound of formula (I), each of $R_6$ and $R_7$ is independently a hydrogen or —$CH_2NR_{13}R_{14}$, and, each of $R_{13}$ and $R_{14}$ is independently a hydrogen or methyl.

In another preferred embodiment, in the compound of formula (I), each of $R_6$ and $R_7$ is independently a hydrogen or —$CH_2NR_{13}R_{14}$, and, $R_{13}$ and $R_{14}$ together with the conjoint nitrogen form a 5-6 membered saturated N-containing heterocyclic ring.

Preferably, the structure of —$CH_2NR_{13}R_{14}$ is shown as formula (a):

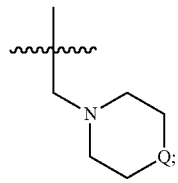
(a)
wherein, Q is O, S, $NC_{1-10}$ alkyl or $C(C_{1-10}$ alkyl$)_2$.
In another preferred embodiment, the compound of formula (I) is selected from the group consisting of:
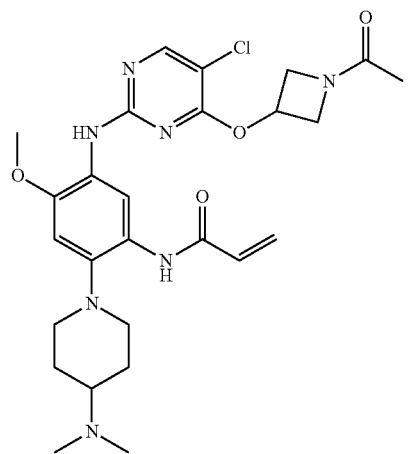
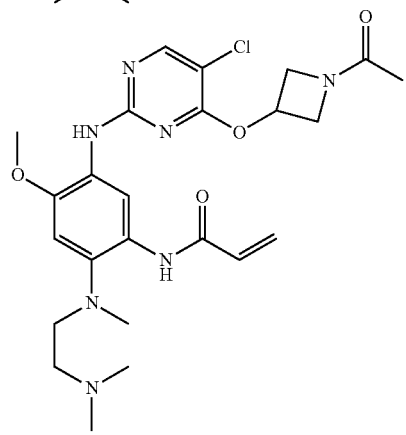
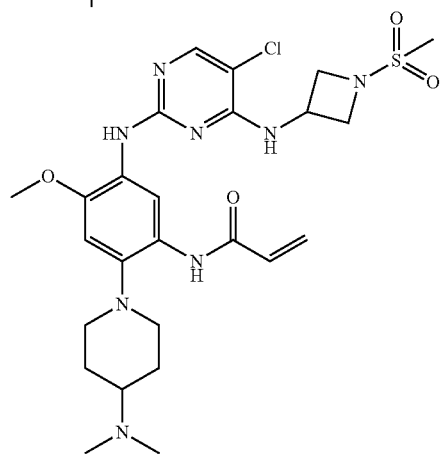
-continued
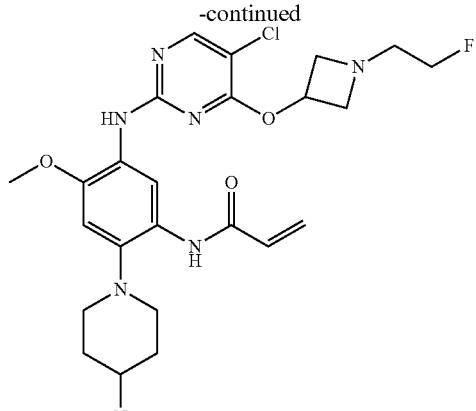
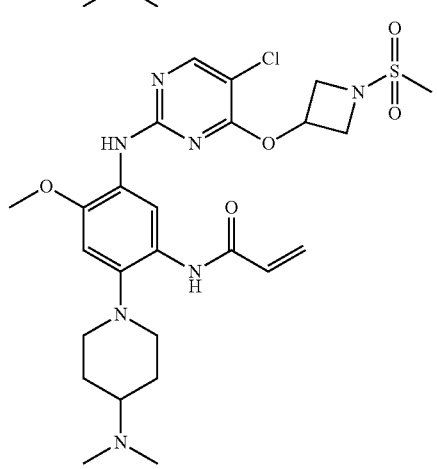
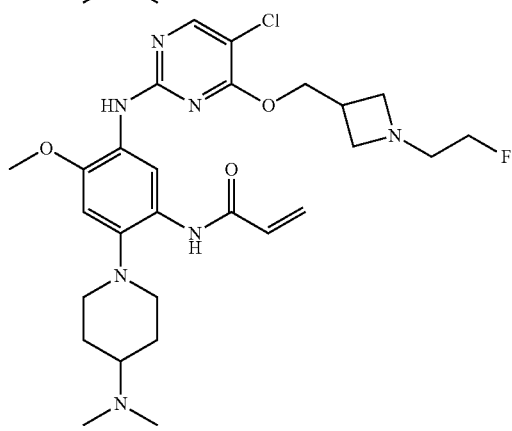
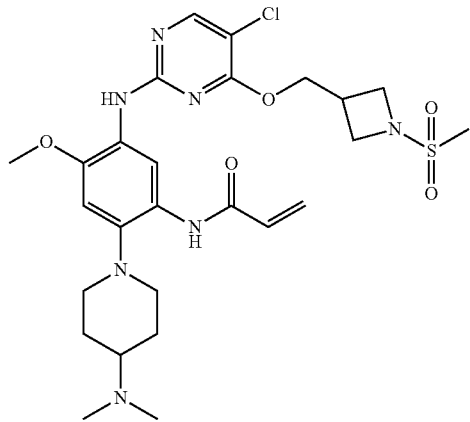

21
-continued
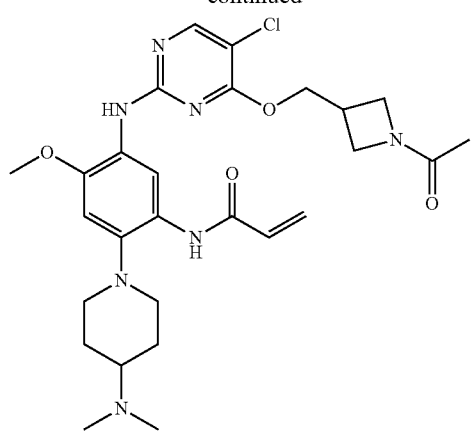
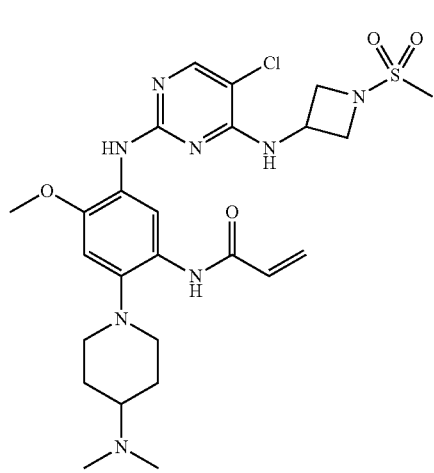
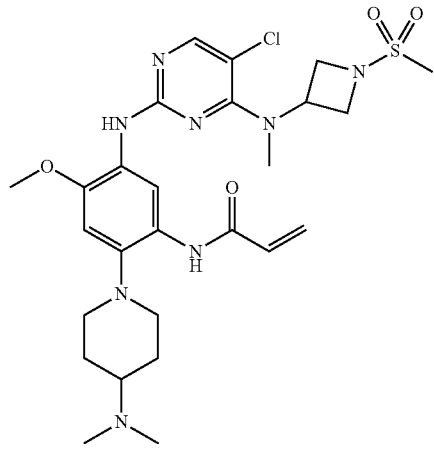
22
-continued
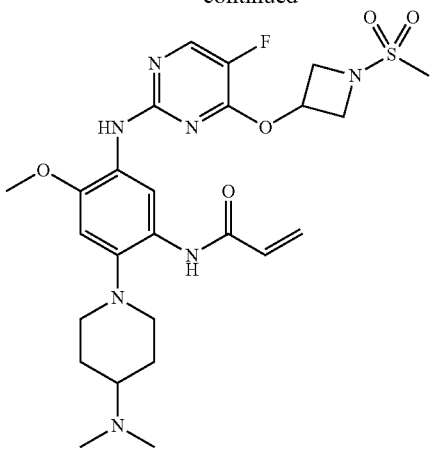
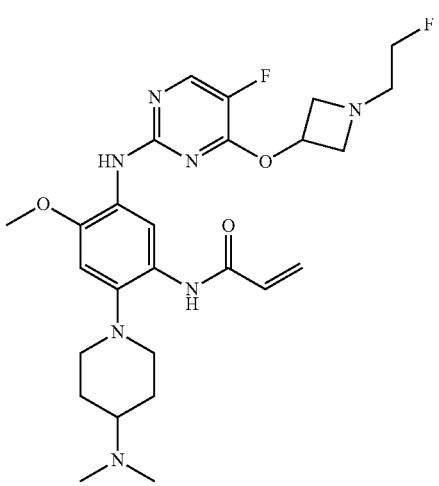
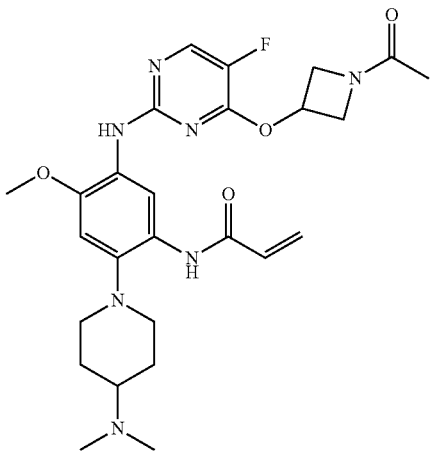

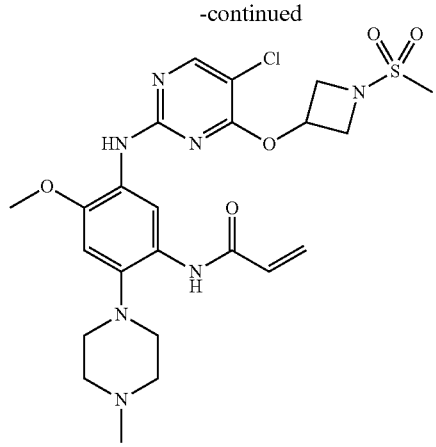
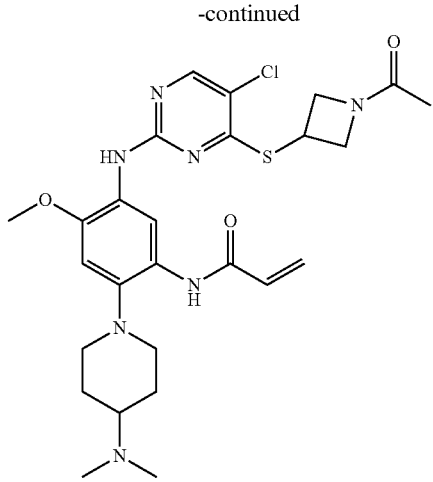
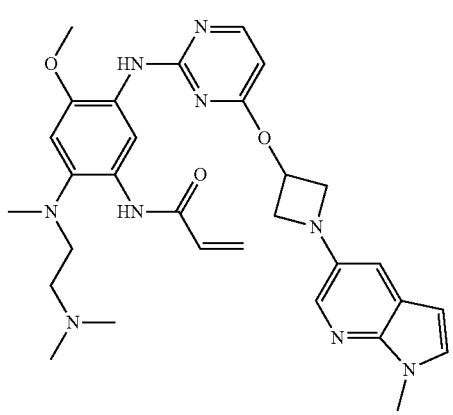
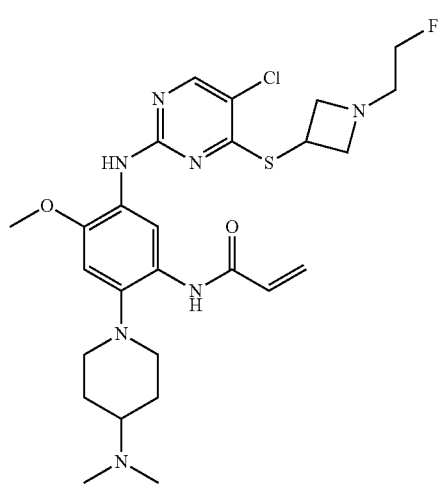
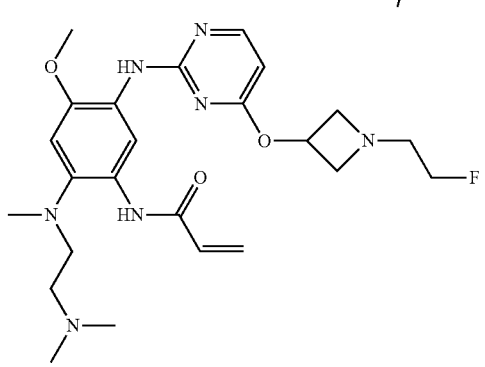
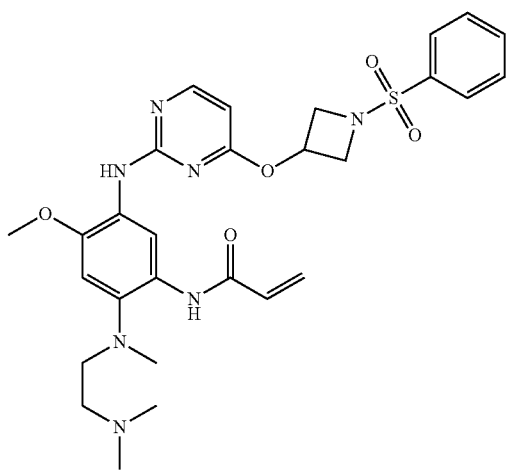

25
-continued
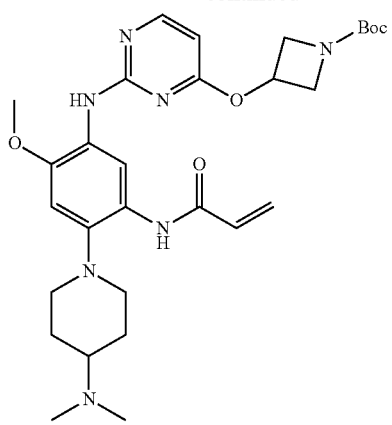
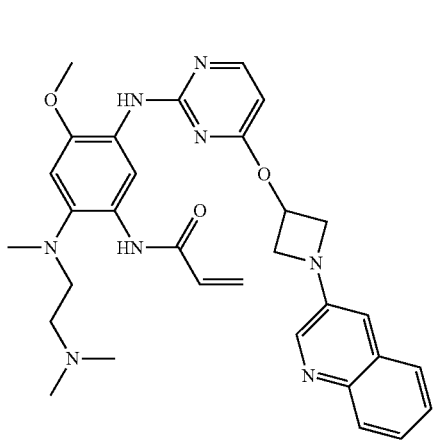
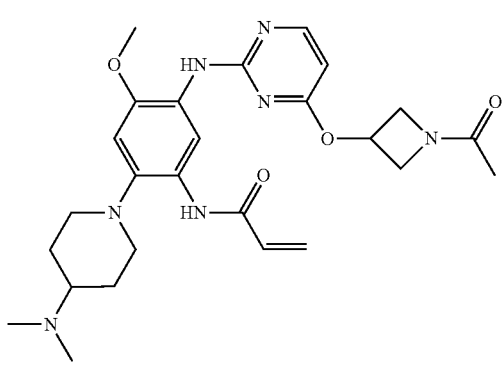
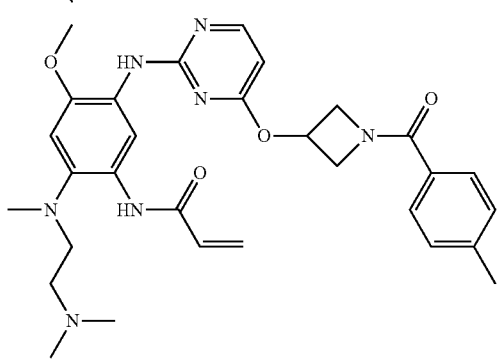
26
-continued
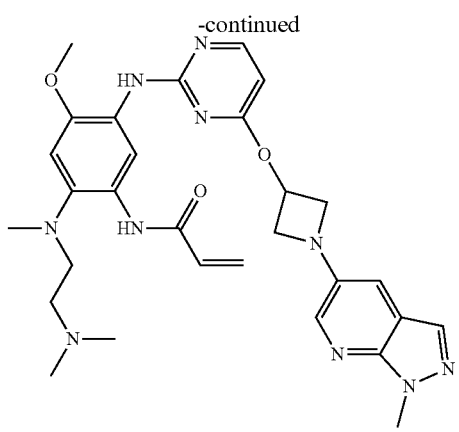
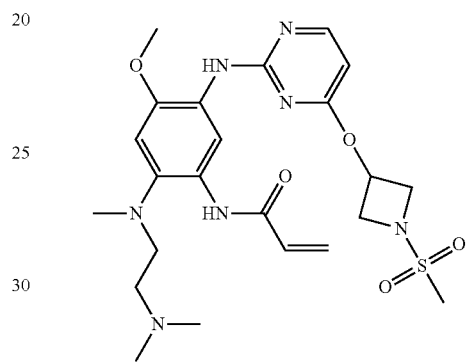
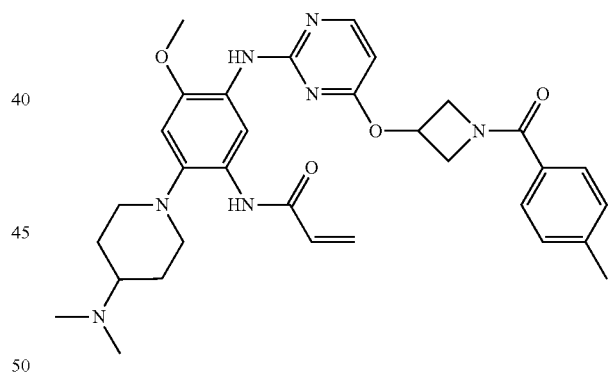
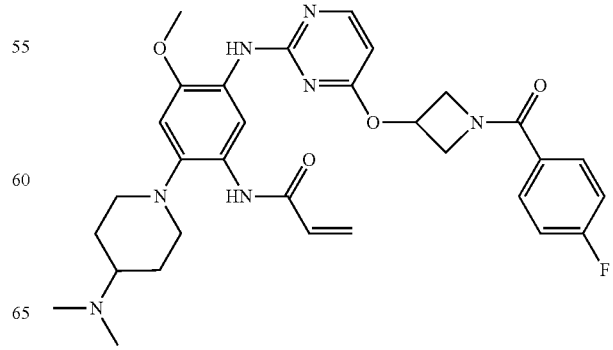

27
-continued
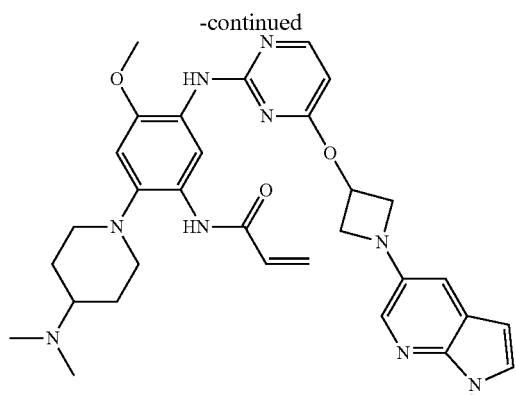
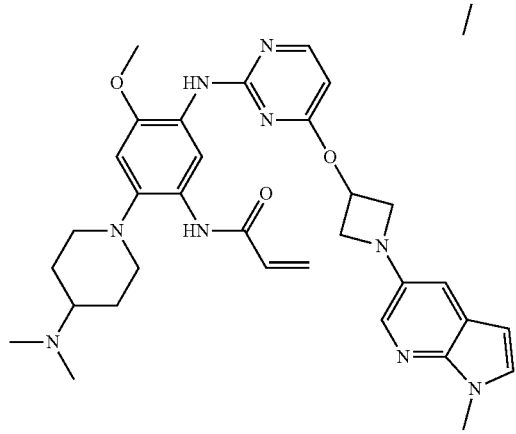
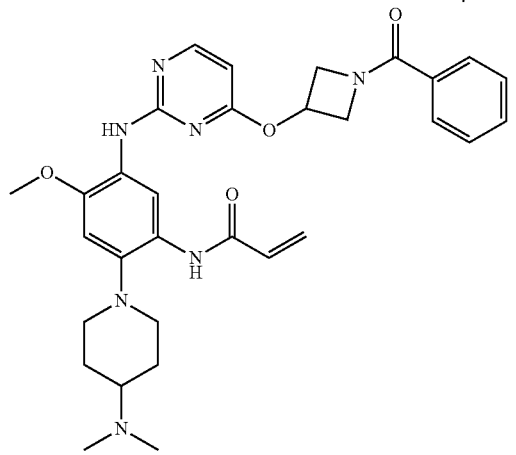
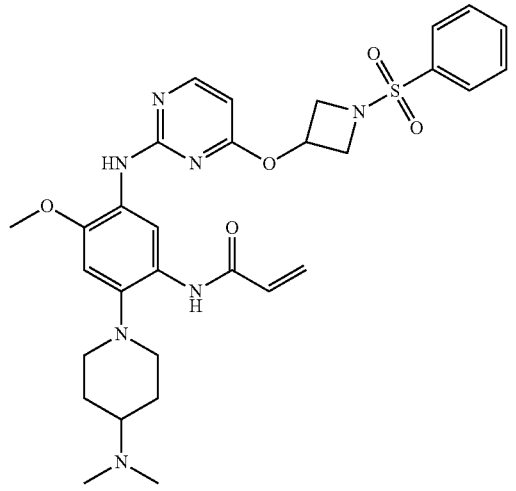
28
-continued
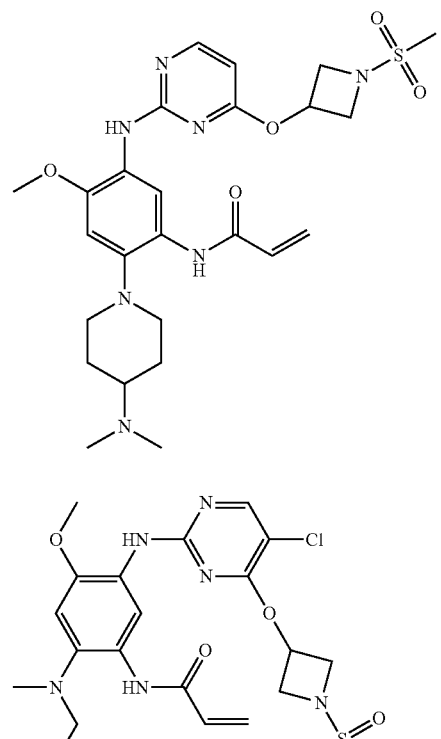
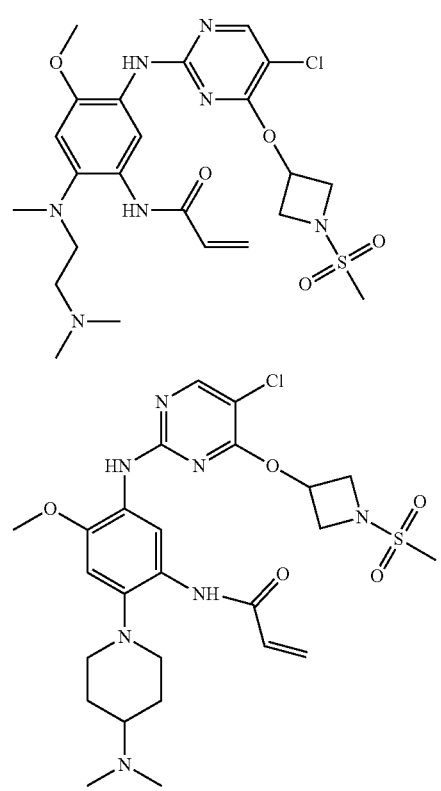
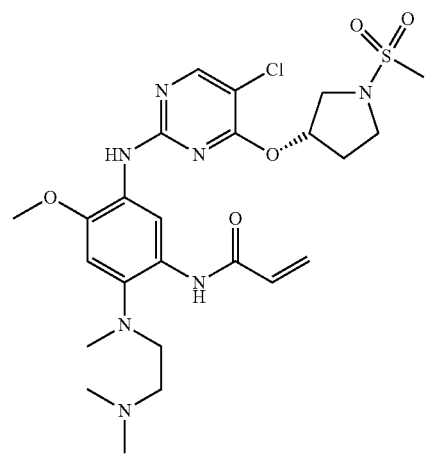

29
-continued
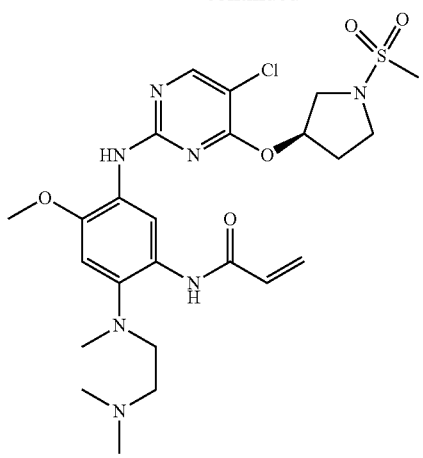
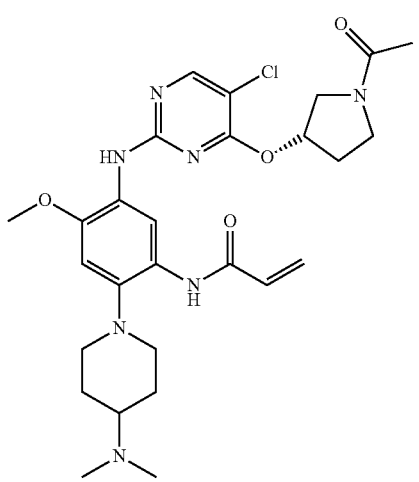
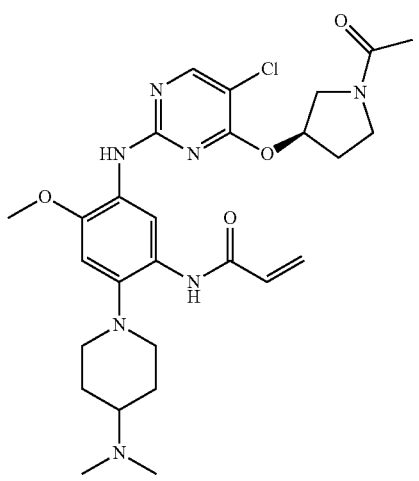
30
-continued
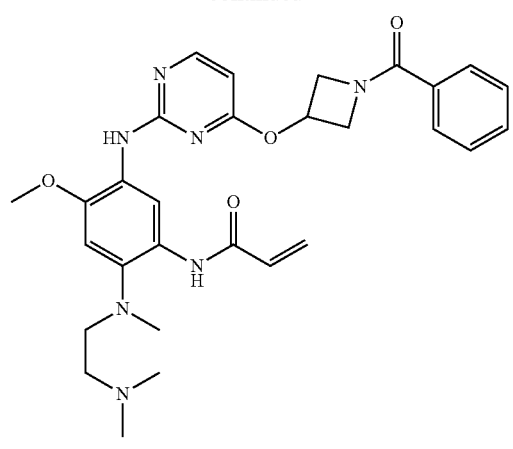
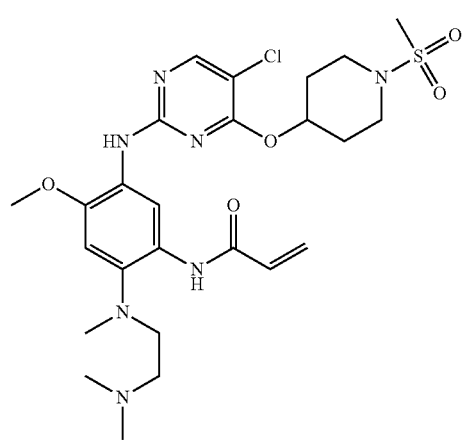
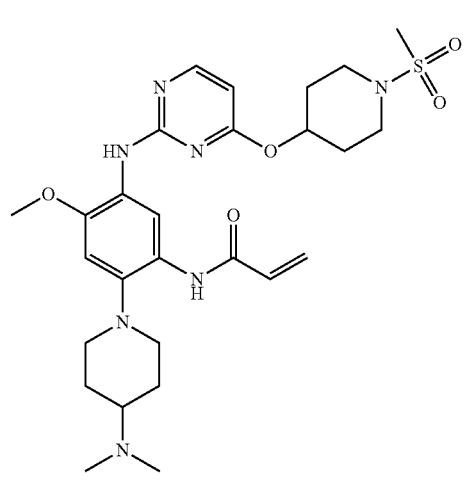

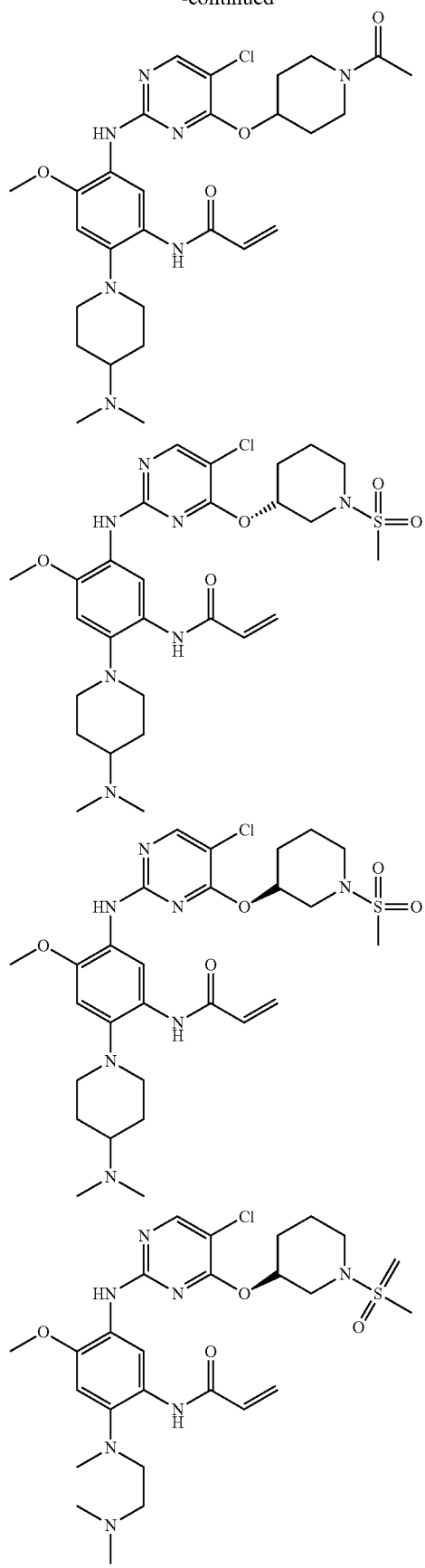
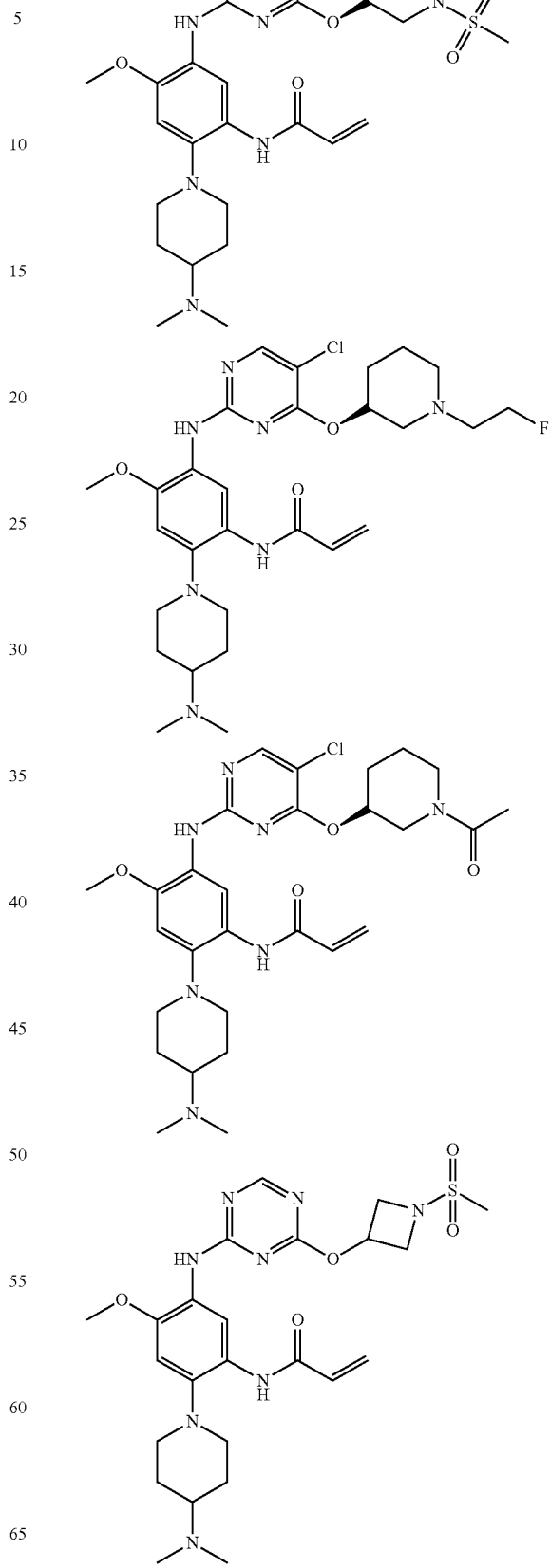

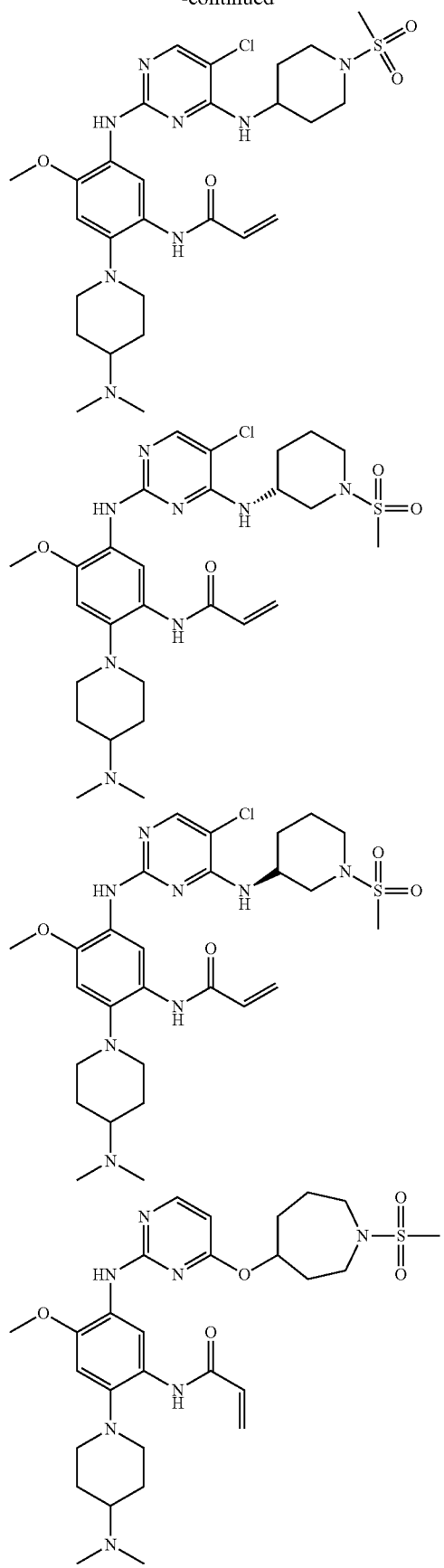
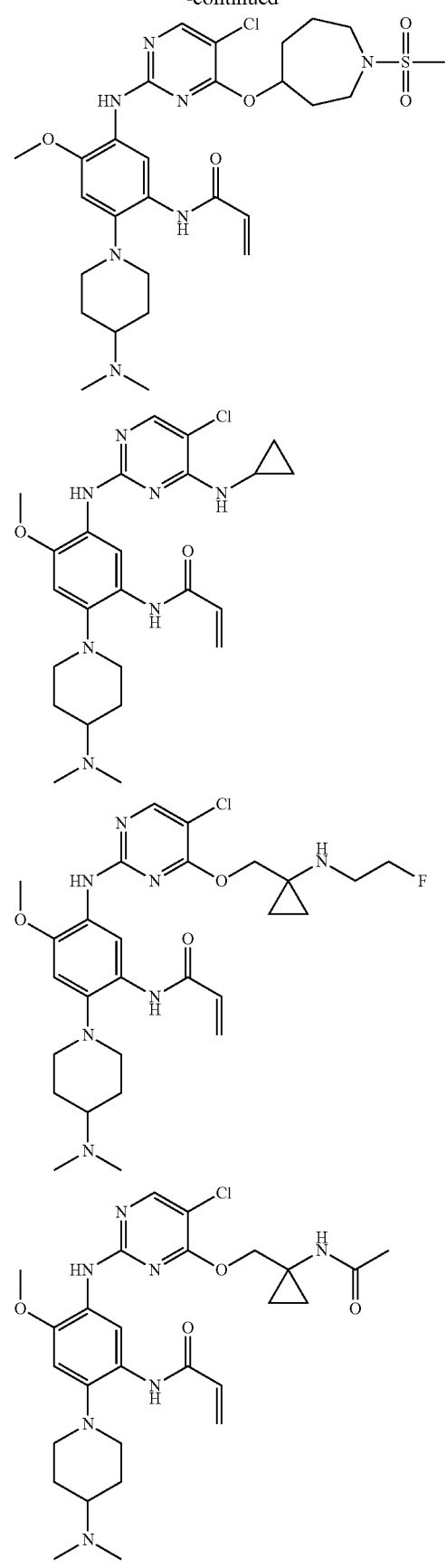

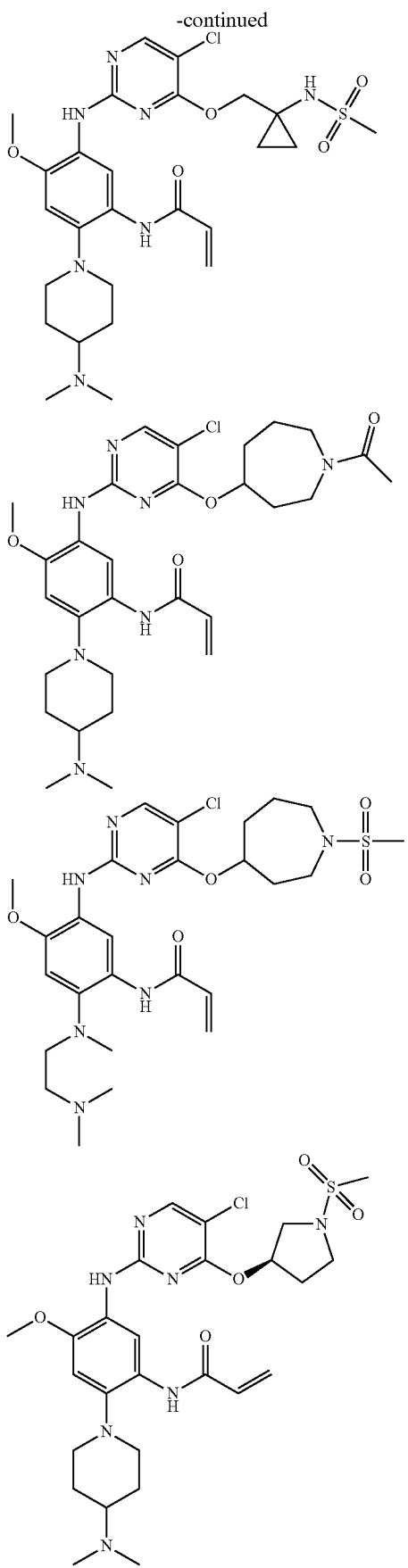
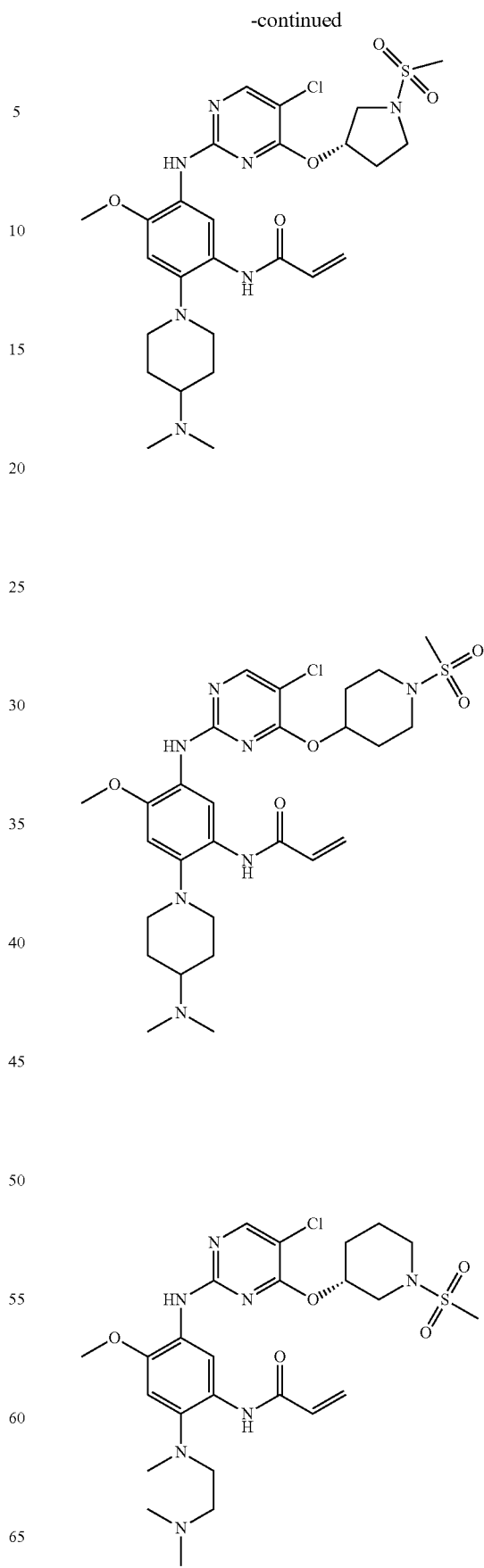

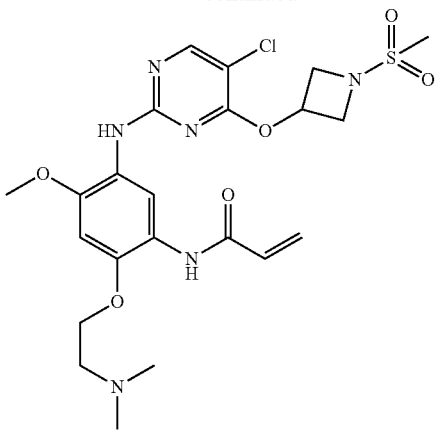

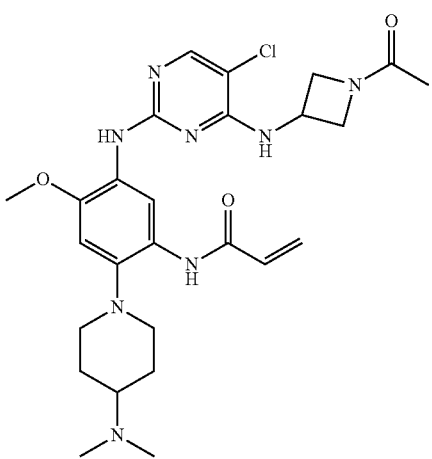

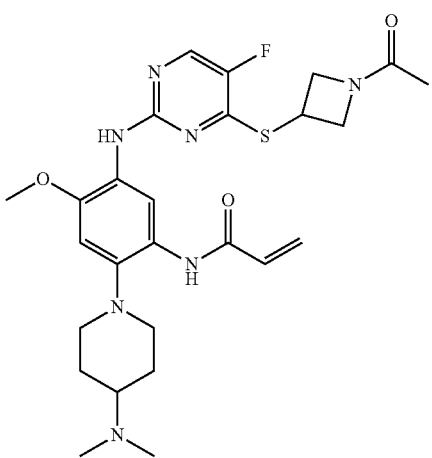

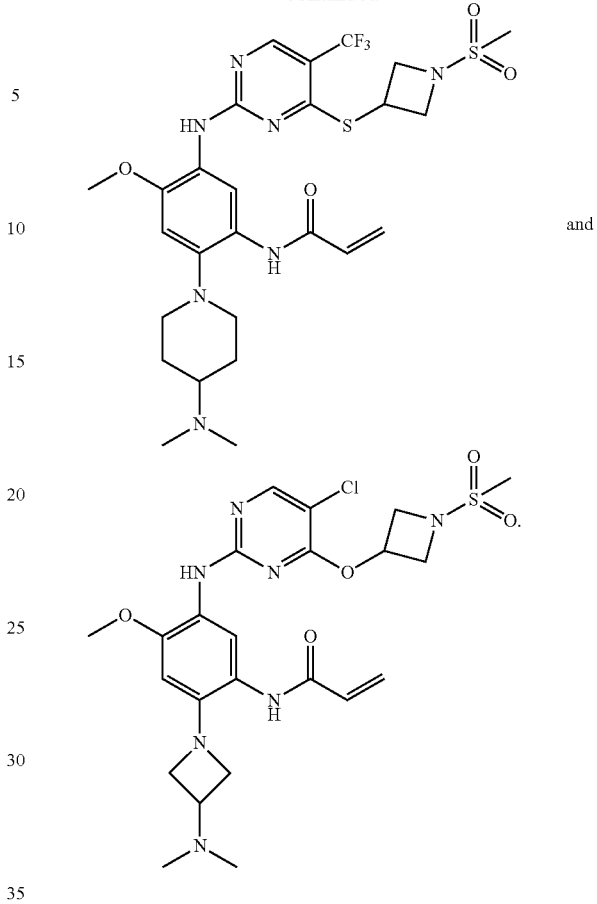

and

In the second aspect of the present invention, a pharmaceutical composition is provided, which comprises the compound of the first aspect of the present invention (such as the compound of formula (I), formula (II), formula (III), formula (IV), formula (V), formula (VI), formula (VII-1), formula (VII-2), formula (VII-3), formula (VII-4), formula (VII-5), formula (VII-6), formula (VII-7), formula (VII-8), formula (VII-9), formula (VII-10), or the exemplary compounds as described above), or a pharmaceutically acceptable salt, solvate, stereoisomer, or prodrug thereof, and a pharmaceutically acceptable carrier.

Generally, the compound of the present invention or a pharmaceutically acceptable salt solvate, stereoisomer, or prodrug thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present invention contained in these formulations may be solid powders or granules; solutions or suspensions in aqueous or non-aqueous liquid; water-in-oil or oil-in-water emulsions etc. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylidene glycol, polyethylidene glycol and the like. The active compounds may form a solution or suspension with the above-mentioned carriers.

The compositions of the present invention are formulated, quantified and administrated in a manner consistent with the practice of medicine. The "effective amount" of the administrated compound depends on the factors such as the specific disease to be treated, the individual being treated, the cause of diseases, the drug targets and the mode of administration, etc.

In the third aspect of the present invention, a use of the compound of the first aspect of the present invention, or a pharmaceutically acceptable salt, solvate, stereoisomer or prodrug thereof for the manufacture of a medicament for adjusting (up-regulating or down-regulating) EGFR tyrosine kinase activity or treating EGFR-related diseases is provided.

Preferably, the EGFR-related disease is cancer, diabetes, immune system disease, neurodegenerative disease or cardiovascular disease, a disease having acquired resistance during the treatment using EGFR modulators.

Preferably, the cancer is non-small cell lung cancer, head and neck cancer, breast cancer, renal cancer, pancreatic cancer, cervical cancer, esophageal cancer, pancreatic cancer, prostate cancer, bladder cancer, colorectal cancer, ovarian cancer, stomach cancer, brain malignancies including glioblastoma, etc., or any combination thereof.

Preferably, the acquired resistance is caused by mutation of T790 encoded by EGFR exon 20, or comprises a resistance caused by mutation of T790 encoded by EGFR exon 20, such as T790M.

Preferably, the non-small cell lung cancer is caused by EGFR mutations, comprising sensitive mutations (such as L858R mutation or exon 19 deletions) and resistant mutations (such as EGFR T790M mutation).

In the present invention, the EGFR modulator refers to a small molecule tyrosine kinase inhibitor which targets EGFR, such as gefitinib, erlotinib, Icotinib, lapatinib or afatinib.

In the fourth aspect of the present invention, a medicinal composition is provided, comprising a therapeutically effective amount of the compound of the first aspect of the present invention, or a pharmaceutically acceptable salt, solvate, stereoisomer or prodrug thereof, as well as a drug selected from the group consisting of gefitinib, erlotinib, icotinib, lapatinib, XL647, NVP-AEE-788, ARRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitors, CNF2024, tanespimycin, alvespimycin, IPI-504, SNX-5422, NVP-AUY922, or combinations thereof. Except for the compound of the present invention, or a pharmaceutically acceptable salt, solvate, stereoisomer or prodrug thereof, the other drugs in the pharmaceutical composition described above are the antitumor drugs well known to those skilled in the art.

Term "therapeutically effective amount" refers to an amount that yields a function or activity to humans and/or animals and may be tolerated by humans and/or animals.

The therapeutically effective amount of the compound of the present invention, or a pharmaceutically acceptable salt, solvate, stereoisomer or prodrug thereof contained in the pharmaceutical composition or medicinal composition of the present invention is preferably 0.1 mg-5 g/kg (body weight).

The medicinal compositions of the present invention are useful for treating EGFR-related diseases such as cancer, diabetes, immune system disorder, neurodegenerative disease or cardiovascular disease, a disease having acquired resistance during the treatment using EGFR modulators.

The disease having acquired resistance is a disease caused by mutation of T790 encoded by EGFR exon 20, or comprises a disease caused by mutation of T790 encoded by EGFR exon 20.

In another preferred embodiment, the T790 encoded by EGFR exon 20 is T790M.

For certain diseases, the compounds of Formula (I) of the present invention may be used in combination with other drugs in order to achieve a desired therapeutic effect. An example of the combination is for treating advanced NSCLC. For example, a therapeutically effective amount of the compound of formula (I) of the present invention is used in combination with mTOR inhibitors (e.g., rapamycin); or Met inhibitors (including Met antibody MetMAb and small molecule Met inhibitors PF02341066); or IGF1R inhibitors (e.g., OSI-906); or heat shock protein inhibitors, and the like.

It should be understood that each of the above technical features of the invention and each technical feature specifically described below (such as in Examples) can be combined with each other within the scope of the present invention so as to constitute new or preferred technical solutions.

DETAIL DESCRIPTION OF INVENTION

Inventors unexpectedly discovered a class of selective inhibitors of EGFR mutations after a long and intensive study. Assays in vitro showed that the selective inhibitors could inhibit the EGFR T790M/L858R double mutant enzyme and the proliferation of H1975 cell line at nanomolar concentrations, and also exhibited a high intensity of inhibition against EGFR sensitive mutant cell line HCC827 (exon 19 deletion) but had a relatively weak inhibition against wild-type EGFR enzyme and A431 cell line. Thus, the compounds with such structures can be used not only for the treatment of EGFR sensitive mutant cancer but also for the treatment of secondary resistance cases generated during the current EGFR-TKI therapy. Meanwhile, the side effects generated by inhibition of wild-type EGFR are greatly reduced due to the mutation selectivity of the compounds. In addition, these compounds exhibit low cytotoxicity in normal cells (such as 3T3 cells), thereby greatly reducing the non-specific side effects, and are the ideal substitutes of the second-generation of EGFR-TKI.

Definition of Terms

"$C_{1-10}$ alkyl" refers to a straight or branched saturated aliphatic hydrocarbon group having 1 to 10 carbon atoms, for example, methyl, ethyl, propyl, iso-propyl, n-butyl, iso-butyl, tert-butyl, pentyl, hexyl and the like, and preferably alkyl having 1 to 6 carbon atoms, and more preferably alkyl having 1 to 3 carbon atoms.

"$C_{2-10}$ alkenyl" refers to a straight or branched unsaturated aliphatic hydrocarbon group having 2 to 10 (preferably 2 to 6) carbon atoms and carbon-carbon double bond (C=C), for example ethenyl, propenyl, iso-propenyl, n-butenyl, iso-butenyl, pentenyl, hexenyl and the like.

"$C_{2-10}$ alkynyl" refers to a straight or branched unsaturated aliphatic hydrocarbon group having 2 to 10 (preferably 2 to 6) carbon atoms and carbon-carbon triple bond, for example ethynyl, propynyl, n-butynyl, iso-butynyl, pentynyl, hexynyl and the like.

"$C_{3-8}$ cycloalkyl" refers to cycloalkyl having 3 to 8 carbon atoms, for example cyclopropyl, cyclobutyl, cyclopentyl, cyclohexyl and the like.

"$C_{1-10}$ alkoxy" refers to $C_{1-10}$ alkyl-O—, for example methoxy, ethoxy, propoxy, butoxy and the like.

"$C_{3-8}$ cycloalkoxy" refers to $C_{3-8}$ cycloalkyl-O—, for example cyclopropyloxy, cyclobutyloxy, cyclopentyloxy, cyclohexyloxy and the like.

"$C_{6-10}$ aryl" refers to aromatic hydrocarbon group having 6 to 10 carbon atoms, for example phenyl, naphthyl and the like.

"Halogen" refers to fluorine, chlorine, bromine or iodine.

"Divalent $C_{1-3}$ hydrocarbyl" refers to a straight or branched alkylidene, alkenylidene or alkynylidene, wherein, "alkylidene" refers to divalent alkyl, for example, methylidene, ethylidene and the like; and "alkenylidene" refers to divalent alkenyl. "Alkylidene is replaced" refers to the methylidene in the divalent straight or branched $C_{1-3}$ hydrocarbyl may be replaced with the groups as defined herein, for example, it is —CH$_2$—S(O)—CH$_2$—, —CH$_2$—O—CH$_2$—, —CH$_2$—C(O)NR$^y$—CH$_2$—, —C(O)—CH$_2$—CH$_2$—, —CH$_2$—C(R$^y$R$^x$)—CH$_2$—, —N(R$^y$)—CH$_2$—CH$_2$—, —C(R$^y$R$^x$)—C(R$^y$R$^x$)—CH$_2$— and the like after replacement.

Term "cyclopropylidene" refer to the structure of

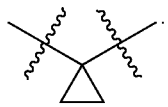 [SMILES: *C1(*)CC1]

Terms "hetero aryl ring" and "hetero aryl" may be used changeably, and refer to a group having 5 to 10 ring atoms (preferably 5, 6, 9 or 10 ring atoms), wherein 1 to 5 of ring atoms are heteroatoms and others are carbon atoms and the ring shares 6, 10 or 14 π electron. Term "heteroatom" refers to nitrogen, oxygen or sulfur.

"5 to 6 membered monocyclic heteroaryl ring" refers to a monocyclic heteroaryl ring having 5 to 6 ring atoms, for example, including (but not limited to): thiophene ring, furan ring, thiazole ring, imidazole ring, oxazole ring, pyrrole ring, imidazole ring, triazole ring, tetrazole ring, isoxazole ring, oxadiazole ring, thiadiazole ring, pyridine ring, pyridazine ring, pyrimidine ring, pyrazine ring and the like.

"8 to 10 membered bicyclic heteroaryl ring" refers to bicyclic hetero aryl ring having 8 to 10 ring atoms, for example, including (but not limited to): benzofuran ring, benzothiophene ring, indole ring, isoindole ring, quinoline ring, isoquinoline ring, indazole ring, benzothiazole ring, benzimidazole ring, quinazoline ring, quinoxaline ring, cinnoline ring, phthalazine ring.

Herein the 5 to 6 membered monocyclic heteroaryl ring or 8 to 10 membered bicyclic heteroaryl ring may be selected from the group consisting of

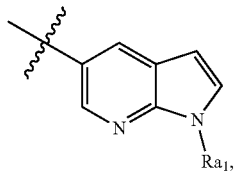 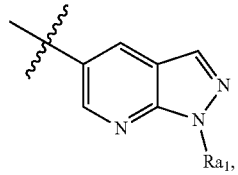

-continued

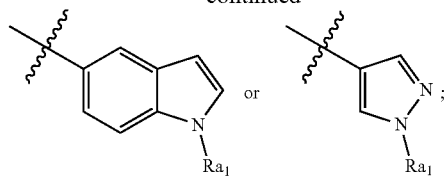

wherein, $R_{a1}$ is a hydrogen, methyl or ethyl.

As used herein, "partially unsaturated" refers to those having one or more unsaturated bonds while do not have fully conjugated π electron system.

"3 to 7 membered saturated or partially unsaturated monocyclic ring" refers to a saturated all-carbon monocyclic ring or partially unsaturated all-carbon monocyclic ring having 3 to 7 ring atoms, for example, including (but not limited to): cyclopropane, cyclobutane, cyclopentane, cyclohexane, cyclohexadiene ring, cycloheptane, cycloheptanetriene ring and the like.

"8 to 10 membered saturated or partially unsaturated bicyclic ring" refers to a saturated all-carbon bicyclic ring or partially unsaturated all-carbon bicyclic ring having 8 to 10 ring atoms.

"3 to 7 membered saturated or partially unsaturated heterocyclic monoring" refers to saturated monocyclic ring or partially unsaturated monocyclic ring having 3 to 7 ring atoms wherein 1 to 3 carbon atoms are substituted by heteroatom(s) selected from nitrogen, oxygen or sulfur. An example of heterocyclic monoring includes (but not limited to): tetrahydrofuran ring, thiophane ring, pyrrolidinyl ring, piperidine ring, pyrroline ring, oxazolidine ring, piperazine ring, dioxalame, morpholine ring.

"8 to 10 membered saturated or partially unsaturated heterocyclic biring" refers to saturated bicyclic ring or partially unsaturated bicyclic ring having 8 to 10 ring atoms wherein 1 to 5 carbon atoms are substituted by heteroatom(s) selected from nitrogen, oxygen or sulfur. An example of heterocyclic biring includes (but not limited to): tetrahydroquinoline ring, tetrahydroisoquinoline ring, decahydroquinoline ring and the like.

"3 to 7 membered saturated or partially unsaturated heterocyclic monoring having 1 or 2 nitrogen atoms and 0 to 3 O or S atoms" refers to a heterocyclic monoring wherein 1 or 2 carbon atom are replaced by nitrogen and 0, 1, 2 or 3 carbon atoms are replaced by oxygen or sulfur.

Pharmaceutical Composition

Term "the active material of the invention" or "the active compound of the invention" refers to the compound of formula (I) of the invention, or a pharmaceutically acceptable salt, solvate, stereoisomer, or prodrug thereof having significant inhibitory activity against resistant EGFR T790M mutation (especially EGFR T790M/L858R double mutation).

As used herein, "pharmaceutically acceptable salt(s)" includes pharmaceutically acceptable acid addition salt(s) and base addition salt(s).

"Pharmaceutically acceptable acid addition salts" refer to salts that are able to retain the biological effectiveness of the free base without other side effects and are formed with inorganic or organic acids. Inorganic acid salts include, but not limited to, hydrochloride, hydrobromide, sulfate, phosphate and the like; organic acid salts include, but not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

"Pharmaceutically acceptable base addition salts" include, but not limited to the salts of inorganic bases such as sodium, potassium, calcium and magnesium salts, and include but not limited to the salts of organic bases, such as ammonium salt, triethylamine salt, lysine salt, arginine salt and the like. These salts can be prepared by the methods known in the art.

As used herein, the compounds of formula (I) may exit in one or more crystalline forms. The active compounds of the present invention include various polymorphs and mixtures thereof.

The "solvate" mentioned in the present invention refers to a complex formed with the compound of the present invention and a solvent. The solvate can be formed either through a reaction in a solvent or precipitated or crystallized from the solvent. For example, a complex formed with water is referred to as "hydrate". The solvates of the compounds of formula (I) are within the scope of the present invention.

The compounds of formula (I) of the invention may contain one or more chiral centers, and may exist in different optically active forms. When the compound contains one chiral center, the compound includes enantiomers. The present invention includes both of two isomers and a mixture thereof, such as racemic mixtures. Enantiomers can be resolved using methods known in the art, such as crystallization and chiral chromatography and the like. When the compound of formula (I) contain more than one chiral centers, the compounds may include diastereomers. The present invention includes specific isomers resolved into optically pure isomers as well as the mixtures of diastereomeric isomers. Diastereomeric isomers can be resolved using methods known in the art, such as crystallization and preparative chromatography.

The present invention includes prodrugs of the above-mentioned compounds. Prodrugs include known amino protecting groups and carboxyl protecting groups which are hydrolyzed under physiologic conditions or released by enzyme reaction to obtain the parent compounds. Specific preparation methods of prodrugs can refer to (Saulnier, M G; Frennesson, D B; Deshpande, M S; Hansel, S B and Vysa, D M Bioorg. Med. Chem Lett. 1994, 4, 1985-1990; and Greenwald, R B; Choe, Y H; Conover, C D; Shum, K.; Wu, D.; Royzen, M. J. Med. Chem. 2000, 43, 475).

Preparation Method

The present invention provides preparation methods of compounds of formula (I). The compounds of the present invention can be easily prepared by a variety of synthetic operations, and these operations are familiar to those skilled in the art. An exemplary preparation of these compounds may include (but not limited to) the processes described below.

Compounds of formula (I) of the present invention can be prepared referring to the following schemes. The procedures of method can be extended or combined as desired in practice.

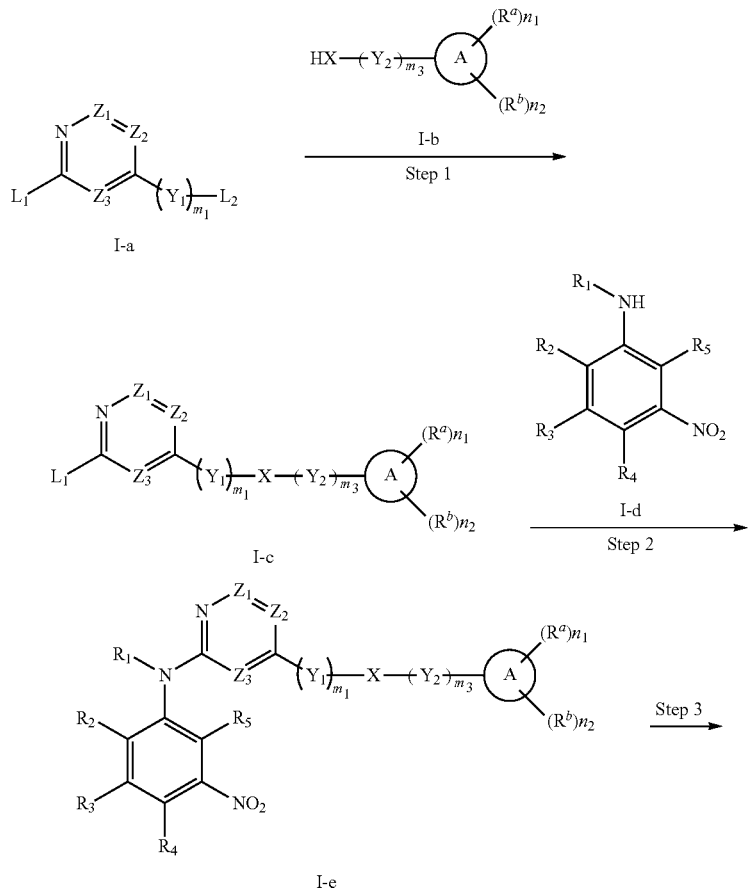

-continued

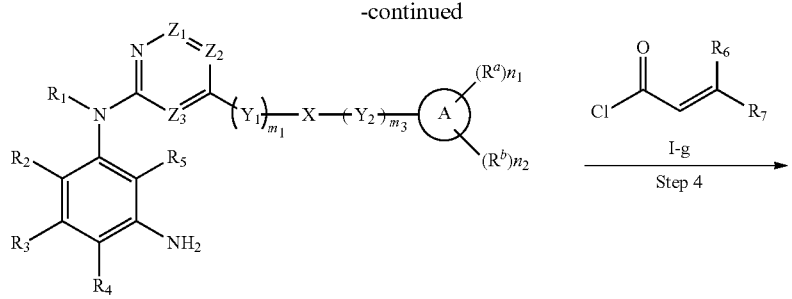

I-f

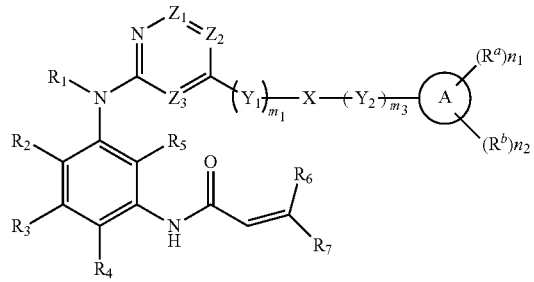

I

Step 1: compound of formula (I-a) may react with compound of formula (I-b) through substitution reaction (for example nucleophilic substitution etc.) or coupling reaction (such as Suzuki coupling etc.) to form compound of formula (I-c), wherein $L_1$ and $L_2$ in compound of formula (I-a) are leaving groups, including (but not limited to) trifluoromethanesulfonate; chlorine, bromine, iodine; sulfonate, such as methane sulfonate, methylbenzenesulfonate, p-bromobenzenesulfonate, p-toluenesulfonate and the like; acyloxy, such as acetoxyl, trifluoroacetoxyl and the like.

Step 2: compound of formula (I-c) may react with compound of formula (I-d) through substitution reaction or coupling reaction to form compound of formula (I-e), for example, at a certain temperature and using suitable catalysts (or comprising suitable ligand) or base and suitable solvent. For example, when using acid catalysis, the catalyst may be but is not limited to TFA or p-toluenesulfonic acid; when using Buchwald-Hartwig amination, the palladium catalyst used may be but is not limited to $Pd_2(dba)_3$, the ligand used may be but is not limited to XantPhos (4,5-bis (diphenylphosphino)-9,9-dimethylxanthene), and the base used may be but is not limited to cesium carbonate.

Step 3: the nitro compound may be conversed into a corresponding amino compound in an acidic condition using metal (including but not limited to iron powder, zinc powder) or stannous chloride as a reductant; or by hydrogenation reduction catalyzed by Palladium/C.

Step 4: the amino compound may react with a corresponding acyl chloride in a basic condition or a corresponding carboxylic acid in the presence of a condensing agent to form amide.

All of the reactions in the above steps are conventional reactions known to the skilled in the art. Compounds of formula (I-a) and formula (I-b) are available commercially or prepared through methods known to the skilled in the art.

Compound of formula (VI) of the present invention may be prepared through the method shown in scheme 1.

Scheme 1

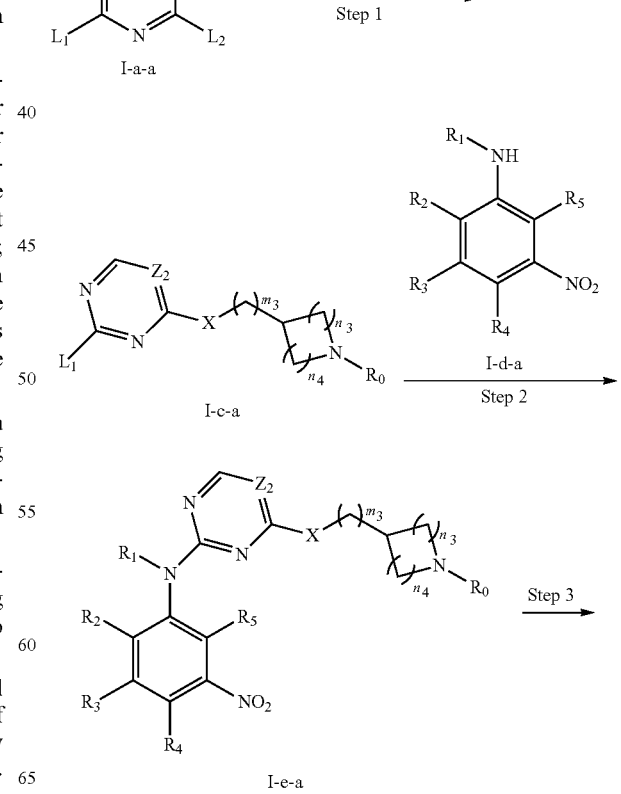

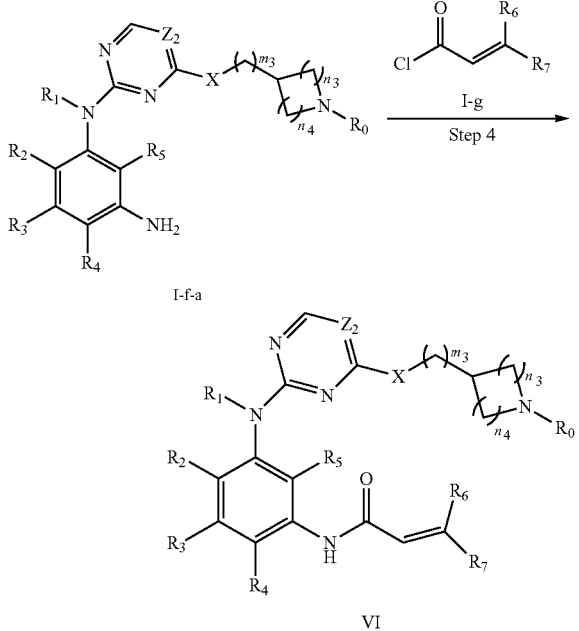

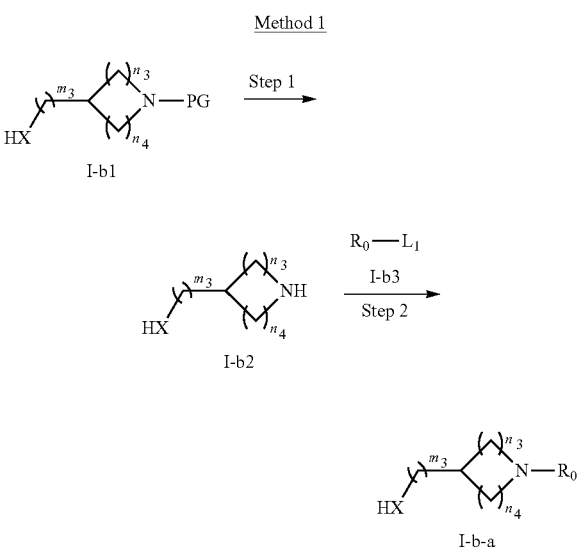

wherein, each of substituent and group is defined as herein.

Step 1: Compound of formula (I-a-a) may react with Compound of formula (I-b-a) through substitution reaction (for example nucleophilic substitution etc.) or coupling reaction (such as Suzuki coupling etc.) to form Compound of formula (I-c-a), wherein $L_1$ and $L_2$ in compound of formula (I-a-a) are leaving groups, including (but not limited to) trifluoromethanesulfonate; chlorine, bromine, iodine; sulfonate, such as methane sulfonate, methylbenzenesulfonate, p-bromobenzenesulfonate, p-toluenesulfonate and the like; acyloxy, such as acetoxyl, trifluoroacetoxyl and the like.

Step 2: Compound of formula (I-c-a) may react with Compound of formula (I-d-a) through substitution reaction or coupling reaction to form Compound of formula (I-e-a), for example, at a certain temperature and using suitable catalysts (or comprising suitable ligand) or base and suitable solvent. For example, when using acid catalysis, the catalyst may be but is not limited to TFA or p-toluenesulfonic acid; when using Buchwald-Hartwig amination, the palladium catalyst used may be but is not limited to $Pd_2(dba)_3$ (tri(dibenzylideneacetone)dipalladium), the ligand used may be but is not limited to XantPhos(4,5-bis(diphenylphosphino)-9,9-dimethylxanthene), and the base used may be but is not limited to cesium carbonate.

Step 3: the nitro compound I-e-a may be conversed into a corresponding amino compound in an acidic condition using metal (including but not limited to iron powder, zinc powder) or stannous chloride as a reductant; or by hydrogenation reduction catalyzed by Palladium/C.

Step 4: the amino compound I-f-a may react with a corresponding acyl chloride in a basic condition or a corresponding carboxylic acid in the presence of a condensing agent to form amide.

In the scheme 1, Compound of formula (I-a-a) is available commercially, and Compound of formula (I-b-a) may be prepared according to the following exemplary method 1.

Step 1: Compound of formula (I-b1) is de-protected to give Compound of formula (I-b2). PG in Compound of formula (I-b1) is amino protecting group, which includes but is not limited to: t-butyloxycarbonyl (Boc); arylmethoxycarbonyl, benzyloxycarbonyl(Cbz) and 9-fluorenyl-methoxycarbonyl (Fmoc); benzyl(Bn), trityl(Tr), 1,1-di-(4'-methoxyphenyl)methyl; trimethylsilyl (TMS) and tert-butyldimethylsilyl(TBS) and the like. The de-protecting method may refer to conventional methods known to the skilled in the art. Compound of formula (I-b1) is available commercially or prepared through methods known to the skilled in the art.

Step 2: Compound of formula (I-b2) reacts with Compound of formula (I-b3) through reactions such as acylation or coupling (such as Suzuki coupling) by suitable methods depending on $R_0$, thereby forming Compound of formula (I-b-a), wherein HX is nucleophilic group with electronegativity, including but not limited to: hydroxy, amino, and sulfydryl.

Compound of formula (I-c-a) also may be prepared according to the following method.

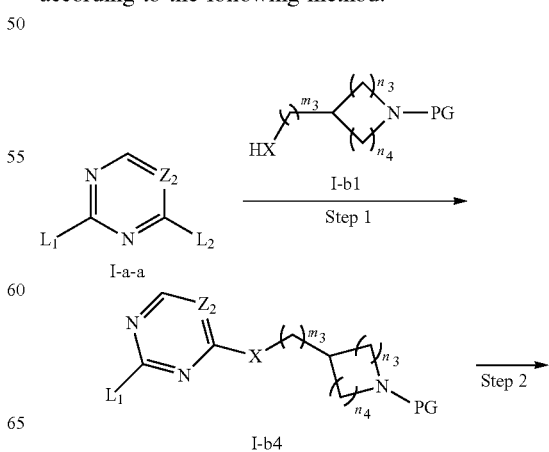

-continued

I-b5

↓ $R_0-L_1$  Step 3

I-c-a

Compound of formula (I-b4) may be obtained through reaction of Compound of formula (I-a-a) with Compound of formula (I-b1) according to the similar method as described in scheme 1. Compound of formula (I-c-a) may be prepared according to the similar method as described in method 1 using Compound of formula (I-b4) as a raw material.

Compound of formula (VI) of the present invention may be prepared through the method shown in scheme 2.

Scheme 2

I-j-a + I-c-a → VI wherein, each of substituent and group is defined as herein.

Compound of formula (I-c-a) may react with Compound of formula (I-j-a) through substitution reaction or coupling reaction to form Compound of formula (VI), for example, at a certain temperature and using suitable catalysts (or comprising suitable ligand) or base and suitable solvent. For example, when using acid catalysis, the catalyst may be but is not limited to TFA or p-toluenesulfonic acid; when using Buchwald-Hartwig amination, the palladium catalyst used may be but is not limited to $Pd_2(dba)_3$ (tri(dibenzylideneacetone)dipalladium), BINAP ((+)-2,2'-bis-(diphenylphosphino)-1,1'-binaphthyl), the ligand used may be but is not limited to XantPhos(4,5-bis(diphenylphosphino)-9,9-dimethylxanthene), and the base used may be but is not limited to cesium carbonate.

In scheme 2, Compound of formula (I-j-a) may be prepared according to the following exemplary method.

I-d1 →Step 1

I-j1 →Step 2

-continued

I-j2 →Step 3

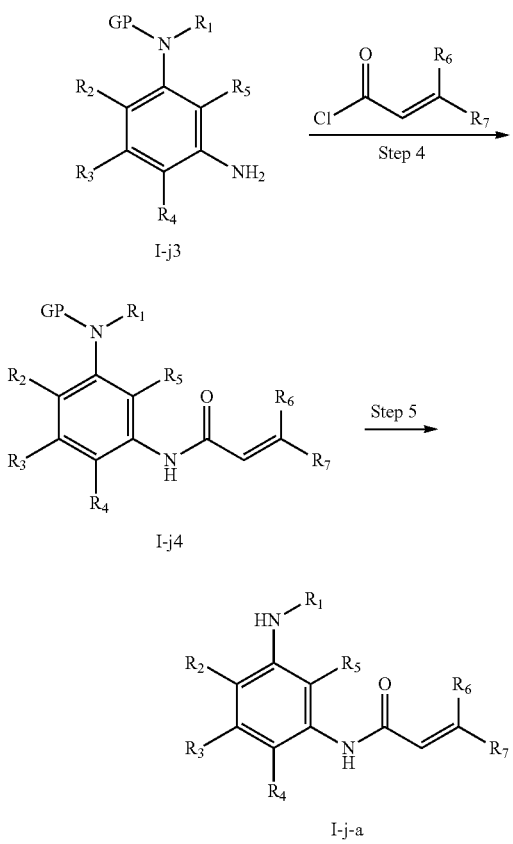

Compound of formula (I-j-a) is prepared through amino-protecting reaction, amino-substituted reaction, nitro-reducting reaction, acylation and amino-deprotecting reaction using Compound of formula (I-d1) as a starting material. The reactions in the above steps are conventional in the art. Compound of formula (I-d1) is available commercially, or prepared through methods known to the skilled in the art (the preparation method of Compound of formula (I-j-a) may refer to WO2013014448A1).

Compounds of formula (I), preparation methods thereof, pharmaceutical compositions and treatment protocols disclosed in the present invention can be achieved by the person skilled in the art through appropriate improvements of process parameters referring to this disclosure of invention. It should be particularly noted that all such alterations and changes are obvious to the skilled artisan, and they are deemed to be included in the present invention. Preferred embodiments of products, methods and applications of the present invention have been described, and relevant personnel can obviously alter or change and combine the methods and uses of the present invention without departing from the content, spirit and scope of the present invention for implementation and application of the present technology.

Compared with the prior art, the main advantages of the present invention include:

(1) The compounds of the present invention show a high inhibitory activity to EGFR T790M mutant (especially EGFR T790M/L858R double mutant) enzymes and cells, but a low inhibitory activity to EGFR wild type (EGFR WT) enzyme and cells, and therefore possess a high selective inhibition.

(2) The compounds of the present invention exhibit not only a high selective inhibition to EGFR double mutant enzymes and cells, but also a low non-specific cytotoxicity.

(3) The compounds of the present invention also exhibit advantageous physical properties (for example, a high aqueous solubility), favorable toxicity profiles (for example, a low hERG blocking liability), and advantageous metabolic profiles (for example, better pharmacokinetic characteristics such as bioavailability) in comparison with other known EGFR-mutant inhibitors.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless defined otherwise, terms used herein are the same as those familiar to the skilled in the art. Moreover, any method or material similar or equivalent to those recorded in the present invention can be used in the present invention.

Reagents and Instruments

$^1$HNMR: Bruker AVANCE-400 NMR machine. The internal standard was tetramethylsilane (TMS).

LC-MS: Agilent 1200 HPLC System/6140 MS liquid-mass spectrometer (available from Agilent), column WatersX-Bridge, 150×4.6 mm, 3.5 μm.

Preparative high performance liquid chromatography (pre-HPLC): Waters PHW007, column XBridge C18, 4.6×150 mm, 3.5 um.

Using ISCO Combiflash-Rf75 or Rf200 automatic eluting column instrument, Agela 4 g, 12 g, 20 g, 40 g, 80 g, 120 g disposable silica gel column.

The known starting materials of the invention are synthesized by the methods known in the art, or are purchased from ABCR GmbH & Co.KG, Acros Organics, Aldrich Chemical Company, Accela ChemBio Inc and Darui Chemical Company etc.

All examples were performed under nitrogen or argon atmosphere and the solution refers to aqueous solution if without special explanation.

In the examples, the reaction process was monitored by thin layer chromatography (TLC), compounds was purified by column chromatography. The eluent used in Column chromatography or TLC were selected from a system of dichloromethane and methanol, n-hexane and ethyl acetate, petroleum ether and ethyl acetate, or acetone and the like, wherein the volume ratio of the solvents might be regulated according to the different polarity of compounds.

DMF refers to dimethylformamide, DMSO refers to dimethylsulfoxide, THF refers to tetrahydrofuran, DIEA refers to N,N-diisopropylethylamine, EA refers to ethyl acetate, PE refers to petroleum ether. BINAP refers to (2R,3S)-2,2'-bis diphenylphosphino-1,1'-binaphthyl, NBS refers to N-bromosuccinimide, NCS refers to N-chlorosuccinimide, $Pd_2(dba)_3$ refers to tris(dibenzylideneacetone)dipalladium, $Pd(dppf)Cl_2$ refers to [1,1'-bis(diphenylphosphino)ferrocene] palladium dichloride.

As used herein, room temperature refers to be about 25° C.

Preparation of Compound a1

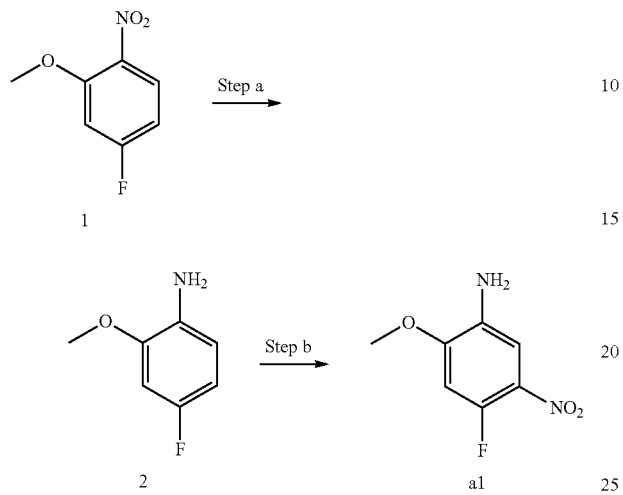

Step a: Compound 1 (10.6 g, 58 mmol) was placed in a 500 ml one-necked reaction flask, and THF/water (100 ml/60 ml) mixed solution was added to dissolve the substrate. Ammonium chloride (15.5 g, 292 mmol) and reductive iron powder (26 g, 467 mmol) were sequentially added with stirring at room temperature, and then the reaction system was heated to 65° C. and stirred continually for 3 h. The reaction progress was monitored by TLC. After the substrate was completely consumed, the excess iron powder was removed by filtration, and the filter cake was washed for three times with ethyl acetate. Filtrate was extracted with ethyl acetate/water system for three times, and the organic layer was separated, washed with water and saturated brine, dried over anhydrous sodium sulfate, and concentrated under reduced pressure to give compound 2 (8.0 g) which was used directly in the next reaction. Yield: 93%; purity: 90%; MS m/z(ESI):142.0 [M+H]$^+$.

Step b: Compound 2 (8.0 g, 43 mmol) was placed in a 500 ml one-necked reaction flask, and concentrated sulfuric acid (100 ml) was added to dissolve the substrate with constant agitation. At −20° C., concentrated nitric acid (6.15 ml, 48 mmol) was slowly added dropwise with stirring, and the reaction mixture was stirred for 5 mins at this temperature. The reaction progress was monitored by TLC. After the substrate was completely consumed, the mixture was poured into ice water. Sodium hydroxide/water solution (150 ml/300 ml) were added slowly to the reaction system which was kept in an ice-water bath at −20° C., and the pH of the mixture was adjusted to 8-9. After the neutralization, the reaction mixture was extracted with ethyl acetate/water system for three times, and the organic layer was separated, washed with water and saturated brine, dried over anhydrous sodium sulfate, and concentrated under reduced pressure to give compound a1 (8.7 g) which was used directly in the next reaction. Yield: 80%; purity: 100%; MS m/z(ESI): 187.0 [M+H]+; $^1$H NMR (400 MHz, DMSO-d$_6$): δ 7.34 (d, J=7.8 Hz, 1H), 7.04 (d, J=13.4 Hz, 1H), 5.25 (brs, 2H), 3.90 (s, 3H).

Preparation of Compound a

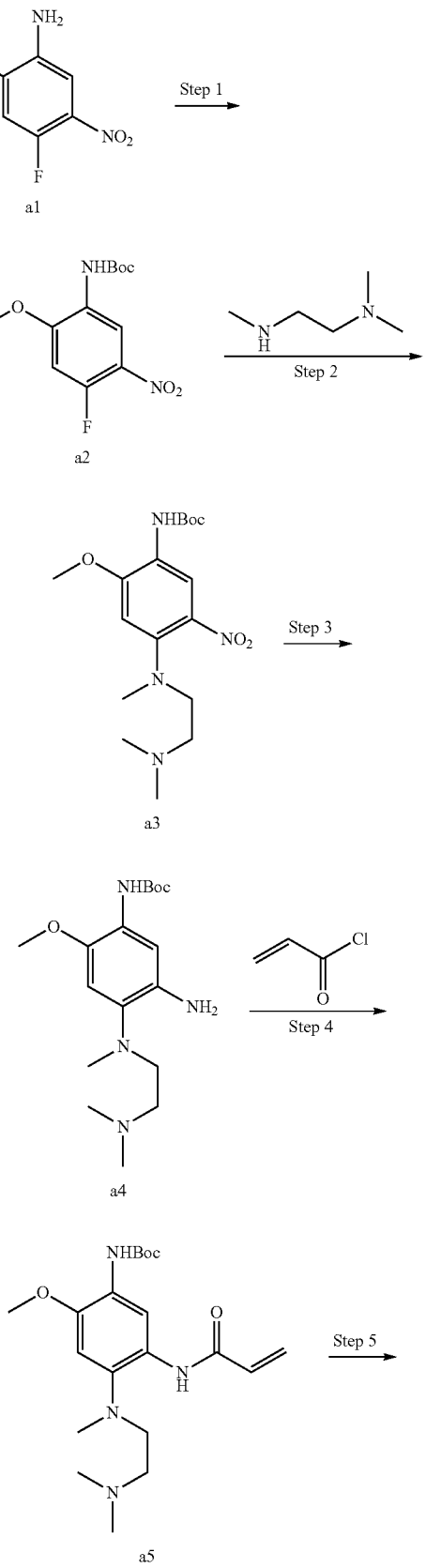

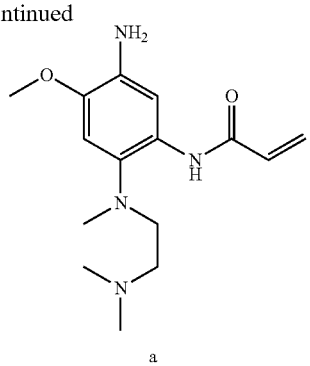

a

Step 1: 4-fluoro-2-methoxy-5-nitroaniline a1 (11.16 g, 60 mmol) was dissolved in 150 ml of dichloromethane. Di-tert-butyl dicarbonate (15.60 g, 72 mmol), triethylamine (12.24 g, 120 mmol) and 4-dimethylaminopyridine (0.74 g of, 6 mmol) were added and the mixture was stirred at room temperature for 18 h. The reaction progress was monitored by TLC. After the substrate was completely consumed, the reaction mixture was concentrated under reduced pressure, isolated and purified by column chromatography [PE:EA=80:20] to give the title compound a2 (12.56 g, 73%). MS m/z(ESI): 285 [M−H]+.

Step 2: The substrate of tert-butyl 4-fluoro-2-methoxy-5-nitrophenyl carbamate a2 (11.46 g, 40 mmol) was dissolved in 60 ml N,N-dimethylacetamide, and N,N,N'-trimethylethylenediamine (4.90 g, 48 mmol) and N,N-diisopropylethylamine (7.74 g, 60 mmol) were added. The mixture was heated to 90° C. and stirred for 6 h. The reaction progress was monitored by TLC. After the substrate was completely consumed, the reaction mixture was cooled to room temperature, poured into ice water, extracted with ethyl acetate, washed with saturated brine, dried over anhydrous sodium sulfate, and concentrated under reduced pressure to give the title product a3 (12.51 g, 85%) which was used directly in the next reaction. MS m/z(ESI): 369 [M+H]+.

Step 3: tert-butyl 4-((2-(dimethylamino)ethyl)(methyl)amino)-2-methoxy-5-nitrophenyl carbamate a3 (12 g, 32.6 mmol) was dissolved in 200 ml of methanol, and 1.0 g 10% Pd/C was added. After air was replaced with hydrogen, the reaction was stirred for 1 h under hydrogenation through a hydrogen balloon at room temperature. The reaction progress was monitored by TLC. After the substrate was completely consumed, the reaction system was filtered by buchuer funnel, the filter cake was washed with little methanol, and the filtrate was concentrated to give the title product a4 (10.70 g, 97%) which was used directly in the next reaction. MS m/z(ESI): 339 [M+H]+.

Step 4: tert-butyl 5-amino-4-((2-(dimethylamino)ethyl)(methyl)amino)-2-methoxyphenyl carbamate a4 (10.1 g, 30 mmol) and triethylamine (6.12 g, 60 mmol) were dissolved in 200 ml of dichloromethane. The mixture was cooled to 0° C., and acryloyl chloride (3.24 g, 36 mmol) was added. The mixture was stirred under nitrogen at room temperature for 3 h. The reaction progress was monitored by TLC. After the substrate was completely consumed, the reaction mixture was washed successively with saturated aqueous sodium bicarbonate solution and saturated brine, dried over anhydrous sodium sulfate, filtered, and concentrated under reduced pressure to give the title product a5 (9.64 g, 82%), which was used directly in the next reaction. MS m/z(ESI): 393 [M+H]+.

Step 5: tert-butyl 5-acrylamido-4-((2-(dimethylamino)ethyl)(methyl)amino)-2-methoxyphenyl carbamate a5 (9.41 g, 24 mmol) was dissolved in 100 ml of dichloromethane. The mixture was cooled to 0° C., and 20 ml of trifluoroacetic acid was added. The reaction was stirred under nitrogen at room temperature for 18 h. The reaction progress was monitored by TLC. After the substrate was completely consumed, the reaction mixture was concentrated under reduced pressure. The residue was dissolved in 300 ml of dichloromethane, washed with saturated aqueous sodium bicarbonate solution and saturated brine successively, dried over anhydrous sodium sulfate, filtered, and concentrated under reduced pressure to give the crude product, which was purified by column chromatography [DCM:MeOH=10:1] to give the title product a, i.e., tert-butyl N-(5-amino-2-((2-(dimethylamino)ethyl)(methyl)amino)-2-methoxyphenyl) acrylamide (3.26 g, 46.5%). MS m/z(ESI): 293 [M+H]+.

Preparation of Compound b

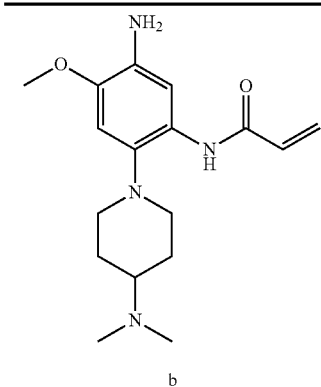

b

The preparation method was similar to that of compound a, except that N,N,N'-trimethyl ethylenediamine in step 2 of preparation method of compound a was replaced by 4-dimethylamino piperidine.

Preparation of Compound 4-a

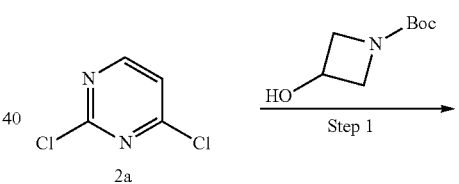

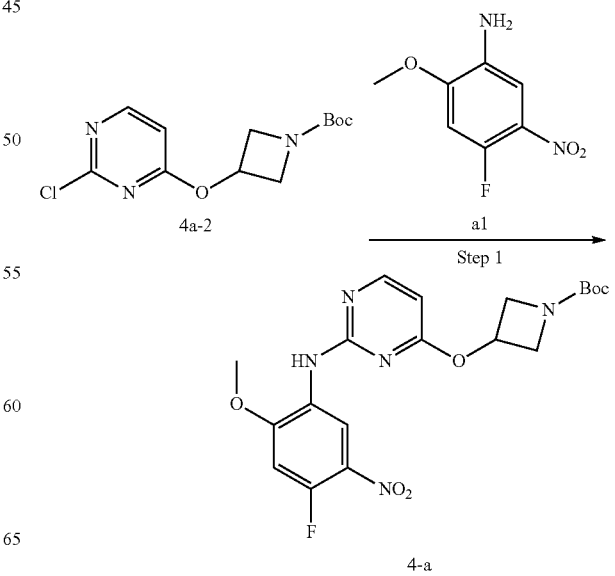

4-a

Step 1: compound 2a (19.7 g, 110 mmol) and cesium carbonate (65.2 g, 200 mmol) were added into a solution of N-Boc-3-hydroxy azetidine (17.3 g, 100 mmol) in 400 ml of DMF. The mixture was stirred at 83° C. with vigorous stirring for 4 hours. The reaction progress was monitored by TLC. After the substrate was completely consumed, the reaction mixture was extracted with ethyl acetate/water system for three times, the organic phase was separated, washed with water and saturated brine, and dried by rotary to obtain crude product, which was purified by Combi-flash column chromatography [PE:EA=100:0-40:60] to obtain compound 4a-2 (25 g, 88%). MS m/z(ESI): 286.1 [M+H]$^+$.

Step 2: compound a1 (1.96 g, 10.5 mmol), Pd$_2$(dba)$_3$ (964 mg, 1.05 mmol), Xantphos (1.219 g, 2.11 mmol) and cesium carbonate (6.86 g, 21.0 mmol) were added into a solution of compound 4a-2 (3 g, 10.5 mmol) in 70 ml of 1,4-dioxane. The mixture was vigorously stirred at 120° C. under N$_2$ for 20 hours. After the reaction was completed, the mixture was filtered and washed with ethyl acetate. The filtrate was concentrated under reduced pressure to obtain a crude product which was purified with Combi-flash column chromatography [PE:EA=100:0-20:80] to obtain compound 4-a (2.86 g, 62%). MS m/z(ESI): 436.2 [M+H]$^+$.

Preparation of Compound 5-a

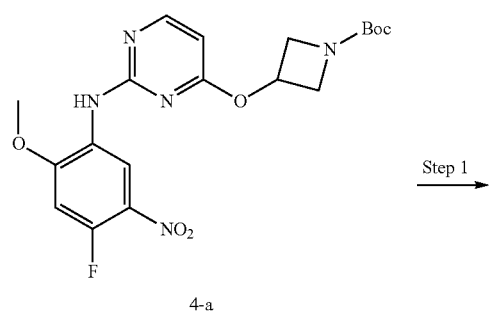

4-a

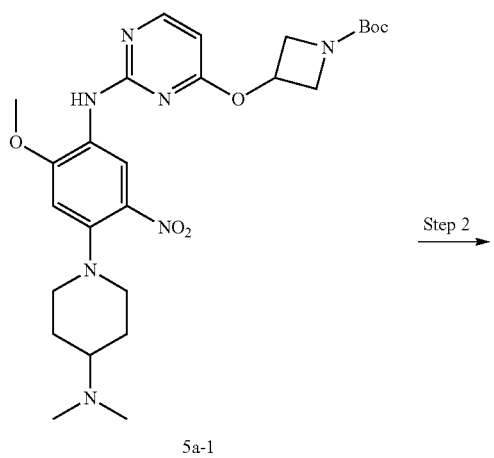

5a-1

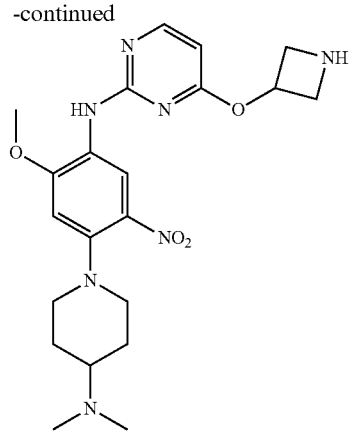

5a

Step 1: 4-dimethylaminopiperidine (106 mg, 0.83 mmol) and potassium carbonate (286 mg, 2.07 mmol) were added into a solution of compound 4-a (300 mg, 0.69 mmol) in 20 ml of DMF. The mixture was vigorously stirred at 100° C. for 4 h. The reaction progress was monitored by TLC. After the substrate was completely consumed, the reaction mixture was extracted with ethyl acetate/water system for three times, the organic phase was separated, and concentrated under reduced pressure to obtain compound 5a-1 (400 mg, 95%), MS m/z(ESI): 544.2[M+H]$^+$.

Step 2: trifluoroacetic acid (3 mL) was added into a solution of compound 5a-1 (1 g, 1.84 mmol) in 30 ml of dichloromethane. The mixture was vigorously stirred for 6 hours at room temperature. The reaction progress was monitored by TLC. After the substrate was completely consumed, extra dichloromethane was removed by rotary under reduced pressure. The mixture was diluted with water, of which pH was adjusted to alkalinity, and extracted with dichloromethane and methanol (10:1). The organic phase was dried by rotary to obtain compound 5-a (1.1 g, 45.8%). MS m/z(ESI): 444.2 [M+H]$^+$.

Preparation of Compound 7-a

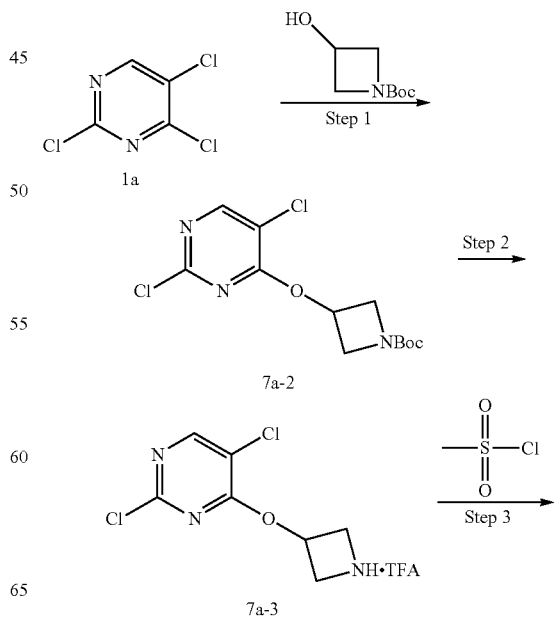

-continued

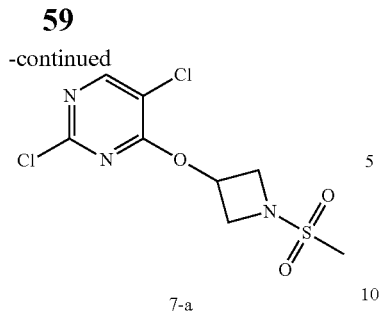

7-a

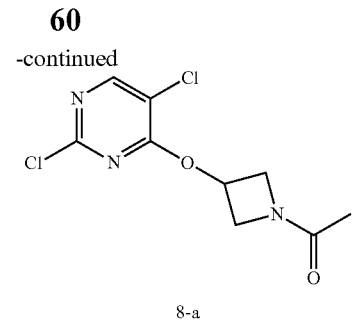

8-a

Step 1: compound 1a (10 g, 54.5 mmol), potassium carbonate (13.7 g, 99.1 mmol) and N-Boc-3-hydroxy azetidine (8.58 g, 49.5 mmol) were placed in 500 ml one-necked reaction flask, and 300 ml of acetonitrile was added. The mixture was heated to 90° C. and stirred for 4 hours. The reaction progress was monitored by TLC. After the substrate was completely consumed, the mixture was extracted with ethyl acetate/water system for three times, the organic phase was separated, washed with water and saturated brine, and concentrated to obtain a crude product, which was isolated and purified by combi-flash column chromatography [PE:EA=100:0-40:60] to obtain the title product 7a-2 (11.6 g, 73.2%). MS m/z(ESI): 320.1 [M+H]$^+$.

Step 2: the substrate 7a-2 (500 mg, 1.56 mmol) was dissolved in 20 ml of dichloromethane, and trifluoroacetic acid (3.5 g, 30.7 mmol) was added slowly. The mixture was stirred at room temperature for 2 hours. The reaction progress was monitored by TLC. After the substrate was completely consumed, the reaction mixture was concentrated under reduced pressure to obtain 800 mg of title crude product 7a-3 which was directly used in the next reaction.

Step 3: The substrate 7a-3 (800 mg, about 1.56 mmol) was dissolved in 25 ml dichloromethane, and N,N-diisopropylethylamine (2.07 g, 16.02 mmol) was added after cooled to 0° C. The mixture was stirred for 10 min, then methylsufonyl chloride (360 mg, 3.14 mmol) was added. The mixture was heated to room temperature and stirred for 2 hours. The reaction progress was monitored by TLC. After the substrate was completely consumed, the reaction was diluted with 25 ml of dichloromethane, washed with water and saturated brine, and concentrated under reduced pressure to obtain a crude product, which was isolated and purified by combi-flash column chromatography [PE:EA=100:0-75:25] to obtain the title product 7-a (362 mg, 77.8%). MS m/z(ESI): 298.0 [M+H]$^+$.

Preparation of Compound 8-a

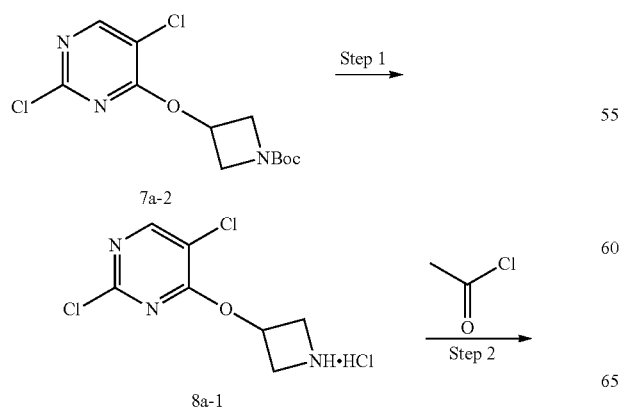

Step 1: At room temperature, a solution of hydrochloric acid/1,4-dioxane (10 ml, 40 mmol) was added dropwise into a solution of compound 7a-2 (640 mg, 2.0 mmol) in 1,4-dioxane (10 ml). The reaction mixture was stirred at room temperature for 3 hours, and then concentrated under reduced pressure to obtain 486 mg of a crude compound 8a-1 which was directly used in the next reaction.

Step 2: At 0° C., a solution of acetyl chloride (165 mg, 2.1 mmol) in dichloromethane (5 ml) was added dropwise into a solution of compound 8a-1 (440 mg, 2.0 mmol) and triethylamine (810 mg, 8.0 mmol) in dichloromethane (35 ml). The reaction mixture was stirred at 0° C. for 1 hour. After the reaction was complete, dichloromethane and water was add into the reaction mixture and the mixture was extracted with dichloromethane. The organic phase was washed with brine, dried with anhydrous sodium sulfate, and concentrated under reduced pressure to obtain 300 mg of a crude product, which was isolated and purified by combi-flash column chromatography to obtain the title product 8-a (148.8 mg, yield 57%). MS m/z(ESI): 262 [M+H]$^+$.

Preparation of Compound 14-a

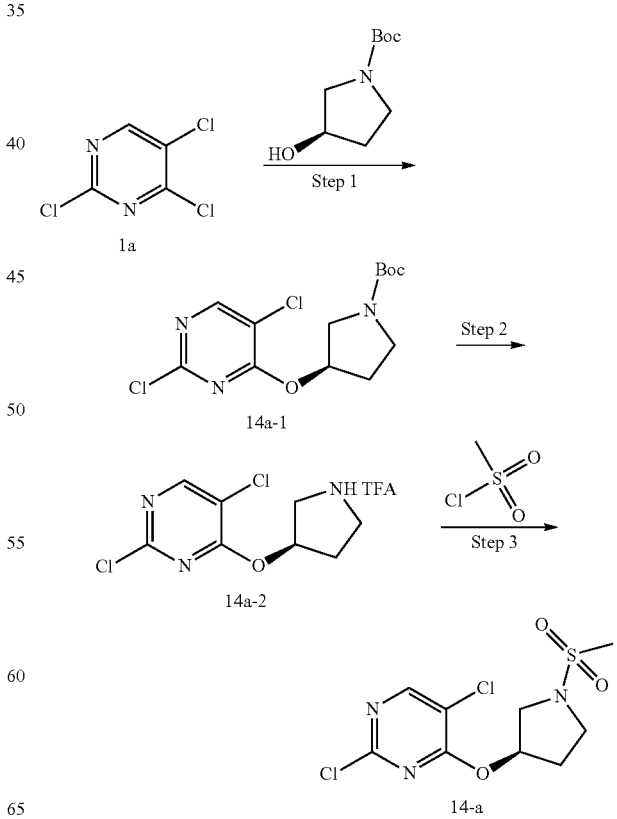

Step 1: compound 1a (3 g, 16.36 mmol), tert-butyl (R)-3-hydroxypyrrolidine-1-formate (3.1 g, 16.56 mmol) and cesium carbonate (8 g, 24.55 mmol) were added into 30 ml of acetonitrile. The reaction mixture was stirred at 80° C. for 3 hours. The reaction was monitored by TLC and LC-MS. After the reaction was complete, the reaction mixture was filtered and washed with dichloromethane. The filtrate was concentrated to obtain a crude product which was purified by combiflash (PE:EA=95:5-80:20) to obtain compound 14a-1 (3.31 g, yield 60.0%). MS m/z(ESI): 278 [M-56+H]$^+$.

Step 2: At 0° C., trifluoroacetic acid (3.50 g, 30.70 mmol) was added into a solution of compound 14a-1 (510 mg, 1.53 mmol) in 5 ml of dichloromethane. The reaction was vigorously stirred at room temperature for 5 hours. After the reaction was complete, the reaction mixture was dried by rotary under reduced pressure to obtain crude compound 14a-2 (831 mg), which was used directly in the next step.

Step 3: At 0° C., N,N-diisopropylethylamine (1.92 g, 14.86 mmol) was added into a solution of compound 14a-2 (831 mg, 1.53 mmol) in 25 ml of dichloromethane. The reaction was vigorously stirred at 0° C. for 30 min and then methylsulfonyl chloride (344 mg, 3.00 mmol) was added. The reaction was vigorously stirred at 0° C. for 2 hours. After the reaction was completed, the reaction was diluted with water and extracted with dichloromethane/water system for three times. The organic phase was concentrated under reduced pressure to obtain a crude product which was purified by combi-flash (PE:EA=100:0-50:50) to obtain compound 14-a (302 mg, yield 70.1%). MS m/z(ESI): 312 [M+H]$^+$.

Preparation of Compounds 15-a, 16-a, and 17-a

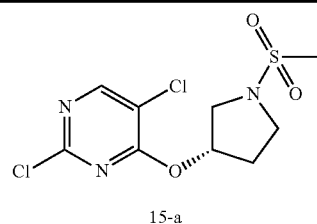

15-a

The preparation method was similar to preparation of compound 14-a, except that (R)-tert butyl-3-hydroxypyrrolidine-1-formate in step 1 was replaced with (S)-tert butyl-3-hydroxypyrrolidine-1-fromate.
MS m/z(ESI): 312 [M + H]$^+$.

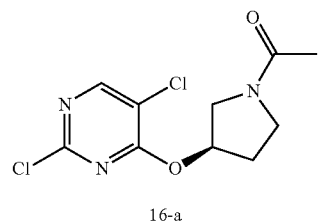

16-a

The preparation method was similar to preparation of compound 14-a, except that methylsulfonyl chloride in step 3 was replaced with acetyl chloride.
MS m/z(ESI): 276 [M + H]$^+$.

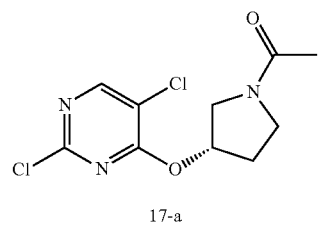

17-a

The preparation method was similar to preparation of compound 14-a, except that tert-butyl (R)-3-hydroxypyrrolidine-1-formate in step 1 was replaced with tert-butyl (S)-3-hydroxypyrrolidine-1-formate, and methylsulfonyl chloride in step 3 was replaced with acetyl chloride.
MS m/z(ESI): 276 [M + H]$^+$.

Preparation of Compound 18-a to Compound 21-a

Preparation methods for compound 18-a to compound 21-a were similar to preparation of compound 14-a, except that:

when preparing compound 18-a, 2,4,5-trichloropyrimidine in step 1 was replaced with 2,4-dichloro-5-fluoropyrimidine, and methylsulfonyl chloride in step 3 was replaced with acetyl chloride;

when preparing compound 19-a, 2,4,5-trichloropyrimidine in step 1 was replaced with 2,4-dichloro-5-fluoropyrimidine, (R)-tert butyl-3-hydroxypyrrolidine-1-formate was replaced with (S)-tert butyl-3-hydroxypyrrolidine-1-formate, and methylsulfonyl chloride in step 3 was replaced with acetyl chloride;

when preparing compound 20-a, 2,4,5-trichloropyrimidine in step 1 was replaced with 2,4-dichloro-5-fluoropyrimidine;

when preparing compound 21-a, 2,4,5-trichloropyrimidine in step 1 was replaced with 2,4-dichloro-5-fluoropyrimidine, and tert-butyl (R)-3-hydroxypyrrolidine-1-formate was replaced with tert-butyl (S)-3-hydroxypyrrolidine-1-formate.

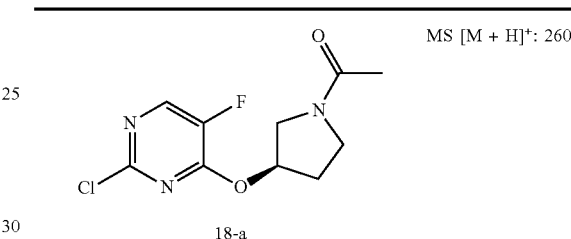

18-a    MS [M + H]$^+$: 260

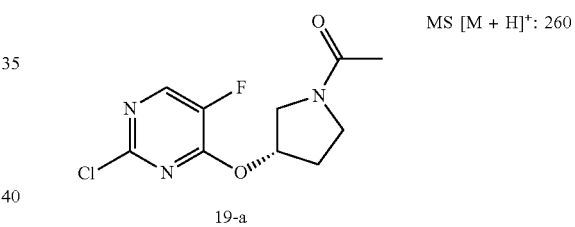

19-a    MS [M + H]$^+$: 260

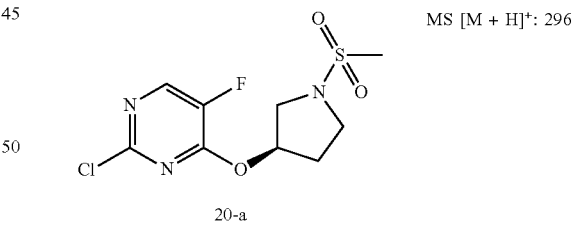

20-a    MS [M + H]$^+$: 296

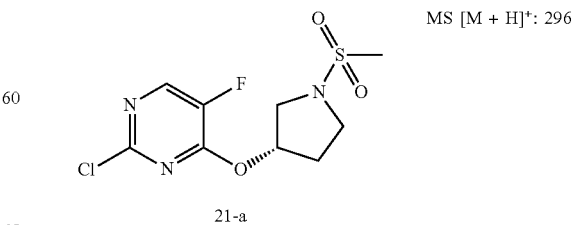

21-a    MS [M + H]$^+$: 296

Preparation of Compound 22-a

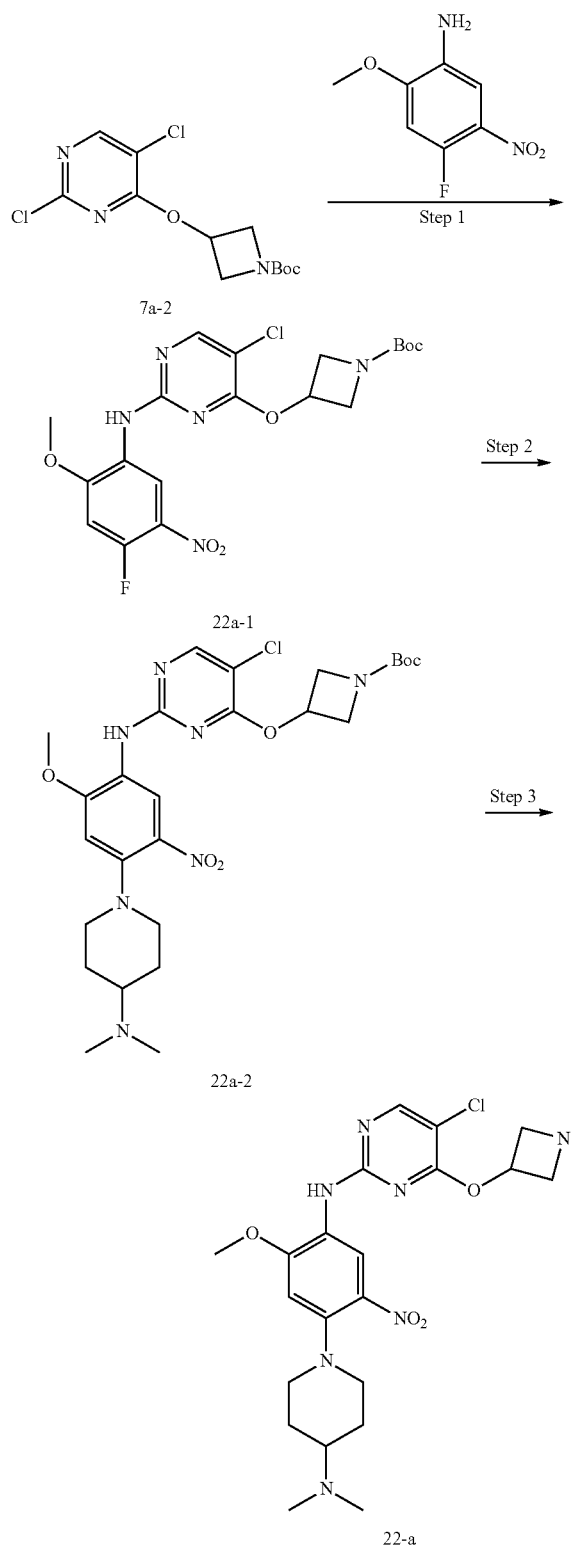

The reaction was microwaved at 160° C. for 20 hours. The reaction was monitored by TLC. After the reaction was complete, the reaction mixture was filtered and washed with ethyl acetate. The filtrate was concentrated under reduced pressure to obtain a crude product which was purified by Combi-flash column chromatography [PE:EA=90:10~50:50] to obtain compound 22a-1 (185.5 mg, yield 39.5%). MS m/z(ESI): 370 [M-100+H]$^+$.

Step 2: 4-dimethylaminopiperidine (106 mg, 0.83 mmol) and potassium carbonate (152 mg, 1.10 mmol) were added to compound 22a-1 (371 mg, 0.55 mmol) in 6 ml of DMF. The reaction was vigorously stirred at 100° C. for 1 h. The reaction progress was monitored by TLC. After the substrate was completely consumed, the reaction mixture was extracted with ethyl acetate/water system for three times, and the organic phase was separated, concentrated under reduced pressure to obtain a crude product which was purified by Combi-flash column chromatography [PE:EA=100:0~85:15] to obtain compound 22a-2 (323 mg, yield 100%). MS m/z(ESI): 578.3 [M+H]$^+$.

Step 3: 216 mg of compound 22-a was prepared by using compound 22a-2 (323 mg, 0.42 mmol) as a raw material according to step 2 in the preparation method of compound 5-a, and compound 22-a was directly used in the next step without purification.

Preparation of Compound 23-a

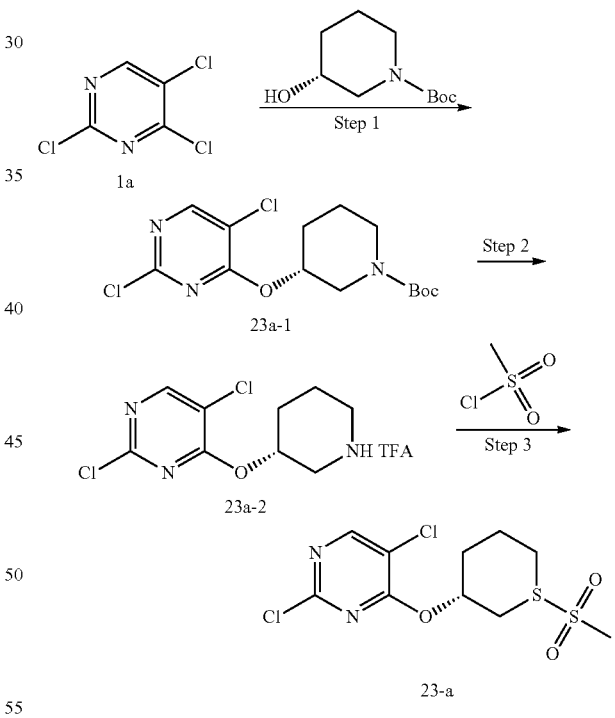

Step 1: Compound a1 (186 mg, 1 mmol), Pd$_2$(dba)$_3$ (92 mg, 0.1 mmol), BINAP (93 mg, 0.15 mmol) and cesium carbonate (652 mg, 2 mmol) were added into a solution of compound 7a-2 (320 mg, 1 mmol) in 11 ml of 1,4-dioxane.

Step 1: At 0° C., into a solution of sodium hydride (220 mg, 5.49 mmol) in THF was added tert-butyl (R)-3-hydroxypiperidine-1-formate (550 mg, 2.75 mmol). The reaction mixture was stirred at 0° C. for 1 hour, and then compound 1a (500 mg, 2.75 mmol) was added. The reaction mixture was stirred at 0° C. for 2 hours, and then at room temperature for 20 hours. After the reaction was complete, the reaction was quenched at 0° C. by water. The reaction mixture was extracted with ethyl acetate, washed with saturated sodium chloride solution and water, and concentrated to obtain a crude product, which was purified by combiflash (PE:EA=80:20) to obtain 500 mg compound 23a-1. MS m/z(ESI): 292 [M-56+H]⁺.

Step 2-3: 240 mg of compound 23-a was prepared by using compound 23a-1 (500 mg, 1.44 mmol) as the raw material according to steps 2 and 3 in preparation method of compound 14-a. MS m/z(ESI): 326 [M+H]⁺.

Preparation of Compound 24-a to Compound 26-a

Preparation of compound 24-a to compound 26-a was similar to preparation of compound 23-a, except that, when preparing compound 24-a, tert-butyl (R)-3-hydroxypiperidine-1-formate in step 1 was replaced with tert-butyl (S)-3-hydroxypiperidine-1-formate;

when preparing compound 25-a, compound 7a-1 in step 1 was replaced with 2,4-dichloro-5-fluoropyrimidine;

when preparing compound 26-a, methylsulfonyl chloride in step 3 was replaced with acetyl chloride.

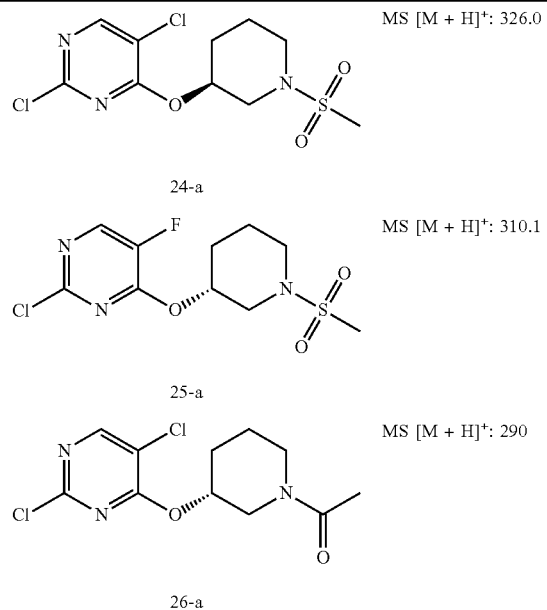

Preparation of Compound 31-a

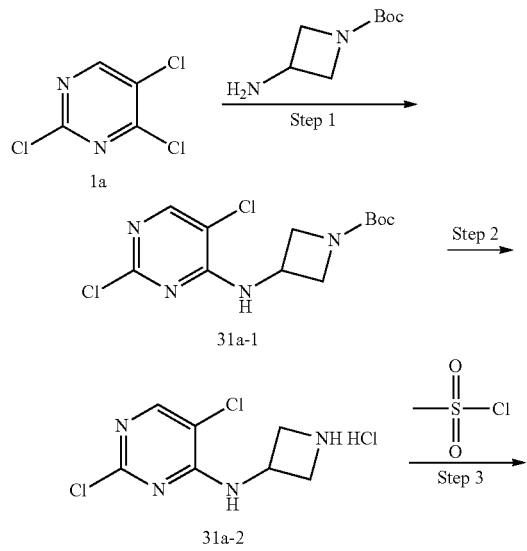

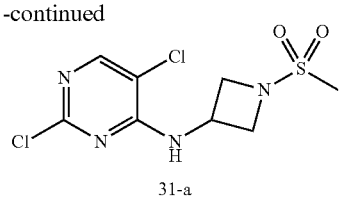

Step 1: At room temperature, into a solution of compound 1a (1.83 g, 10 mmol) and N,N-diisopropylethylamine (2.58 g, 20 mmol) in dichloromethane (90 ml) was added dropwise a solution of tert-butyl 3-aminoazetidine-1-carboxylate (1.89 g, 11 mmol) in dichloromethane (10 ml). The reaction mixture was stirred at room temperature for 5 hours. After the reaction was complete, the reaction mixture was extracted with water and dichloromethane. The organic phase was dried with anhydrous sodium sulfate and then concentrated under reduced pressure to obtain 2.85 g crude product 31a-1 which was directly used in the next reaction without purification. MS m/z(ESI): 319 [M+H]⁺.

Step 2: At room temperature, into a solution of compound 31a-1 (638 mg, 2.0 mmol) in 1,4-dioxane (20 ml) was added dropwise a solution of hydrochloric acid/1,4-dioxane (10 ml, 40 mmol). The reaction mixture was stirred at room temperature for 3 hours, and then concentrated under reduced pressure to obtain 680 mg of crude compound 31a-2 which was directly used in the next reaction.

Step 3: Compound 31-a was prepared by using compound 31a-2 as the raw material according to step 3 in preparation of compound 7-a. MS m/z(ESI): 297 [M+H]⁺.

Preparation of Compound 32-a

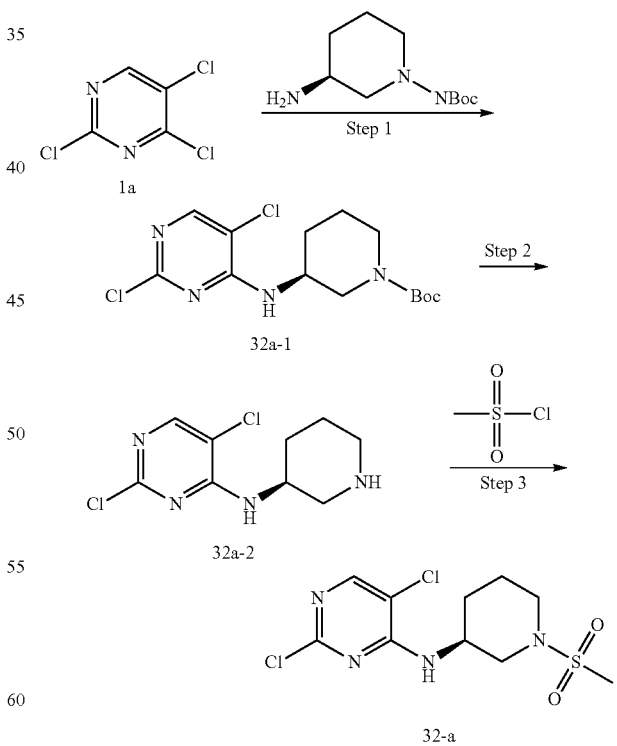

Step 1: Compound 32a-1 was prepared by using compound 1a and tert-butyl (S)-3-aminopiperidine-1-formate according to step 1 in preparation of compound 31-a. MS m/z(ESI): 347 [M+H]⁺.

Step 2-3: Compound 32-a was prepared by using compound 32a-1 as the raw material according to steps 2 and 3 in preparation of compound 7-a. MS m/z(ESI): 325.0 [M+H]⁺.

Preparation of Compounds 33-a and 34-a

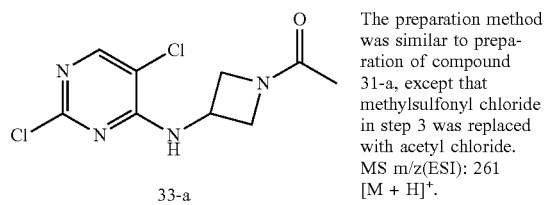

The preparation method was similar to preparation of compound 31-a, except that methylsulfonyl chloride in step 3 was replaced with acetyl chloride. MS m/z(ESI): 261 [M + H]⁺.

33-a

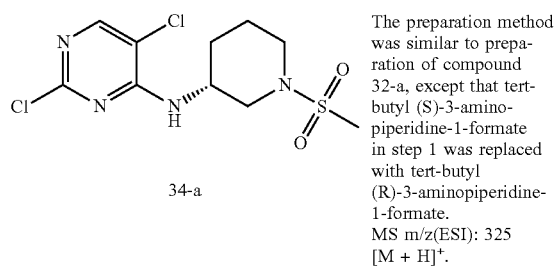

The preparation method was similar to preparation of compound 32-a, except that tert-butyl (S)-3-amino-piperidine-1-formate in step 1 was replaced with tert-butyl (R)-3-aminopiperidine-1-formate. MS m/z(ESI): 325 [M + H]⁺.

34-a

Preparation of Compound 35-a

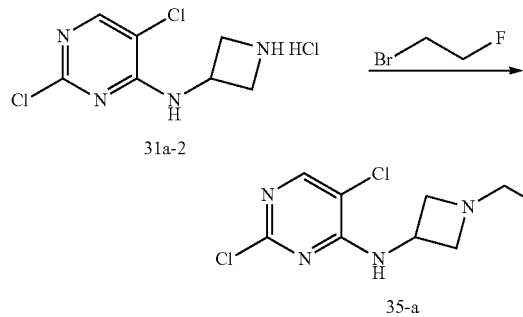

A solution of compound 31a-2 (584 mg, 2.0 mmol), 1-bromo-2-fluoroethane (280 mg, 2.2 mmol) and potassium carbonate (1.1 g, 8.0 mmol) in acetonitrile (40 ml) was stirred in a sealed tube at 50° C. overnight. The reaction mixture was extracted with water and ethyl acetate. The organic phase was dried with anhydrous sodium sulfate and concentrated under reduced pressure to obtain a crude product, which was isolated and purified by combi-flash column chromatography [PE:EA=100:0~90:10] to obtain the title product 35-a (71 mg, yield 13.4%). MS m/z(ESI): 265 [M+H]⁺.

Preparation of Compound 36-a

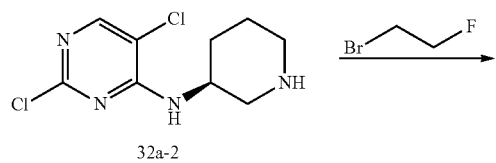

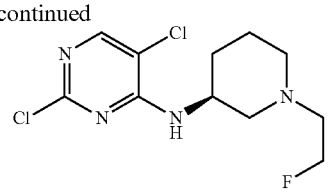

36-a

Compound 36-a was prepared by using compound 32a-2 as the raw material according to preparation of compound 35-a. MS m/z(ESI): 293 [M+H]⁺.

Preparation of Compound 37-a

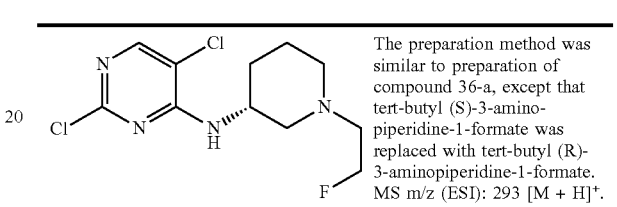

The preparation method was similar to preparation of compound 36-a, except that tert-butyl (S)-3-amino-piperidine-1-formate was replaced with tert-butyl (R)-3-aminopiperidine-1-formate. MS m/z (ESI): 293 [M + H]⁺.

37-a

Preparation of Compound 38-a

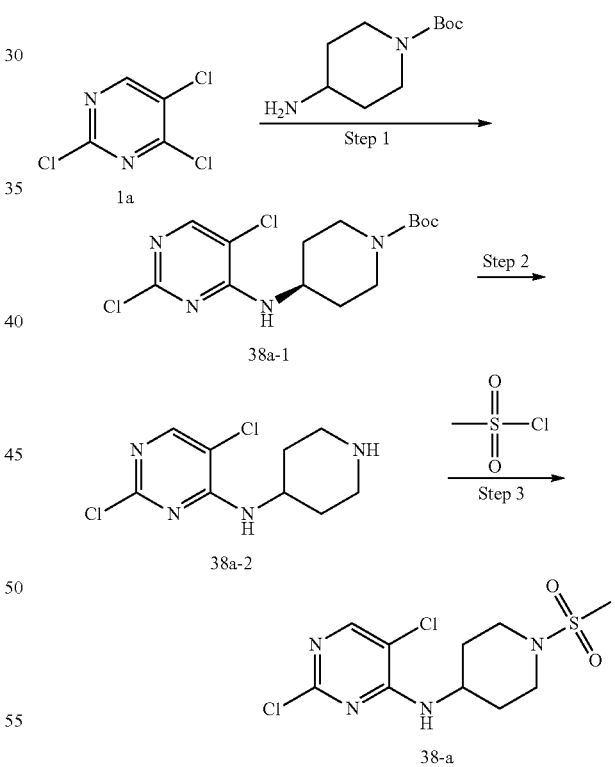

Step 1: Into a solution of tert-butyl 4-aminopiperidine-1-formate (550 mg, 2.75 mmol) in acetonitrile (10 ml) was added compound 1a (500 mg, 2.75 mmol) and potassium carbonate (758 mg, 5.49 mmol). The reaction mixture was stirred at 90° C. for 2 hours. After the reaction was complete, the reaction mixture was filtered and concentrated, and isolated and purified by combi-flash column chromatography [PE:EA=80:20] to obtain 700 mg of the title product 38a-1, MS m/z(ESI): 347.2 [M+H]⁺.

Step 2-3: Compound 38-a was prepared by using compound 38a-1 as the raw material, successively according to steps 2 and step 3 in preparation of compound 7-a. MS m/z(ESI): 325.0 [M+H]$^+$.

Preparation of Compound 39-a

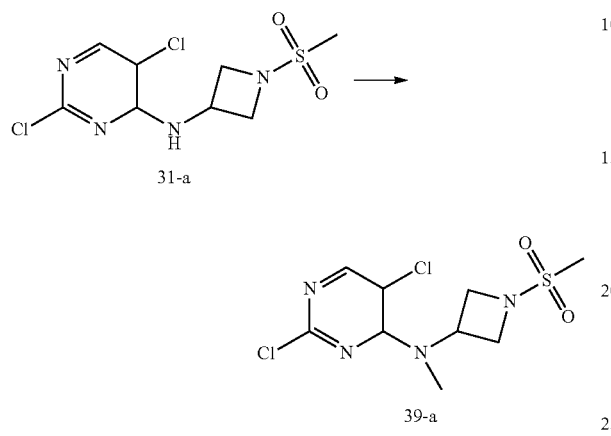

A solution of compound 31-a (500 mg, 1.68 mmol) in 5 ml of dimethylformamide was added dropwise into a solution of sodium hydride (80 mg, 2 mmol) in 10 ml of dimethylformamide at 0° C. The reaction mixture was stirred at 0° C. for 1 hour, and then iodomethane (286 mg, 2 mmol) was added dropwise under stirring at room temperature. The reaction mixture was stirred at room temperature for 3 hours. After the reaction was complete, ice-water was added into the reaction mixture, which was extracted with dichloromethane and water. The organic phase was dried with anhydrous sodium sulfate, filtered and concentrated under reduced pressure to obtain a crude product which was purified by Combi-flash column chromatography to obtain compound 39-a (260 mg) as a solid which was directly used in the next reaction. yield: 49.8%, MS m/z (ESI):311[M+H]$^+$.

Preparation of Compound 40-a

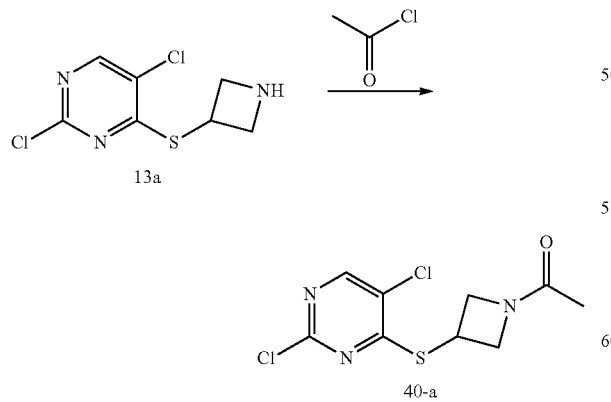

It was prepared by using compound 13e as the raw material according to step 2 in preparation of compound 8-a. MS m/z(ESI):278 [M+H]$^+$.

Preparation of Compound 41-a

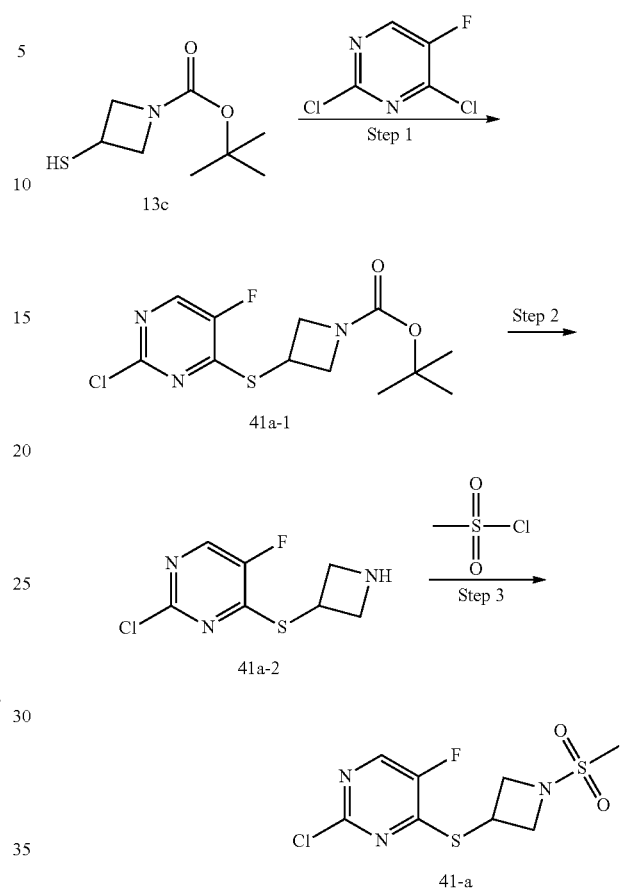

Compound 41-a was prepared by using compound 13c and 2,4-dichloro-5-fluoropyrimidine as the starting materials successively according to steps 3, 4 and 5 in preparation of compound 13f. MS m/z(ESI):298 [M+H]$^+$.

Preparation of Compound 42-a

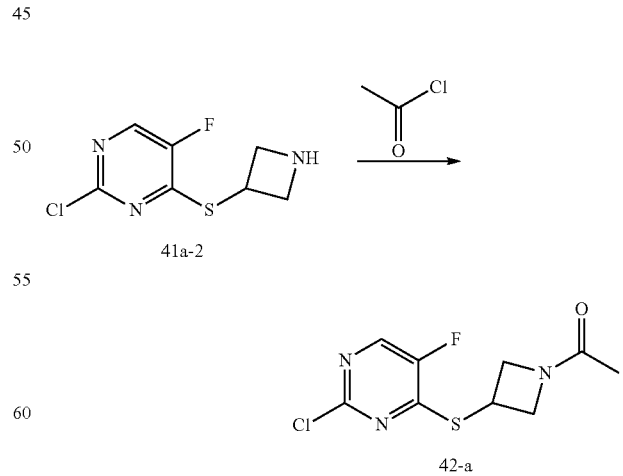

It was prepared by using compound 41a-2 as the raw material according to step 2 in preparation of compound 8-a. MS m/z(ESI):262 [M+H]$^+$.

Preparation of Compound 43-a

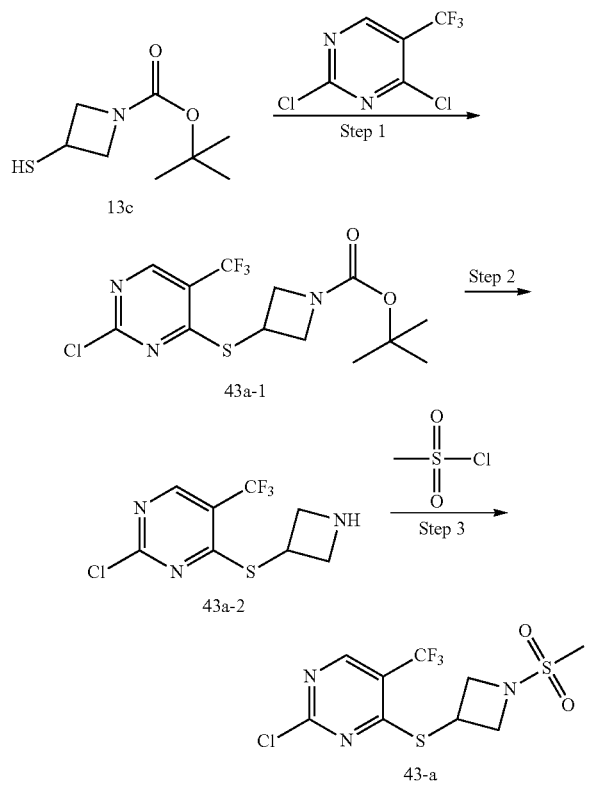

Step 1: At 0° C., into a solution of compound 13c (1.6 g, 8.5 mmol) in acetonitrile (50 ml) was added 2,4-dichloro-5-(trifluoromethyl)pyrimidine (1.84 g, 8.5 mmol) and potassium carbonate (2.35 g, 17 mmol). The reaction mixture was stirred at 0° C. for 1 hour. After the reaction was complete, the reaction was quenched with water, and extracted with ethyl acetate. The organic phase was concentrated to obtain a crude product, which was isolated and purified by combi-flash column chromatography to obtain the title product 43a-1 (2.5 g, yield 67%). MS m/z(ESI): 370[M+H]$^+$.

Step 2-3: It was conducted by using compound 43a-1 as the raw material according to steps 4 and 5 in preparation of compound 13f. MS m/z(ESI):348 [M+H]$^+$.

Preparation of Compound 44-a

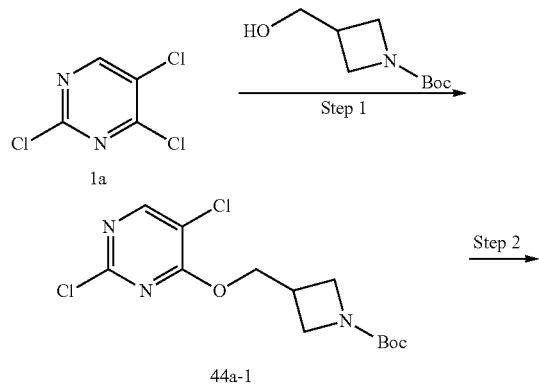

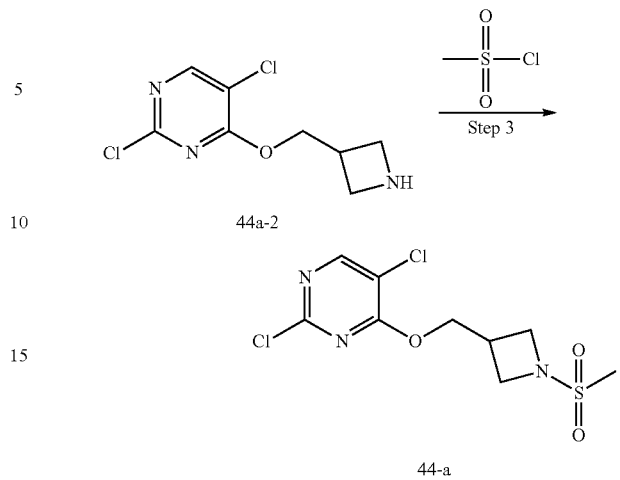

Step 1: Compound 1a (1 g, 5.45 mmol), 3-(hydroxymethyl) azetidine-1-formic acid (1 g, 5.34 mmol) and cesium carbonate (2.67 g, 8.19 mmol) were added to 15 ml of acetonitrile. The reaction mixture was stirred at 80° C. for 3 hours. After the reaction was complete, the reaction mixture was filtered, washed with dichloromethane, concentrated and isolated and purified by combi-flash column chromatography [PE:EA=100:0~80:20] to obtain the title product 44a-1 (1.06 g, yield 58.18%). MS m/z(ESI):278 [M-55]$^+$.

Step 2-3: It was conducted by using compound 44a-1 as the raw material according to steps 4 and 5 in preparation of compound 13f. MS m/z(ESI):312 [M+H]$^+$.

Preparation of Compound 45-a

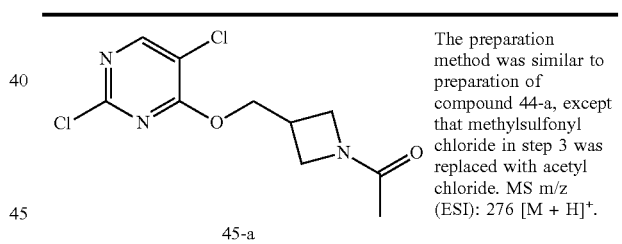

The preparation method was similar to preparation of compound 44-a, except that methylsulfonyl chloride in step 3 was replaced with acetyl chloride. MS m/z (ESI): 276 [M + H]$^+$.

Preparation of Compound 46-a

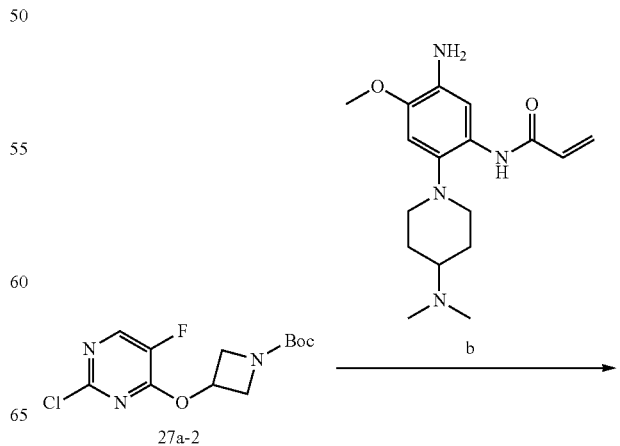

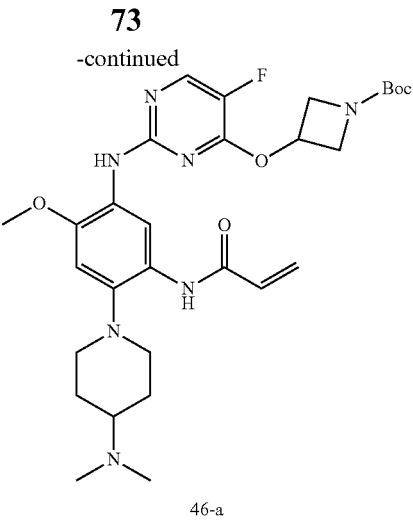

46-a

Compound 46-a was prepared by using compound 27a-2 and compound b as the raw material according to preparation of compound J-27. MS m/z(ESI):586.3 [M+H]⁺.

Preparation of Compound 47-a

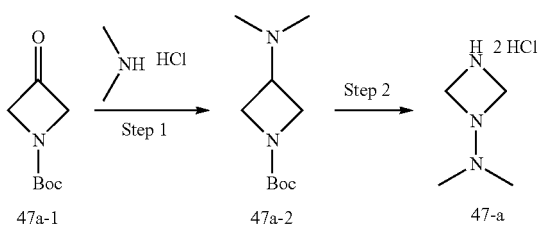

Step 1: Under hydrogen atmosphere, compound 47a-1 (5.0 g, 0.0292 mmol), dimethylamine hydrochloride (4.77 g, 0.0584 mmol), 2.1 g of Pd/C and 2.5 ml of acetic acid were added into 100 ml of methanol. The air in the system was replaced by hydrogen and then the reaction was conducted at room temperature for 48 hours. After the reaction was complete, the reaction mixture was filtered, and concentrated to obtain a crude product, which was extracted with saturated NaHCO₃ and ethyl acetate. The organic phase was washed with brine and concentrated to obtain the title compound 47a-2 (5.0 g, yield 85%). MS m/z(ESI): 201 [M+H]⁺.

Step 2: At 0° C., into a solution of compound 47a-2 (5.0 g, 0.025 mmol) in dichloromethane (100 ml) was added a solution of HCl/1,4-dioxane (4M). The reaction mixture was stirred at room temperature for 3 hours. After the reaction was complete, the reaction mixture was concentrated to obtain the title compound 47-a (3.5 g, 82%). MS m/z(ESI): 173 [M+H]⁺.

Preparation of Compound 48-a

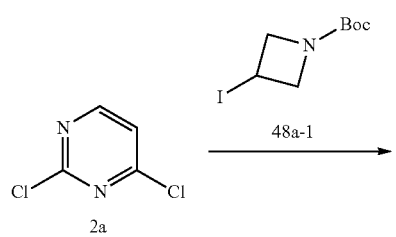

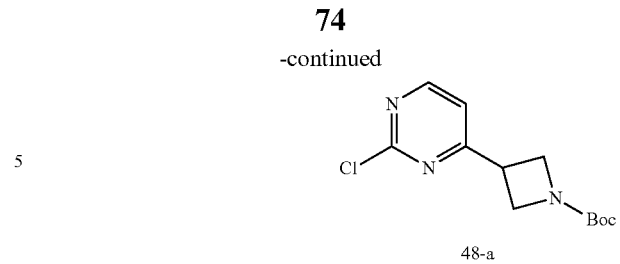

48-a

Zinc powder (980 mg, 15.08 mmol), trimethylchlorosilane (175 mg, 1.61 mmol), 1,2-dibromoethane (303 mg, 1.61 mmol) were added successively into 20 ml of DMF. The air in the system was replaced with argon and then the reaction mixture was stirred at room temperature for 3 min. Then a solution of compound 48a-1 (3.95 g, 13.95 mmol) in 10 ml of DMF was added. The reaction mixture was stirred at room temperature for 1.5 hours. The above reaction mixture was added into a mixture of compound 2a (1.6 g, 10.74 mmol), Pd(dppf)Cl₂ (393 mg, 0.54 mmol), cuprous iodide (102 mg, 0.54 mmol) and 20 ml of DMF. The air in the system was replaced with argon and then the reaction was conducted in a sealed tube at 100° C. for 16 hours. After the reaction was complete, the reaction mixture was filtered and concentrated. The residue was dissolved in dichloromethane. The resultant mixture was washed with saturated sodium bicarbonate and brine, and concentrated to give a residue isolated and purified by combi-flash column chromatography to obtain the title product 48-a. MS m/z(ESI): 214 [M-55]⁺.

Preparation of Compounds 49-a and 50-a

Preparation of compounds 49-a and 50-a followed preparation of compound 31-a, except that compound 7a-1 in step 1 was replaced with 2,4-dichloro-5-fluoropyrimidine and 2,4-dichloro-5-(trifluoromethyl)pyrimidine, respectively.

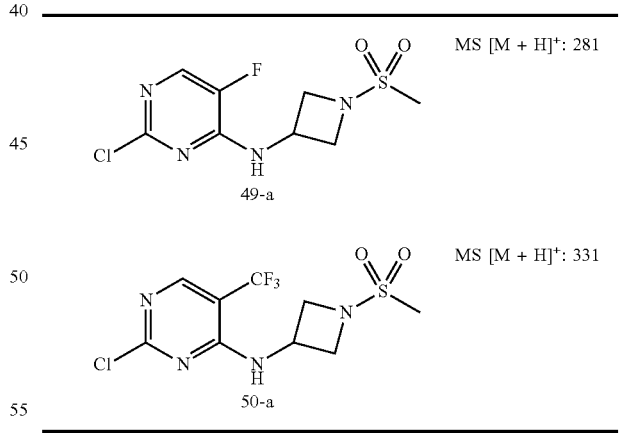

Preparation of Compounds 51-a and 52-a

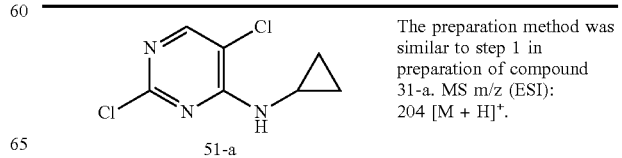

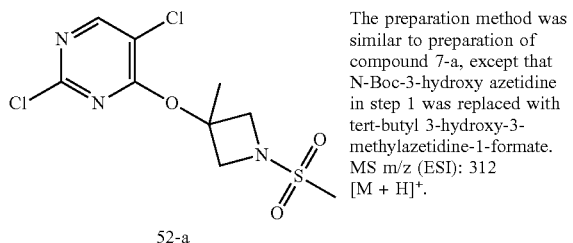

The preparation method was similar to preparation of compound 7-a, except that N-Boc-3-hydroxy azetidine in step 1 was replaced with tert-butyl 3-hydroxy-3-methylazetidine-1-formate. MS m/z (ESI): 312 [M + H]+.

52-a

Example 1 Preparation of N-(5-(5-chloro-4-(1-(methylsulfonyl)azacycloheptane-4-oxy)pyrimidine-2-amino)-2-((2-(dimethylamino)ethyl)(methyl)amino)-4-methoxyl phenyl)acrylamide (J-1)

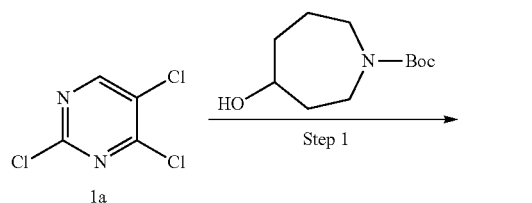

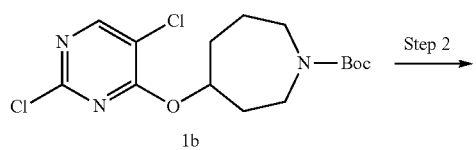

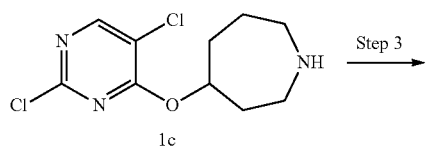

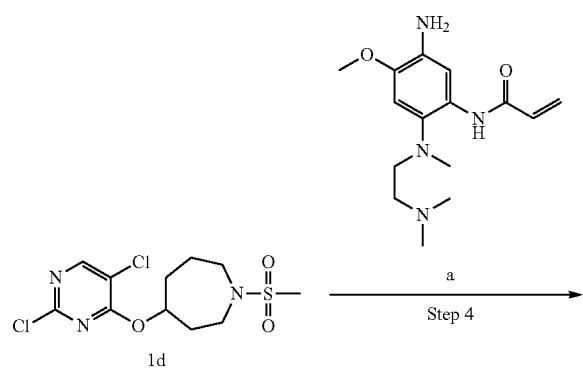

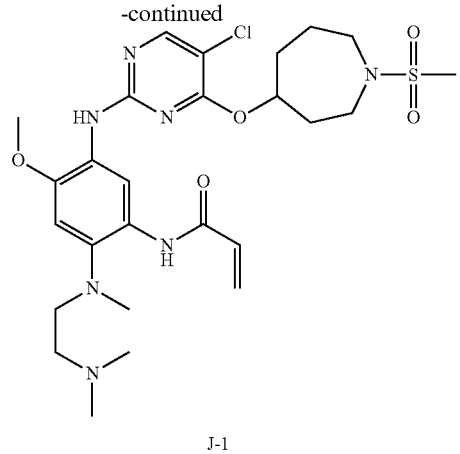

J-1

Step 1: 2,4,5-trichloropyrimidinela (2 g, 10.9 mmol) and cesium carbonate (10.2 g, 31.2 mmol) were added into a solution of tert-butyl 4-hydroxyazacycloheptane-1-carboxylate (2.24 g, 10.9 mmol) in 100 ml of acetonitrile. The reaction mixture was vigorously stirred at 85° C. for 5 hours. After the reaction was complete, the undissolved substance was removed by filtration and the filter cake was washed with ethyl acetate. The organic phase was concentrated under reduced pressure and purified by combi-flash to obtain compound tert-butyl 4-(2,5-dichloropyrimidine-4-oxy) azacycloheptane-1-carboxylate 1b (200 mg, 5%). MS m/z(ESI): 306.0 [M-56]+.

Step 2: At 0° C., trifluoroacetic acid (1.89 g, 16.7 mmol) was added into a solution of tert-butyl 4-(2,5-dichloropyrimidine-4-oxy)azacycloheptane-1-formate 1b (300 mg, 0.83 mmol) in 10 ml of dichloromethane. The reaction mixture was vigorously stirred at room temperature for 5 hours. After the reaction was complete, the reaction mixture was dried by rotary under reduced pressure to obtain compound 4-(2,5-dichloropyrimidine-4-oxy)azacycloheptane 1c (380 mg), which was used directly in the next step. MS m/z(ESI): 262.0 [M+1]+.

Step 3: At 0° C., N,N-diisopropylethylamine (4 g, 30.5 mmol) was added into a solution of compound 4-(2,5-dichloropyrimidine-4-oxy)azacycloheptane 1c (400 mg, 1.53 mmol) in 12 ml of dichloromethane. The reaction mixture was vigorously stirred at 0° C. for 30 min, and then methylsulfonyl chloride (350 mg, 3.05 mmol) was added. The reaction mixture was vigorously stirred at 0° C. for 2 hours. After the reaction was complete, the reaction mixture was diluted with water, and extracted with dichloromethane/water system for three times. The organic phase was concentrated under reduced pressure and purified by combiflash to obtain compound 4-(2,5-dichloropyrimidine-4-oxy)-1-(methylsulfonyl)azacycloheptane 1d (360 mg, 70%). MS m/z(ESI): 362.0 [M+1]+.

Step 4: N-(5-amino-2-((2-(dimethylamino)ethyl)(methyl)amino)-4-methoxylphenyl)acrylamidea (155 mg, 0.53 mmol), Pd$_2$(dba)$_3$ (49 mg, 0.05 mmol), BINAP (66 mg, 0.10 mmol) and cesium carbonate (345 mg, 1.06 mmol) were added into a solution of compound 4-(2,5-dichloropyrimidine-4-oxy)-1-(methylsulfonyl)azacycloheptane 1d (180 mg, 0.53 mmol) in 5 ml of 1,4-dioxane. The reaction mixture was vigorously stirred under microwave at 160° C. for 30 min. After the reaction was complete, the reaction mixture was filtered. The filtrate was extracted with ethyl acetate/water system for three times. The organic phase was concentrated under reduced pressure to obtain a crude product which was isolated and purified by preparative liquid phase chromatography to obtain compound N-(5-(5-chloro-4-(1-(methylsulfonyl)azacycloheptane-4-oxy)pyrimidine-2- amino)-2-((2-(dimethylamino)ethyl)(methyl)amino)-4-methoxylphenyl)acrylamide J-1 (84.24 mg). MS m/z(ESI): 596.3 [M+1]+; ¹HNMR (400 MHz, DMSO-d₆) δ 10.12 (s, 1H), 8.75 (s, 1H), 8.29 (s, 1H), 8.26 (s, 1H), 8.25 (s, 1H), 6.99 (s, 1H), 6.44 (dd, J=16.9, 10.1 Hz, 1H), 6.23 (dd, J=16.9, 1.8 Hz, 1H), 5.75 (dd, J=10.1, 1.7 Hz, 1H), 5.46 (dd, J=7.6, 3.8 Hz, 1H), 3.83 (s, 3H), 3.39-3.32 (m, 1H), 3.27 (t, J=6.3 Hz, 3H), 2.90 (d, J=6.0 Hz, 2H), 2.87 (s, 3H), 2.68 (s, 3H), 2.37 (t, J=5.6 Hz, 2H), 2.24 (s, 6H), 2.13-2.03 (m, 1H), 1.98-1.79 (m, 4H), 1.72-1.58 (m, 1H).

Example 2 Preparation of tert-butyl 4-(2-(5-acrylamido-4-(4-(dimethylamino) piperidine-1-yl)-2-methoxyphenylamino)pyrimidine-4-oxy)piperidine-1-formate (J-2)

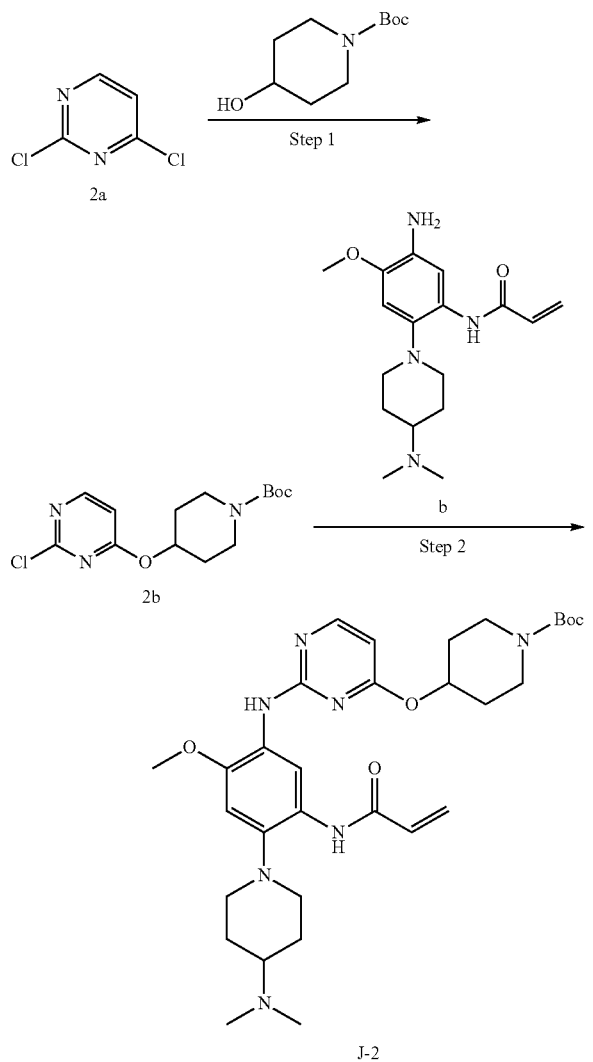

Step 1: 2,4-dichloropyrimidine 2a (10 g, 67.11 mmol) and cesium carbonate (39.8 g, 122.09 mmol) were added into a solution of tert butyl-4-hydroxypiperidine-1-formate (12.8 g, 63.68 mmol) in 300 ml of DMF. The reaction mixture was vigorously stirred at 80° C. for 8 hours. After the reaction was complete, the reaction mixture was diluted with water, extracted with ethyl acetate/water system for three times, and washed with water and saturated sodium chloride for three times. The organic phase was concentrated under reduced pressure and purified by combiflash [PE:EA=100: 0~50:50] to obtain compound tert-butyl 4-(2-chloropyrimidine-4-oxy)piperidine-1-formate 2b (7.6 g, 40%). MS m/z (ESI): 314.1 [M+1]+.

Step 2: compound N-(5-amino-2-(4-(dimethylamino) piperidine-1-yl)-4-methoxyphenyl)acrylamide b (250 mg, 0.80 mmol), Pd₂(dba)₃ (80 mg, 0.08 mmol), Xantphos (100 mg, 0.16 mmol) and cesium carbonate (520 mg, 1.60 mmol) were added into a solution of compound tert-butyl 4-(2-chloropyrimidine-4-oxy)piperidine-1-formate 2b (250 mg, 0.80 mmol) in 5 ml of 1,4-dioxane. The reaction mixture was vigorously stirred under microwave at 160° C. for 30 min. After the reaction was complete, the reaction mixture was filtered. The filtrate was extracted with ethyl acetate/water system for three times. The organic phase was concentrated under reduced pressure to obtain a crude product isolated and purified by preparative liquid phase chromatography to obtain tert-butyl 4-(2-(5-acrylamido-4-(4-(dimethylamino) piperidine-1-yl)-2-methoxyphenylamino)pyrimidine-4-oxy)piperidine-1-formate J-2 (34.91 mg, 7%). MS m/z(ESI): 596.3 [M+1]+; ¹HNMR (400 MHz, DMSO-d₆) δ9.02 (s, 1H), 8.66 (s, 1H), 8.15 (d, J=5.6 Hz, 1H), 7.90 (s, 1H), 6.83 (s, 1H), 6.68 (dd, J=17.0, 10.2 Hz, 1H), 6.25-6.15 (m, 2H), 5.71 (d, J=10.2 Hz, 1H), 5.34 (s, 1H), 3.85 (s, 3H), 3.71 (d, J=13.3 Hz, 2H), 3.01 (d, J=11.6 Hz, 4H), 2.65 (t, J=10.6 Hz, 2H), 2.22 (s, 6H), 2.17 (s, 1H), 1.94 (d, J=8.9 Hz, 2H), 1.82 (d, J=11.0 Hz, 2H), 1.68 (d, J=9.3 Hz, 2H), 1.49 (d, J=9.6 Hz, 2H), 1.40 (s, 9H).

Example 3 Preparation of N-(5-(5-chloro-4-(1-(methylsulfonyl) piperidine-4-oxy)pyrimidine-2-amino)-2-((2-(dimethylamino)ethyl)(methyl)amino)-4-methoxylphenyl) acrylamide (J-3)

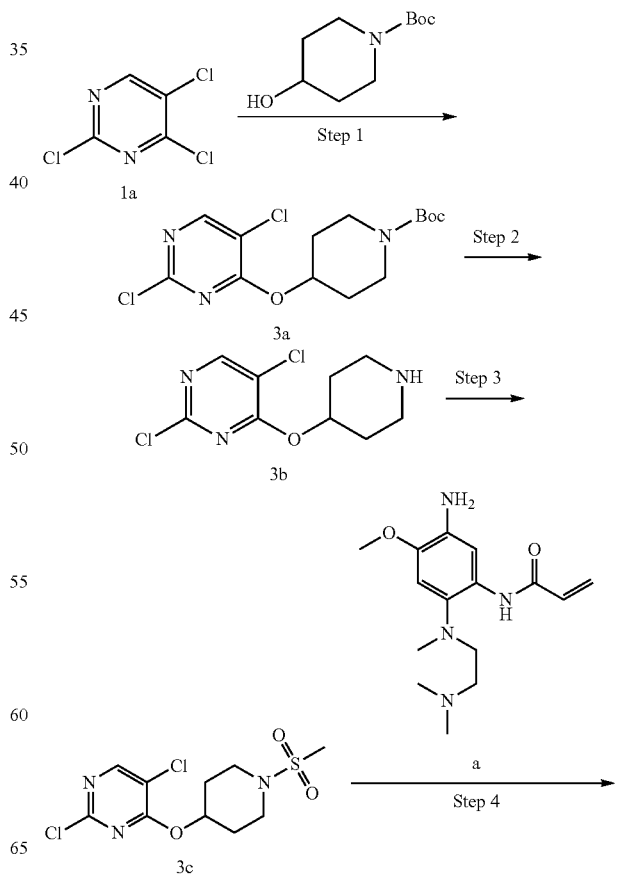

-continued

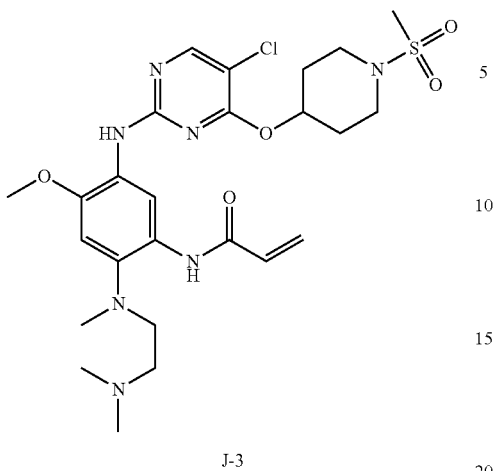

J-3

Step 1: At 0° C., tert-butyl 4-hydroxypiperidine-1-formate (10 g, 49.8 mmol) was added into a solution of sodium hydride (2.4 g, 59.8 mmol) in 200 ml of THF. The reaction mixture was stirred at 0° C. for 1 h, and then 2,4,5-trichloropyrimidine 1a (10 g, 54.7 mmol) was added. The reaction mixture was vigorously stirred at room temperature for 8 hours. After the reaction was complete, the reaction mixture was diluted with water, extracted with ethyl acetate/water system for three times, washed with water and saturated sodium chloride for three times. The organic phase was concentrated under reduced pressure and purified by combiflash [PE:EA=100:0~50:50] to obtain compound tert-butyl 4-(2,5-dichloropyrimidine-4-oxy) piperidine-1-formate 3a (7.6 g, 52%). MS m/z(ESI): 292.0 [M+1]$^+$.

Step 2: Compound 2,5-dichloro-4-(piperidine-4-oxy)pyrimidine 3b (2.4 g, 100%) was prepared by using tert-butyl 4-(2,5-dichloropyrimidine-4-oxy)piperidine-1-formate 3a (1.5 g, 4.32 mmol) as the raw material according to step 2 in Example 1, and the product was used directly in the next step. MS m/z(ESI):248.0 [M+1]+.

Step 3: Compound 2,5-dichloro-4-(1-(methylsulfonyl)piperidine-4-oxy) pyrimidine 3c (150 mg, 28%) was prepared using 2,5-dichloro-4-(piperidine-4-oxy) pyrimidine 3b (908 mg, 1.62 mmol) as the raw material according to step 3 in Example 1. MS m/z(ESI):326.0 [M+1]$^+$.

Step 4: compound N-(5-(5-chloro-4-(1-(methylsulfonyl)piperidine-4-oxy) pyrimidine-2-amino)-2-((2-(dimethylamino)ethyl)(methyl)amino)-4-methoxyphenyl)acryl amide J-3 (75.60 mg, 33%) was prepared by using 2,5-dichloro-4-(1-(methylsulfonyl)piperidine-4-oxy)pyrimidine 3c (130 mg, 0.40 mmol) as the raw material according to step 4 in Example 1. MS m/z(ESI):582.2 [M+1]$^+$; $^1$HNMR (400 MHz, DMSO-d$_6$) δ9.92 (s, 1H), 8.72 (s, 1H), 8.27 (d, J=9.5 Hz, 2H), 8.19 (s, 1H), 6.99 (s, 1H), 6.54 (dd, J=16.9, 10.1 Hz, 1H), 6.26 (dd, J=16.9, 1.8 Hz, 1H), 5.77 (dd, J=10.2, 1.7 Hz, 1H), 5.47-5.32 (m, 1H), 3.84 (s, 3H), 3.40-3.34 (m, 2H), 3.03 (dt, J=11.8, 7.3 Hz, 4H), 2.87 (s, 3H), 2.66 (s, 5H), 2.41 (s, 6H), 2.10-2.00 (m, 2H), 1.84-1.72 (m, 2H).

Example 4 Preparation of N-(2-((2-(dimethylamino)ethyl)(methyl)amino)-4-methoxy-5-(4-(1-(methylsulfonyl)piperidine-4-oxy)pyrimidine-2-amino)phenyl) acrylamide (J-4)

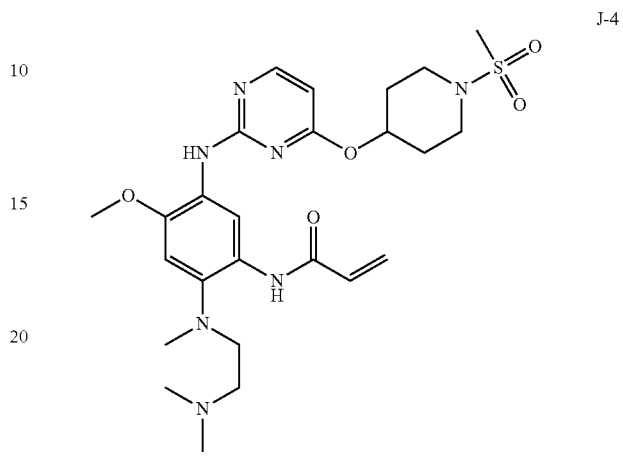

J-4

Compound N-(2-((2-(dimethylamino)ethyl)(methyl)amino)-4-methoxy-5-(4-(1-(methylsulfonyl)piperidine-4-oxy)pyrimidine-2-amino)phenyl)acrylamide J-4 (93.42 mg, 33%) was prepared by using compound 2a (10 g, 67.11 mmol) as the raw material according to Example 1, except that tert-butyl 4-hydroxyazacycloheptane-1-carboxylate in step 1 of Example 1 was replaced with tert-butyl 4-hydroxypiperidine-1-formate (12.8 g, 63.68 mmol).

MS m/z(ESI):548.3 [M+1]$^+$; $^1$HNMR (400 MHz, DMSO-d$_6$) δ10.15 (s, 1H), 8.96 (s, 1H), 8.17 (d, J=5.6 Hz, 1H), 7.94 (s, 1H), 7.00 (s, 1H), 6.40 (dd, J=16.9, 10.0 Hz, 1H), 6.25 (td, J=6.6, 2.0 Hz, 2H), 5.76 (dd, J=10.0, 1.9 Hz, 1H), 5.45-5.32 (m, 1H), 3.85 (s, 3H), 3.38 (dd, J=11.6, 5.6 Hz, 2H), 3.02 (t, J=9.1 Hz, 2H), 2.86 (d, J=9.0 Hz, 5H), 2.70 (s, 3H), 2.28 (t, J=5.7 Hz, 2H), 2.19 (s, 6H), 2.09-2.01 (m, 2H), 1.77-1.66 (m, 2H).

Example 5 Preparation of N-(2-(4-(dimethylamino)piperidine-1-yl)-4-methoxy-5-(4-(1-(methylsulfonyl)piperidine-4-oxy)pyrimidine-2-amino)phenyl)acrylamide (J-5)

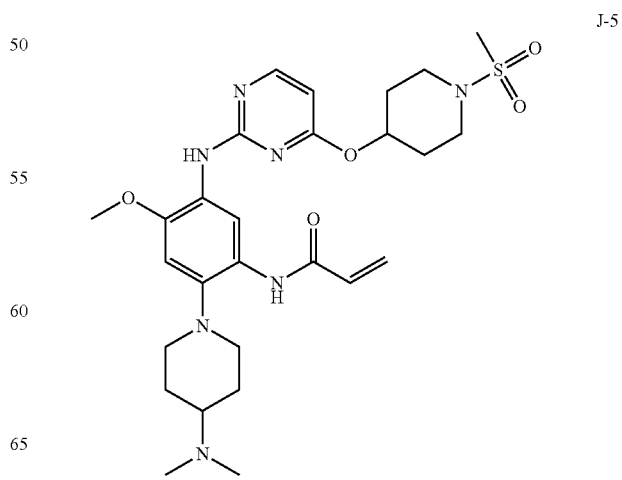

J-5

Compound N-(2-(4-(dimethylamino)piperidine-1-yl)-4-methoxy-5-(4-(1-(methylsulfonyl)piperidine-4-oxy)pyrimidine-2-amino)phenyl)acrylamide (142.64 mg, 47%) was prepared by using compound 2a (10 g, 67.11 mmol) as the raw material referring to Example 1, except that tert-butyl 4-hydroxyazacycloheptane-1-carboxylate in step 1 of Example 1 was replaced with tert-butyl 4-hydroxypiperidine-1-formate (12.8 g, 63.68 mmol), and compound a in step 4 of Example 1 was replaced with compound b (164 mg, 0.52 mmol).

MS m/z(ESI):574.3 [M+1]$^+$; $^1$HNMR (400 MHz, DMSO-d$_6$) δ 9.01 (s, 1H), 8.67 (s, 1H), 8.16 (d, J=5.6 Hz, 1H), 7.92 (s, 1H), 6.84 (s, 1H), 6.67 (dd, J=16.9, 10.1 Hz, 1H), 6.29-6.19 (m, 2H), 5.75 (d, J=10.3 Hz, 1H), 5.31 (s, 1H), 3.85 (s, 3H), 3.44-3.35 (m, 2H), 3.33 (s, 3H), 3.01 (s, 4H), 2.87 (s, 3H), 2.66 (t, J=10.7 Hz, 2H), 2.23 (s, 6H), 2.20-2.14 (m, 1H), 2.05 (d, J=11.2 Hz, 2H), 1.84 (d, J=10.4 Hz, 2H), 1.78-1.62 (m, 4H).

Example 6 Preparation of N-(5-(4-(1-benzoylaza-3-oxy)pyrimidine-2-amino)-2-((2-dimethylamino)ethyl)(methyl)amino)-4-methoxylphenyl)acrylamide (J-6)

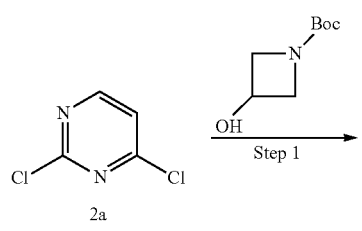

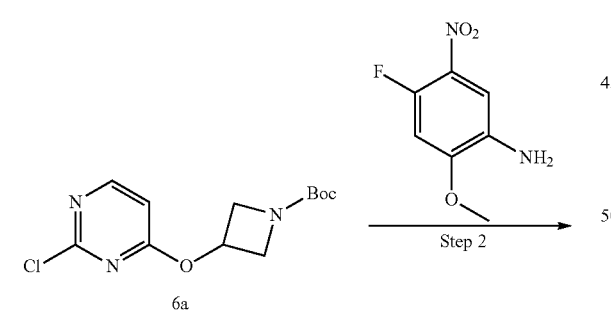

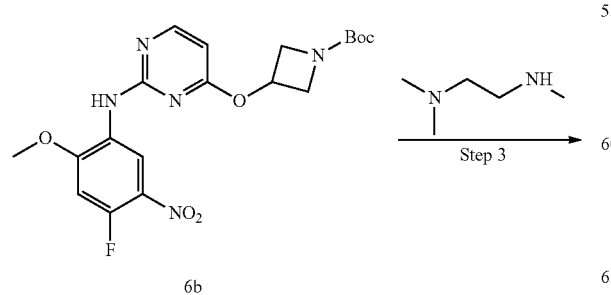

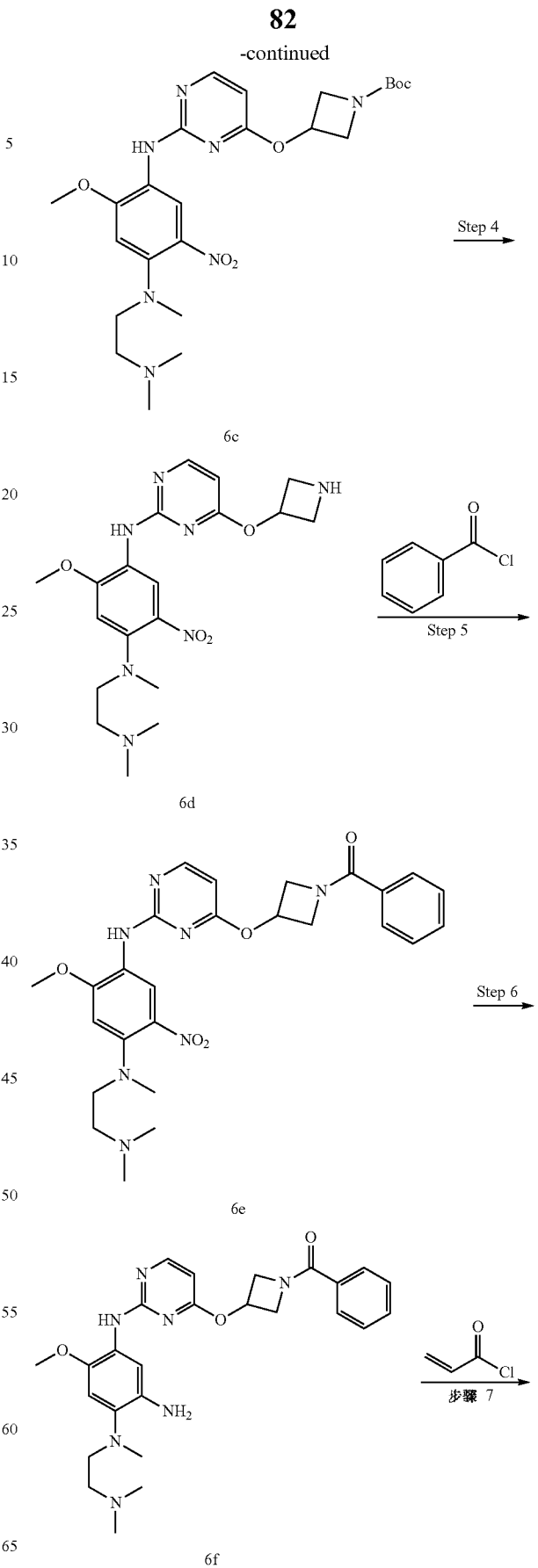

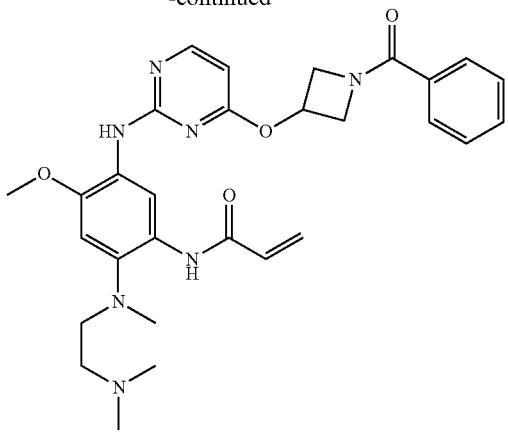

J-6

Step 1: Compound 2, 4-dichloropyrimidine 2a (19.7 g, 110 mmol) and cesium carbonate (65.2 g, 200 mmol) were added into a solution of N-Boc-3-hydroxy azetidine (17.3 g, 100 mmol) in 400 ml of DMF. The reaction mixture was vigorously stirred at 83° C. for 4 hours. The reaction progress was monitored by TLC. After the substrate was completely consumed, the reaction mixture was extracted with ethyl acetate/water system for three times. The organic phase was separated, washed with water and saturated brine, and dried by rotary to obtain a crude product purified by Combi-flash column chromatography [PE:EA=100:0-40:60] to obtain compound tert-butyl 3-(2-chloropyrimidine-4-oxy) azetidine-1-formate 6a (25 g, 88%). MS m/z(ESI): 286.1 [M+1]$^+$.

Step 2: Compound 4 fluoro-2-methoxy-5-nitroaniline (1.96 g, 10.5 mmol), Pd$_2$(dba)$_3$ (964 mg, 1.05 mmol), Xantphos (1.219 g, 2.11 mmol) and cesium carbonate (6.86 g, 21.0 mmol) were added into a solution of compound tert-butyl 3-(2-chloropyrimidine-4-oxy) azetidine-1-formate 6a (3 g, 10.5 mmol) in 70 ml of 1,4-dioxane. At 120° C., under N$_2$ atmosphere, the reaction mixture was vigorously stirred for 20 hours. After the reaction was complete, the reaction mixture was filtered and washed with ethyl acetate. The filtrate was concentrated under reduced pressure to obtain a crude product purified by Combi-flash column chromatography [PE:EA=100:0-20:80] to obtain compound tert-butyl 3-(2-(4-fluoro-2-methoxy-5-nitrophenylamino) pyrimidine-4-oxy) azetidine-1-formate 6b (2.86 g, 62%). MS m/z(ESI): 436.2 M+1]$^+$.

Step 3: N,N,N'-trimethylethylenediamine (4.08 g, 40.0 mmol) and potassium carbonate (13.8 g, 100 mmol) were added into a solution of compound tert-butyl 3-(2-(4-fluoro-2-methoxy-5-nitrophenylamino)pyrimidine-4-oxy) azetidine-1-formate 6b (14.5 g, 33.3 mmol) in 170 ml of DMF. The reaction mixture was vigorously stirred at 100° C. for 4 h. The reaction progress was monitored by TLC. After the substrate was completely consumed, the reaction mixture was extracted with ethyl acetate/water system for three times. The organic phase was separated and concentrated under reduced pressure to obtain compound tert-butyl 3-(2-(4-((2-(dimethylamino)ethyl)(methyl)amino)-2-methoxy-5-nitrophenylamino)pyrimidine-4-oxy) azetidine-1-formate 6c (9.2 g, 54%), MS m/z (ESI): 518.3 [M+1]$^+$.

Step 4: Trifluoroacetic acid (27 mL, 356.0 mmol) was added into a solution of compound tert-butyl 3-(2-(4-((2-(dimethylamino)ethyl)(methyl)amino)-2-methoxy-5-nitrop-henylamino)pyrimidine-4-oxy) azetidine-1-formate 6c (9.2 g, 17.8 mmol) in 250 ml of dichloromethane. The reaction mixture was vigorously stirred at room temperature for 6 hours. The reaction progress was monitored by TLC. After the substrate was completely consumed, extra dichloromethane was removed by rotary under reduced pressure. The residue was diluted with water and pH was adjusted to alkalinity. The resultant mixture was extracted with dichloromethane and methanol (10:1). The organic phase was dried by rotary to obtain compound N1-(4-(azetidine-3-oxy) pyrimidine-2-yl)-N4-(2-(dimethylamino)ethyl)-2-methoxy-N4-methyl-5-nitrophenyl-1,4-diamine 6d (5.2 g, 70%). MS m/z(ESI): 418.2 [M+1]$^+$.

Step 5: At 0° C., triethylamine (1.01 g, 10 mmol) was added into a solution of compound N1-(4-(azetidine-3-oxy) pyrimidine-2-yl)-N4-(2-(dimethylamino)ethyl)-2-methoxy-N4-methyl-5-nitrophenyl-1,4-diamine 6d (1.4 g, 1 mmol) in 10 ml of dichloromethane. The reaction mixture was vigorously stirred at 0° C. for 30 min and then benzoyl chloride (140 mg, 1.2 mmol) was added. After the reaction was complete, the reaction mixture was diluted with water, extracted with dichloromethane/water system for three times. The organic phase was concentrated under reduced pressure to obtain compound (3-(2-(4-((2-(dimethylamino) ethyl)(methyl)amino)-2-methoxy-5-nitrophenylamino)py-rimidine-4-oxy)azetidine-1-yl)(phenyl)ketone 6e (660 mg, 99%). The product was used directly in the next step. MS m/z(ESI): 522.3 [M+1]$^+$.

Step 6: Pd/C (110 mg) were added into a solution of compound (3-(2-(4-((2-(dimethylamino)ethyl)(methyl) amino)-2-methoxy-5-nitrophenylamino)pyrimidine-4-oxy) azetidine-1-yl)(phenyl)ketone 6e (650 mg, 1 mmol) in 50 ml of methanol. The reaction mixture was vigorously stirred at room temperature under H$_2$ atmosphere for 4 hours. After the reaction was complete, the reaction mixture was filtered. The filtrate was concentrated to obtain compound (3-(2-(5-amino-4-((2-(dimethylamino)ethyl)(methyl) amino)-2-methoxyphenylamino)pyrimidine-4-oxy) azetidine-1-yl) (phenyl)ketone 6f (630 mg, 99%), The product was used directly in the next step. MS m/z(ESI): 492.3 [M+1].

Step 7: At 0° C., acryloyl chloride (138 mg, 1.54 mmol) and triethylamine (195 mg, 1.92 mmol) were added into a solution of compound (3-(2-(5-amino-4-((2-(dimethyl-amino)ethyl)(methyl)amino)-2-methoxyphenylamino)py-rimidine-4-oxy) azetidine-1-yl)(phenyl)ketone 6f (630 mg, 1 mmol) in 10 ml of dichloromethane. The reaction mixture was vigorously stirred at 0° C. for 2 hours. After the reaction was complete, the reaction mixture was diluted with water, and extracted with dichloromethane/water system for three times. The organic phase was concentrated under reduced pressure to obtain a crude product, which was isolated and purified by preparative liquid phase chromatography to obtain compound N-(5-(4-(1-benzoylaza-3-oxy)pyrimidine-2-amino)-2-((2-(dimethylamino)ethyl)(methyl)amino)-4-methoxylphenyl)acrylamide J-6 (70.67 mg, 13%). MS m/z (ESI): 545.8 [M+1]$^+$; $^1$HNMR (400 MHz, DMSO-d$_6$) δ10.14 (s, 1H), 8.93 (s, 1H), 8.22 (d, J=5.6 Hz, 1H), 8.04 (s, 1H), 7.59 (d, J=7.1 Hz, 2H), 7.50 (t, J=7.3 Hz, 1H), 7.42 (t, J=7.4 Hz, 2H), 6.97 (s, 1H), 6.35 (d, J=5.6 Hz, 1H), 6.34-6.27 (m, 1H), 6.18 (dd, J=16.9, 2.1 Hz, 1H), 5.76-5.66 (m, 2H), 4.50 (d, J=25.3 Hz, 2H), 4.35 (s, 1H), 4.05 (s, 1H), 3.83 (s, 3H), 2.82 (d, J=3.9 Hz, 2H), 2.66 (s, 3H), 2.23 (s, 2H), 2.14 (s, 6H).

Example 7 Preparation of N-(2-((2-(dimethylamino) ethyl)(methyl)amino)-4-methoxy-5-(4-(1-(phenylsulfonyl) azetidine-3-oxy)pyrimidine-2-amino)phenyl) acrylamide (J-7)

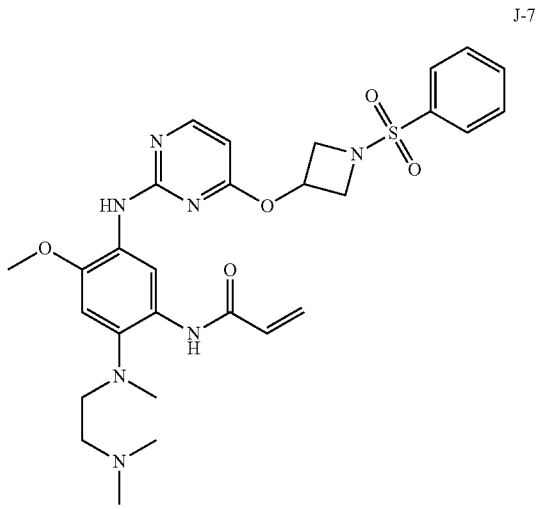 [SMILES: C=CC(=O)Nc1cc(Nc2nccc(OC3CN(S(=O)(=O)c4ccccc4)C3)n2)c(OC)cc1N(C)CCN(C)C]

J-7

Compound N-(2-((2-(dimethylamino)ethyl)(methyl) amino)-4-methoxy-5-(4-(1-(phenylsulfonyl) azetidine-3-oxy)pyrimidine-2-amino)phenyl)acrylamide J-7 (44.30 mg, 7%) was prepared by using compound 6b (14.5 g, 33.3 mmol) as the raw material according to the method in Example 6, except that benzoyl chloride in step 5 of Example 6 was replaced with phenylsulfonyl chloride (210 mg, 1.2 mmol).

MS m/z(ESI): 582.3 [M+1]$^+$; $^1$H NMR (400 MHz, DMSO-d$_6$) δ9.98 (s, 1H), 8.65 (s, 1H), 8.15 (s, 1H), 8.17 (d, J=5.6 Hz, 1H), 7.79 (m, 3H), 7.69 (t, J=7.5 Hz, 2H), 6.98 (s, 1H), 6.82-6.36 (m, 1H), 6.25 (d, J=16.7 Hz, 1H), 6.12 (d, J=5.6 Hz, 1H), 5.74 (d, J=11.8 Hz, 1H), 5.29 (s, 1H), 4.09 (t, J=15.6 Hz, 2H), 3.83 (s, 3H), 3.59 (m, 2H), 2.99 (s, 2H), 2.67 (s, 3H), 2.50-2.14 (m, 8H).

Example 8 Preparation of N-(5-(4-(1-benzoylaza-3-oxy)pyrimidine-2-amino)-2-(4-(dimethylamino)piperidine-1-yl)-4-methoxylphenyl)acrylamide (J-8)

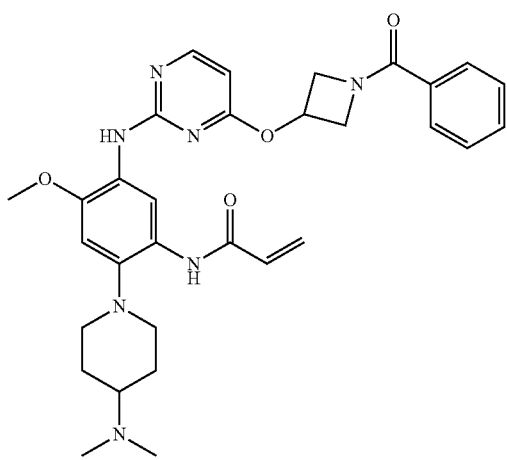

J-8

Compound N-(5-(4-(1-benzoylaza-3-oxy)pyrimidine-2-amino)-2-(4-(dimethylamino) piperidine-1-yl)-4-methoxylphenyl)acrylamide J-8 (33.46 mg, 15%) was prepared by using compound 6b (6.7 g, 15.4 mmol) as the raw material according to the method of Example 6, except that N,N,N'-trimethylethylenediamine in step 3 of Example 6 was replaced with 4-dimethylaminopiperidine (2.37 g, 18.5 mmol).

MS m/z(ESI): 572.8 [M+1]$^+$; $^1$H NMR (400 MHz, DMSO-d$_6$) δ 8.95 (s, 1H), 8.58 (s, 1H), 8.20 (d, J=5.6 Hz, 1H), 8.04 (s, 1H), 7.65-7.58 (m, 2H), 7.51 (t, J=7.3 Hz, 1H), 7.44 (t, J=7.4 Hz, 2H), 6.79 (s, 1H), 6.62 (dd, J=16.9, 10.2 Hz, 1H), 6.33 (d, J=5.6 Hz, 1H), 6.17 (dd, J=16.9, 1.9 Hz, 1H), 5.68 (d, J=10 Hz, 1H), 5.63 (s, 1H), 4.49 (d, J=19.8 Hz, 2H), 4.33 (s, 1H), 4.03 (d, J=7.7 Hz, 1H), 3.82 (s, 3H), 2.95 (d, J=12.6 Hz, 2H), 2.69-2.53 (m, 2H), 2.22 (s, 6H), 2.16 (t, J=10.9 Hz, 1H), 1.81 (d, J=11.1 Hz, 2H), 1.66 (d, J=9.6 Hz, 2H).

Example 9 Preparation of N-(2-(4-(dimethylamino) piperidine-1-yl)-4-methoxy-5-(4-(1-(phenylsulfonyl) azetidine-3-oxy)pyrimidino)phenyl)acrylamide (J-9)

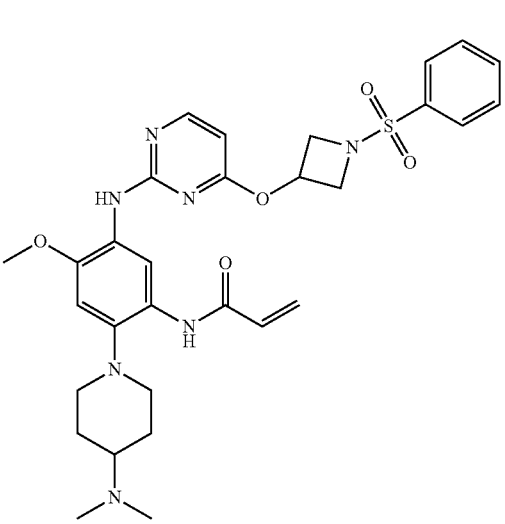

J-9

Compound N-(2-(4-(dimethylamino)piperidine-1-yl)-4-methoxy-5-(4-(1-(phenylsulfonyl)azetidine-3-oxy)pyrimidine-2-amino)phenyl)acrylamide J-9 (78.86 mg, 34%) was prepared by using compound 6b (6.7 g, 15.4 mmol) as the raw material according to the method of Example 6, except that N,N,N'-trimethylethylenediamine in step 3 of Example 6 was replaced with 4-dimethylaminopiperidine (2.37 g, 18.5 mmol), and benzoyl chloride in step 5 of Example 6 was replaced with phenylsulfonyl chloride (88 mg, 0.45 mmol).

MS m/z(ESI): 608.3 [M+1]$^+$; $^1$H NMR (400 MHz, DMSO-d$_6$) δ8.96 (s, 1H), 8.41 (s, 1H), 8.12 (s, 2H), 7.75 (m, 5H), 6.73 (d, J=60.1 Hz, 2H), 6.17 (d, J=58.5 Hz, 2H), 5.73 (d, J=20.8 Hz, 1H), 5.25 (s, 1H), 4.08 (d, J=7.2 Hz, 2H), 3.82 (d, J=14.9 Hz, 3H), 3.59 (s, 2H), 3.03 (s, 2H), 2.66 (s, 2H), 2.26 (s, 7H), 1.85 (s, 2H), 1.72 (s, 2H).

Example 10 Preparation of N-(2-(4-(dimethylamino)piperidine-1-yl)-4-methoxy-5-(4-(1-(methylsulfonyl) azetidine-3-oxy)pyrimidine-2-amino)phenyl)acrylamide (J-10)

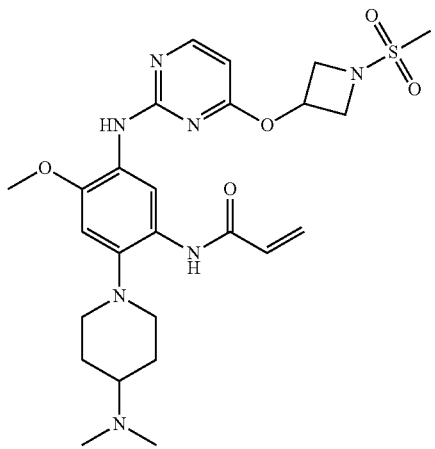

Compound N-(2-(4-(dimethylamino)piperidine-1-yl)-4-methoxy-5-(4-(1-(methylsulfonyl)azetidine-3-oxy)pyrimidine-2-amino)phenyl)acrylamide J-10 (93.21 mg, 45%) was prepared by using compound 6b (6.7 g, 15.4 mmol) as the raw material according to the method of Example 6, except that N,N,N'-trimethylethylenediamine in step 3 of Example 6 was replaced with 4-dimethylaminopiperidine (2.37 g, 18.5 mmol), and benzoyl chloride in step 5 of Example 6 was replaced with methylsulfonyl chloride (57 mg, 0.50 mmol).

MS m/z(ESI): 546.3 [M+1]$^+$; $^1$H NMR (400 MHz, DMSO-d$_6$) δ 9.01 (s, 1H), 8.51 (s, 1H), 8.20 (d, J=4.5 Hz, 1H), 8.10 (s, 1H), 6.83 (s, 1H), 6.76-6.59 (m, 1H), 6.30 (d, J=5.6 Hz, 1H), 6.26 (d, J=16.4 Hz, 2H), 5.74 (d, J=9.9 Hz, 1H), 5.45 (s, 1H), 4.23-4.14 (t, J=7.8 Hz, 2H), 3.95-3.89 (m, 2H), 3.83 (s, 3H), 3.04 (s, 2H), 3.01 (s, 3H), 2.66 (t, J=10.8 Hz, 2H), 2.24 (s, 7H), 1.82 (d, J=12.4 Hz, 2H), 1.69 (m, 2H).

Example 11 Preparation of N-(5-(5-chloro-4-(1-(methylsulfonyl) azetidine-3-oxy) pyrimidine-2amino)-2-((2-(dimethylamino)ethyl)(methyl) amino)-4-methoxyphenyl)acrylamide 1-11

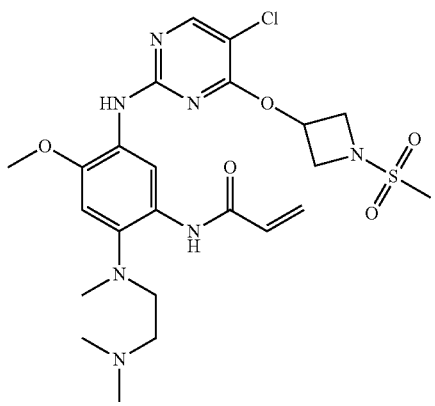

N-(5-(5-chloro-4-(1-(methylsulfonyl) azetidine-3-oxy) pyrimidine-2amino)-2-((2-(dimethylamino)ethyl)(methyl)amino)-4-methoxyphenyl)acrylamide J-11 (56.2 mg, 31.5%) was prepared by using compound 1a (10 g, 54.5 mmol) as the raw material according to the method of Example 1, except that tert-butyl 4-hydroxyazacycloheptane-1-carboxylate in step 1 of Example 1 was replaced with N-Boc-3-hydroxy azetidine (8.58 g, 49.5 mmol).

MS m/z(ESI): 553.6 [M+H]$^+$; $^1$H NMR (400 MHz, CDCl$_3$): δ 12.37 (s, 1H), 9.50 (s, 1H), 9.14 (s, 1H), 8.08 (s, 1H), 7.29-7.31 (m, 1H), 6.63 (s, 1H), 6.37-6.41 (d, J=16.4 Hz, 1H), 5.99 (s, 1H), 5.67-5.70 (dd, J=11.6 Hz, 2 Hz, 1H), 4.27-4.31 (t, J=8 Hz, 2H), 4.00-4.04 (q, J=4.6 Hz, 2H), 3.85 (s, 3H), 3.27-3.29 (m, 2H), 3.07-3.09 (m, 2H), 2.82 (s, 3H), 2.77 (s, 3H), 2.76 (s, 3H), 2.71 (s, 3H).

Example 12 Preparation of N-(5-(5-chloro-4-(1-(methylsulfonyl) azetidine-3-oxy) pyrimidine-2-amino)-2-(4-(dimethylamino)piperidine-1-yl)-4-methoxylphenyl)acrylamide formate (J-12)

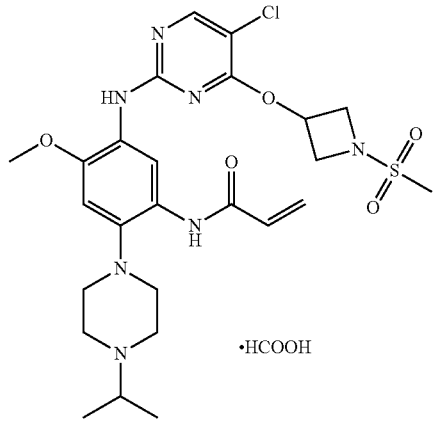

Compound N-(5-(5-chloro-4-(1-(methylsulfonyl) azetidine-3-oxy)pyrimidine-2-amino)-2-(4-(dimethylamino)piperidine-1-yl)-4-methoxylphenyl)acrylamide formate J-12 (81.9 mg, 30.7%) was prepared by using compound 1a (10 g, 54.5 mmol) as the raw material according to the method of Example 1, except that tert-butyl 4-hydroxyazacycloheptane-1-carboxylate in step 1 of Example 1 was replaced with N-Boc-3-hydroxy azetidine (8.58 g, 49.5 mmol), and compound a in step 4 of Example 1 was replaced with compound b (160 mg, 0.50 mmol).

MS m/z(ESI): 580.2 [M+H]$^+$; $^1$H NMR (400 MHz, DMSO-d$_6$): δ 9.02 (s, 1H), 8.43 (s, 1H), 8.34 (s, 1H), 8.28 (s, 1H), 8.16 (s, 1H), 6.83 (s, 1H), 6.63-6.70 (dd, J=17.2 Hz, 10.8 Hz, 1H), 6.24-6.29 (dd, J=17.2 Hz, 2 Hz, 1H), 5.72-5.75 (d, J=11.6 Hz, 1H), 5.42-5.45 (m, 1H), 4.15-4.19 (t, J=8 Hz, 2H), 3.93-3.97 (q, J=4.8 Hz, 2H), 3.81 (s, 3H), 3.12-3.16 (m, 2H), 3.02 (s, 3H), 2.66-2.71 (t, J=10.8 Hz, 2H), 2.54-2.59 (m, 1H), 2.42 (s, 6H), 1.89-1.92 (d, J=11.2 Hz, 2H), 1.72-1.80 (m, 2H).

Example 13 Preparation of N-(5-(5-chloro-4-(1-(methylsulfonyl) azetidine-3-thio) pyrimidine-2-amino)-2-(4-(dimethylamino)piperidine-1-yl)-4-methoxylphenyl)acrylamide (J-13)

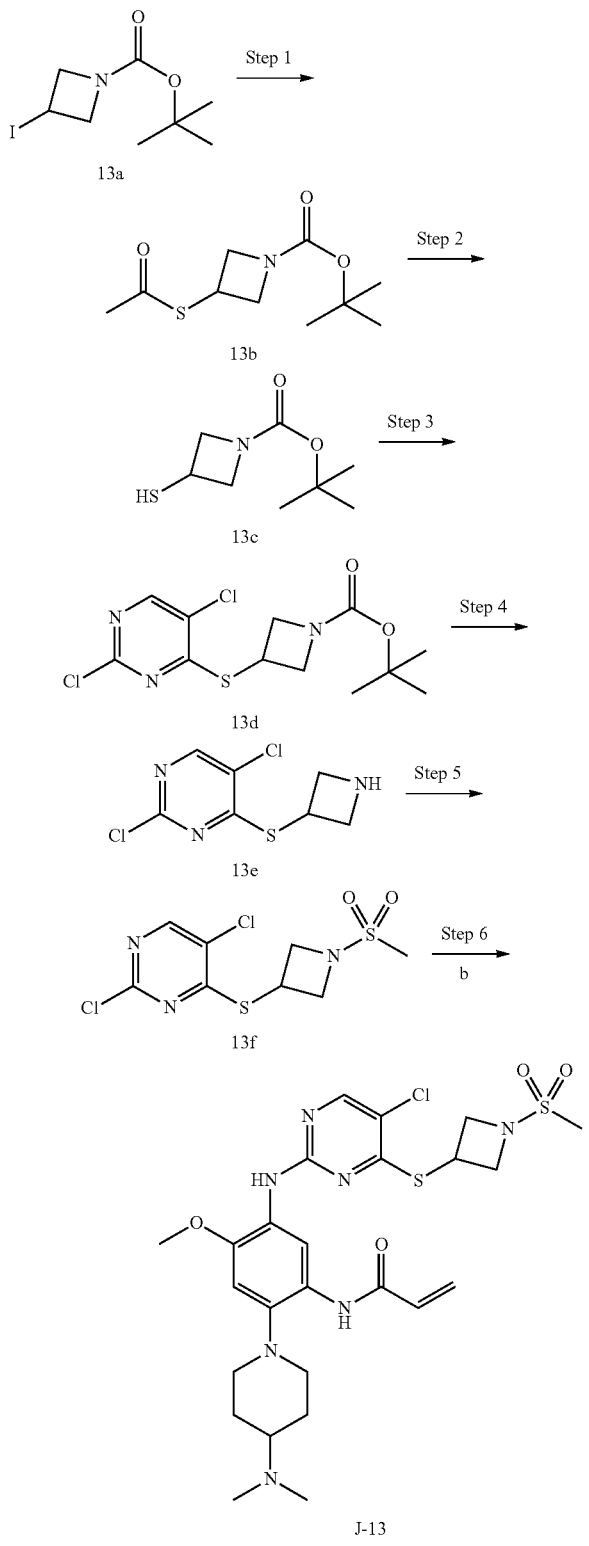

Step 1: Tert-butyl 3-iodoazetidine-1-formate 13a (2 g, 7.2 mmol) and cesium carbonate (4.72 g, 14.4 mmol) were added into a solution of compound thioacetic acid (1.1 g, 14.4 mmol) in 10 ml of N, N-dimethylformamide. The reaction mixture was vigorously stirred at 70° C. for 4 hours. After the reaction was complete, undissloved substance was removed by filtration. The filter cake was washed with ethyl acetate. The organic phase was concentrated under reduced pressure and purified by combiflash to obtain compound tert-butyl 3-(acetylthio)azetidine-1-formate 13b (700 mg, 43%). MS m/z(ESI):232 [M+H]$^+$.

Step 2: Tert-butyl 3-(acetylthio) azetidine-1-formate 13b (0.7 g, 3.03 mmol) and potassium carbonate (0.836 g, 6.05 mmol) were added into 10 ml of methanol. The reaction mixture was vigorously stirred at 50° C. for 2 hours. After the reaction was complete, the reaction mixture was cooled to room temperature and pH value was adjusted to 2-3 with 2M hydrochloric acid aqueous solution. Then The mixture was diluted with water, retracted with ethyl acetate/water system for two times. The organic phase was concentrated under reduced pressure to obtain compound tert-butyl 3-mercaptoazetidine-1-formate 13c (450 mg, 78%), which was directly used in the next step without purification. MS m/z(ESI):190 [M+1]$^+$.

Step 3: Tert-butyl 3-mercaptoazetidine-1-carboxylate 13c (0.45 g, 2.38 mmol), 2,4,5-trichloropyrimidine (0.46 g, 2.5 mmol) and sodium carbonate (0.631 g, 5.96 mmol) were added into 20 ml of acetonitrile. The reaction mixture was vigorously stirred at 70° C. for 3 hours. After the reaction was complete, the reaction mixture was cooled, filtered, concentrated and purified by combi-flash to obtain compound tert-butyl 3-(2,5-dichloropyrimidine-4-thio)azetidine-1-formate 13d (580 mg, 72%). MS m/z(ESI):337 [M+1]$^+$.

Step 4: Tert-butyl 3-(2,5-dichloropyrimidine-4-thio) azetidine-1-formate 13d (0.58 g, 1.73 mmol) was added into 10 ml of dichloromethane. Into the reaction mixture was added dropwise trifluoroacetic acid (5 g, 43.9 mmol) at 0° C. under stirring. The reaction was warmed to room temperature and conducted for 3 hours. After completion, the reaction mixture was concentrated to obtain crude compound 3-(2,5-dichloropyrimidine-4-thio) azetidine 13e (1.5 g), which was directly used in the next step without purification. MS m/z(ESI):237 [M+1]$^+$.

Step 5: Compound 2,5-dichloro-4-(1-(methylsulfonyl) azetidine-3-thio)pyrimidine 13 f was prepared by using compound 13e (1.5 g) as the raw material according to step 3 in Example 1. MS m/z(ESI):314 [M+1]$^+$.

Step 6: Compound N-(5-(5-chloro-4-(1-(methylsulfonyl) azetidine-3-thio)pyrimidine-2-amino)-2-(4-(dimethylamino)piperidine-1-yl)-4-methoxylphenyl)acrylamide J-13 (89.06 mg) was prepared by using compound 13f (314 mg, 1 mmol) and compound b (318 mg, 1 mmol) as the raw materials according to step 2 in Example 2.

MS m/z(ESI):596 [M+1]$^+$; $^1$HNMR (400 MHz, DMSO-d6) δ9.94 (s, 1H), 9.05 (s, 1H), 8.68 (s, 1H), 8.25 (s, 1H), 8.23 (s, 1H), 8.15 (s, 1H), 6.85 (s, 1H), 6.69 (dd, J=16.4, 10.0 Hz, 1H), 6.28 (d, J=16.0 Hz, 1H), 5.75 (d, J=11.6 Hz, 1H), 4.44 (f, 1H), 4.08 (br, s, 2H), 3.84-3.72 (m, 5H), 3.40-3.20 (m, 1H), 3.16 (d, J=11.6 Hz, 2H), 3.00 (s, 3H), 2.81 (d, J=4.8 Hz, 6H), 2.75 (t, J=11.6 Hz, 2H), 2.05 (d, J=9.6 Hz, 2H), 1.85-2.00 (m, 2H).

Example 14 Preparation of N-(2-((2-(dimethylamino)ethyl)(methyl)amino)-4-methoxy-5-(4-(1-(quinoline-3-yl)azetidine-3-oxy)pyrimidine-2-amino)phenyl)acrylamide (J-14)

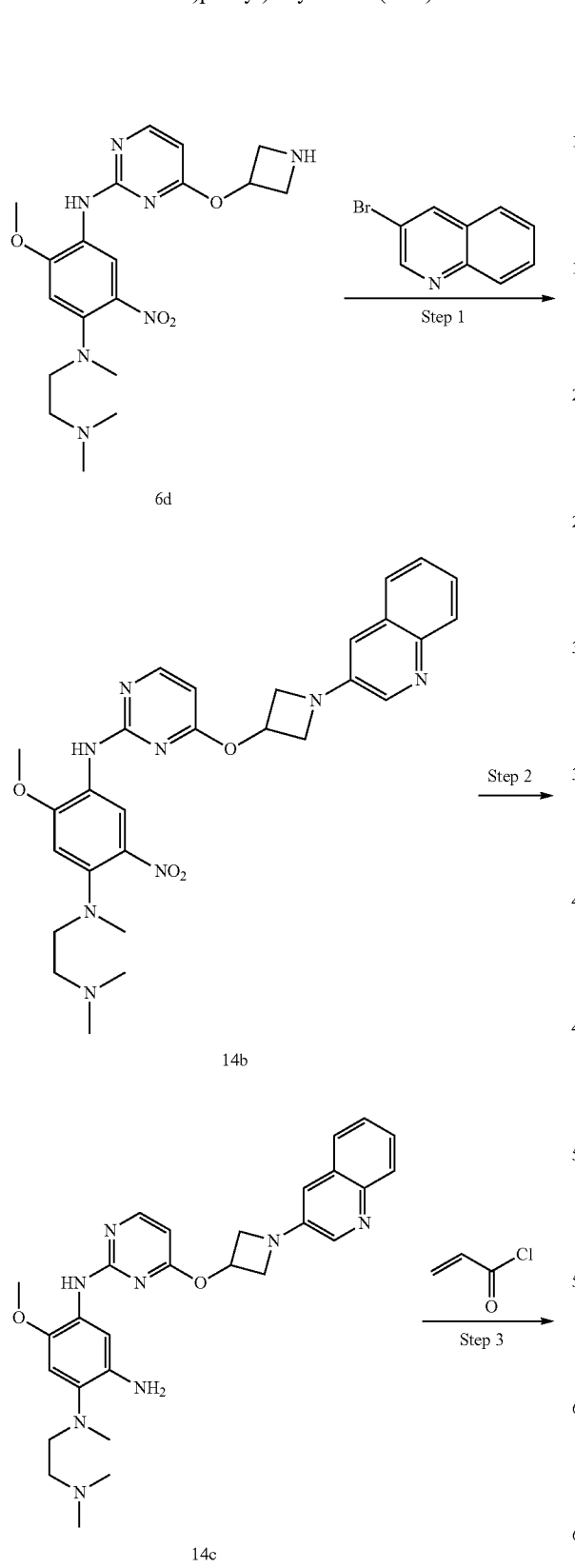

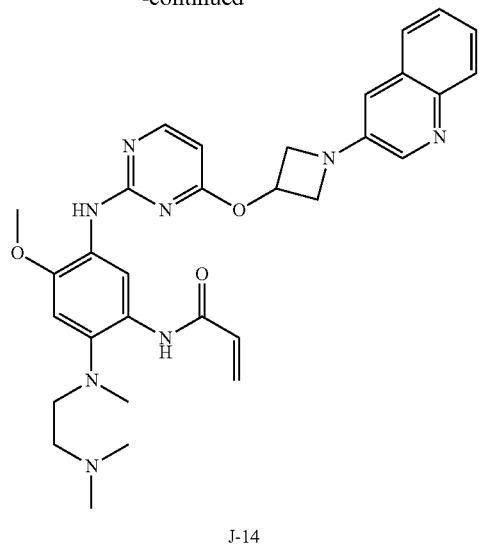

Step 1: 3-bromoquinoline (0.31 g, 1.473 mmol), Pd$_2$(dba)$_3$ (0.135 g, 0.1473 mmol), Xantphos (0.171 g, 0.2946 mmol) and cesium carbonate (1.92 g, 5.69 mmol) were added into a solution of compound 6d (1.0 g, 1.473 mmol) in 50 ml of 1,4-dioxane. The reaction mixture was vigorously stirred at 120° C. under N$_2$ atmosphere for 20 hours. After the reaction was complete, the reaction mixture was filtered, and washed with ethyl acetate. The filtrate was concentrated under reduced pressure to obtain a crude product, which was purified by Combi-flash column chromatography [PE:EA=100:0-20:80] to obtain compound 14b (0.42 g, 52.8%). MS m/z(ESI): 545 [M+H]$^+$.

Step 2: 70 mg of crude product of compound 14c was prepared by using compound 14b (80 mg, 0.15 mmol) as the raw material according to step 6 in Example 6 and was directly used in the next step without purification. MS m/z(ESI): 515 [M+H]$^+$.

Step 3: Compound 14c (70 mg, 0.11 mmol) was used as the raw material according to step 7 in Example 6 to obtain a crude product, which was isolated and purified by preparative liquid phase chromatography to obtain the title compound J-14 (13 mg, yield 16.9%). MS m/z(ESI): 569 [M+H]$^+$; $^1$H NMR (400 MHz, CDCl$_3$) δ 10.12 (s, 1H), 9.51 (s, 1H), 8.33 (d, J=2.6 Hz, 1H), 8.19 (d, J=5.6 Hz, 1H), 7.99-7.92 (m, 1H), 7.65 (s, 1H), 7.60 (dd, J=5.9, 3.4 Hz, 1H), 7.42 (dd, J=6.3, 3.3 Hz, 2H), 6.93 (s, 1H), 6.78 (s, 1H), 6.25 (d, J=5.6 Hz, 1H), 6.18 (d, J=15.6 Hz, 2H), 5.36 (s, 1H), 4.57-4.50 (m, 2H), 4.10 (dd, J=8.6, 4.0 Hz, 2H), 3.89 (s, 3H), 2.88 (s, 2H), 2.71 (s, 3H), 2.22 (s, 6H), 2.01 (s, 2H).

Examples 15-19

Compounds J-15, J-16 and J-17 were prepared by using compound 6d as the starting material according to the method of Example 14, except that 3-bromoquinoline in step 1 was replaced with 5-bromo-1-methyl-1H-pyrazolo[3,4-b]pyridine, 5-bromo-1-methyl-1H-pyrrolo[2,3-b]pyridine and 3-bromopyridine, respectively.

Compounds J-18 and J-19 were prepared by using compound 5-a as the starting material according to the method of Example 14, except that 3-bromoquinoline in step 1 was replaced with 5-bromo-1-methyl-1H-pyrrolo[2,3-b]pyridine and 5-bromo-1-methyl-1H-pyrazolo[3,4-b]pyridine, respectively.

| | | |
|---|---|---|
| Example 15 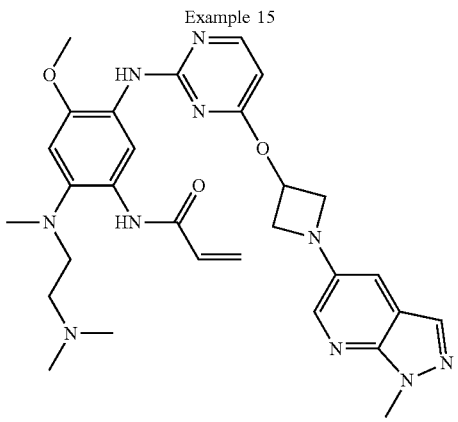 J-15 | | MS [M + H]⁺: 573; ¹H NMR (400 MHz, CDCl₃) δ 10.12 (s, 1H), 9.47 (s, 1H), 8.17 (dd, J = 8.2, 4.2 Hz, 2H), 7.62 (d, J = 10.7 Hz, 2H), 6.80-6.76 (m, 2H), 6.22 (dd, J = 8.5, 4.0 Hz, 3H), 6.18 (d, J = 9.4 Hz, 1H), 5.44 (dd, J = 9.3, 2.4 Hz, 1H), 4.44-4.39 (m, 2H), 4.18 (s, 3H), 3.99 (dd, J = 8.5, 3.9 Hz, 2H), 3.88 (s, 3H), 2.89-2.85 (m, 2H), 2.70 (s, 3H), 2.29-2.25 (m, 2H), 2.22 (s, 6H). |
| Example 16 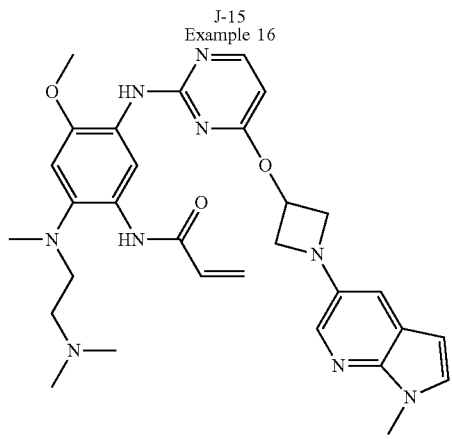 J-16 | | MS [M + H]⁺: 572; ¹H NMR (400 MHz, CDCl₃) δ 10.09 (s, 1H), 9.49 (s, 1H), 8.18 (d, J = 5.6 Hz, 1H), 7.71 (d, J = 2.5 Hz, 1H), 7.57 (s, 1H), 7.09 (d, J = 3.3 Hz, 1H), 6.99 (d, J = 2.5 Hz, 1H), 6.78 (s, 1H), 6.30-6.21 (m, 4H), 6.04 (s, 1H), 5.48 (d, J = 11.7 Hz, 1H), 4.39-4.34 (m, 2H), 3.95 (dd, J = 8.4, 3.8 Hz, 2H), 3.88 (s, 3H), 3.83 (s, 3H), 2.88 (s, 2H), 2.70 (s, 3H), 2.23 (s, 8H). |
| Example 17 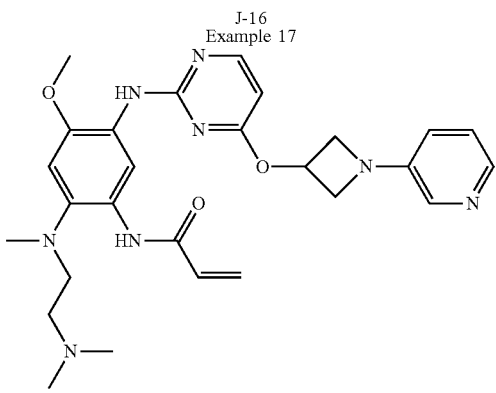 J-17 | | MS [M + H]⁺: 519; ¹H NMR (400 MHz, CDCl₃) δ 10.10 (s, 1H), 9.47 (s, 1H), 8.18-8.17 (d, J = 5.6 Hz, 1H), 7.98-7.97 (d, J = 4.7 Hz, 1H), 7.83-7.83 (d, J = 2.6 Hz, 1H), 7.61 (s, 1H), 7.08-7.05 (dd, J1 = 4.8 Hz, J2 = 8.3 Hz, 1H), 6.78 (s, 1H), 6.72-6.69 (dd, J1 = 6.9 Hz, J2 = 8.4 Hz, 1H), 6.23-6.22 (d, J = 5.7 Hz, 1H), 6.20-6.18 (d, J = 4.9 Hz, 2H), 6.11 (s, 1H), 5.51-5.48 (t, J = 6.1 Hz, 1H), 4.40-4.37 (t, J = 7.6 Hz, 2H), 3.99-3.96 (dd, J1 = 3.9 Hz, J2 = 8.5 Hz, 2H), 3.87 (s, 3H), 2.87 (s, 2H), 2.70 (s, 3H), 2.24 (s, 8H). |
| Example 18 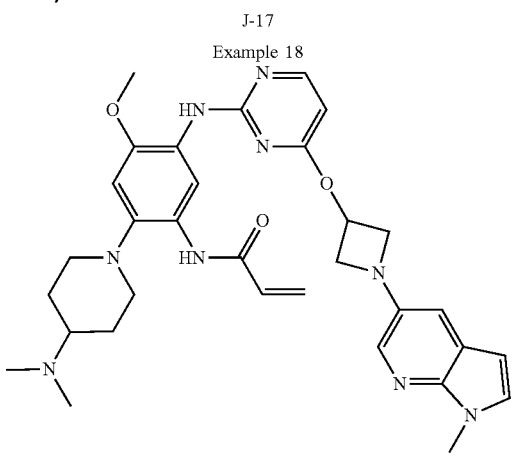 J-18 | | MS [M + H]⁺: 598; ¹H NMR (400 MHz, CDCl₃) δ 9.42 (s, 1H), 8.45 (s, 1H), 8.18 (d, J = 5.6 Hz, 1H), 7.71 (d, J = 2.5 Hz, 1H), 7.55 (s, 1H), 7.10 (d, J = 3.3 Hz, 1H), 7.00 (d, J = 2.6 Hz, 1H), 6.74 (s, 1H), 6.27 (d, J = 3.4 Hz, 1H), 6.23 (q, J = 4.7 Hz, 2H), 6.17 (d, J = 9.7 Hz, 1H), 6.01 (s, 1H), 5.54 (d, J = 9.7 Hz, 1H), 4.39-4.33 (m, 2H), 3.95 (dd, J = 8.3, 3.9 Hz, 2H), 3.88 (s, 3H), 3.83 (s, 3H), 3.06 (d, J = 12.1 Hz, 2H), 2.73 (t, J = 11.2 Hz, 2H), 2.41 (s, 7H), 2.07 (d, J = 10.6 Hz, 2H), 1.68 (s, 2H). |

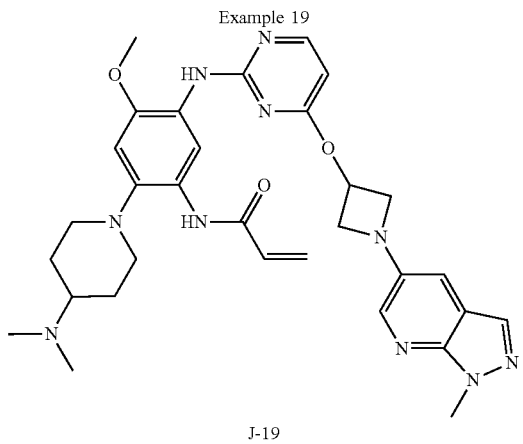

Example 19

J-19

MS [M + H]⁺: 599; $^1$H NMR (400 MHz, CDCl$_3$) δ 9.42 (s, 1H), 8.48 (s, 1H), 8.19-8.16 (m, 2H), 7.64 (s, 1H), 7.58 (s, 1H), 6.78 (d, J = 2.8 Hz, 1H), 6.74 (s, 1H), 6.24 (d, J = 5.6 Hz, 1H), 6.19-6.13 (m, 2H), 6.06 (s, 1H), 5.52 (d, J = 11.1 Hz, 1H), 4.43-4.38 (m, 2H), 4.18 (s, 3H), 3.99 (dd, J = 8.4, 3.9 Hz, 2H), 3.88 (s, 3H), 3.05 (d, J = 12.4 Hz, 2H), 2.71 (d, J = 11.1 Hz, 2H), 2.38 (s, 7H), 2.05 (d, J = 12.6 Hz, 2H), 1.65 (s, 2H).

Examples 20-34

Compounds J-20 to J-32 were prepared by using various 5-substituted or unsubstituted 2,4-dichloropyrimidine and N-Boc-3-hydroxy azetidine as the starting material according to the method of Example 6. According to the different structure of the compounds, N,N,N'-trimethylethylenediamine and benzoyl chloride in step 3 and step 5 of Example 6 were replaced with the corresponding amine and acyl chloride.

Compounds J-33, J-34, and J-75 were prepared by using compounds 45-a, 44-a and 52-a as the raw material which was reacted with compound b. The reaction steps and conditions referred to step 2 of Example 2.

Preparation of compound J-76 was similar to that of compound J-12.

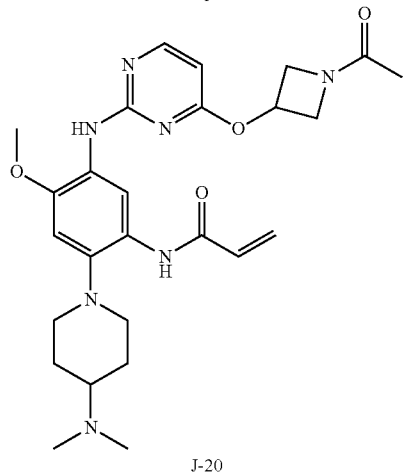

Example 20

J-20

MS [M + H]⁺: 510; $^1$H NMR (400 MHz, CDCl$_3$) δ 9.34 (s, 1H), 8.48 (s, 1H), 8.11-8.10 (d, J = 5.6 Hz, 1H), 7.56 (s, 1H), 6.66 (s, 1H), 7.74 (s, 1H), 6.30-6.26 (d, J = 15.4 Hz, 1H), 6.16-6.15 (d, J = 5.6 Hz, 1H), 5.95 (s, 1H), 5.68-5.65 (dd, J1 = 1.5 Hz, J2 = 9.8 Hz, 1H), 4.57-4.53 (t, J = 9.5 Hz, 1H), 4.39-4.35 (dd, J1 = 7.1 Hz, J2 = 10.5 Hz, 1H), 4.16-4.13 (m, 2H), 4.03-3.94 (m, 2H), 3.80 (s, 3H), 2.98 (s, 2H), 2.70-2.63 (t, J = 12.6 Hz, 2H), 2.35 (s, 6H), 2.03-2.00 (d, J = 11.0 Hz, 1H), 1.77 (s, 3H), 1.63-1.60 (t, J = 5.8 Hz, 2H).

Example 21

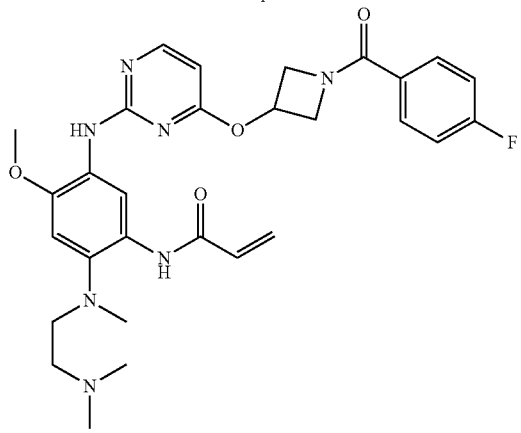

J-21

MS [M + H]⁺: 564; ¹H NMR (400 MHz, CDCl₃) δ 10.13 (s, 1H), 9.48 (s, 1H), 8.18-8.16 (d, J = 5.6 Hz, 1H), 7.67 (s, 1H), 7.64-7.60 (dd, J1 = 5.4 Hz, J2 = 8.8 Hz, 2H), 7.05-7.00 (t, J = 8.7 Hz, 2H), 6.76 (s, 1H), 6.36-6.31 (d, J = 16.9 Hz, 1H), 6.23-6.22 (d, J = 5.6 Hz, 2H), 6.18 (s, 1H), 5.64-5.61 (d, J = 9.9 Hz, 1H), 4.82-4.78 (t, J = 8.1 Hz, 1H), 4.70-4.66 (t, J = 10.9 Hz, 1H), 4.26-4.22 (dd, J1 = 3.7 Hz, J2 = 10.6 Hz, 2H), 3.86 (s, 3H), 2.85 (s, 2H), 2.68 (s, 3H), 2.25 (s, 2H), 2.22 (s, 6H).

Example 22

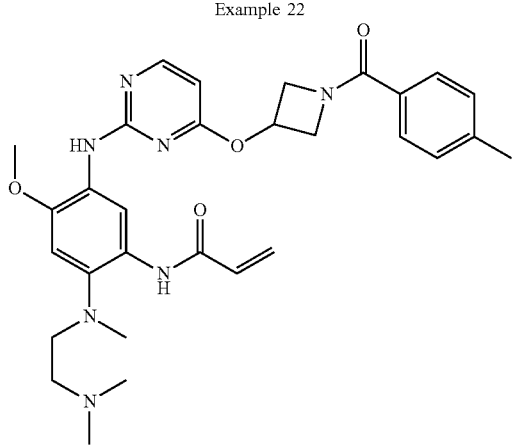

J-22

MS [M + H]⁺: 560; ¹H NMR (400 MHz, CDCl₃) δ 9.73 (s, 1H), 9.48 (s, 1H), 8.17-8.16 (d, J = 5.6 Hz, 1H), 7.65 (s, 1H), 7.52-7.50 (d, J = 8.1 Hz, 2H), 7.17-7.15 (d, J = 8.0 Hz, 2H), 6.71 (s, 1H), 6.58-6.51 (dd, J1 = 10.4 Hz, J2 = 17.4 Hz, 1H), 6.38-6.33 (d, J = 16.9 Hz, 1H), 6.23-6.22 (d, J = 5.6 Hz, 1H), 6.13 (s, 1H), 5.66-5.63 (d, J = 10.0 Hz, 1H), 4.76-4.74 (d, J = 9.0 Hz, 1H), 4.67-4.62 (dd, J1 = 7.0 Hz, J2 = 9.0 Hz, 1H), 4.27-4.20 (dd, J1 = 7.3 Hz, J2 = 17.4 Hz, 2H), 3.86 (s, 3H), 3.04-3.01 (t, J = 4.9 Hz, 2H), 2.65 (s, 3H), 2.61 (s, 2H), 2.44 (s, 6H), 2.35 (s, 3H).

Example 23

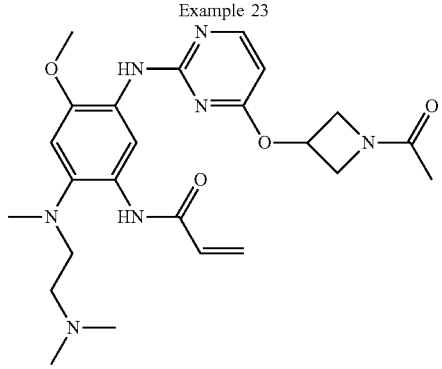

J-23

MS [M + H]⁺: 484.2; ¹HNMR (400 MHz, CDCl₃) δ 10.15 (s, 1H), 8.87 (s, 1H), 8.21-8.19 (d, J = 5.6 Hz, 1H), 8.04 (s, 1H), 6.99 (s, 1H), 6.40-6.34 (dd, J1 = 10.0 Hz, J2 = 16.8 Hz, 1H), 6.32-6.31 (d, J = 5.6 Hz, 1H), 6.23-6.19 (d, J = 16.9 Hz, 1H), 5.73-5.70 (d, J = 9.9 Hz, 1H), 5.57 (s, 1H), 4.42-4.38 (t, J = 9.3 Hz, 1H), 4.18-4.14 (dd, J1 = 7.0 Hz, J2 = 10.5 Hz, 1H), 4.08-4.05 (dd, J1 = 3.9 Hz, J2 = 9.7 Hz, 1H), 3.83 (s, 3H), 3.79-3.76 (dd, J1 = 4.0 Hz, J2 = 10.7 Hz, 1H), 2.87-2.84 (t, J = 5.5 Hz, 2H), 2.69 (s, 3H), 2.28-2.25 (t, J = 5.7 Hz, 2H), 2.18 (s, 6H), 1.71 (s, 3H).

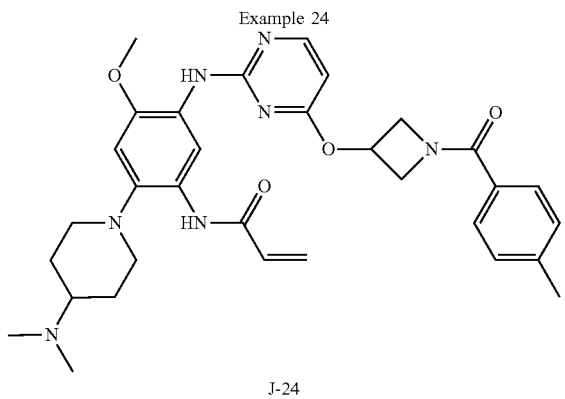
Example 24
J-24
MS [M + H]⁺: 586; ¹H NMR (400 MHz, CDCl₃) δ 9.43 (s, 1H), 8.52 (s, 1H), 8.17-8.16 (d, J = 5.6 Hz, 1H), 7.61 (s, 1H), 7.52-7.50 (d, J = 8.1 Hz, 2H), 7.18-7.16 (d, J = 8.0 Hz, 2H), 6.72 (s, 1H), 6.26-6.22 (d, J = 15.4 Hz, 1H), 6.17-6.10 (m, 2H), 6.03 (s, 1H), 5.64-5.61 (d, J = 9.8 Hz, 1H), 4.70-4.56 (m, 2H), 4.20-4.11 (dd, J1 = 6.1 Hz, J2 = 24.1 Hz, 2H), 3.79 (s, 3H), 2.95 (s, 2H), 2.65 (s, 2H), 2.31 (s, 6H), 2.29 (s, 3H), 2.21 (s, 1H), 1.99-1.96 (d, J = 11.2 Hz, 2H), 1.60 (s, 2H).
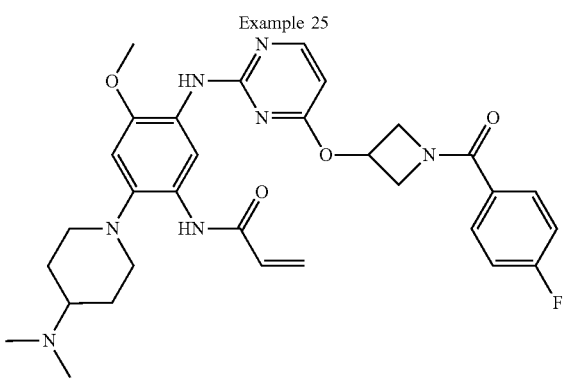
Example 25
J-25
MS [M + H]⁺: 590; ¹H NMR (400 MHz, CDCl₃) δ 9.40 (s, 1H), 8.53 (s, 1H), 8.18-8.16 (d, J = 5.6 Hz, 1H), 7.64-7.60 (m, 3H), 7.06-7.02 (t, J = 8.6 Hz, 2H), 6.72 (s, 1H), 6.32-6.28 (d, J = 16.8 Hz, 1H), 6.24-6.16 (m, 2H), 6.12 (s, 1H), 5.71-5.68 (dd, J1 = 1.5 Hz, J2 = 9.9 Hz, 1H), 4.78-4.65 (m, 2H), 4.24-4.21 (m, 2H), 3.86 (s, 3H), 3.01-2.95 (m, 2H), 2.75-2.66 (m, 2H), 2.36 (s, 6H), 2.25 (s, 1H), 2.06-2.03 (d, J = 11.9 Hz, 2H), 1.66 (s, 2H).
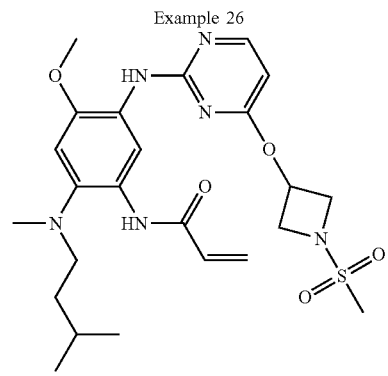
Example 26
J-26
MS [M + H]⁺: 520; ¹H NMR (400 MHz, CDCl₃) δ 10.18 (s, 1H), 9.43 (s, 1H), 8.18 (d, J = 5.6 Hz, 1H), 7.64 (s, 1H), 6.78 (s, 1H), 6.42 (dd, J = 16.9, 1.9 Hz, 1H), 6.35-6.21 (m, 2H), 6.06 (s, 1H), 5.69 (dd, J = 9.9, 1.9 Hz, 1H), 4.43 (dd, J = 9.5, 6.8 Hz, 2H), 4.00 (dd, J = 9.7, 4.2 Hz, 2H), 3.87 (s, 3H), 2.90-2.85 (m, 5H), 2.71 (s, 3H), 2.31-2.23 (m, 8H).

| Example 27 | 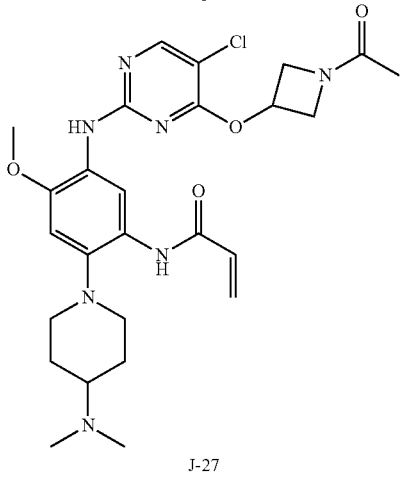 J-27 | MS [M + H]⁺: 544.2; ¹H NMR (400 MHz, DMSO-d$_6$) δ 9.01 (s, 1H), 8.38 (s, 1H), 8.34 (s, 1H), 8.28 (s, 1H), 6.81 (s, 1H), 6.69-6.62 (dd, J1 = 9.8 Hz, J2 = 16.6 Hz, 1H), 6.23-6.18 (d, J = 16.9 Hz, 1H), 5.72-5.69 (d, J = 10.1 Hz, 1H), 5.50 (s, 1H), 4.42-4.38 (t, J = 8.7 Hz, 1H), 4.18-4.10 (m, 2H), 3.81-3.79 (m, 4H), 3.04-3.02 (d, J = 11.0 Hz, 2H), 2.69-2.60 (dd, J1 = 11.2 Hz, J2 = 23.5 Hz, 1H), 2.21 (s, 6H), 2.17 (s, 1H), 1.83-1.81 (d, J = 11.3 Hz, 2H), 1.73 (s, 3H), 1.68-1.66 (d, J = 8.8 Hz, 2H). |
|---|---|---|
| Example 28 | 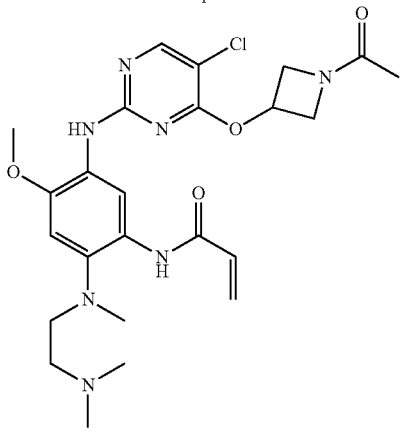 J-28 | MS [M + H]⁺: 518.2; ¹H NMR (400 MHz, DMSO-d$_6$) δ 10.13 (s, 1H), 8.70 (s, 1H), 8.36 (s, 1H), 8.29 (s, 1H), 6.99 (s, 1H), 6.41-6.35 (dd, J1 = 10.5 Hz, J2 = 16.8 Hz, 1H), 6.24-6.19 (d, J = 16.8 Hz, 1H), 5.74-5.71 (d, J = 10.0 Hz, 1H), 5.55 (s, 1H), 4.41-4.37 (t, J = 9.0 Hz, 1H), 4.18-4.10 (m, 2H), 3.82-3.79 (m, 4H), 2.86(s, 2H), 2.69 (s, 3H), 2.29 (s, 2H), 2.19 (s, 6H), 1.71 (s, 3H). |
| Example 29 | 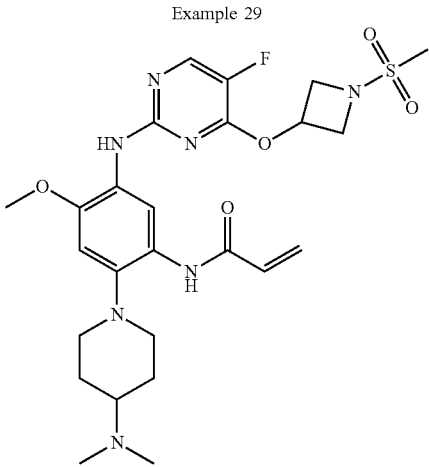 J-29 | MS [M + H]⁺: 564.2; ¹H NMR (400 MHz, DMSO-d$_6$) δ 9.01 (s, 1H), 8.44 (s, 1H), 8.30 (d, J = 3.1 Hz, 1H), 8.15 (s, 1H), 6.83 (s, 1H), 6.67 (dd, J = 16.9, 10.3 Hz, 1H), 6.26 (dd, J = 17.0, 1.7 Hz, 1H), 5.81-5.68 (m, 1H), 5.50 (d, J = 5.0 Hz, 1H), 4.21 (dd, J = 9.8, 6.7 Hz, 2H), 4.01 (dd, J = 9.9, 4.7 Hz, 2H), 3.82 (s, 3H), 3.04 (s, 3H), 3.01 (s, 2H), 2.66 (t, J = 10.7 Hz, 2H), 2.23 (s, 6H), 2.17 (d, J = 11.0 Hz, 1H), 1.83 (d, J = 10.7 Hz, 2H), 1.77-1.60 (m, 2H). |

Example 30
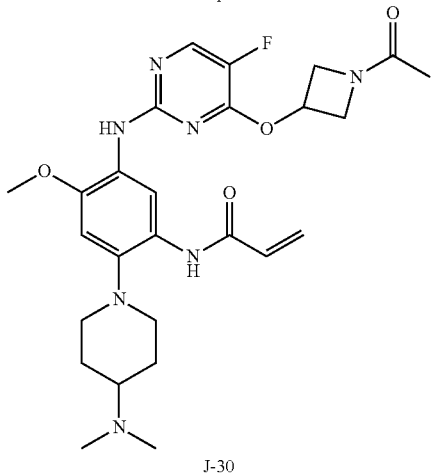
J-30
MS [M + H]+: 528.2; 1H NMR (400 MHz, DMSO-d6) δ 9.03 (s, 1H), 8.49 (s, 1H), 8.31 (d, J = 2.4 Hz, 1H), 8.10 (s, 1H), 6.82 (s, 1H), 6.67 (dd, J = 16.8, 10.2 Hz, 1H), 6.22 (d, J = 16.9 Hz, 1H), 5.72 (d, J = 9.9 Hz, 1H), 5.57 (s, 1H), 4.53-4.37 (m, 1H), 4.20 (d, J = 10.6 Hz, 2H), 3.87 (s, 1H), 3.83 (s, 3H), 3.03 (d, J = 10.0 Hz, 2H), 2.65 (dd, J = 23.2, 11.6 Hz, 2H), 2.22 (s, 6H), 2.19-2.15 (m, 1H), 1.81 (s, 2H), 1.75 (s, 3H), 1.68 (d, J = 10.7 Hz, 2H).
Example 31
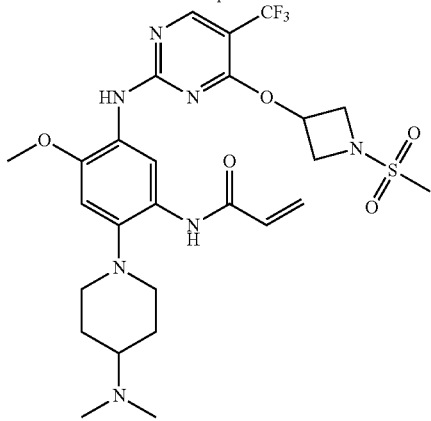
J-31
MS [M + H]+: 614.2; 1H NMR (400 MHz, DMSO-d6) δ 9.09 (s, 1H), 9.03 (s, 1H), 8.49 (s, 1H), 8.19 (s, 1H), 6.84 (s, 1H), 6.71~6.64 (dd, J = 17.2, 10.4 Hz, 1H), 6.27~6.23 (d, J = 17.6 Hz, 1H), 5.75~5.73 (d, J = 11.2 Hz, 1H), 5.42~5.40 (t, J = 5.2 Hz, 1H), 4.08~3.92 (m, 4H), 3.81 (m, 3H), 3.08~3.06 (d, J = 9.2 Hz, 2H), 3.00 (s, 3H), 2.70~2.64 (t, J = 10.8 Hz, 2H), 2.26 (s, 6H), 2.03~1.96 (m, 1H), 1.86~1.83 (d, J = 11.2 Hz, 2H), 1.76~1.66 (m, 2H).
Example 32
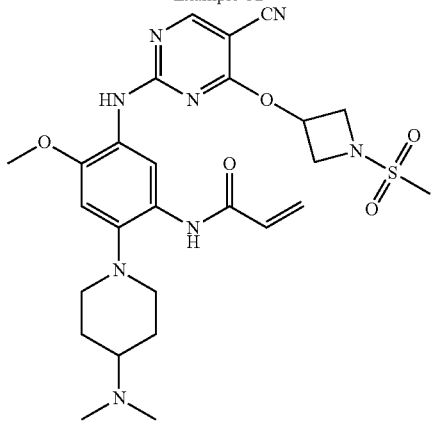
J-32
MS [M + H]+: 571.2; 1H NMR (400 MHz, DMSO-d6) δ 9.44 (s, 1H), 9.06 (s, 1H), 8.68 (s, 1H), 8.19 (s, 1H), 6.83 (s, 1H), 6.70~6.63 (m, 1H), 6.30~6.25 (m, 1H), 5.77~5.75 (d, J = 9.6 Hz, 1H), 5.38~5.32 (m, 1H), 3.96 (m, 4H), 3.81 (s, 3H), 3.19~3.09 (m, 2H), 3.00 (s, 3H), 2.76~2.67 (m, 8H), 2.03~1.96 (m, 4H), 1.90~1.87 (m, 1H).

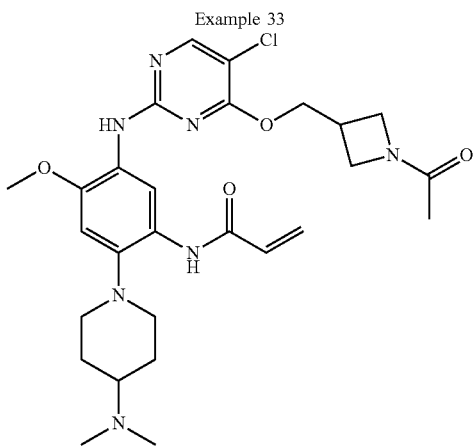
Example 33
J-33
MS [M + H]⁺: 558.3; ¹H NMR (400 MHz, DMSO-d₆) δ 8.97 (s, 1H), 8.66 (s, 1H), 8.26 (s, 1H), 8.21 (s, 0.5H), 8.16 (s, 1H), 6.85 (s, 1H), 6.70-6.63 (dd, J = 17.0, 1.6 Hz, 1H), 6.21 (dd, J = 17.0, 1.7 Hz, 1H), 5.73 (d, J = 11.6 Hz, 1H), 4.63 (d, J = 6.9 Hz, 2H), 4.20 (t, J = 8.4 Hz, 1H), 3.97-3.88 (m, 2H), 3.84 (s, 3H), 3.68 (dd, J = 9.6, 5.4 Hz, 1H), 3.01 (d, J = 11.5 Hz, 3H), 2.65 (t, J = 11.1 Hz, 2H), 2.25 (s, 6H), 2.00 (dd, J = 14.4, 6.7 Hz, 1H), 1.84 (d, J = 10.8 Hz, 2H), 1.70 (d, J = 15.1 Hz, 5H).
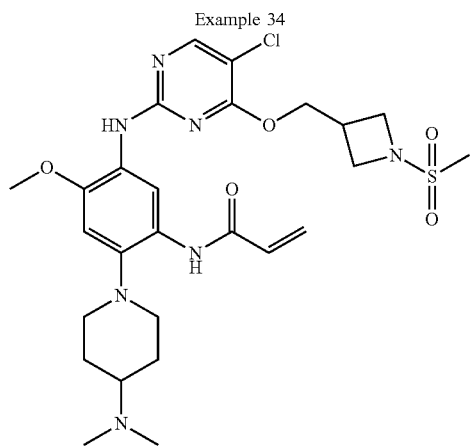
Example 34
J-34
MS [M + H]⁺: 594.2; ¹H NMR (400 MHz, DMSO-d₆) δ 8.99 (s, 1H), 8.65 (s, 1H), 8.26 (s, 1H), 8.16 (s, 1H), 6.84 (s, 1H), 6.66 (dd, J = 16.8, 10.3 Hz, 1H), 6.26-6.20 (m, 1H), 5.73 (d, J = 11.5 Hz, 1H), 4.62 (d, J = 6.7 Hz, 2H), 3.97 (t, J = 8.3 Hz, 2H), 3.83 (d, J = 8.3 Hz, 5H), 3.08 (d, J = 6.5 Hz, 1H), 3.01 (s, 5H), 2.64 (d, J = 10.2 Hz, 2H), 2.03-1.96 (m, 1H), 1.83 (d, J = 10.8 Hz, 2H), 1.73-1.66 (m, 2H).
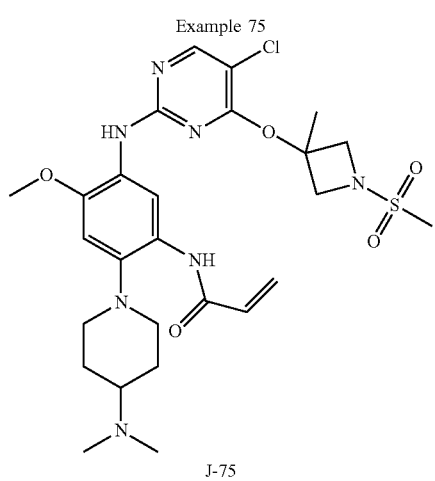
Example 75
J-75
MS [M + H]⁺: 594.3; ¹H NMR (400 MHz, DMSO-d₆) δ 9.04 (s, 1H), 8.62 (s, 1H), 8.24 (s, 1H), 7.98 (s, 1H), 6.80 (s, 1H), 6.70 (dd, J = 17.2, 10.4 Hz, 1H), 6.23 (d, J = 17.2 Hz, 1H), 5.74 (d, J = 10.0 Hz, 1H), 4.05 (m, 2H), 3.78 (s, 3H), 3.68 (m, 2H), 3.07 (m, 2H), 3.00 (s, 3H), 2.68 (m, 2H), 2.24 (s, 7H), 1.84 (m, 2H), 1.73 (m, 2H).

| Example 76 | MS [M + H]⁺: 550.2; ¹H NMR (400 MHz, DMSO-d₆) δ 9.69 (s, 1H), 9.09 (s, 1H), 8.42 (s, 1H), 8.34 (s, 1H), 7.31 (s, 1H), 7.14 (d, J = 8.8 Hz, 1H), 6.72 (dd, J = 16.8, 10.0 Hz, 1H), 6.32 (d, J = 17.2 Hz, 1H), 5.80 (d, J = 10.0 Hz, 1H), 5.55 (s, 1H), 4.30 (m, 2H), 4.03 (m, 2H), 3.03 (s, 3H), 3.00 (m, 2H), 2.64 (m, 2H), 2.22 (s, 6H), 2.03 (m, 1H), 1.84 (m, 2H), 1.72 (m, 2H). |
|---|---|

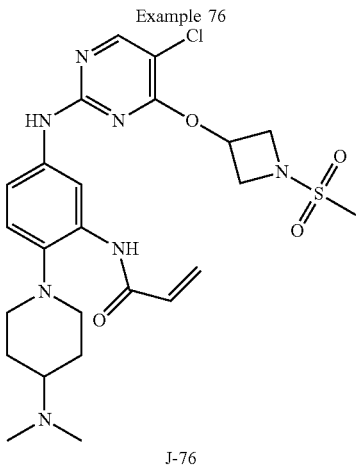

J-76

Examples 35-37

Compounds J-35, J-36 and J-37 were prepared by using various 5-chloro or unsubstituted 2,4-dichloropyrimidine and tert-butyl 4-hydroxyazacycloheptane-1-carboxylate as the starting materials according to the method of Example 1. According to the different structure of the compounds, methylsulfonyl chloride and compound a in step 3 and step 4 of Example 1 were replaced with corresponding methylsulfonyl chloride and compound b.

| Example 35 | MS [M + H]⁺: 586.4; ¹H NMR (400 MHz, DMSO-d₆) δ 8.98 (s, 1H), 8.47 (d, J = 8.6 Hz, 1H), 8.22 (t, J = 8.9 Hz, 2H), 6.83 (s, 1H), 6.67 (dd, J = 15.9, 11.0 Hz, 1H), 6.21 (d, J = 16.9 Hz, 1H), 5.73 (d, J = 10.3 Hz, 1H), 5.40 (s, 1H), 3.83 (s, 3H), 3.57-3.33 (m, 4H), 3.02 (d, J = 11.2 Hz, 2H), 2.66 (t, J = 11.1 Hz, 2H), 2.22 (s, 6H), 2.15 (s, 1H), 1.97 (d, J = 16.2 Hz, 4H), 1.89-1.54 (m, 9H) |
|---|---|

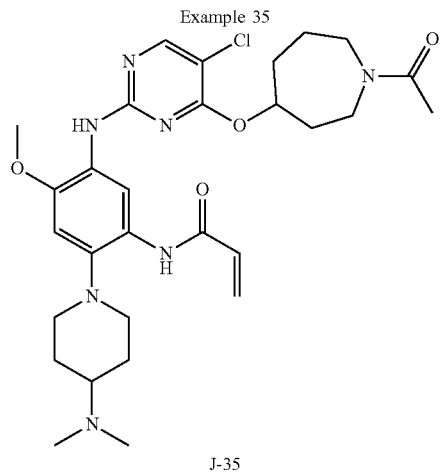

J-35

| Example 36 | MS [M + H]⁺: 562.2; ¹H NMR (400 MHz, DMSO-d₆) δ 10.11 (s, 1H), 8.88 (s, 1H), 8.23 (s, 1H), 8.13 (d, J = 5.6 Hz, 1H), 7.93 (s, 1H), 6.98 (s, 1H), 6.43 (dd, J = 16.9, 10.1 Hz, 1H), 6.22 (dd, J = 21.1, 3.7 Hz, 2H), 5.77-5.72 (m, 1H), 5.41 (d, J = 3.9 Hz, 1H), 3.84 (s, 3H), 3.42-3.34 (m, 1H), 3.23 (dt, J = 24.4, 9.7 Hz, 3H), 2.89 (t, J = 5.7 Hz, 2H), 2.86 (s, 3H), 2.67 (s, 3H), 2.36 (t, J = 5.6 Hz, 2H), 2.24 (s, 6H), 2.13-2.04 (m, 1H), 1.99-1.91 (m, 1H), 1.80 (dd, J = 19.7, 10.2 Hz, 3H), 1.67 (dd, J = 13.6, 8.0 Hz, 1H). |
|---|---|

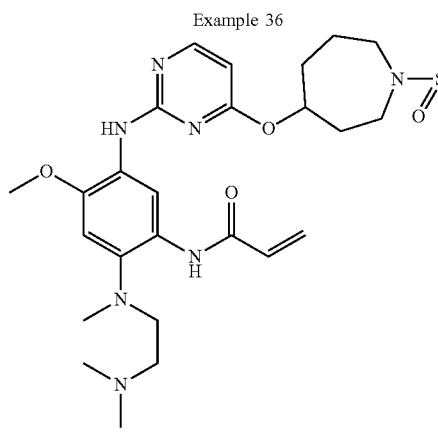

J-36

| Example 37 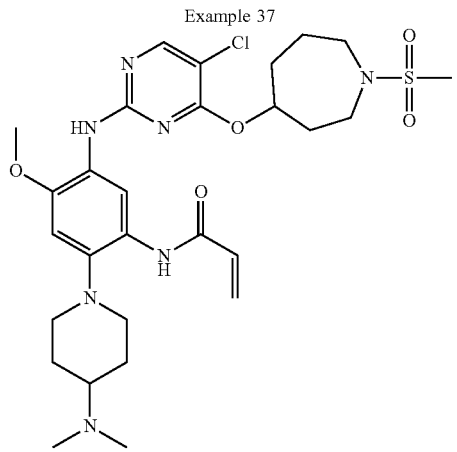 J-37 | MS [M + H]⁺: 622.2; ¹H NMR (400 MHz, DMSO-d$_6$) δ 9.00 (s, 1H), 8.43 (s, 1H), 8.34 (s, 1H), 8.25 (s, 1H), 8.24 (s, 1H), 6.82 (s, 1H), 6.67 (dd, J = 17.0, 10.3 Hz, 1H), 6.22 (dd, J = 17.0, 1.7 Hz, 1H), 5.74 (d, J = 11.7 Hz, 1H), 5.42 (s, 1H), 3.82 (s, 3H), 3.33-3.24 (m, 4H), 3.03 (d, J = 11.6 Hz, 2H), 2.88 (s, 3H), 2.65 (t, J = 10.8 Hz, 2H), 2.23 (s, 6H), 2.18 (d, J = 11.1 Hz, 1H), 2.13-2.02 (m, 1H), 1.87 (dd, J = 25.3, 10.7 Hz, 6H), 1.75-1.59 (m, 3H). |

Examples 38-39

Compound J-38 and J-39 were prepared according to the method of Example 3. According to the different structure of the compounds, methylsulfonyl chloride and compound a in step 3 and step 4 of Example 3 were replaced with corresponding acetyl chloride and compound b.

| Example 38 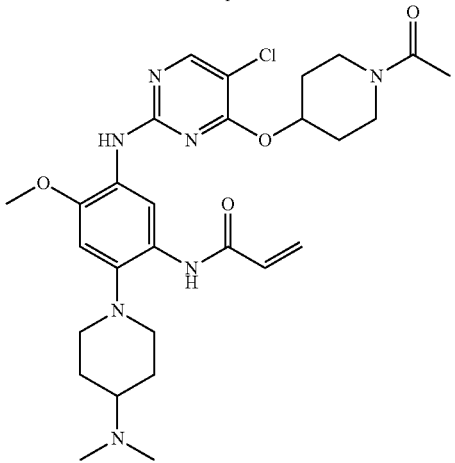 J-38 | MS [M + H]⁺: 572.3; ¹H NMR (400 MHz, DMSO-d$_6$) δ 9.01 (s, 1H), 8.52 (s, 1H), 8.26 (s, 1H), 8.20 (s, 1H), 6.84 (s, 1H), 6.67 (dd, J = 17.0, 10.2 Hz, 1H), 6.20 (dd, J = 16.9, 1.6 Hz, 1H), 5.73 (d, J = 11.5 Hz, 1H), 5.44 (s, 1H), 3.89 (d, J = 13.3 Hz, 1H), 3.84 (s, 3H), 3.66 (d, J = 14.1 Hz, 1H), 3.28 (d, J = 12.5 Hz, 1H), 3.12 (t, J = 10.0 Hz, 1H), 3.02 (d, J = 11.3 Hz, 2H), 2.66 (dd, J = 19.2, 9.9 Hz, 2H), 2.22 (s, 6H), 2.18 (s, 1H), 2.01 (s, 3H), 1.91 (s, 2H), 1.83 (d, J = 10.5 Hz, 2H), 1.63 (dt, J = 54.9, 9.9 Hz, 4H). |
| Example 39 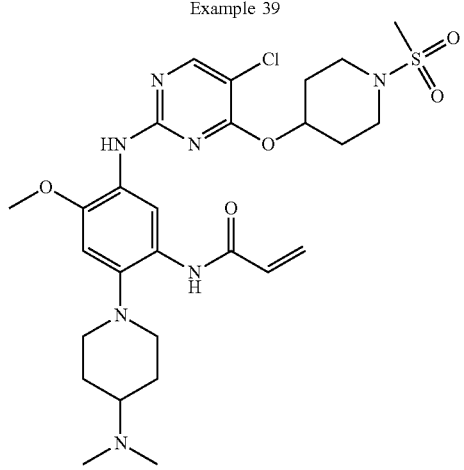 J-39 | MS [M + H]⁺: 608.4; ¹H NMR (400 MHz, DMSO-d$_6$) δ 9.02 (s, 1H), 8.51 (s, 1H), 8.27 (s, 1H), 8.23 (d, J = 4.4 Hz, 2H), 6.84 (s, 1H), 6.68 (dd, J = 16.9, 10.1 Hz, 1H), 6.32-6.19 (m, 1H), 5.75 (d, J = 11.5 Hz, 1H), 5.35 (s, 1H), 3.83 (s, 3H), 3.39-3.34 (m, 2H), 3.05 (t, J = 10.8 Hz, 4H), 2.88 (s, 3H), 2.67 (t, J = 11.0 Hz, 2H), 2.29 (s, 7H), 2.03 (s, 2H), 1.86 (d, J = 10.3 Hz, 2H), 1.82-1.66 (m, 4H). |

Example 40 Preparation of (R)—N-(5-(5-chloro-4-(1-(methylsulfonyl)piperidine-3-oxy) pyrimidine-2-amino)-2-((2-(dimethylamino)ethyl)(methyl)amino)-4-methoxyphenyl)acrylamide (J-40)

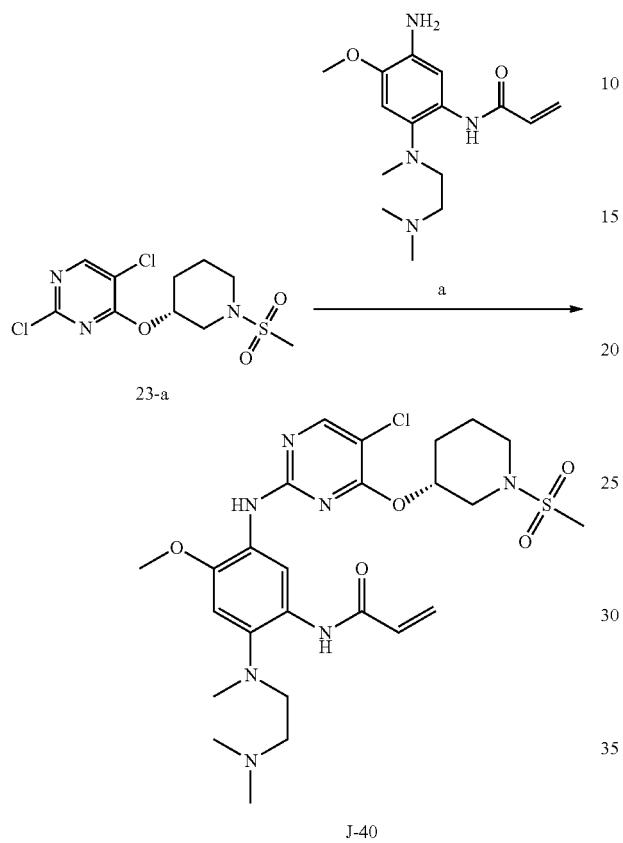

Into a solution of compound 23-a (109 mg, 0.38 mmol) and compound a (120 mg, 0.38 mmol) in 4 ml of 1,4-dioxane was added $Pd_2(dba)_3$ (35 mg, 0.04 mmol), BINAP (47 mg, 0.08 mmol) and cesium carbonate (247 mg, 0.75 mmol). The reaction mixture was microwaved at 140° C. for 20 min. After the reaction was complete, the reaction mixture was filtered and washed with dichloromethane. The filtrate was concentrated under reduced pressure to obtain a crude product, which was isolated and purified by preparative liquid phase chromatography to obtain 93 mg of the title compound J-40. MS m/z(ESI): 582.2[M+H]$^+$; $^1$HNMR (400 MHz, DMSO-d$_6$) δ 10.09 (s, 1H), 8.72 (s, 1H), 8.29 (s, 1H), 8.27 (s, 1H), 8.23 (s, 1H), 6.98 (s, 1H), 6.50-6.36 (m, 1H), 6.25 (dd, J=16.9, 2.0 Hz, 1H), 5.74 (dd, J=10.0, 2.0 Hz, 1H), 5.41 (s, 1H), 3.83 (s, 3H), 3.36 (d, J=5.4 Hz, 2H), 3.23-3.09 (m, 2H), 2.88 (s, 5H), 2.67 (d, J=11.6 Hz, 3H), 2.38 (s, 2H), 2.25 (d, J=1.8 Hz, 6H), 1.97-1.88 (m, 1H), 1.86-1.71 (m, 2H), 1.60 (s, 1H).

Examples 41-44

Compounds J-41, J-42, J-43, and J-44 were prepared by using compounds 23-a, 24-a, 25-a, and 26-a as the raw materials each of which was reacted with compound b. The reaction steps and conditions referred to Example 40.

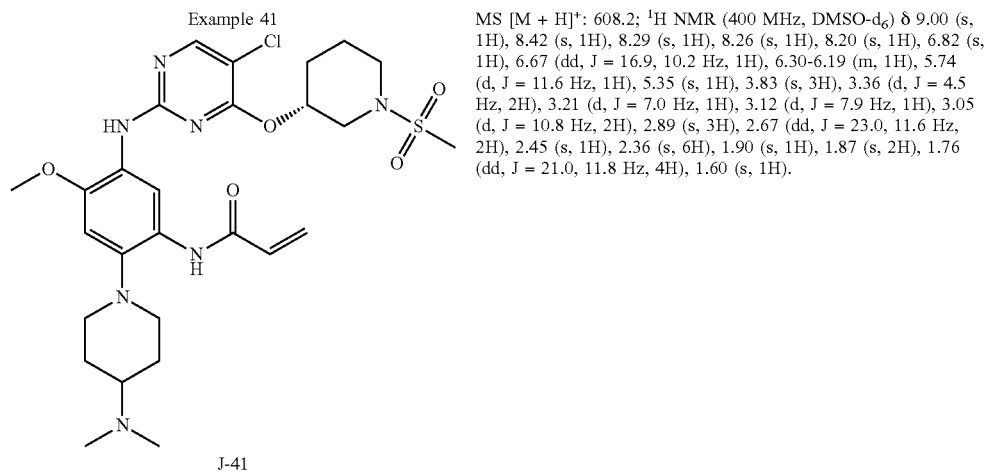

Example 41

MS [M + H]$^+$: 608.2; $^1$H NMR (400 MHz, DMSO-d$_6$) δ 9.00 (s, 1H), 8.42 (s, 1H), 8.29 (s, 1H), 8.26 (s, 1H), 8.20 (s, 1H), 6.82 (s, 1H), 6.67 (dd, J = 16.9, 10.2 Hz, 1H), 6.30-6.19 (m, 1H), 5.74 (d, J = 11.6 Hz, 1H), 5.35 (s, 1H), 3.83 (s, 3H), 3.36 (d, J = 4.5 Hz, 2H), 3.21 (d, J = 7.0 Hz, 1H), 3.12 (d, J = 7.9 Hz, 1H), 3.05 (d, J = 10.8 Hz, 2H), 2.89 (s, 3H), 2.67 (dd, J = 23.0, 11.6 Hz, 2H), 2.45 (s, 1H), 2.36 (s, 6H), 1.90 (s, 1H), 1.87 (s, 2H), 1.76 (dd, J = 21.0, 11.8 Hz, 4H), 1.60 (s, 1H).

| Example | Structure | Data |
|---|---|---|
| Example 42 | 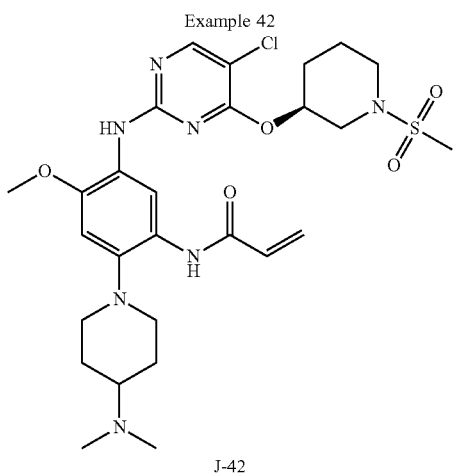<br>J-42 | MS [M + H]⁺: 608.2; ¹H NMR (400 MHz, DMSO-d₆) δ 9.00 (s, 1H), 8.42 (s, 1H), 8.29 (s, 1H), 8.26 (s, 2H), 6.82 (s, 1H), 6.67 (dd, J = 17.0, 10.2 Hz, 1H), 6.24 (dd, J = 17.0, 1.8 Hz, 1H), 5.73 (d, J = 11.8 Hz, 1H), 5.35 (s, 1H), 3.82 (s, 3H), 3.36 (d, J = 4.5 Hz, 2H), 3.21 (d, J = 7.1 Hz, 1H), 3.12 (d, J = 7.7 Hz, 1H), 3.04 (d, J = 10.5 Hz, 2H), 2.89 (s, 3H), 2.66 (q, J = 11.8 Hz, 2H), 2.36 (s, 1H), 2.31 (s, 6H), 1.85 (t, J = 15.4 Hz, 4H), 1.78-1.66 (m, 3H), 1.60 (s, 1H). |
| Example 43 | 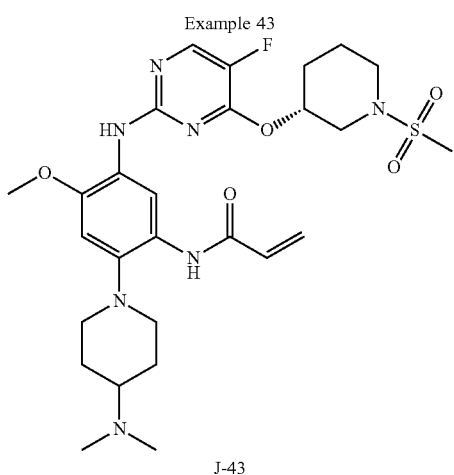<br>J-43 | MS [M + H]⁺: 592.3; ¹H NMR (400 MHz, DMSO-d₆) δ 8.99 (s, 1H), 8.52 (s, 1H), 8.27 (d, J = 3.1 Hz, 1H), 8.24 (s, 1H), 8.04 (s, 1H), 6.82 (s, 1H), 6.67 (dd, J = 16.9, 10.2 Hz, 1H), 6.34-6.15 (m, 1H), 5.74 (d, J = 10.1 Hz, 1H), 5.40 (s, 1H), 3.84 (s, 3H), 3.38 (s, 2H), 3.23 (d, J = 7.2 Hz, 1H), 3.16-3.08 (m, 1H), 3.04 (d, J = 10.7 Hz, 2H), 2.89 (s, 3H), 2.66 (q, J = 10.1 Hz, 2H), 2.42 (s, 1H), 2.34 (s, 6H), 1.90 (dd, J = 16.0, 7.5 Hz, 3H), 1.84-1.77 (m, 2H), 1.73 (d, J = 9.8 Hz, 2H), 1.60 (s, 1H). |
| Example 44 | 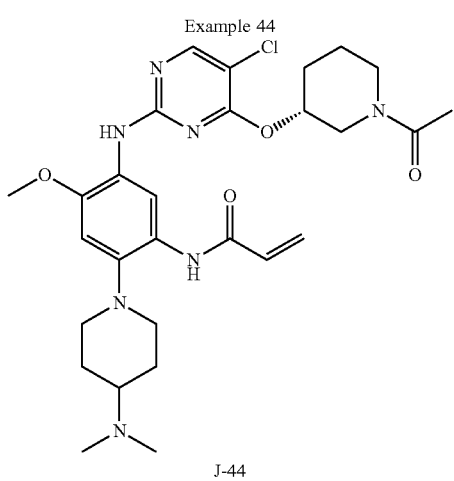<br>J-44 | MS [M + H]⁺: 572.3; ¹H NMR (400 MHz, DMSO-d₆) δ 8.97 (d, J = 7.8 Hz, 1H), 8.49 (d, J = 11.1 Hz, 1H), 8.24 (dd, J = 35.7, 21.8 Hz, 2H), 6.82 (s, 1H), 6.66 (dd, J = 16.9, 10.4 Hz, 1H), 6.29-6.15 (m, 1H), 5.73 (d, J = 10.2 Hz, 1H), 5.32 (s, 1H), 3.83 (d, J = 7.3 Hz, 3H), 3.67-3.43 (m, 3H), 3.30-3.22 (m, 1H), 3.02 (d, J = 10.1 Hz, 2H), 2.71-2.60 (m, 2H), 2.24 (s, 7H), 1.98 (s, 2H), 1.83 (s, 2H), 1.81 (s, 3H), 1.69 (d, J = 11.5 Hz, 3H), 1.46 (s, 1H). |

Example 45 Preparation of (R)—N-(5-(5-chloro-4-(1-(methylsulfonyl)pyrrolidine-3-oxy)pyrimidine-2-amino)-2-(4-(dimethylamino)piperidine-1-yl)-4-methoxyphenyl)acrylamide (J-45)

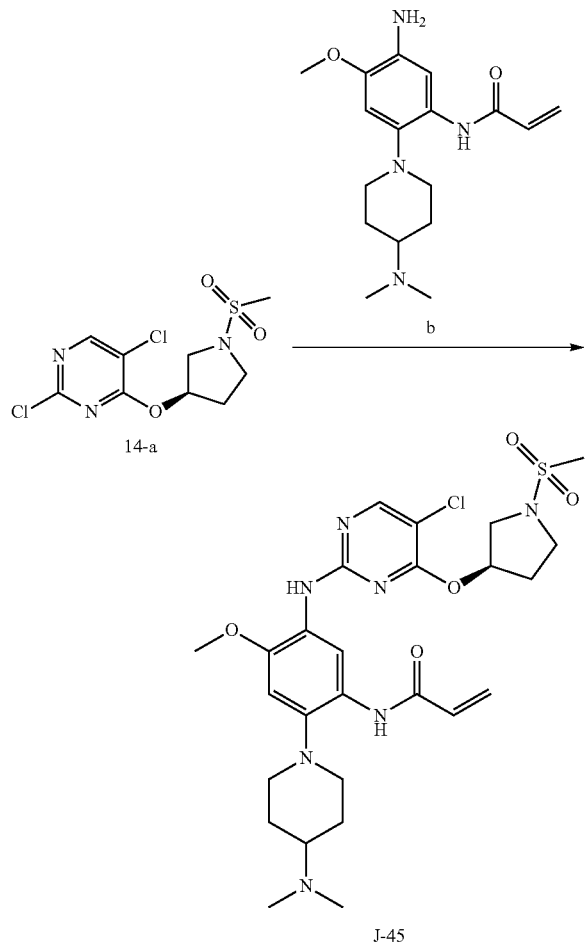

Compound b (159 mg, 0.48 mmol), Pd$_2$(dba)$_3$ (44 mg, 0.048 mmol), Xantphos (42 mg, 0.073 mmol), cesium carbonate (315 mg, 0.97 mmol) and compound 14-a (150 mg, 0.48 mmol) were added into 5 ml of 1,4-dioxane. After the air in the system was replaced with argon, the reaction was stirred in a sealed tube at 120° C. overnight. The reaction was monitored by LC-Ms. After the reaction was complete, the reaction mixture was filtered and washed with dichloromethane. The filtrate was concentrated to obtain a crude product, which was isolated and purified by preparative liquid phase chromatography to obtain the title compound J-45 (63.77 mg, yield 20.7%). MS m/z(ESI): 594.3 [M+H]$^+$; $^1$HNMR (400 MHz, DMSO-d$_6$) δ 9.00 (s, 1H), 8.49 (s, 1H), 8.26 (s, 2H), 8.23 (s, 1H), 6.82 (s, 1H), 6.66 (dd, J=16.9, 10.3 Hz, 1H), 6.22 (d, J=17.0 Hz, 1H), 5.79 (s, 1H), 5.73 (d, J=11.6 Hz, 1H), 3.83 (s, 3H), 3.57 (dd, J=12.3, 4.4 Hz, 2H), 3.03 (d, J=11.2 Hz, 2H), 2.90 (s, 3H), 2.64 (d, J=11.0 Hz, 2H), 2.23 (d, J=13.0 Hz, 9H), 1.84 (d, J=11.3 Hz, 2H), 1.68 (d, J=8.9 Hz, 2H).

Examples 46-52

Compounds J-46, J-47, J-48, J-49, J-50, J-51 and J-52 were prepared by using compound 15-a, 16-a, 17-a, 18-a, 19-a, 20-a and 21-a as the raw materials, each of which was reacted with compound b. The reaction steps and conditions referred to Example 45.

| Example 46 | | |
|---|---|---|
| 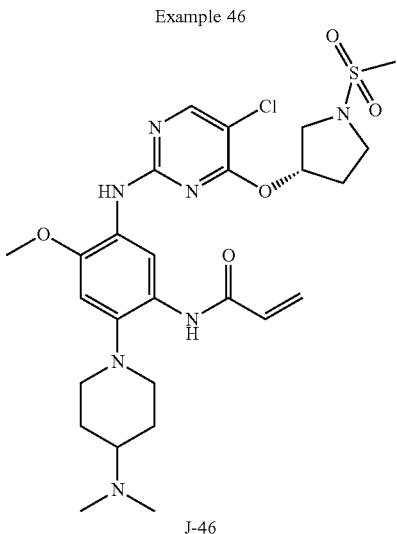 | MS [M + H]$^+$: 594.4; $^1$H NMR (400 MHz, DMSO-d$_6$) δ 9.00 (s, 1H), 8.48 (s, 1H), 8.26 (s, 2H), 6.82 (s, 1H), 6.66 (dd, J = 16.7, 10.0 Hz, 1H), 6.22 (d, J = 16.7 Hz, 1H), 5.79 (s, 1H), 5.73 (d, J = 10.2 Hz, 1H), 3.83 (s, 3H), 3.59-3.55 (m, 1H), 3.02 (d, J = 11.0 Hz, 2H), 2.90 (s, 3H), 2.65 (s, 2H), 2.24-2.17 (m, 9H), 1.81 (s, 2H), 1.67 (d, J = 8.9 Hz, 2H). | |

Example 47

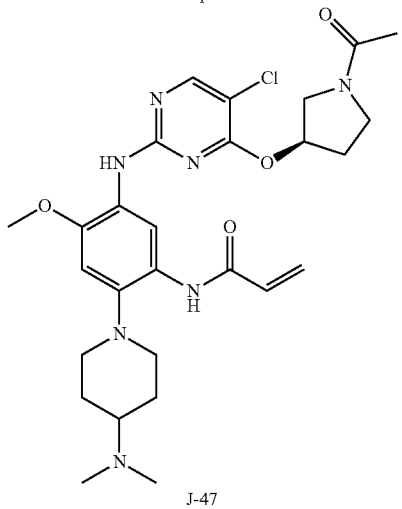

J-47

MS [M + H]+: 558.2; 1H NMR (400 MHz, DMSO-$d_6$) δ 8.98 (s, 1H), 8.53 (d, J = 18.9 Hz, 1H), 8.26 (d, J = 2.0 Hz, 1H), 8.22 (d, J = 7.0 Hz, 1H), 6.83 (s, 1H), 6.65 (dd, J = 16.9, 10.2 Hz, 1H), 6.20 (d, J = 16.9 Hz, 1H), 5.79 (d, J = 16.9 Hz, 1H), 5.72 (d, J = 10.6 Hz, 1H), 3.84 (d, J = 1.7 Hz, 3H), 3.82-3.77 (m, 0.5H), 3.53 (ddd, J = 28.9, 22.8, 9.8 Hz, 3.5H), 3.02 (d, J = 11.4 Hz, 2H), 2.65 (d, J = 14.9 Hz, 2H), 2.24-2.12 (m, 9H), 1.93 (d, J = 23.7 Hz, 3H), 1.82 (d, J = 11.5 Hz, 2H), 1.73-1.61 (m, 2H).

Example 48

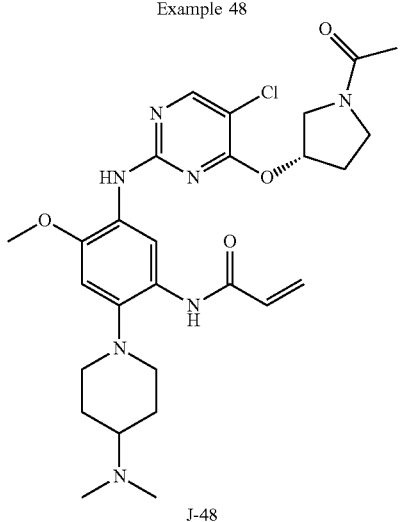

J-48

MS [M + H]+: 558.3; 1H NMR (400 MHz, DMSO-$d_6$) δ 8.98 (s, 1H), 8.53 (d, J = 18.9 Hz, 1H), 8.26 (d, J = 1.9 Hz, 1H), 8.22 (d, J = 6.9 Hz, 1H), 6.83 (s, 1H), 6.62 (d, J = 10.1 Hz, 1H), 6.20 (d, J = 16.8 Hz, 1H), 5.79 (d, J = 15.4 Hz, 1H), 5.72 (d, J = 10.2 Hz, 1H), 3.84 (s, 3H), 3.79 (s, 0.5H), 3.62-3.46 (m, 3.5H), 3.02 (d, J = 12.4 Hz, 2H), 2.65 (d, J = 15.1 Hz, 2H), 2.19 (d, J = 17.8 Hz, 9H), 1.93 (d, J = 23.8 Hz, 3H), 1.81 (s, 2H), 1.67 (d, J = 9.8 Hz, 2H).

Example 49

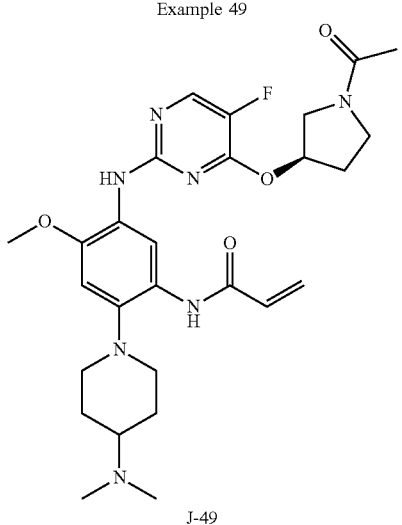

J-49

MS [M + H]+: 542.3; 1H NMR (400 MHz, DMSO-$d_6$) δ 8.99 (s, 1H), 8.62 (d, J = 19.4 Hz, 1H), 8.26 (dd, J = 5.1, 2.4 Hz, 2H), 8.01 (d, J = 4.9 Hz, 1H), 6.82 (s, 1H), 6.65 (dd, J = 16.8, 10.2 Hz, 1H), 6.20 (d, J = 17.1 Hz, 1H), 5.83 (d, J = 16.7 Hz, 1H), 5.72 (d, J = 10.3 Hz, 1H), 3.83 (t, J = 5.5 Hz, 3.5H), 3.62-3.51 (m, 3H), 3.34 (dd, J = 19.4, 8.8 Hz, 0.5H), 3.02 (d, J = 11.4 Hz, 2H), 2.65 (d, J = 14.0 Hz, 2H), 2.27 (s, 8H), 2.14-2.10 (m, 1H), 1.94 (d, J = 21.5 Hz, 3H), 1.84 (d, J = 11.3 Hz, 2H), 1.74-1.67 (m, 2H).

-continued

Example 50

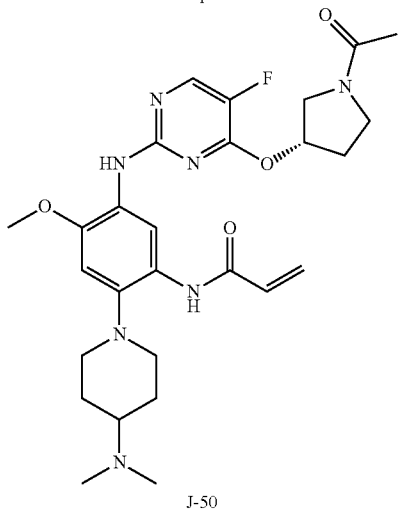

J-50

MS [M + H]⁺: 542.3; ¹H NMR (400 MHz, DMSO-d₆) δ 8.99 (s, 1H), 8.62 (d, J = 19.3 Hz, 1H), 8.27 (t, J = 2.6 Hz, 2H), 8.00 (d, J = 5.0 Hz, 1H), 6.82 (s, 1H), 6.65 (dd, J = 16.8, 10.1 Hz, 1H), 6.20 (d, J = 17.0 Hz, 1H), 5.83 (d, J = 17.0 Hz, 1H), 5.72 (d, J = 10.4 Hz, 1H), 3.84 (d, J = 1.5 Hz, 3H), 3.79 (d, J = 4.8 Hz, 0.5H), 3.64-3.48 (m, 4H), 3.34 (dd, J = 18.6, 9.8 Hz, 0.5H), 3.02 (d, J = 10.7 Hz, 2H), 2.70-2.60 (m, 2H), 2.30-2.21 (m, 8H), 2.17-2.10 (m, 1H), 1.94 (d, J = 21.4 Hz, 3H), 1.85 (d, J = 11.9 Hz, 2H), 1.70 (dd, J = 20.2, 11.2 Hz, 2H).

Example 51

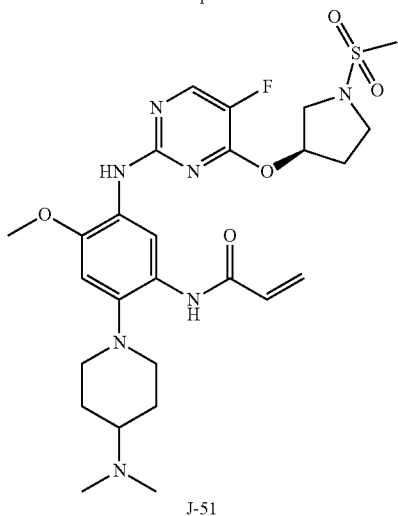

J-51

MS [M + H]⁺: 578.3; ¹H NMR (400 MHz, DMSO-d₆) δ 9.00 (s, 1H), 8.57 (s, 1H), 8.27 (d, J = 3.1 Hz, 1H), 8.03 (s, 1H), 6.82 (s, 1H), 6.66 (dd, J = 17.0, 10.2 Hz, 1H), 6.22 (d, J = 18.5 Hz, 1H), 5.82 (s, 1H), 5.73 (d, J = 11.4 Hz, 1H), 3.83 (s, 3H), 3.59 (dd, J = 12.2, 4.5 Hz, 1H), 3.43 (dd, J = 17.2, 7.8 Hz, 3H), 3.01 (d, J = 11.7 Hz, 2H), 2.89 (s, 3H), 2.64 (t, J = 10.6 Hz, 2H), 2.22 (d, J = 11.1 Hz, 9H), 1.83 (d, J = 11.7 Hz, 2H), 1.73-1.65 (m, 2H).

Example 52

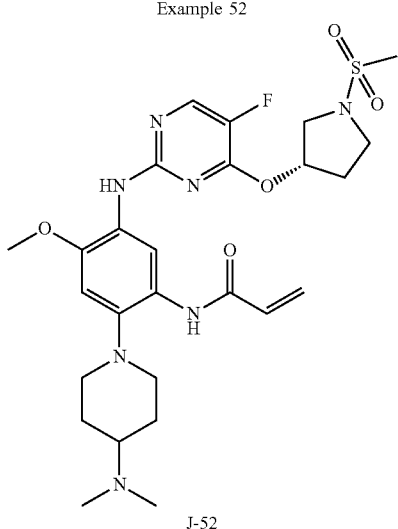

J-52

MS [M + H]⁺: 578.2; ¹H NMR (400 MHz, DMSO-d₆) δ 9.00 (s, 1H), 8.57 (s, 1H), 8.27 (d, J = 3.1 Hz, 1H), 8.03 (s, 1H), 6.82 (s, 1H), 6.66 (dd, J = 17.0, 10.2 Hz, 1H), 6.22 (dd, J = 17.0, 1.8 Hz, 1H), 5.82 (s, 1H), 5.73 (dd, J = 10.2, 1.6 Hz, 1H), 3.83 (s, 3H), 3.59 (dd, J = 12.2, 4.6 Hz, 1H), 3.43 (dd, J = 17.3, 7.9 Hz, 3H), 3.01 (d, J = 11.4 Hz, 2H), 2.89 (s, 3H), 2.68-2.60 (m, 2H), 2.23-2.16 (m, 9H), 1.82 (d, J = 10.9 Hz, 2H), 1.72-1.64 (m, 2H).

121

Example 53 Preparation of N-(2-((2-(dimethyl-amino)ethyl)(methyl) amino)-5-(4-(1-(2-fluroethyl) azetidine-3-oxy)pyrimidine-2-amino)-4-methoxy-phenyl) acrylamide (J-53)

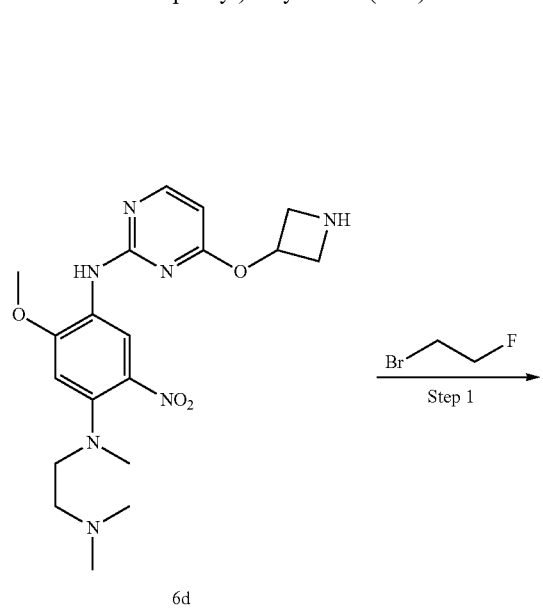

6d

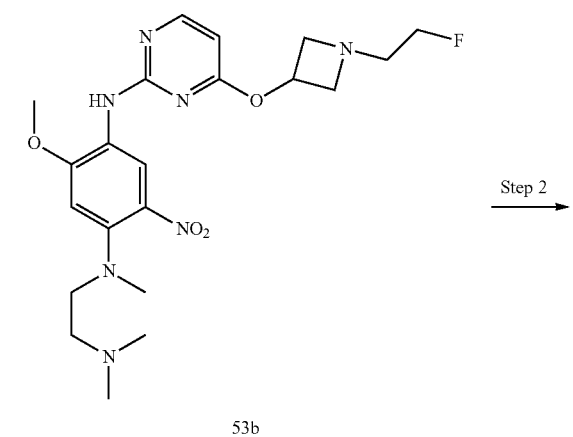

53b

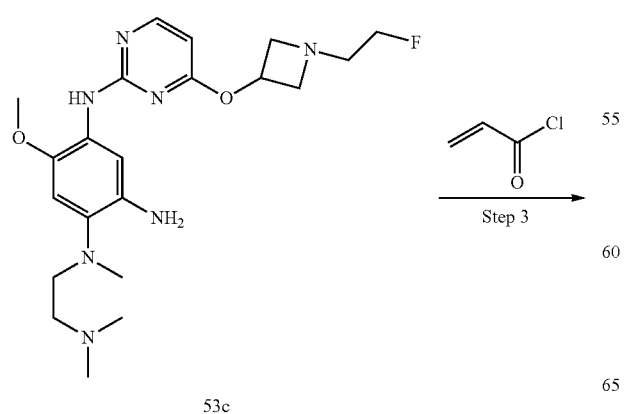

53c

122

-continued

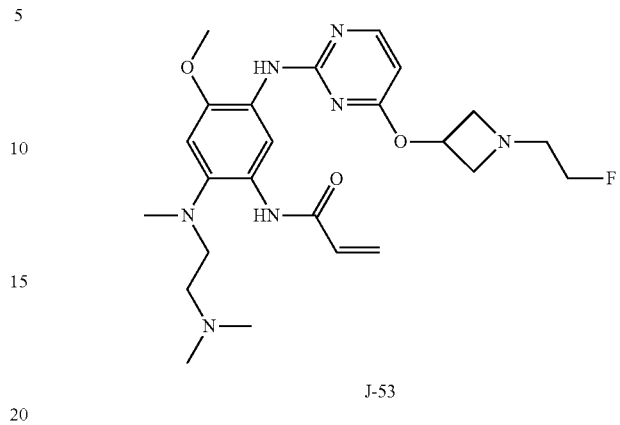

J-53

Step 1: A solution of compound 6d (210 mg, 0.5 mmol), 1-bromo-2-fluoroethane (75 mg, 0.6 mmol) and potassium carbonate (205 mg, 1.5 mmol) in acetonitrile (5 ml) was stirred in a sealed tube at 50° C. overnight. After the reaction was complete, the reaction mixture was extracted with dichloromethane/water system for three times. The organic phase was separated, washed with saturated brine, dried over anhydrous sodium sulfate and concentrated to obtain a crude product of compound 53b, which was purified by Combi-flash column chromatography to obtain compound 53b (115 mg, yield 50%). MS m/z(ESI): 464 [M+H]$^+$.

Step 2-3: The title compound J-53 (35 mg, yield 31%) was prepared by using compound 53b as the raw material according to step 6 and step 7 of Example 6, and was isolated and purified by preparative liquid phase chromatography.

MS m/z(ESI): 488 [M+H]; $^1$H NMR (400 MHz, CDCl$_3$) δ 10.02 (s, 1H), 9.38 (s, 1H), 8.17-8.16 (d, J=5.6 Hz, 1H), 7.49 (s, 1H), 6.74 (s, 1H), 6.47 (s, 1H), 6.43 (s, 1H), 6.20-6.19 (d, J=5.6 Hz, 1H), 5.71-5.68 (d, J=11.9 Hz, 2H), 4.52-4.50 (t, J=4.9 Hz, 1H), 4.40-4.38 (t, J=4.9 Hz, 1H), 3.86 (s, 3H), 3.84-3.80 (t, J=8.2 Hz, 2H), 3.41 (s, 2H), 2.93 (s, 2H), 2.85-2.77 (m, 2H), 2.70 (s, 3H), 2.34 (s, 8H).

Examples 54-55

Compound J-54 was prepared by using compound 22-a as the raw material according to the method of Example 53. Compound J-55 was prepared by using compound 46-a as the raw material successively according to step 2 of Example 3 and step 1 of Example 53.

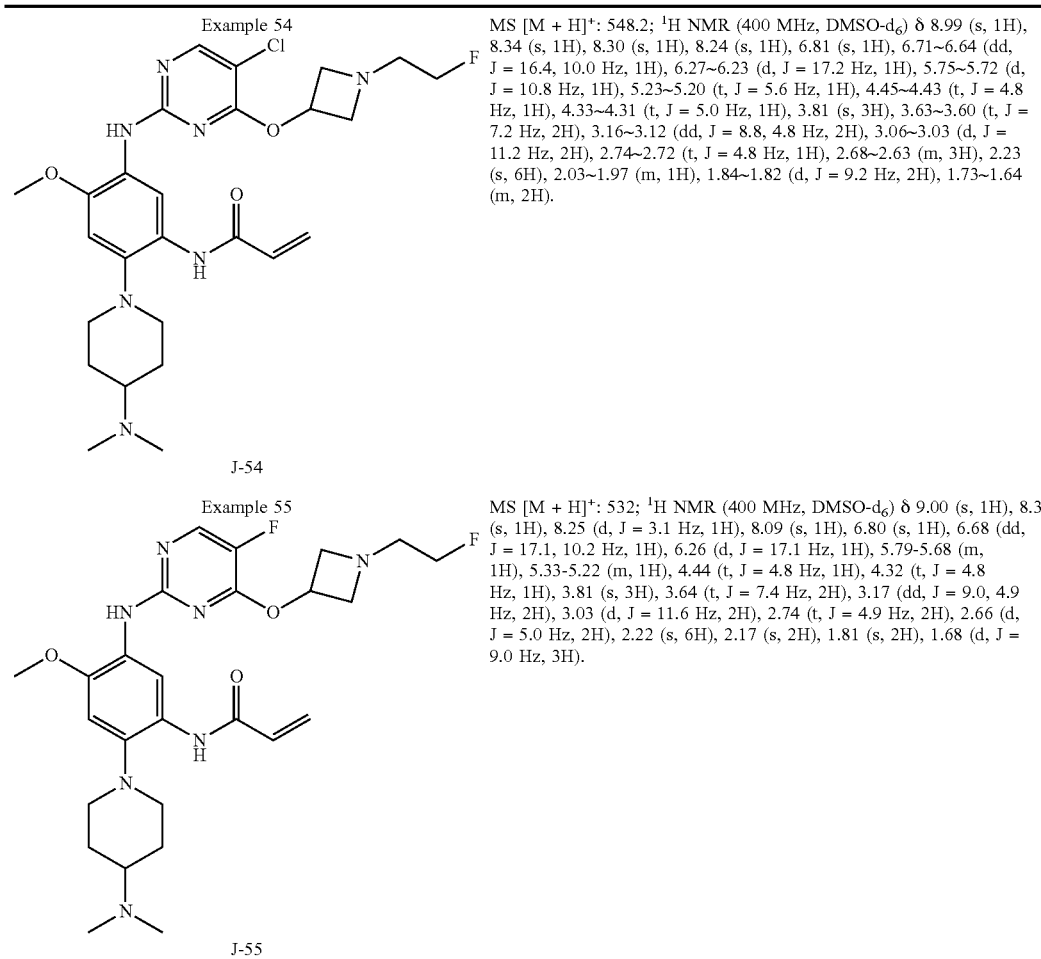

Example 54 — J-54

MS [M + H]⁺: 548.2; $^1$H NMR (400 MHz, DMSO-$d_6$) δ 8.99 (s, 1H), 8.34 (s, 1H), 8.30 (s, 1H), 8.24 (s, 1H), 6.81 (s, 1H), 6.71~6.64 (dd, J = 16.4, 10.0 Hz, 1H), 6.27~6.23 (d, J = 17.2 Hz, 1H), 5.75~5.72 (d, J = 10.8 Hz, 1H), 5.23~5.20 (t, J = 5.6 Hz, 1H), 4.45~4.43 (t, J = 4.8 Hz, 1H), 4.33~4.31 (t, J = 5.0 Hz, 1H), 3.81 (s, 3H), 3.63~3.60 (t, J = 7.2 Hz, 2H), 3.16~3.12 (dd, J = 8.8, 4.8 Hz, 2H), 3.06~3.03 (d, J = 11.2 Hz, 2H), 2.74~2.72 (t, J = 4.8 Hz, 1H), 2.68~2.63 (m, 3H), 2.23 (s, 6H), 2.03~1.97 (m, 1H), 1.84~1.82 (d, J = 9.2 Hz, 2H), 1.73~1.64 (m, 2H).

Example 55 — J-55

MS [M + H]⁺: 532; $^1$H NMR (400 MHz, DMSO-$d_6$) δ 9.00 (s, 1H), 8.38 (s, 1H), 8.25 (d, J = 3.1 Hz, 1H), 8.09 (s, 1H), 6.80 (s, 1H), 6.68 (dd, J = 17.1, 10.2 Hz, 1H), 6.26 (d, J = 17.1 Hz, 1H), 5.79-5.68 (m, 1H), 5.33-5.22 (m, 1H), 4.44 (t, J = 4.8 Hz, 1H), 4.32 (t, J = 4.8 Hz, 1H), 3.81 (s, 3H), 3.64 (t, J = 7.4 Hz, 2H), 3.17 (dd, J = 9.0, 4.9 Hz, 2H), 3.03 (d, J = 11.6 Hz, 2H), 2.74 (t, J = 4.9 Hz, 2H), 2.66 (d, J = 5.0 Hz, 2H), 2.22 (s, 6H), 2.17 (s, 2H), 1.81 (s, 2H), 1.68 (d, J = 9.0 Hz, 3H).

Examples 56-59

Compounds J-56, J-57, J-58 and J-59 were prepared by using compounds 40-a, 41-a, 42-a and 43-a as the raw material which were reacted with compound b respectively. The reaction steps and conditions referred to Example 13.

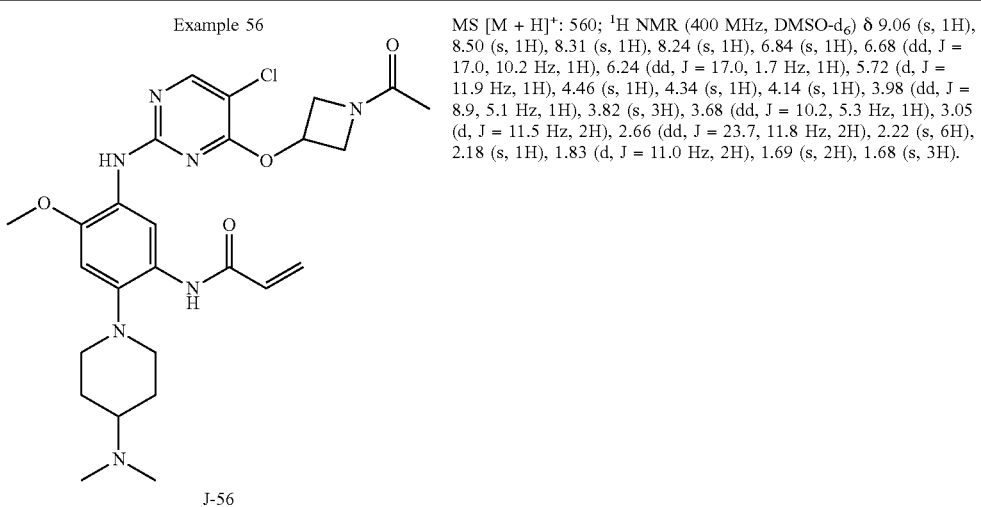

Example 56 — J-56

MS [M + H]⁺: 560; $^1$H NMR (400 MHz, DMSO-$d_6$) δ 9.06 (s, 1H), 8.50 (s, 1H), 8.31 (s, 1H), 8.24 (s, 1H), 6.84 (s, 1H), 6.68 (dd, J = 17.0, 10.2 Hz, 1H), 6.24 (dd, J = 17.0, 1.7 Hz, 1H), 5.72 (d, J = 11.9 Hz, 1H), 4.46 (s, 1H), 4.34 (s, 1H), 4.14 (s, 1H), 3.98 (dd, J = 8.9, 5.1 Hz, 1H), 3.82 (s, 3H), 3.68 (dd, J = 10.2, 5.3 Hz, 1H), 3.05 (d, J = 11.5 Hz, 2H), 2.66 (dd, J = 23.7, 11.8 Hz, 2H), 2.22 (s, 6H), 2.18 (s, 1H), 1.83 (d, J = 11.0 Hz, 2H), 1.69 (s, 2H), 1.68 (s, 3H).

Example 57
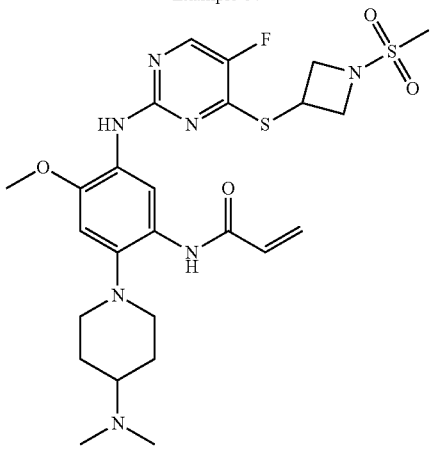
J-57
MS [M + H]+: 580; 1H NMR (400 MHz, DMSO-d6) δ 9.02 (s, 1H), 8.39 (s, 1H), 8.32 (s, 2H), 8.24 (d, J = 1.8 Hz, 1H), 6.84 (s, 1H), 6.69 (dd, J = 16.9, 10.2 Hz, 1H), 6.26 (dd, J = 17.0, 1.7 Hz, 1H), 5.74 (d, J = 11.8 Hz, 1H), 4.54 (t, J = 6.0 Hz, 1H), 4.18 (t, J = 8.4 Hz, 2H), 3.83 (dd, J = 8.8, 5.6 Hz, 3H), 3.80 (d, J = 6.1 Hz, 3H), 3.05 (d, J = 11.4 Hz, 2H), 3.00 (d, J = 7.3 Hz, 3H), 2.67 (t, J = 10.8 Hz, 2H), 2.26 (s, 6H), 2.25-2.18 (m, 1H), 1.85 (d, J = 10.2 Hz, 2H), 1.79-1.65 (m, 2H).
Example 58
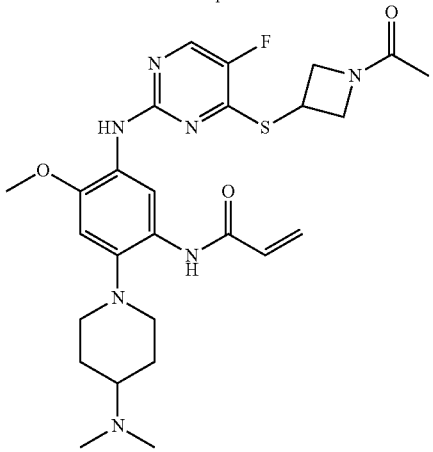
J-58
MS [M + H]+: 544; 1H NMR (400 MHz, DMSO-d6) δ 9.06 (s, 1H), 8.42 (s, 1H), 8.29 (s, 1H), 8.26 (d, J = 1.5 Hz, 2H), 6.84 (s, 1H), 6.68 (dd, J = 17.0, 10.2 Hz, 1H), 6.25 (dd, J = 17.0, 1.7 Hz, 1H), 5.76-5.67 (m, 1H), 4.56 (dd, J = 11.5, 6.4 Hz, 1H), 4.42 (t, J = 8.5 Hz, 1H), 4.20 (d, J = 9.6 Hz, 1H), 4.04-4.00 (m, 1H), 3.83 (s, 3H), 3.73-3.69 (m, 1H), 3.05 (d, J = 11.1 Hz, 2H), 2.67 (dd, J = 24.1, 11.9 Hz, 2H), 2.31 (d, J = 13.4 Hz, 1H), 2.28 (s, 6H), 1.85 (d, J = 10.9 Hz, 2H), 1.72 (d, J = 13.1 Hz, 2H), 1.69 (s, 3H).
Example 59
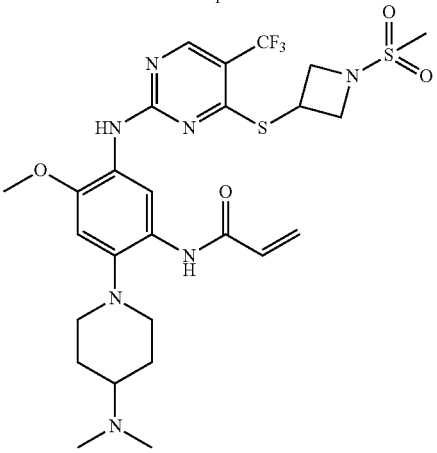
J-59
MS [M + H]+: 630; 1H NMR (400 MHz, DMSO-d6) δ 9.35 (s, 1H), 9.02 (s, 1H), 8.44 (s, 1H), 8.03 (s, 1H), 6.86 (s, 1H), 6.80-6.59 (m, 1H), 6.26 (s, 1H), 5.75 (s, 1H), 4.53-4.37 (m, 1H), 3.79 (s, 5H), 3.02 (d, J = 53.0 Hz, 6H), 2.68 (s, 4H), 2.23 (s, 7H), 1.77 (d, J = 42.2 Hz, 4H).

Example 60 Preparation of N-(5-(5-chloro-4-(1-(methylsulfonyl) azetidine-3-amino) pyrimidine-2-amino)-2-(4-(dimethylamino)piperidine-1-yl)-4-methoxyphenyl)acrylamide (J-60)

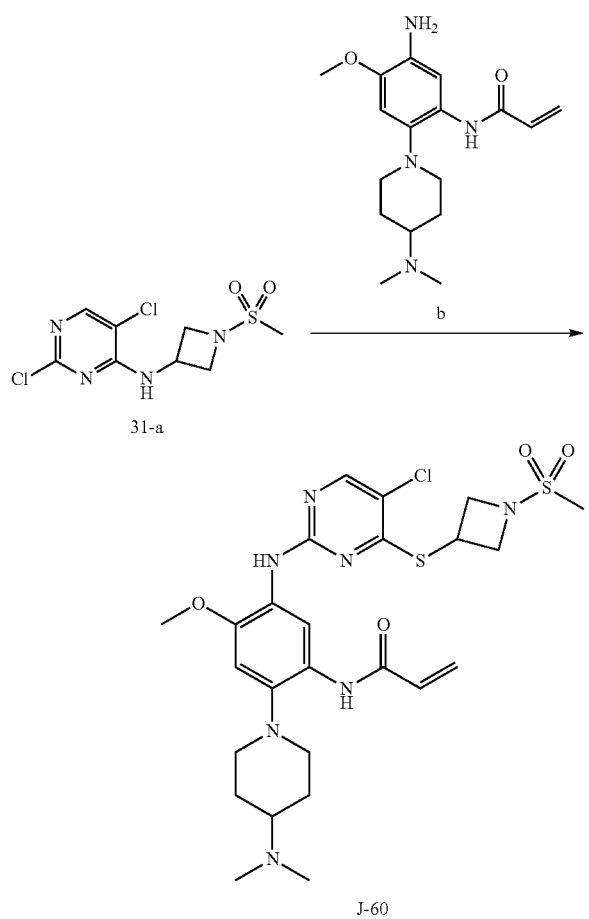

Under argon atmosphere and at room temperature, into a solution of compound b (143 mg, 0.45 mmol), compound 31-a (135 mg, 0.45 mmol), Xantphos (52 mg, 0.09 mmol) and cesium carbonate (293 mg, 0.9 mmol) in 1,4-dioxane (10 ml) was added $Pd_2(dba)_3$ (41 mg, 0.045 mmol). The reaction mixture was microwaved at 160° C. for 15 min. After the reaction was complete, the reaction mixture was filtered. The filtrate was concentrated under reduced pressure to obtain a crude product, which was isolated and purified by preparative liquid phase chromatography to obtain the title compound J-60 (44.03 mg, yield 15.6%). MS m/z(ESI): 579 [M+H]$^+$; $^1$HNMR (400 MHz, DMSO-d$_6$) δ 8.99 (s, 1H), 8.66 (s, 1H), 8.23 (s, 1H), 7.96 (s, 1H), 7.72-7.71 (d, J=6.6 Hz, 1H), 7.69 (s, 1H), 6.80 (s, 1H), 6.69-6.62 (dd, J1=10.2 Hz, J2=17.0 Hz, 1H), 6.30-6.26 (d, J=16.8 Hz, 1H), 5.73-5.70 (d, J=10.2 Hz, 1H), 4.99-4.94 (m, 1H), 4.05-4.01 (t, J=8.0 Hz, 2H), 3.96-3.92 (t, J=6.9 Hz, 2H), 3.83 (s, 3H), 3.02-2.99 (m, 5H), 2.67-2.62 (t, J=10.1 Hz, 2H), 2.26 (s, 7H), 1.85-1.82 (d, J=11.1 Hz, 2H), 1.73-1.66 (m, 2H).

Examples 61-64 and Example 73

Compounds J-61, J-62, J-63, J-64, J-73 and J-74 were prepared by using compounds 33-a, 49-a, 35-a, 50-a, 39-a and 51-a as the raw material which were reacted with compound b, respectively. The reaction steps and conditions referred to Example 60.

Example 61

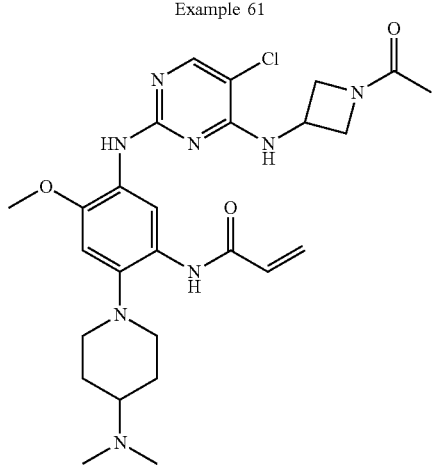

J-61

MS [M + H]$^+$: 543.2; $^1$H NMR (400 MHz, DMSO-d$_6$) δ 9.02 (s, 1H), 8.73 (s, 1H), 8.20 (s, 1H), 7.95 (s, 1H), 7.74-7.73 (d, J = 6.8 Hz, 1H), 7.63 (s, 1H), 6.80 (s, 1H), 6.69-6.63 (dd, J1 = 10.2 Hz, J2 = 16.9 Hz, 1H), 6.23-6.19 (d, J = 16.8 Hz, 1H), 5.71-5.68 (d, J = 10.2 Hz, 1H), 5.04-5.03 (m, 1H), 4.34-4.30 (t, J = 8.2 Hz, 1H), 4.05-4.02 (m, 2H), 3.90-3.88 (m, 1H), 3.84 (s, 3H), 3.16 (s, 1H), 3.05-3.02 (d, J = 10.8 Hz, 2H), 2.69-2.62 (m, 2H), 2.37 (s, 6H), 1.90-1.87 (d, J = 11.1 Hz, 2H), 1.75-1.71 (m, 5H).

Example 62
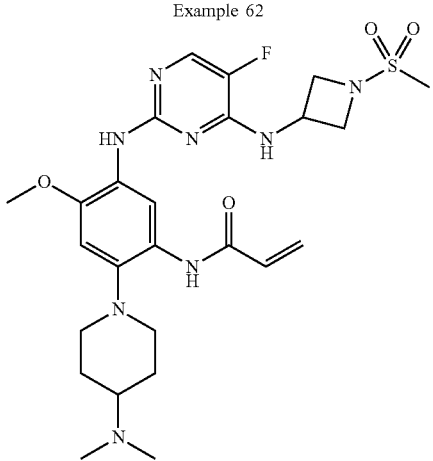
J-62
MS [M + H]+: 563; 1H NMR (400 MHz, DMSO-d6) δ 8.98 (s, 1H), 8.77 (s, 1H), 8.09-8.07 (d, J = 7.0 Hz, 1H), 7.93-7.92 (d, J = 3.6 Hz, 1H), 7.47 (s, 1H), 6.80 (s, 1H), 6.68-6.62 (dd, J1 = 10.1 Hz, J2 = 16.8 Hz, 1H), 6.31-6.26 (d, J = 16.7 Hz, 1H), 5.73-5.70 (d, J = 11.3 Hz, 1H), 5.03-4.98 (m, 1H), 4.12-4.08 (t, J = 8.1 Hz, 2H), 3.92-3.89 (t, J = 14.6 Hz, 2H), 3.83 (s, 3H), 3.00-2.97 (m, 4H), 2.66-2.61 (t, J = 10.7 Hz, 2H), 2.21 (s, 6H), 2.17 (s, 1H), 1.83-1.80 (d, J = 10.4 Hz, 2H), 1.70-1.63 (m, 2H).
MS [M + H]+: 547;
Example 63
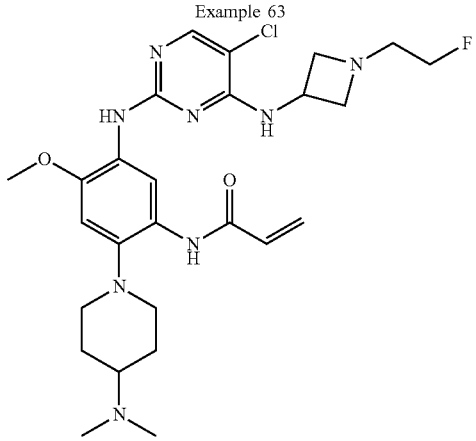
J-63
MS [M + H]+: 613; 1H NMR (400 MHz, DMSO-d6) δ 9.05 (s, 1H), 8.67 (s, 1H), 8.32 (s, 1H), 8.23 (s, 2H), 7.79 (s, 1H), 6.86 (s, 1H), 6.70-6.64 (dd, J1 = 10.2 Hz, J2 = 17.0 Hz, 1H), 6.32-6.27 (d, J = 17.2 Hz, 1H), 5.74-5.71 (d, J = 11.8 Hz, 1H), 4.69 (s, 1H), 3.96-3.92 (t, J = 8.0 Hz, 2H), 3.84 (s, 3H), 3.77-3.73 (t, J = 6.5 Hz, 2H), 3.06-3.03 (d, J = 11.2 Hz, 2H), 2.94 (s, 3H), 2.68-2.63 (t, J = 8.6 Hz, 2H), 2.22 (s, 7H), 1.84-1.82 (d, J = 10.8 Hz, 2H), 1.73-1.68 (t, J = 10.8 Hz, 2H).
Example 64
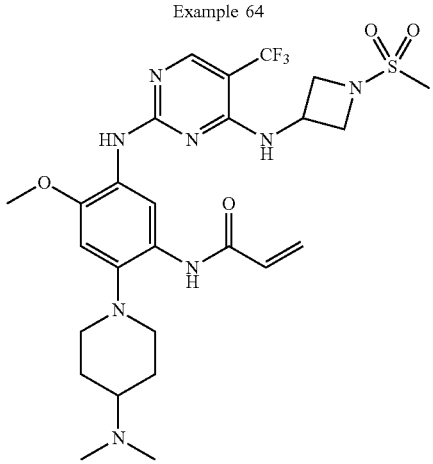
J-64

| Example 73 | MS [M + H]⁺: 593; ¹H NMR (400 MHz, DMSO-d$_6$) δ 8.97 (s, 1H), 8.35 (s, 1H), 8.27 (s, 1H), 8.05-8.02 (d, J = 12.4 Hz, 2H), 6.80 (s, 1H), 6.68-6.62 (dd, J1 = 10.2 Hz, J2 = 16.7 Hz, 1H), 6.25-6.21 (d, J = 17.2 Hz, 1H), 5.73-5.71 (d, J = 9.9 Hz, 1H), 4.63-4.60 (t, J = 7.0 Hz, 2H), 3.97-3.93 (t, J = 7.6 Hz, 2H), 3.85-3.79 (m, 5H), 3.05 (s, 3H), 3.00 (s, 2H), 2.97 (s, 3H), 2.67-2.62 (t, J = 10.4 Hz, 2H), 2.23 (s, 7H), 1.84-1.81 (d, J = 9.3 Hz, 2H), 1.70-1.67 (m, 2H). |
|---|---|
| 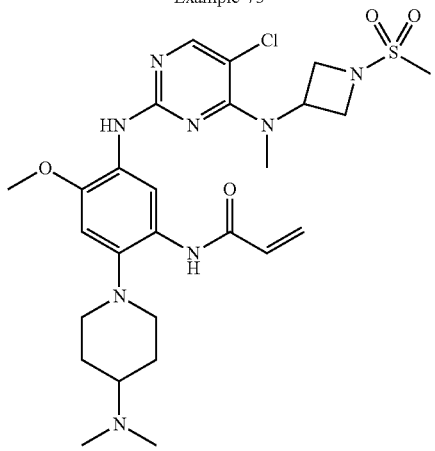<br>J-73 | |
| Example 74 | MS [M + H]⁺: 486; ¹H NMR (400 MHz, DMSO-d$_6$) δ 9.00 (s, 1H), 8.86 (s, 1H), 7.90 (s, 1H), 7.53 (s, 1H), 7.25 (s, 1H), 6.78 (s, 1H), 6.62 (dd, J = 16.7, 10.2 Hz, 1H), 6.15 (d, J = 16.8 Hz, 1H), 5.68 (d, J = 10.0 Hz, 1H), 3.87 (s, 3H), 3.02 (d, J = 11.4 Hz, 3H), 2.62 (t, J = 11.0 Hz, 2H), 2.21 (s, 6H), 2.16 (s, 1H), 1.81 (d, J = 10.1 Hz, 2H), 1.64 (d, J = 10.3 Hz, 2H), 0.69-0.55 (m, 4H). |
| 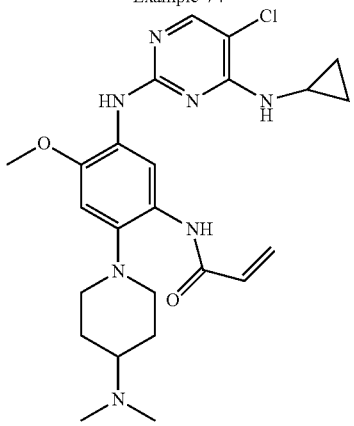<br>J-74 | |

Example 65 Preparation of N-(5-(5-chloro-4-(1-(methylsulfonyl) piperidine-3-amino)pyrimidine-2-amino)-2-(4-(dimethylamino)piperidine-1-yl)-4-methoxy phenyl)acrylamide (J-65)

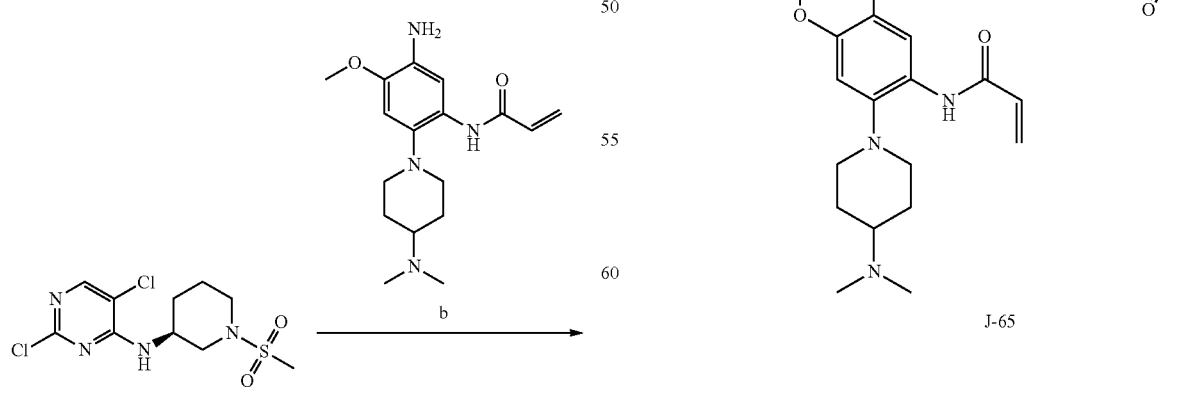

Into a solution of compound 32-a (150 mg, 0.46 mmol) in 1,4-dioxane were added compound b (147 mg, 0.46 mmol), Pd$_2$(dba)$_3$ (43 mg, 0.046 mmol), BINAP (58 mg, 0.092 mmol) and cesium carbonate (301 mg, 0.922 mmol). The reaction mixture was stirred under microwave at 130° C. for 25 min. After the reaction was complete, the reaction mixture was filtered and concentrated to obtain a crude product, which was isolated and purified by preparative liquid phase chromatography to obtain the title compound J-65 (28.56 mg). MS m/z(ESI):607.3 [M+H]+. $^1$H NMR (400 MHz, DMSO-d$_6$) δ 8.95 (s, 1H), 8.58 (s, 1H), 8.21 (s, 1H), 7.95 (s, 1H), 7.67 (s, 1H), 6.80 (s, 1H), 6.74 (d, J=8.3 Hz, 1H), 6.65 (dd, J=16.9, 10.1 Hz, 1H), 6.23 (d, J=16.9 Hz, 1H), 5.72 (d, J=11.4 Hz, 1H), 4.28 (s, 1H), 3.84 (s, 3H), 3.47 (d, J=7.9 Hz, 1H), 3.35 (d, J=11.1 Hz, 1H), 3.03 (s, 2H), 2.83 (s, 3H), 2.76 (dd, J=17.4, 7.5 Hz, 2H), 2.72-2.58 (m, 2H), 2.40 (s, 6H), 1.88 (d, J=10.2 Hz, 3H), 1.64 (dd, J=40.4, 31.7 Hz, 6H).

Examples 66-69

Compounds J-66, J-67, J-68 and J-69 were prepared by using compound 34-a, 37-a, 36-a and 38-a as the raw materials which were reacted with compound b, respectively. The reaction steps and conditions referred to Example 65.

Example 66

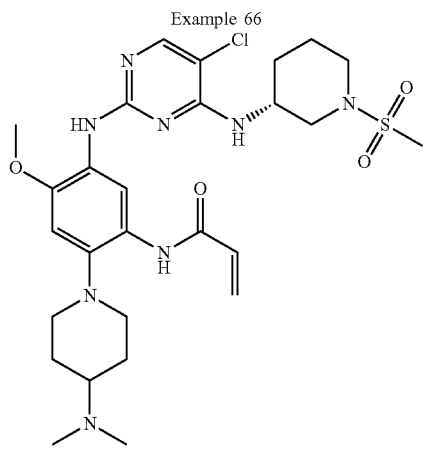

J-66

MS [M + H]$^+$: 607.2; $^1$H NMR (400 MHz, DMSO-d$_6$) δ 8.95 (s, 1H), 8.56 (s, 1H), 7.94 (s, 1H), 7.66 (s, 1H), 6.79 (s, 1H), 6.73 (d, J = 8.2 Hz, 1H), 6.65 (dd, J = 17.0, 10.2 Hz, 1H), 6.27-6.17 (m, 1H), 5.71 (d, J = 11.6 Hz, 1H), 4.28 (s, 1H), 3.83 (s, 3H), 3.47 (d, J = 7.7 Hz, 1H), 3.36 (s, 1H), 3.00 (s, 2H), 2.83 (s, 3H), 2.81-2.72 (m, 2H), 2.61 (dd, J = 28.4, 16.4 Hz, 2H), 2.22 (s, 6H), 1.89-1.74 (m, 4H), 1.74-1.53 (m, 5H).

Example 67

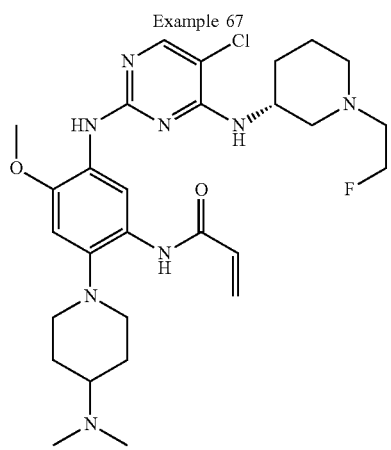

J-67

MS [M + H]$^+$: 575.3; $^1$H NMR (400 MHz, DMSO-d$_6$) δ 8.97 (s, 1H), 8.58 (s, 1H), 8.26 (s, 1H), 7.92 (s, 1H), 7.62 (s, 1H), 6.79 (s, 1H), 6.65 (dd, J = 16.9, 10.2 Hz, 1H), 6.54 (d, J = 8.3 Hz, 1H), 6.22 (dd, J = 17.0, 1.8 Hz, 1H), 5.72 (d, J = 11.7 Hz, 1H), 4.56 (t, J = 4.9 Hz, 1H), 4.45 (t, J = 5.0 Hz, 1H), 4.25 (s, 1H), 3.84 (s, 3H), 3.03 (d, J = 11.1 Hz, 2H), 2.63 (ddd, J = 19.8, 14.9, 8.5 Hz, 5H), 2.46 (s, 1H), 2.36 (s, 6H), 2.34-2.22 (m, 2H), 1.87 (s, 2H), 1.65 (ddd, J = 60.8, 29.6, 9.6 Hz, 7H).

| Example 68 | MS [M + H]⁺: 575.3; ¹H NMR (400 MHz, DMSO-d₆) δ 8.98 (s, 1H), 8.59 (s, 1H), 8.26 (s, 1H), 7.92 (s, 1H), 7.63 (s, 1H), 6.79 (s, 1H), 6.66 (dd, J = 16.9, 10.2 Hz, 1H), 6.55 (d, J = 8.3 Hz, 1H), 6.22 (dd, J = 17.0, 1.7 Hz, 1H), 5.77-5.68 (m, 1H), 4.56 (t, J = 4.9 Hz, 1H), 4.45 (t, J = 4.9 Hz, 1H), 4.25 (s, 1H), 3.84 (s, 3H), 3.04 (d, J = 9.7 Hz, 2H), 2.63 (ddd, J = 24.3, 10.7, 6.2 Hz, 7H), 2.44 (s, 6H), 2.29 (d, J = 24.1 Hz, 2H), 1.91 (s, 2H), 1.77 (d, J = 9.6 Hz, 2H), 1.57 (dd, J = 46.0, 15.5 Hz, 4H). |
|---|---|
| 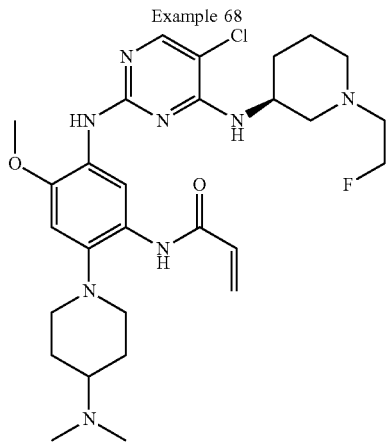  J-68 | |
| Example 69 | MS [M + H]⁺: 607.3; ¹H NMR (400 MHz, DMSO-d₆) δ 9.02 (s, 1H), 8.70 (s, 1H), 7.93 (s, 1H), 7.57 (s, 1H), 6.91 (d, J = 7.8 Hz, 1H), 6.82 (s, 1H), 6.66 (dd, J = 17.0, 10.2 Hz, 1H), 6.24 (d, J = 17.0 Hz, 1H), 5.75 (d, J = 11.8 Hz, 1H), 4.18 (s, 1H), 3.85 (s, 3H), 3.57 (d, J = 12.1 Hz, 2H), 2.99 (d, J = 11.8 Hz, 2H), 2.85 (s, 3H), 2.74 (t, J = 11.3 Hz, 2H), 2.65 (t, J = 11.1 Hz, 2H), 2.22 (s, 6H), 2.18 (s, 1H), 1.91 (d, J = 10.3 Hz, 2H), 1.83 (d, J = 10.8 Hz, 2H), 1.74-1.57 (m, 4H). |
| 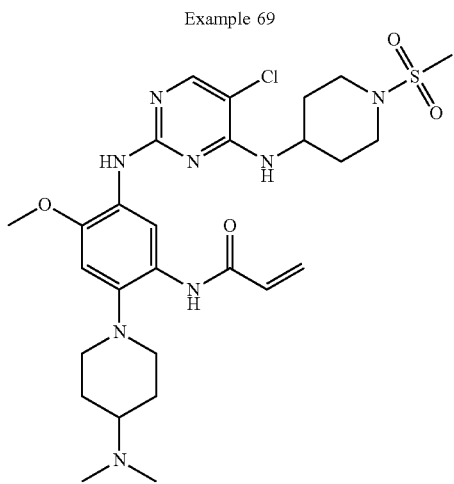  J-69 | |

Example 70 Preparation of N-(5-(5-chloro-4-(1-(methylsulfonyl) azetidine-3-oxy) pyrimidine-2-amino)-4-methoxy-2-(4-methylpiperazine-1-yl)phenyl)acrylamide (J-70)

-continued

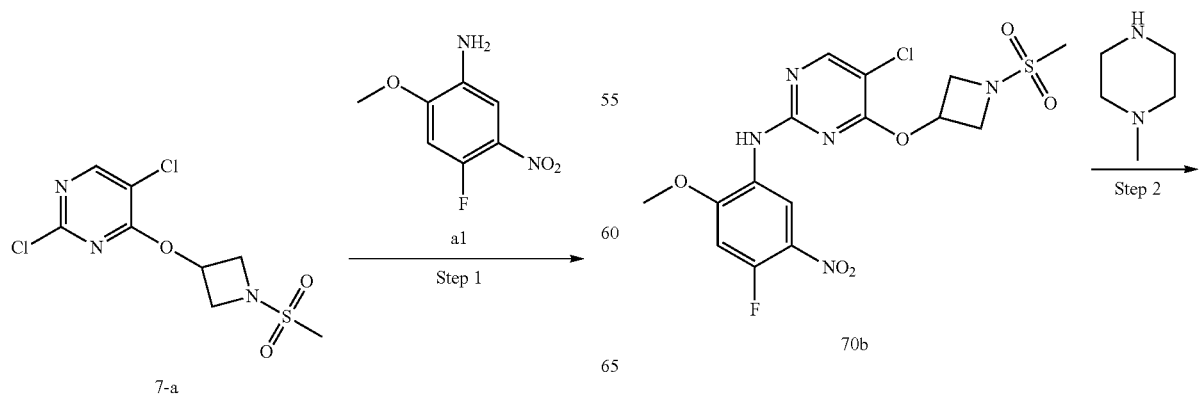

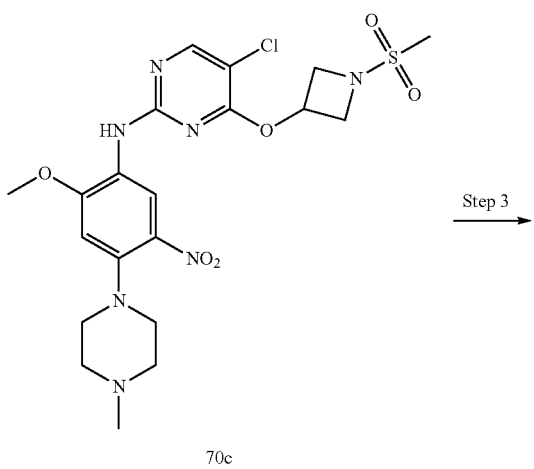

70c

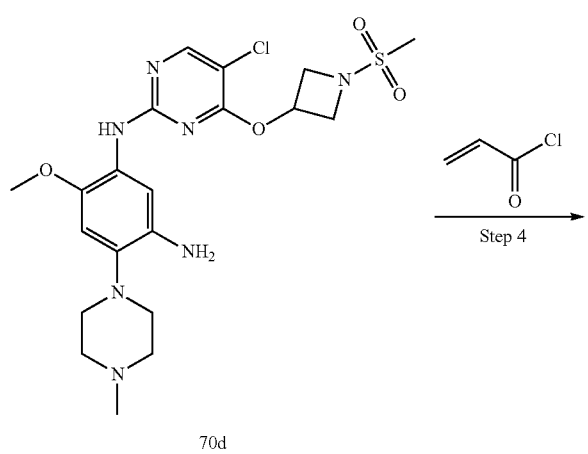

70d

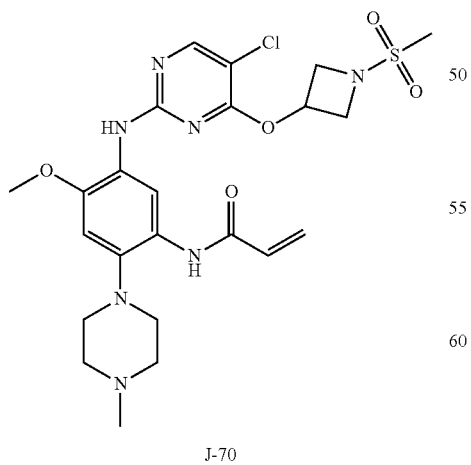

J-70

Step 1: Compound a1 (186 mg, 1 mmol), Pd$_2$(dba)$_3$ (92 mg, 0.1 mmol), Xantphos (90 mg, 0.15 mmol) and cesium carbonate (652 mg, 2 mmol) were added into a solution of compound 7-a (298 mg, 1 mmol) in 4 ml of 1,4-dioxane. The reaction mixture was microwaved at 160° C. for 20 min. After the reaction was complete, the reaction mixture was filtered and washed with ethyl acetate. The filtrate was concentrated under reduced pressure to obtain a crude product, which was purified by Combi-flash column chromatography to obtain compound 70b (160 mg, yield 35.8%). MS m/z(ESI): 448 [M+H]$^+$.

Step 2: 1-methylpiperazine (72 mg, 0.72 mmol) and potassium carbonate (99.5 mg, 0.72 mmol) were added into a solution of compound 70b (160 mg, 0.36 mmol) in 3 ml of DMF. The reaction mixture was vigorously stirred at 100° C. for 2 h. The reaction progress was monitored by TLC. After the substrate was completely consumed, the reaction mixture was extracted with ethyl acetate/water system for three times. The organic phase was separated, and concentrated under reduced pressure to obtain 180 mg of crude product of compound 70c, which was used in the next step without purification. MS m/z(ESI): 528 [M+H]$^+$.

Step 3-4: The title compound J-70 (74.5 mg, yield 37%) was prepared by using compound 70c (180 mg, 0.34 mmol) as the raw material according to step 6 and step 7 of Example 6. MS m/z(ESI): 552 [M+H]; $^1$HNMR (400 MHz, DMSO-d$_6$) δ 9.01 (s, 1H), 8.43 (s, 1H), 8.31 (s, 1H), 8.29 (s, 1H), 6.85 (s, 1H), 6.61 (dd, J=17.0, 10.2 Hz, 1H), 6.25 (d, J=16.9 Hz, 1H), 5.74 (d, J=11.7 Hz, 1H), 5.50-5.38 (m, 1H), 4.25-4.14 (m, 2H), 3.96 (dd, J=9.8, 4.7 Hz, 2H), 3.83 (s, 3H), 3.03 (s, 3H), 2.86 (t, J=4.6 Hz, 4H), 2.52 (s, 4H), 2.26 (s, 3H).

Examples 71-72

Compound J-71 and J-72 were prepared according to the method of Example 70, except that 1-methylpiperazine in step 2 Example 70 was replaced with 2-(dimethylamino)ethanol and compound 47-a, respectively.

| Example 71 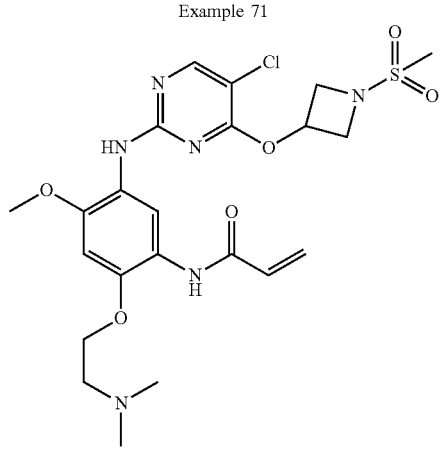  J-71 | MS [M + H]⁺: 541; ¹H NMR (400 MHz, DMSO-d₆) δ 9.73 (s, 1H), 8.48 (s, 1H), 8.35 (s, 1H), 8.27 (s, 1H), 6.91 (s, 1H), 6.46 (dd, J = 17.0, 10.2 Hz, 1H), 6.25 (d, J = 16.9 Hz, 1H), 5.80-5.68 (m, 1H), 5.39 (t, J = 5.0 Hz, 1H), 4.18 (t, J = 5.6 Hz, 3H), 4.15-4.11 (m, 1H), 3.95 (dd, J = 9.7, 4.8 Hz, 2H), 3.81 (s, 3H), 3.02 (s, 3H), 2.60 (s, 2H), 2.27 (s, 6H). |
|---|---|
| Example 72 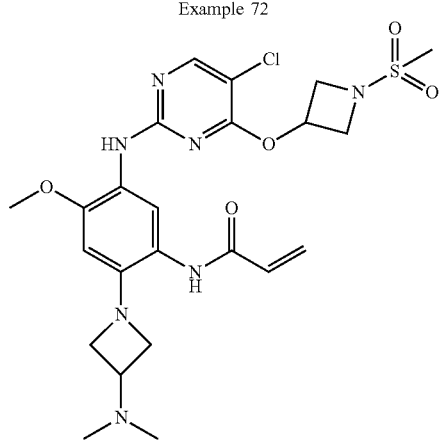  J-72 | MS [M + H]⁺: 552; ¹H NMR (400 MHz, DMSO-d₆) δ 9.34 (s, 1H), 8.38 (s, 1H), 8.24 (s, 1H), 7.46 (s, 1H), 6.57-6.42 (m, 1H), 6.23 (dd, J = 11.1, 5.9 Hz, 2H), 5.70 (dd, J = 10.2, 1.9 Hz, 1H), 5.30 (s, 1H), 4.18 (s, 2H), 3.97 (dd, J = 15.0, 10.4 Hz, 4H), 3.81 (s, 3H), 3.72 (s, 2H), 3.06 (s, 3H), 2.21 (d, J = 97.4 Hz, 6H). |
Preparation of Comparative Compound 2
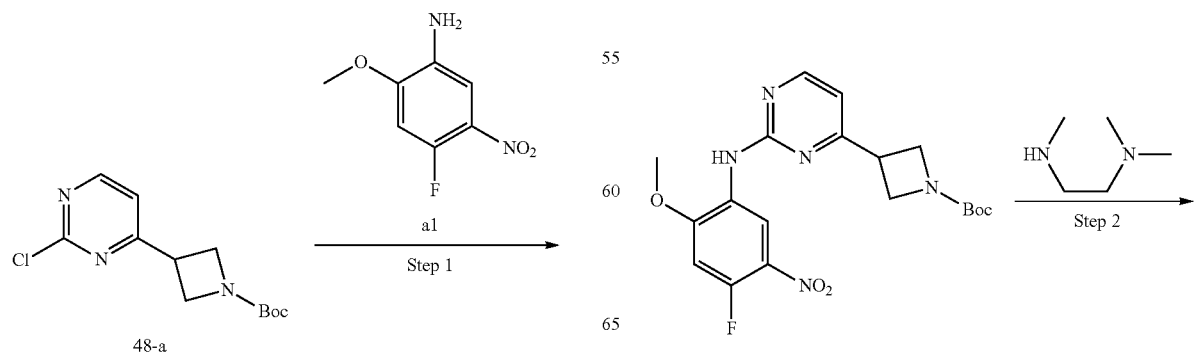

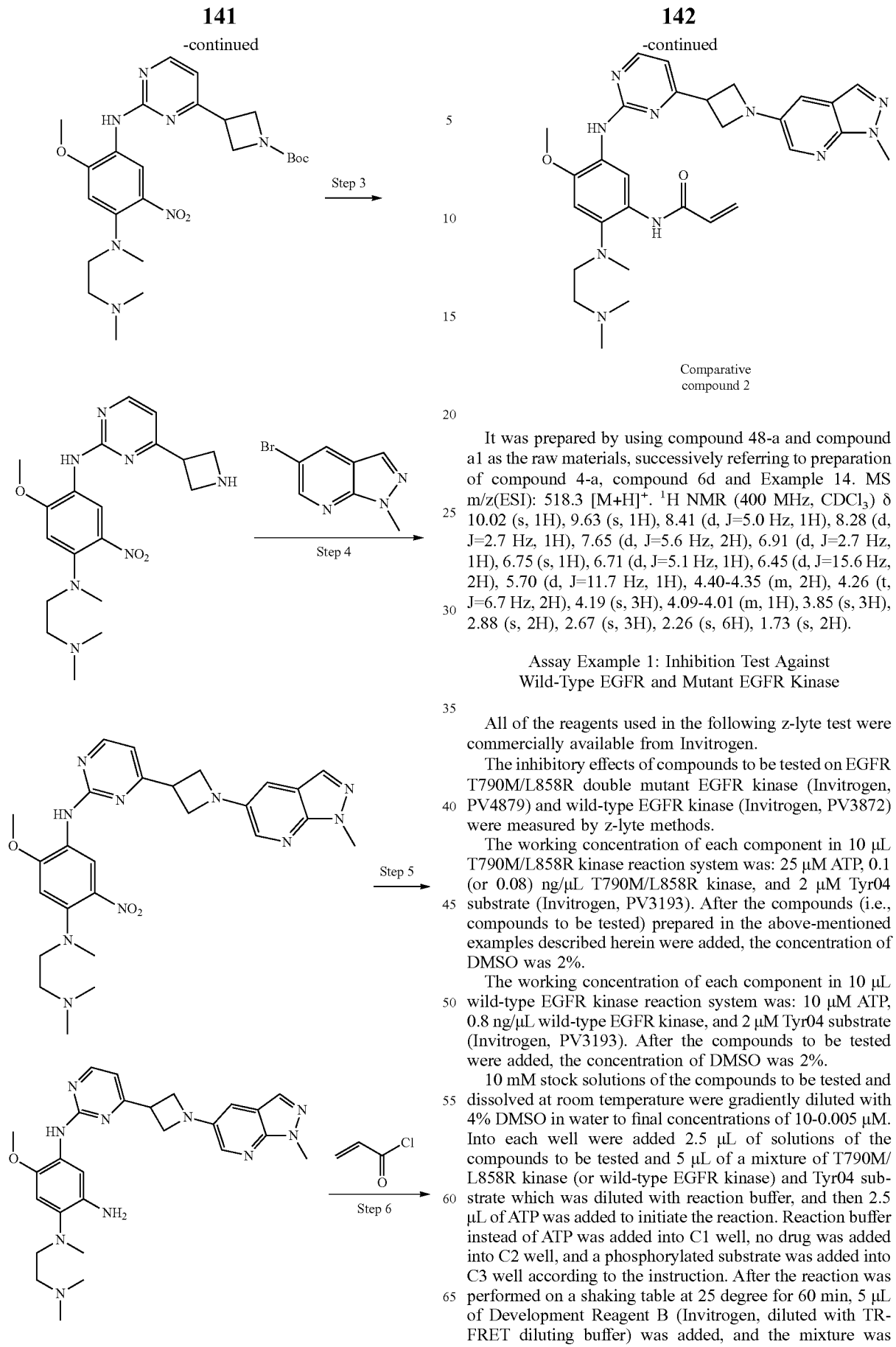

Comparative compound 2

It was prepared by using compound 48-a and compound a1 as the raw materials, successively referring to preparation of compound 4-a, compound 6d and Example 14. MS m/z(ESI): 518.3 [M+H]$^+$. $^1$H NMR (400 MHz, CDCl$_3$) δ 10.02 (s, 1H), 9.63 (s, 1H), 8.41 (d, J=5.0 Hz, 1H), 8.28 (d, J=2.7 Hz, 1H), 7.65 (d, J=5.6 Hz, 2H), 6.91 (d, J=2.7 Hz, 1H), 6.75 (s, 1H), 6.71 (d, J=5.1 Hz, 1H), 6.45 (d, J=15.6 Hz, 2H), 5.70 (d, J=11.7 Hz, 1H), 4.40-4.35 (m, 2H), 4.26 (t, J=6.7 Hz, 2H), 4.19 (s, 3H), 4.09-4.01 (m, 1H), 3.85 (s, 3H), 2.88 (s, 2H), 2.67 (s, 3H), 2.26 (s, 6H), 1.73 (s, 2H).

Assay Example 1: Inhibition Test Against Wild-Type EGFR and Mutant EGFR Kinase

All of the reagents used in the following z-lyte test were commercially available from Invitrogen.

The inhibitory effects of compounds to be tested on EGFR T790M/L858R double mutant EGFR kinase (Invitrogen, PV4879) and wild-type EGFR kinase (Invitrogen, PV3872) were measured by z-lyte methods.

The working concentration of each component in 10 μL T790M/L858R kinase reaction system was: 25 μM ATP, 0.1 (or 0.08) ng/μL T790M/L858R kinase, and 2 μM Tyr04 substrate (Invitrogen, PV3193). After the compounds (i.e., compounds to be tested) prepared in the above-mentioned examples described herein were added, the concentration of DMSO was 2%.

The working concentration of each component in 10 μL wild-type EGFR kinase reaction system was: 10 μM ATP, 0.8 ng/μL wild-type EGFR kinase, and 2 μM Tyr04 substrate (Invitrogen, PV3193). After the compounds to be tested were added, the concentration of DMSO was 2%.

10 mM stock solutions of the compounds to be tested and dissolved at room temperature were gradiently diluted with 4% DMSO in water to final concentrations of 10-0.005 μM. Into each well were added 2.5 μL of solutions of the compounds to be tested and 5 μL of a mixture of T790M/L858R kinase (or wild-type EGFR kinase) and Tyr04 substrate which was diluted with reaction buffer, and then 2.5 μL of ATP was added to initiate the reaction. Reaction buffer instead of ATP was added into C1 well, no drug was added into C2 well, and a phosphorylated substrate was added into C3 well according to the instruction. After the reaction was performed on a shaking table at 25 degree for 60 min, 5 μL of Development Reagent B (Invitrogen, diluted with TR-FRET diluting buffer) was added, and the mixture was reacted on a shaking table at room temperature for 60 min. The plate was read by using VictorX5 Fluoresence Microplate Reader (PerkinElmer) and the absorbance was measured at a excitation wavelength of 405 nm, and emission wavelengths of 450 nm and 520 nm. (For example, $C3_{520nm}$ represented the reading at 520 nm for C3 well).

Inhibition ratio was calculated as follows (referring to the instruction of PV3193, Invitrogen):

$ER$=Coumarin Emission(450 nm)/Fluorescein Emission(520 nm)    1.

Phosphorylation ratio=$(1-((ER \times C3_{520nm}-C3_{450nm})/((C1_{450nm}-C3_{450nm})+ER \times (C3_{520nm}-C1_{520nm})))) \times 100\%$    2.

Inhibition ratio(IR)=(1−Phosphorylation ratio of the compound to be tested)/(phosphorylation ratio of C2))×100%    3.

Half maximal inhibitory concentration of $IC_{50}$ was determined by fitting calculation with XLFIT 5.0 (IDBS Company, UK). The results of inhibitory activity and selective inhibitory activity against enzyme were shown in Table 1.

TABLE 1

Inhibitory activity and selective inhibitory activity against enzyme

| Compound | T790M/L858R ($IC_{50}$/nM) | EGFR WT ($IC_{50}$/nM) | Selective inhibitory activity against enzyme [$IC_{50}$(EGFR WT)/$IC_{50}$(T790M/L858R)] |
|---|---|---|---|
| J-1 | 3 | 20 | 6.7 |
| J-2 | 66 | 154 | 2.3 |
| J-3 | 9 | 38 | 4.2 |
| J-9 | 40 | 72 | 1.8 |
| J-11 | 2 | 12 | 6 |
| J-4 | 34 | 52 | 1.53 |
| J-5 | 25 | 51 | 2.04 |
| J-12 | 1 | 10 | 10 |
| J-13 | <0.5 | 16 | >32 |
| J-17 | 6 | 8 | 1.3 |
| J-18 | 29 | 30 | 1.03 |
| J-20 | 31 | 69 | 2.2 |
| J-23 | 15 | 32 | 2.1 |
| J-24 | 50 | 119 | 2.4 |
| J-27 | 9 | 114 | 12.7 |
| J-28 | 3 | 49 | 16.3 |
| J-29 | 1 | 6 | 6 |
| J-30 | 22 | 95 | 4.3 |
| J-31 | 2 | 27 | 13.5 |
| J-32 | 6 | 11 | 1.8 |
| J-33 | 55 | 597 | 10.9 |
| J-34 | 11 | 113 | 10.3 |
| J-35 | 7 | 80 | 11.4 |
| J-36 | 11 | 17 | 1.55 |
| J-37 | 2 | 22 | 11 |
| J-38 | 13 | 170 | 13.1 |
| J-39 | 3 | 39 | 13 |
| J-40 | 8 | 47 | 5.9 |
| J-45 | 3 | 41 | 13.7 |
| J-46 | 3 | 49 | 16.3 |
| J-47 | 17 | 227 | 13.3 |
| J-48 | 39 | 610 | 15.6 |
| J-49 | 61 | 259 | 4.2 |
| J-51 | 6 | 26 | 4.3 |
| J-52 | 8 | 47 | 6 |
| J-54 | 36 | 376 | 10.4 |
| J-56 | 7 | 176 | 25.1 |
| J-57 | 1 | 4 | 4 |
| J-58 | 13 | 69 | 5.3 |
| J-59 | 1 | 23 | 23 |
| J-60 | 1 | 6 | 6 |
| J-61 | 18 | 181 | 10.1 |
| J-62 | 3 | 6 | 2 |
| J-67 | 1 | 2 | 2 |

TABLE 1-continued

Inhibitory activity and selective inhibitory activity against enzyme

| Compound | T790M/L858R ($IC_{50}$/nM) | EGFR WT ($IC_{50}$/nM) | Selective inhibitory activity against enzyme [$IC_{50}$(EGFR WT)/$IC_{50}$(T790M/L858R)] |
|---|---|---|---|
| J-68 | 14 | 41 | 2.9 |
| J-69 | 17 | 105 | 6.2 |
| J-70 | 1 | 14 | 14 |
| J-71 | 4 | 23 | 5.8 |
| J-73 | 3 | 24 | 8 |
| J-74 | 33 | 216 | 6.5 |
| J-75 | 47 | 463 | 9.9 |
| J-76 | 1 | 14 | 14 |
| Comparative compound 1 | 2 | 3 | 1.5 |
| BIBW2992 | 5 | 1 | 0.2 |

It can be seen from Table 1 that the exemplary compounds of the invention can inhibit EGFR mutant enzyme (T790M/L858R) at a concentration of 100 nM (some compounds below a concentration of 10 nM) and show fairly strong inhibitory activities, but show weaker inhibitory activities against EGFR wild-type enzyme (T790M WT). The compounds of the present invention have significant selective inhibitory activities against EGFR mutant enzyme compared with the positive control BIBW2992 (Afatinib), and the selective inhibitory activities of the exemplary compounds of the invention against EGFR mutant enzyme are greater than that of the comparative compound 1 (the specific structure is shown as below and can be found in WO2013014448A1), and the highest selectivity is 21 times higher than that of the comparative compound 1. It is also found that when the substituent $R_0$ is replaced with hetero aryl ring, the selective inhibitory activities against EGFR mutant is obviously reduced when compared with comparative compound 1.

comparative compound 1

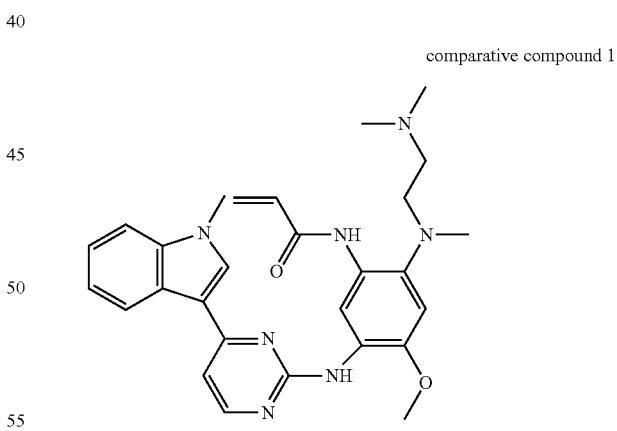

Assay Example 2: Test of Cytostatic Activity by MTT (3-(4,5-dimethyl-thiazol-2)-2,5-diphenyl tetrazolium bromide) Method MTT assay was conducted using the methods well known to those skilled in the art, and all of the reagents used in the method were commercially obtained.

Firstly, the medium was removed and 0.25% trypsin/EDTA (Gibco, 25200-056) was added. After rinsed once, 1.5 mL of trypsin/EDTA was added to digest the adherent cells until the cells detached, and then 3.5 mL of medium was added to terminate the digestion. The digested cell suspension was transferred to a 15 mL centrifugal tube, and centrifuged at 1300 rpm for 3 min, then the supernatant was discarded and cells were suspended in a fresh medium. The cells were then counted, and diluted to the following concentrations: H1975 cell at $2.78 \times 10^4$ cells/mL and A431 cell and NIH3T3 cell at $3.33 \times 10^4$ cells/mL. The cells were seeded into 96-well plates (BD 3072), 90 μL/well, and incubated overnight.

The medium for A431 cell: 10% FBS (Gibco, 10099-141) DMEM (Hyclone SH30243.01B);

The medium for NIH3T3 cell: 10% FBS (Gibco, 10099-141), DMEM (Hyclone SH30243.01B);

The medium for H1975 cell: 10% FBS (Gibco, 10099-141), RPMI-1640 (Hyclone SH30809.01B);

20 μL of 10 mM compound to be tested was take and the compound solution (10×) was diluted according to the following concentration gradient (2000, 666.67, 222.22, 74.07, 24.69, 8.23, 2.74, 0.91 μM). Serum-free medium was then added (the final concentration: 10, 3.333, 1.111, 0.370, 0.123, 0.041, 0.014, 0.005 μM), and 10 μL of the compound to be tested in each well was added into the cell culture plates, in which the final concentration of DMSO was 0.5%.

The cells were placed in an incubator after addition of the compound to be tested, and incubated for 72 h. Then 10 μL of MTT (Sigma, M5655) solution at 5 mg/ml was added into each well, and the 96-well plate was placed in an incubator and incubated at 37° C. under 5% $CO_2$ for 4 h.

The plates were centrifuged at 2000 rpm for 5 min. After the supernatant was removed, 150 μL of DMSO was added to each well, and the plate was shaken on a shaker until the purple crystal completely dissolved. Finally, the absorbance at 492 nm was measured by using a microplate reader, and $IC_{50}$ was calculated with XLFIT 5.0 software (IDBS Company, UK). The inhibitory activity and selective inhibitory activity of the exemplary compounds against cells were shown in Table 2 and Table 3.

TABLE 2

Compound's Inhibitory activity and selective inhibitory activity against cells

| Compound | H1975 cell ($IC_{50}$/nM) | A431 cell ($IC_{50}$/nM) | Selective inhibitory activity against cells [$IC_{50}$(A431 cell)/$IC_{50}$(H1975 cell)] |
|---|---|---|---|
| J-7 | 66 | 989 | 15 |
| J-10 | 31 | 596 | 19.2 |
| J-11 | 14 | 1583 | 113 |
| J-12 | 7 | 814 | 116 |
| J-1 | 22 | 1145 | 52 |
| J-13 | 7 | 926 | 132.3 |
| J-17 | 121 | 1880 | 15.5 |
| J-18 | 184 | 2960 | 16.1 |
| J-20 | 138 | 5353 | 38.8 |
| J-27 | 57 | 3053 | 53.6 |
| J-28 | 11 | 3149 | 286.3 |
| J-29 | 17 | 1097 | 64.5 |
| J-30 | 121 | 6010 | 50 |
| J-31 | 4 | 1716 | 429 |
| J-35 | 35 | 2899 | 82.8 |
| J-36 | 69 | 3264 | 47.3 |
| J-37 | 27 | 2144 | 79.4 |
| J-38 | 66 | 4673 | 71 |
| J-39 | 72 | 4299 | 60 |
| J-40 | 50 | 2948 | 59 |
| J-45 | 19 | 2738 | 144.1 |
| J-46 | 17 | 2921 | 171.8 |
| J-47 | 46 | 7382 | 160.5 |

TABLE 2-continued

Compound's Inhibitory activity and selective inhibitory activity against cells

| Compound | H1975 cell ($IC_{50}$/nM) | A431 cell ($IC_{50}$/nM) | Selective inhibitory activity against cells [$IC_{50}$(A431 cell)/$IC_{50}$(H1975 cell)] |
|---|---|---|---|
| J-48 | 56 | 4615 | 82.4 |
| J-54 | 92 | 6083 | 66.1 |
| J-56 | 20 | 3952 | 198 |
| J-57 | 7 | 534 | 76.3 |
| J-58 | 23 | 2261 | 98.3 |
| J-59 | <5 | 1951 | >390 |
| J-60 | 24 | 1341 | 56 |
| J-70 | 6 | 971 | 162 |
| J-71 | 21 | 1797 | 86 |
| Comparative compound 1 | 13 | 478 | 36.77 |
| Comparative compound 2 | 359 | 5062 | 14.1 |
| BIBW2992 | 88 | 29 | 0.33 |

TABLE 3

Results of cytotoxicity of the compounds against NIH3T3 cells

| Compound | MTT assay against NIH3T3 cell ($IC_{50}$/nM) |
|---|---|
| J-7 | >10000 |
| J-8 | >10000 |
| J-9 | >10000 |
| J-10 | >10000 |
| J-11 | >10000 |
| J-12 | >10000 |
| J-1 | >10000 |
| J-3 | >10000 |
| J-4 | >10000 |
| J-5 | >10000 |
| J-6 | >10000 |
| J-13 | >10000 |
| J-14 | >10000 |
| J-15 | >10000 |
| J-16 | >10000 |
| J-17 | >10000 |
| J-19 | >10000 |
| J-20 | >10000 |
| J-21 | >10000 |
| J-22 | >10000 |
| J-23 | >10000 |
| J-24 | 5997 |
| J-26 | >10000 |
| J-27 | 9829 |
| J-28 | >10000 |
| J-29 | >10000 |
| J-30 | >10000 |
| J-31 | >3000 |
| J-32 | >10000 |
| J-33 | >10000 |
| J-34 | >10000 |
| J-35 | >10000 |
| J-36 | >10000 |
| J-37 | >10000 |
| J-38 | >10000 |
| J-39 | >10000 |
| J-40 | >10000 |
| J-42 | >10000 |
| J-45 | 8203 |
| J-46 | >10000 |
| J-47 | >10000 |
| J-48 | >10000 |
| J-51 | >10000 |
| J-52 | >10000 |
| J-53 | >10000 |

TABLE 3-continued

Results of cytotoxicity of the
compounds against NIH3T3 cells

| Compound | MTT assay against NIH3T3 cell (IC$_{50}$/nM) |
| --- | --- |
| J-54 | >10000 |
| J-56 | 9042 |
| J-57 | >10000 |
| J-58 | >10000 |
| J-59 | 9628 |
| J-60 | >10000 |
| J-61 | >10000 |
| J-62 | >10000 |
| J-68 | 7602 |
| J-69 | >10000 |
| J-70 | >10000 |
| J-71 | >10000 |
| J-73 | >10000 |
| Comparative compound 1 | 3552 |
| BIBW2992 | 2750 |

It can be seen from Table 2 that the exemplary compounds of the invention can inhibit the activity of H1975 cell at and below a concentration of 100 nM (some compounds below a concentration of 10 nM) and show fairly strong inhibitory activities against EGFR mutant cells (H1975 cells) but weaker inhibitory activities against EGFR wild-type cells (A431 cells). The compounds of the present invention have significant selective inhibitory activities against EGFR mutant cell growth compared with the positive control BIBW2992. The selective inhibitory activities against EGFR mutant cell growth are greater than those of comparative compounds 1 and 2. The highest selectivity are improved to nearly 10 times when compared with comparative compound 1. It is found in the study that the activities against H1975 cell and selective inhibitory activities against cell growth significantly are reduced after the nitrogen-containing ring is linked directly to pyridine or quinoline and/or the substitutent R$_0$ is replaced with hetero aryl ring.

It can be seen from Table 3 that the exemplary compounds of the invention possess higher IC$_{50}$ values against NIH3T3 cells compared with the positive comparative compound 1, thereby showing less toxicity.

Assay Example 3: ELISA Assay for Testing Cell Activity of EGFR T790M Inhibitor

Reagents, preparation methods of solution, as well as cell treating procedures and preparing procedures of lysate, and steps of ELISA assay in the following method were conducted according to the instructions of R&D DYC3570, R&D DYC1095E and R&D DYC1095BE 1. Reagents and Solutions Cell lysis buffer: 1% NP-40, 20 mM Tris (pH 8.0), 137 mM NaCl, 10% glycerol, 1 mM NaVO$_3$, 2 mM EDTA.

Cell lysates: cell lysis buffer+10 µg/mL Aprotinin (Sigma), 10 µg/mL Leupeptin (Sigma), which was prepared when needed.

1×PBS buffer: NaCl: 0.137 M, KCl: 0.0027 M, Na$_2$PO$_4$·12H$_2$O: 0.01M, KH$_2$PO$_4$: 0.0015M, pH7.4.

Wash buffer: 0.05% Tween-20 in PBS buffer.

Diluent for detecting antibody: 20 mM Tris, 137 mM NaCl, 0.05% Tween-20, 0.1% BSA, pH 7.2-7.4.

Blocking Buffer: 1% BSA in PBS buffer.

ELISA kits: R&D DYC3570, R&D DYC1095E and R&D DYC1095BE.

2. H1975 cells 2.1 Treatment of H1975 cells and Preparation of lysates (1) H1975 cells were seeded in 96-well plate at 1×10$^4$ cells/well with 90 ul of 1640 medium containing 10% FBS in each well, and incubated at 37° C. with 5% CO$_2$ overnight.

(2) The compounds to be tested were diluted according to the method in MTT assay, and 10 mL of diluted compound or DMSO was added into the corresponding plate well, which was incubated at 37° C. with 5% CO$_2$ for 1 h. The final concentration of DMSO was 0.5%. Cell culture system merely treated with DMSO was used as cell control.

(3) 100 µL of cell lysate was added after aspirating the medium. The plate was sealed and placed in a refrigerator at −80° C. overnight. Cell lysis buffer was used as blank control.

2.2 Procedure of ELISA Assay

The assay was operated according to the instructions of R&D DYC1095E or R&D DYC1095BE.

(1) R&D capture antibody ((DYC1095BE or DYC1095E)) was diluted with PBS by 1:180, and ELISA plate (Corning costar 42592) was coated with 100 µL/well of the diluted antibody, and incubated at 25° C. overnight under shaking;

(2) 360 µL of wash buffer was used for washing for three times;

(3) 300 µL of blocking buffer was added, and the plate was incubated at 25° C. for 2 hours under shaking;

(4) 360 µL of wash buffer was used for washing for three times;

(5) 40 µL of cell lysis buffer and 60 µL of cell lysates were added, and the plate was incubated at 25° C. for 2 h under shaking;

(6) 360 µL of wash buffer was used for washing for three times;

(7) Detecting antibody was diluted according to a predetermined ratio as stipulated in kit instructions by using diluent for detecting antibody, and 100 µL of the diluted detecting antibody was added into each well, and incubated at 25° C. for 1 h under shaking in darkness;

(8) 360 µL of wash buffer was used for washing for three times;

(9) reagent A and reagent B of TMB substrate (R & D DY999) were mixed at a ratio of 1:1, 100 µL of which was added into each well, and incubated at 25° C. for 20 minutes under shaking in darkness;

(10) 50 µL of 2N H$_2$SO$_4$ was added into each well;

(11) OD450 values and OD570 values of the cell control, the blank control and the compound-treated sample were measured respectively by using microplate reader (Thermo Multiskan K3), and OD450 values subtracted the corresponding OD570 values of the same wells to get the OD$_{cell}$, OD$_{blank}$ and OD$_{compound-treated}$, respectively.

2.3 Data Analysis

Inhibition ratio (%)=100%×(OD$_{cell}$−OD$_{compound-treated}$)/(OD$_{cell}$−OD$_{blank}$)

2.4 IC$_{50}$ values were calculated with XLFIT 5.0 software from the resulted inhibition ratio and shown in Table 4.

3. A431 cells 3.1 Treating and detecting procedure of A431 cells (1) A431 cells were seeded in 96-well plate at 1×10$^4$ cells/well with 90 uL/well of DMEM medium containing 10% FBS, and incubated at 37° C. with 5% CO$_2$ overnight.

(2) The medium for A431 cells was replaced by 90 uL of serum-free DMEM medium, and incubated overnight.

(3) The compounds to be tested were diluted according to the method in MTT assay, 10 μL of diluted compound or DMSO was added to the corresponding plate well, and incubated at 37° C. with 5% $CO_2$ for 1 h. The final concentration of DMSO was 0.5%. 10 μL of 2 μg/L EGF was then added to each well except the cell control well. Into the cell well was added 10 μL of serum-free DMEM, and incubated for 45 min; the EGF-free and compound treatment-free cells were used as cell control, and the compound treatment-free but only EGF-treated cells were used as EGF control.

(4) 100 μL of cell lysate was added after aspirating the medium. The plate was sealed and placed in refrigerator at −80° C. overnight.

3.2 Procedure of ELISA Assay

The assay was operated according to the instruction of R&D DYC3570E.

(1) R&D capture antibody (DYC3570E) was diluted with PBS by 1:180, and ELISA plate (Corning costar 42592) was coated with 100 μL/well of the diluted antibody, and incubated at 25° C. overnight under shaking;

(2) 360 μL of wash buffer was used for washing for three times;

(3) 200 μL of blocking buffer was added, and the plate was incubated at 25° C. for 2 hours under shaking;

(4) 360 μL of wash buffer was used for washing for three times;

(5) 40 μL of cell lysis buffer and 60 μL of cell lysates were added, and the plate was incubated at 25° C. for 2 h under shaking;

(6) 360 μL of wash buffer was used for washing for three times;

(7) Detecting antibody was diluted according to a predetermined ratio as stipulated in kit instruction by using diluent for detecting antibody, and 100 μL of the diluted detecting antibody was added to each well, and incubated at 25° C. for 1 h under shaking in darkness;

(8) 360 μL of wash buffer was used for washing for three times;

(9) reagent A and reagent B of TMB substrate (R & D DY999) were mixed at a ratio of 1:1, 100 μL of which was added into each well, and incubated at 25° C. for 20 minutes under shaking in darkness;

(10) 50 μL of 2N $H_2SO_4$ was added into each well;

(11) The OD450 values and OD570 values of the cell control, blank control and compound-treated sample were measured respectively by using microplate reader (Thermo Multiskan K3), and OD450 values subtracted the corresponding OD570 values of the same wells to get the $OD_{EGF}$, $OD_{compound}$ and $OD_{cell}$, respectively.

3.3 Data Analysis

Inhibition ratio (%)=100%×($OD_{EGF}$−$OD_{compound}$)/($OD_{EGF}$−$OD_{cell}$)

3.4 $IC_{50}$ values were calculated with XLFIT 5.0 software from the resulted inhibition ratio and shown in Table 4.

TABLE 4

Results of cell activities measured by ELISA Assay

| Compound No. | H1975 cell ($IC_{50}$/nM) | A431 cell ($IC_{50}$/nM) | Selective inhibitory activities against cell [$IC_{50}$(A431 cell)/$IC_{50}$(H1975 cell)] |
|---|---|---|---|
| J-7 | 70 | 234 | 3.3 |
| J-11 | 38 | 379 | 10 |
| J-1 | 13 | 383 | 29.5 |
| J-12 | 8 | 715 | 89.4 |
| J-13 | 20 | 458 | 23 |
| J-15 | 75 | 835 | 11.1 |
| J-17 | 129 | 155 | 1.2 |
| J-18 | 256 | 1099 | 4.3 |
| J-27 | 30 | 2550 | 85 |
| J-28 | 20 | 649 | 32.5 |
| J-29 | 23 | 156 | 7 |
| J-30 | 113 | 1907 | 17 |
| J-31 | 5 | 419 | 84 |
| J-35 | 52 | 2972 | 57.2 |
| J-37 | 36 | 919 | 26 |
| J-38 | 75 | 4.487 | 60 |
| J-39 | 123 | 1321 | 11 |
| J-40 | 95 | 670 | 7.1 |
| J-45 | 18 | 784 | 44 |
| J-46 | 13 | 832 | 64 |
| J-47 | 97 | 2735 | 28.2 |
| J-48 | 102 | 3789 | 37.1 |
| J-51 | 64 | 937 | 15 |
| J-52 | 47 | 700 | 15 |
| J-53 | 30 | 225 | 7.5 |
| J-56 | 24 | 1474 | 61.4 |
| J-57 | 11 | 49 | 4.5 |
| J-58 | 24 | 991 | 41.3 |
| J-59 | 6 | 757 | 126 |
| J-60 | 30 | 272 | 9.1 |
| J-68 | 48 | 388 | 8.1 |
| J-70 | 13 | 460 | 35.4 |
| J-71 | 32 | 539 | 17 |
| J-73 | 26 | 494 | 19 |
| J-74 | 264 | 2028 | 7.7 |
| J-75 | 438 | >10000 | >22.8 |
| Comparative compound 1 | 29 | 114 | 3.9 |
| Comparative compound 2 | 1342 | 1765 | 1.3 |
| BIBW2992 | 21 | 5 | 0.24 |

It can be seen from Table 4 that the exemplary compounds of the invention can inhibit the activity of H1975 cell at or below a concentration of 100 nM (some of the compounds below 10 nM) and show stronger inhibitory activities against target on mutant cellular level. Compared with the positive control BIBW2992, the exemplary compounds of the invention have obvious selective inhibitory activities against target on cellular level. The highest selective inhibitory activity against target on cellular level is increased 32 times when compared with comparative compounds 1 or 2. It is found in the study that the inhibitory activities against H1975 cell and the selective inhibitory activities against target on cellular level is not efficiently improved, or even significantly reduced after the nitrogen-containing ring A is directly linked to pyridine and/or the substituent $R_0$ is replaced by hetero aryl ring.

The enzyme and cell growth inhibition tests in vitro have showed that the compounds of the invention exhibit stronger inhibitory activities against EGFR mutant enzyme and cells but show weak inhibitory activities against EGFR wild-type enzyme and cells, and thus possessing better selectivity to EGFR mutant cells. In addition, the compounds show very weak inhibitory effect on NIH-3T3 cells in cytotoxicity test, thus exhibiting lower cytotoxicity. Therefore, such compounds have better selective inhibitory activities against T790M mutations and lower cytotoxicity.

Assay Example 4

In Vivo Test in Rats or Mice

LC/MS/MS method was applied for determining the drug concentration in plasma at different times after the exemplary compounds were intragastrically and intravenously administered respectively to rats or mice in order to study the pharmacokinetic behavior of the compounds of the invention in vivo in rats or mice and to evaluate their pharmacokinetic characteristics.

Protocol:

Test Animals: healthy adult male SD rats (weight 200-300 g, 6, fasted) or male CD1 mice (weight 20-30 g, 18 mice, free access to water and food), provided by SLAC company.

Administration and Dosage: SD rats were administered intravenously on foot dorsal (1 mg/kg, 5 mL/kg, 5% DMAC (dimethylacetamide), 5% Solutol HS 15 (polyethylene glycol-15 hydroxystearate) and 90% saline); and were administered intragastrically (20 mg/kg, 10 mL/kg, 0.5% sodium carboxymethylcellulose aqueous solution); CD1 mice were administered intravenously via tail (1 mg/kg, 5 ml/kg, 5% DMAC, 5% Solutol HS 15 and 90% Saline) and were administered intragastrically (5 mg/kg, 10 mL/kg, 0.5% DMAC, 5% Solutol HS 15 and 90% saline).

Blood collection: Firstly, the animals which were selected prior to administration and met testing requirements were weighted. The rats or mice were bound before collecting blood. Blood from each administered rat was taken at predetermined time points (intravenous administration on foot dorsal: blood was collected before administration and at 0.083, 0.25, 0.5, 1, 2, 4, 8, 24 h after administration respectively, 9 time points in total; intragastrical administration: blood was collected before administration and at 0.083, 0.25, 0.5, 1, 2, 4, 8, 24 h after administration respectively, 9 time points in total), about 150 μL of blood was collected via tail vein or heart (collecting terminal blood). Blood from each administered mouse was taken at predetermined time points (intravenous administration via tail: blood was collected at 0.083, 0.25, 0.5, 1, 2, 4, 8, 24 h, 8 time points in total; intragastrical administration: blood was collected at 0.25, 0.5, 1, 2, 4, 8, 24 h, 7 time points in total), about 150 μL of blood was collected via orbit or heart (collecting terminal blood). Blood was transferred to a 1.5 mL tube to which $K_2EDTA$ was added previously. The collected blood sample was put on wet ice, centrifuged for 5 min (2000 g, at 4° C.), and then the plasma sample was taken. The whole operation was finished within 15 minutes. All of the samples were stored in a refrigerator at −70° C. until analysis.

The concentration of the drug was determined using LC/MS/MS. The pharmacokinetic parameters of some exemplary compounds of the invention in vivo in rats and mice at same doses and through same administration were shown in Table 5:

TABLE 5

Pharmacokinetic parameters of compounds in rats and mice in vivo

|  | rat | | | mice | | |
| --- | --- | --- | --- | --- | --- | --- |
|  | J-12 | J-13 | Comparative compound 1 | J-12 | J-13 | Comparative compound 1 |
| Clearance CL (mL/min/kg) | 56.5 | 71.2 | 54.3 | 57.9 | 42.5 | 89.0 |
| Half-life $T_{1/2}$ (hr) | 3.84 | 3.73 | 4.13 | 3.82 | 3.40 | 1.54 |
| Oral relative bioavailability F | 44.3% | 128% | 18.5% | 42.6% | 66.6% | 30.2% |
| Maximum plasma concentration $C_{max}$ (ng/mL) | 188 | 482 | 118 | 70.6 | 139 | 67.9 |
| Area under the curve AUC (hr*ng/mL) | 2619 | 5980 | 1119 | 605 | 1294 | 272 |

It can be seen from Table 5 that the exemplary compounds of the present invention are well absorbed, have obvious absorption effect and exhibit excellent bioavailability.

All publications mentioned herein are incorporated by reference as if each individual document was cited as a reference, as in the present application. It should also be understood that, after reading the above teachings of the present invention, those skilled in the art can make various changes or modifications, equivalents of which fall in the scope of claims as defined in the appended claims.

What is claimed:

1. A compound of formula (VI), or a pharmaceutically acceptable salt, a solvate, a stereoisomer or a prodrug thereof:

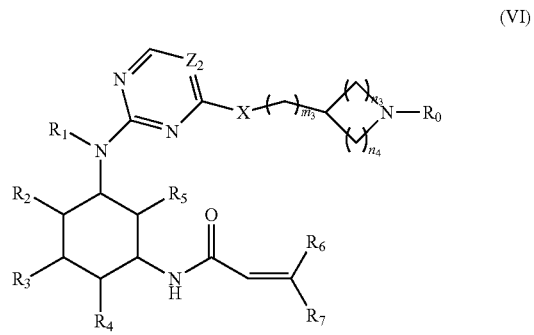

(VI)

wherein, $Z_2$ is $CR_{10}$, $R_{10}$ is a hydrogen, hydroxy, $NO_2$, fluorine, chlorine, $-NH_2$, $-N(CH_3)_2$, $C_{1-3}$ alkyl, cyclopropyl, cyclopropyloxy, $C_{1-3}$ alkoxy, $-CHO$, $-COCH_3$, $-CO$-phenyl, phenyl, $-CONH_2$, $-CON(CH_3)_2$, $-C(O)OCH_3$, $-OC(O)CH_3$, $-SO_2CH_3$, $-SO_2$-phenyl or t-butyloxycarbonyl; wherein each of alkyl, cyclopropyl, alkoxy and phenyl is unsubstituted or substituted with 1-3 substituents selected from the group consisting of fluorine, chlorine, nitro, phenyl, methyl, methoxy, cyclopropyl, cyclopropyloxy, $-CONH_2$, $-CON(CH_3)_2$, $-C(O)OCH_3$, $-CHO$, $-OC(O)CH_3$, $-SO_2CH_3$, $-SO_2$-phenyl, and $-CO$-phenyl;

X is NH, N(C$_{1-3}$ alkyl), O or S;

m$_3$ is 0 or 1;

R$_0$ is a hydrogen, hydroxy, C$_{1-3}$ alkyl, cyclopropyl, —CHO, —COC$_{1-3}$ alkyl, —CO— phenyl, phenyl, —CONH$_2$, —CON(CH$_3$)$_2$, —C(O)OCH$_3$, —SO$_2$C$_{1-3}$ alkyl, —SO$_2$-phenyl, —S(O)C$_{1-3}$ alkyl, —S(O)-phenyl, or t-butyloxycarbonyl; wherein, each of alkyl and phenyl is unsubstituted or substituted with 1-3 substituent selected from the group consisting of fluorine, chlorine, hydroxy, NO$_2$, phenyl, methyl, methoxy, cyclopropyl, cyclopropyloxy, —CONH$_2$, —CON(CH$_3$)$_2$, —C(O)OCH$_3$, —CHO, —OC(O)CH$_3$, —SO$_2$CH$_3$, —SO$_2$-phenyl, —CO-phenyl; or R$_0$ is selected from: pyridyl,

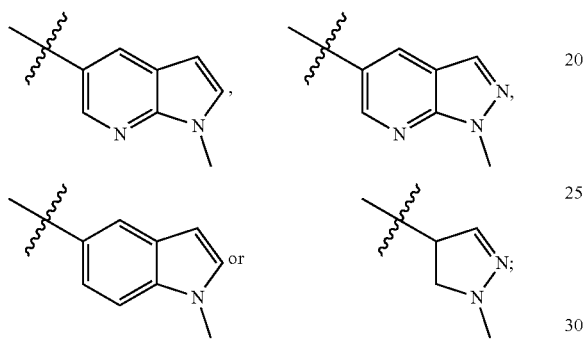

each of n$_3$ and n$_4$ is independently 0, 1, 2 or 3, and n$_3$ and n$_4$ are not 0 simultaneously;

R$_1$ is a hydrogen;

R$_2$ is methoxy;

each of R$_3$ and R$_5$ are independently a hydrogen;

R$_4$ is a group selected from

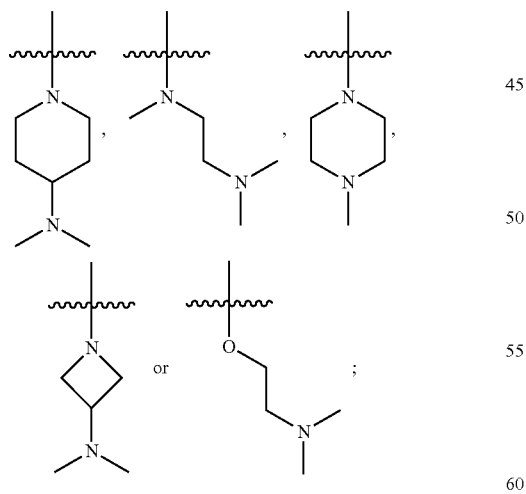

each of R$_6$ and R$_7$ is independently a hydrogen.

2. The compound of claim 1, or a pharmaceutically acceptable salt, a solvate, a stereoisomer or a prodrug thereof, wherein, the compound of formula (I) is selected from the group consisting of

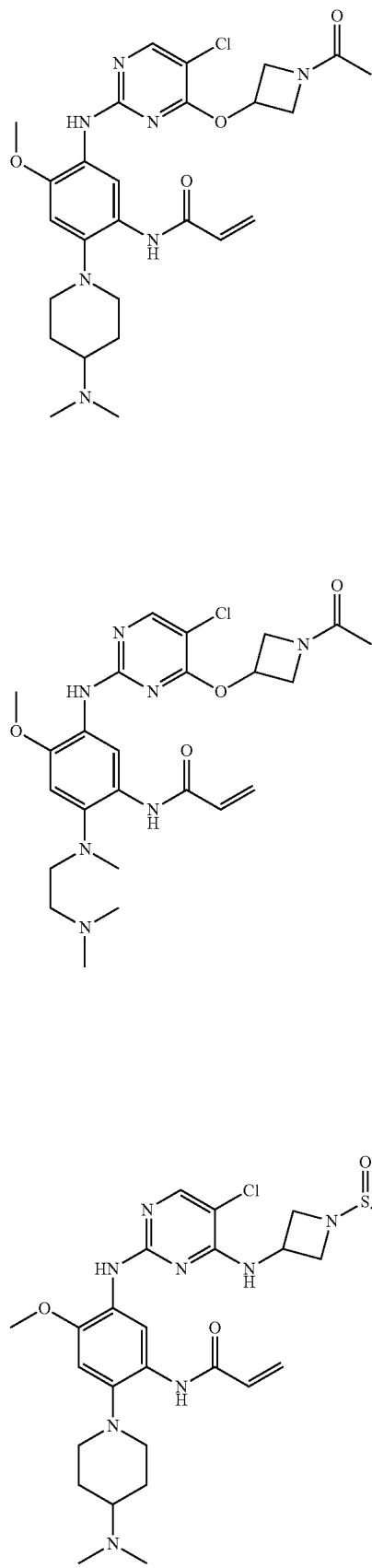

-continued
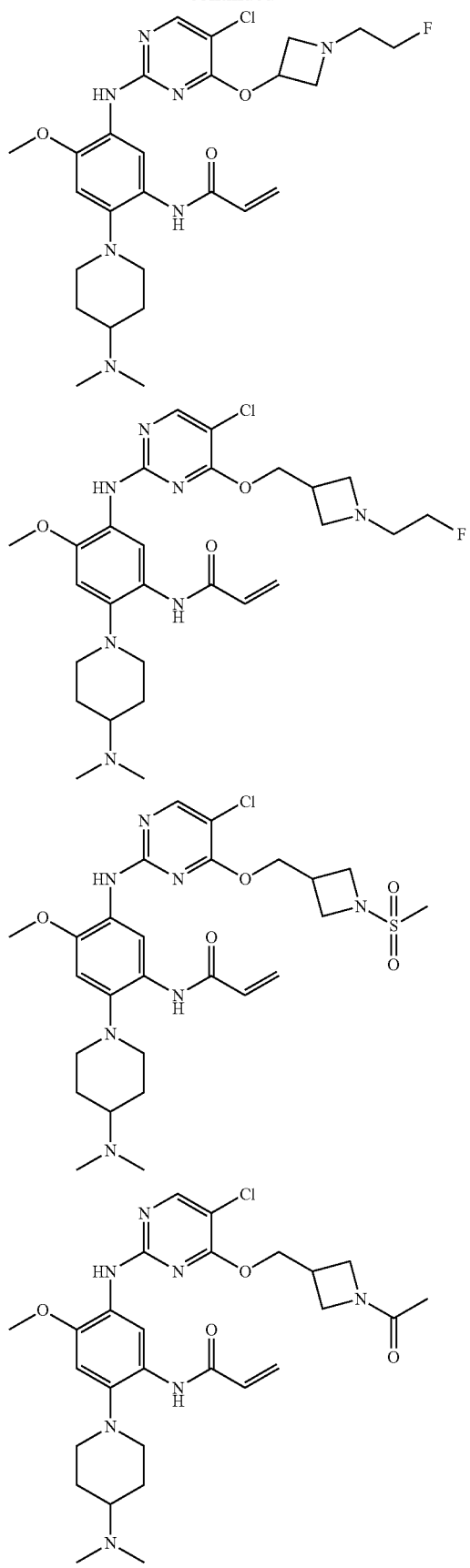
-continued
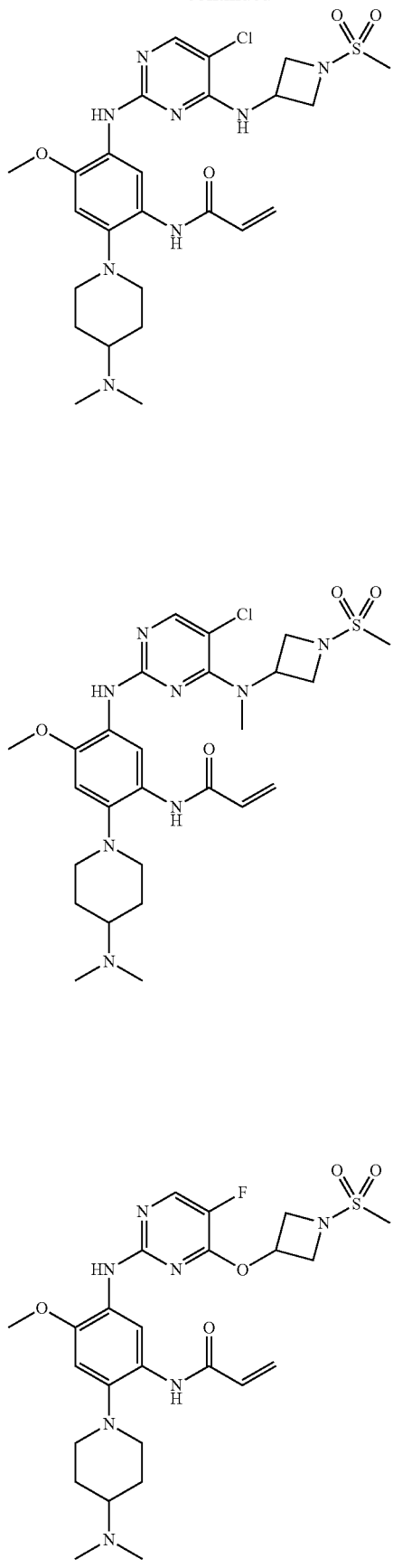

157
-continued
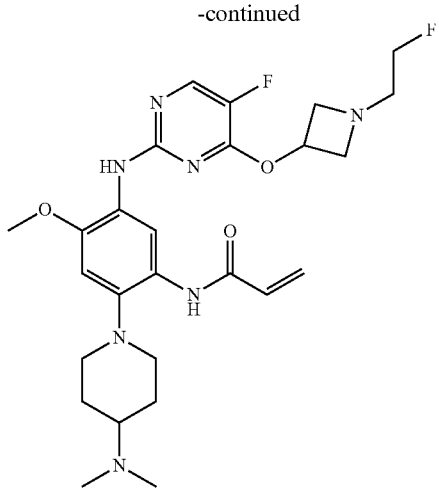
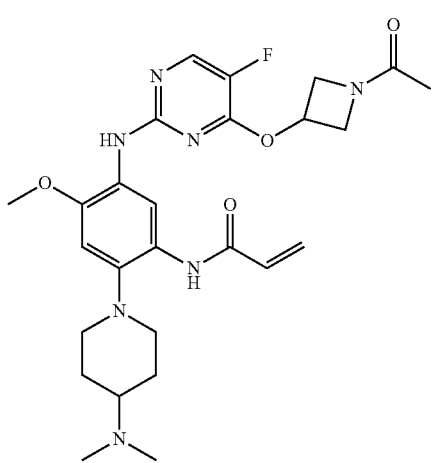
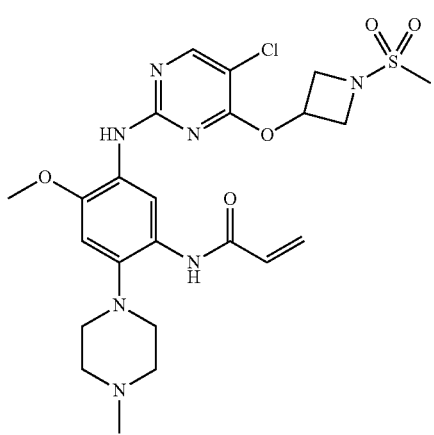
158
-continued
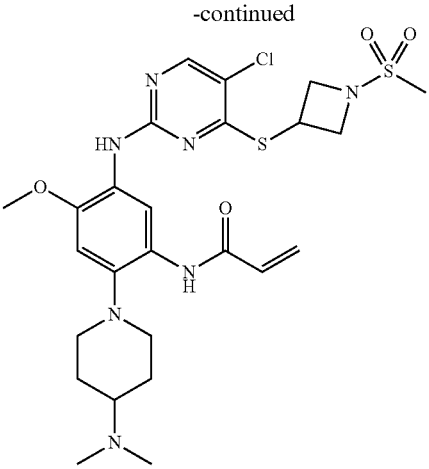
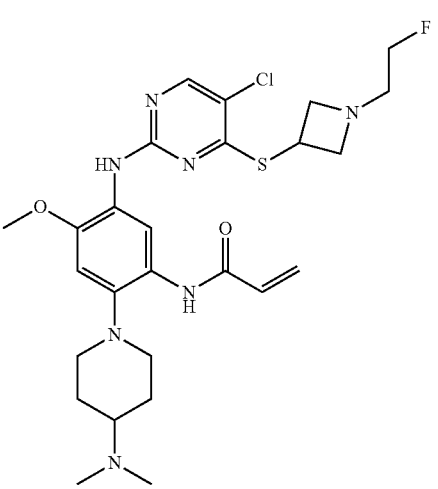

159
-continued
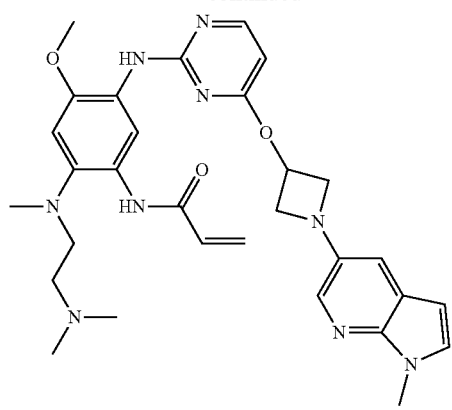
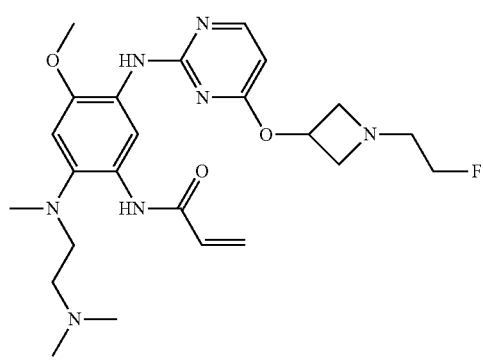
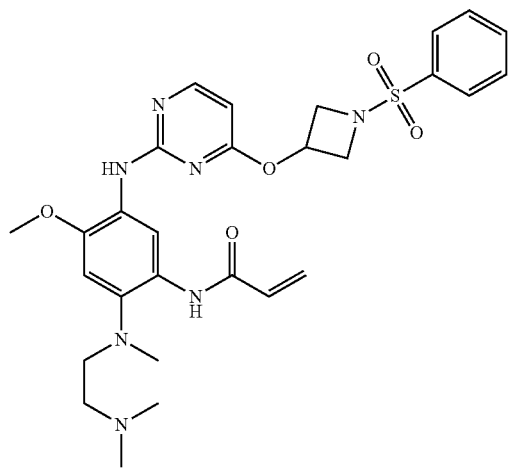
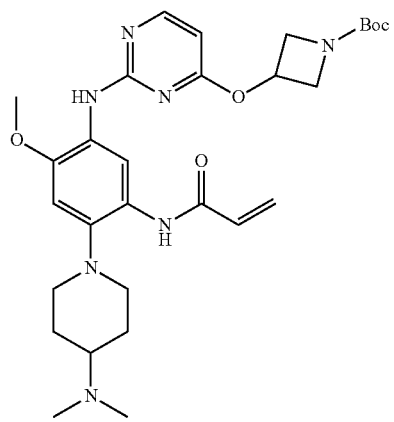
160
-continued
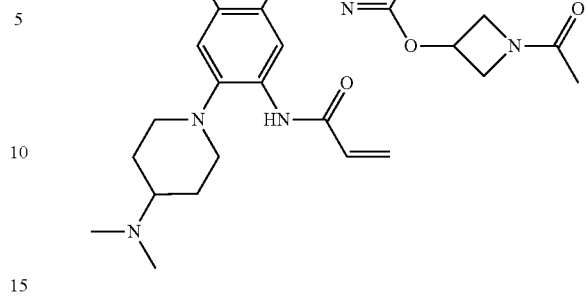
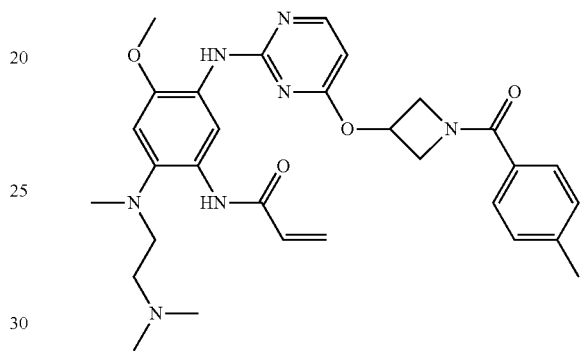
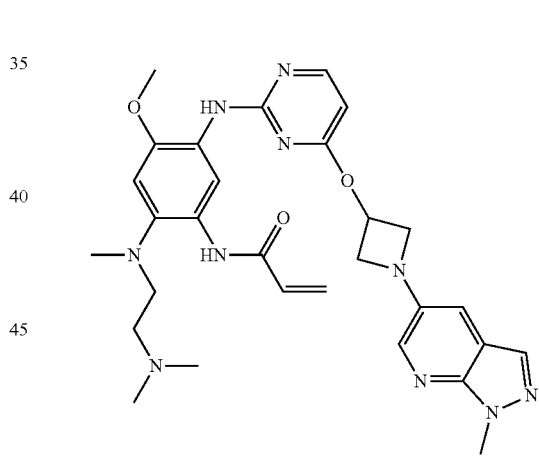
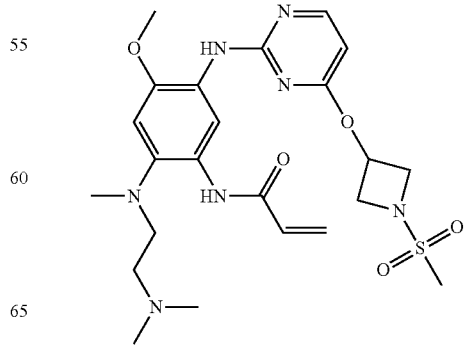

161
-continued
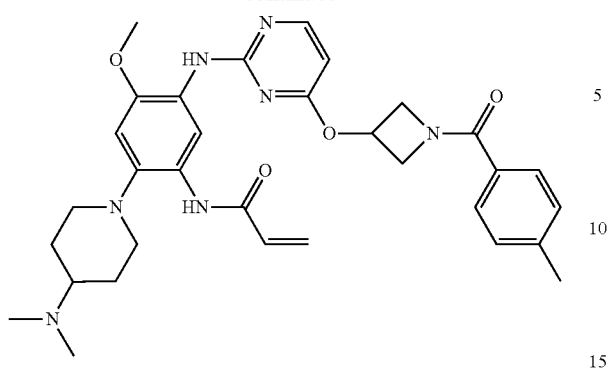
162
-continued
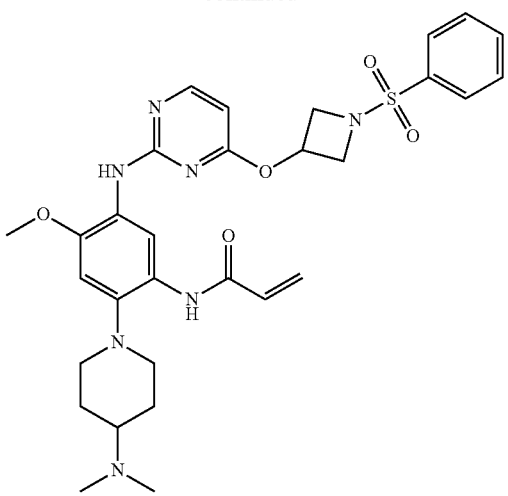
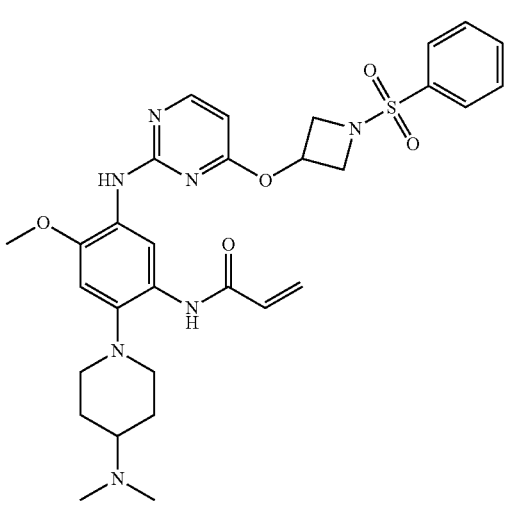
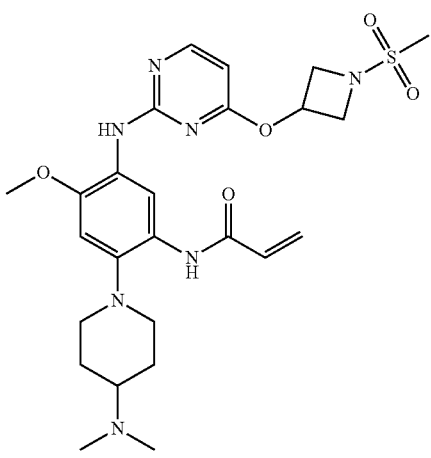

163
-continued
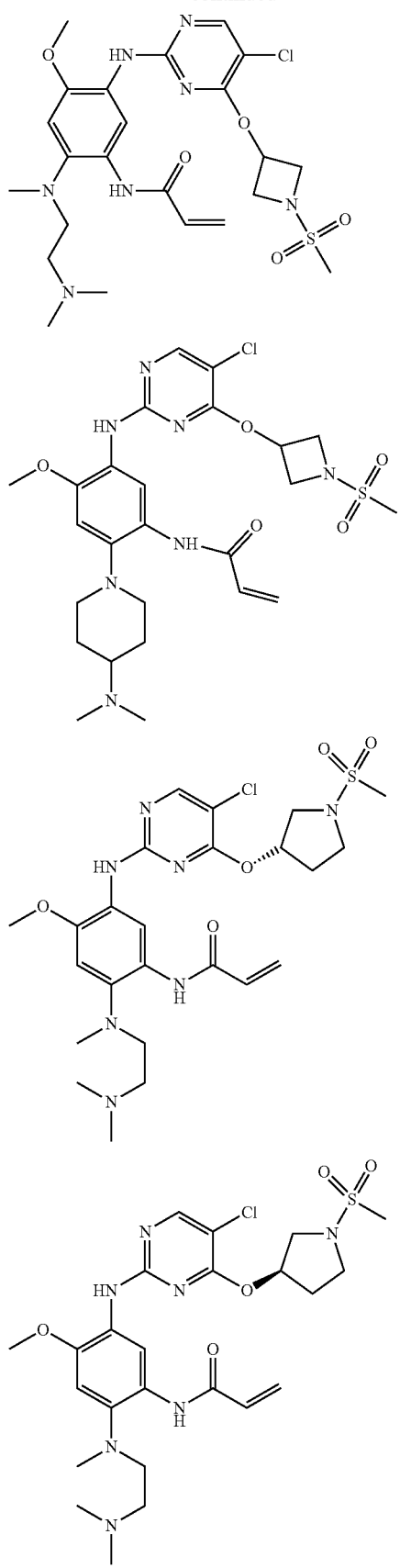
164
-continued
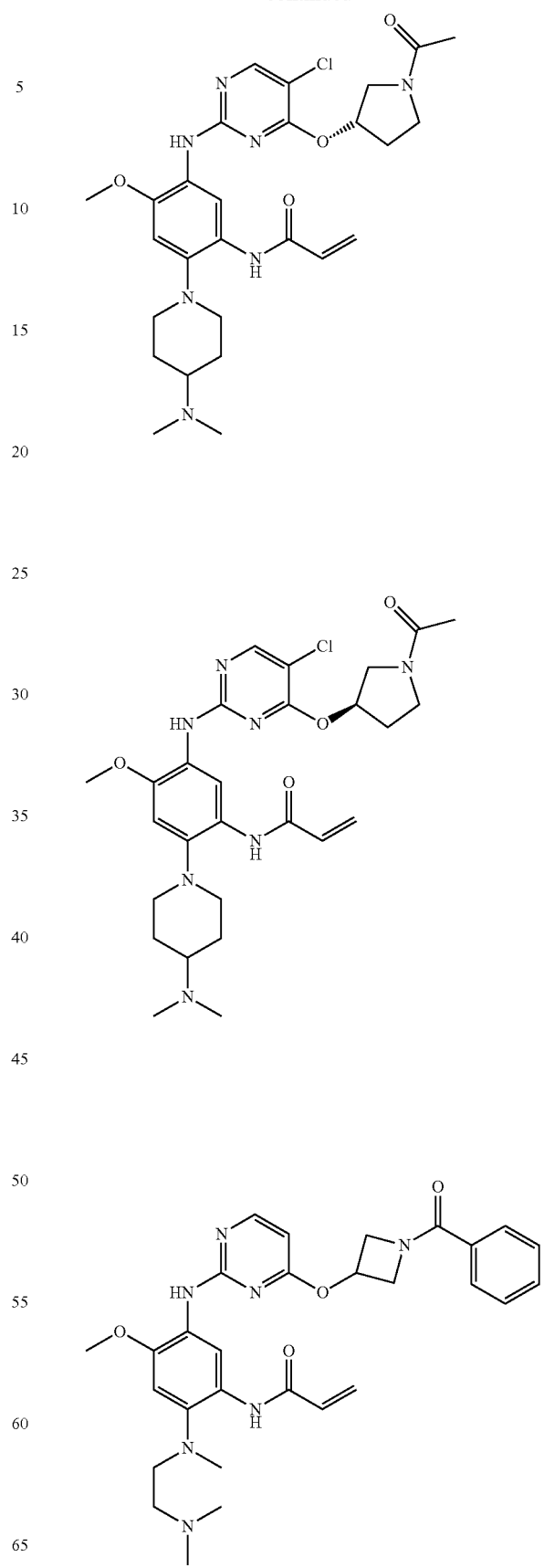

165
-continued
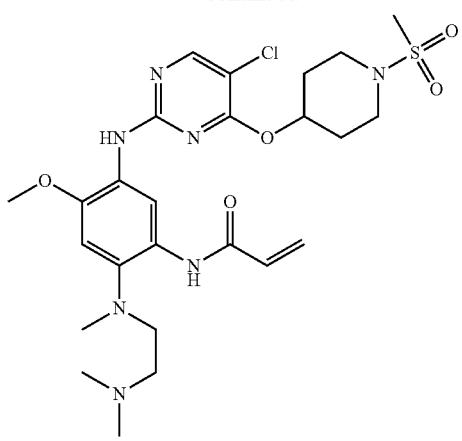
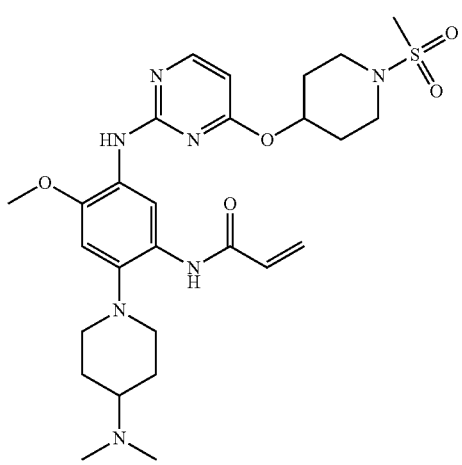
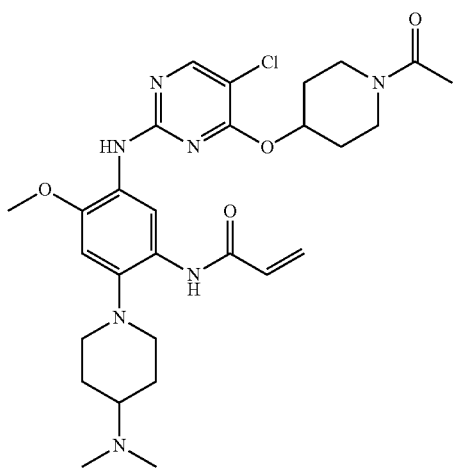 [SMILES: C=CC(=O)Nc1cc(Nc2ncc(Cl)c(OC3CCN(C(C)=O)CC3)n2)c(OC)cc1N1CCC(N(C)C)CC1]
166
-continued
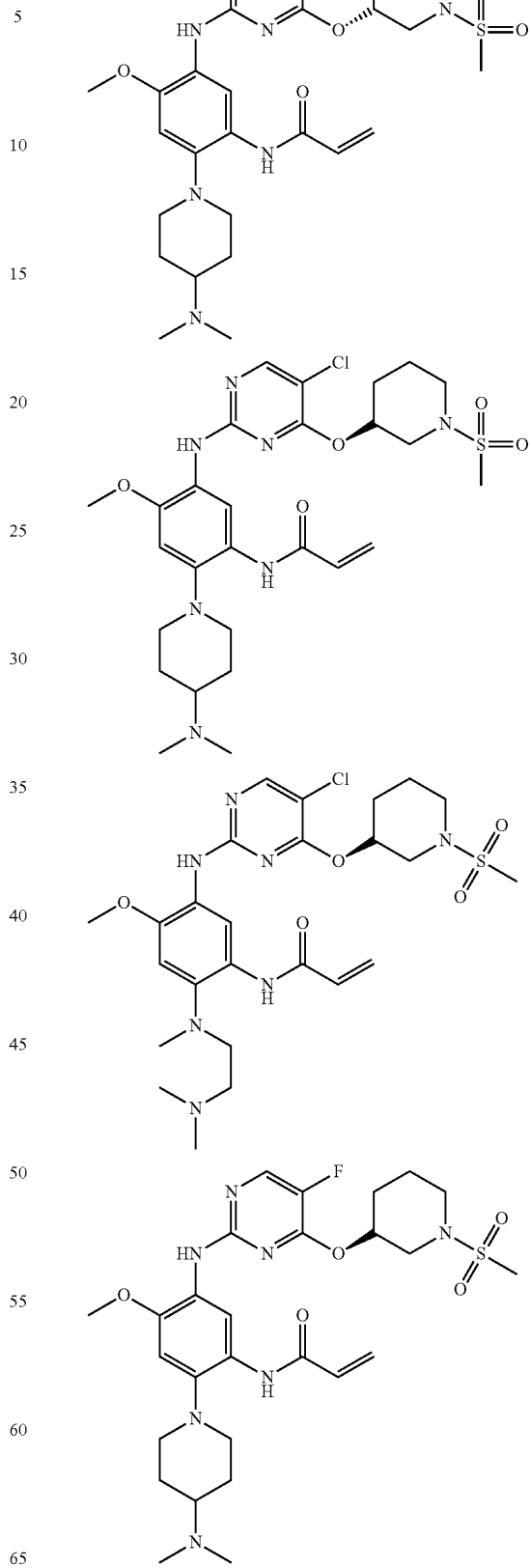

167
-continued
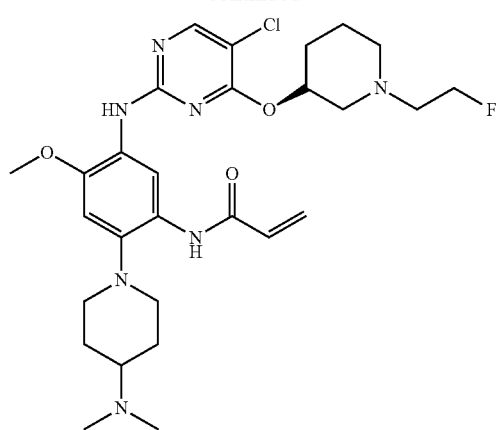
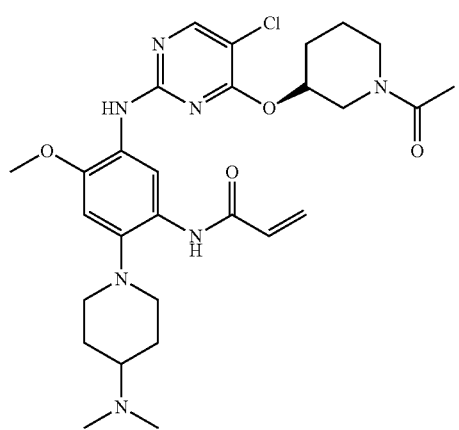
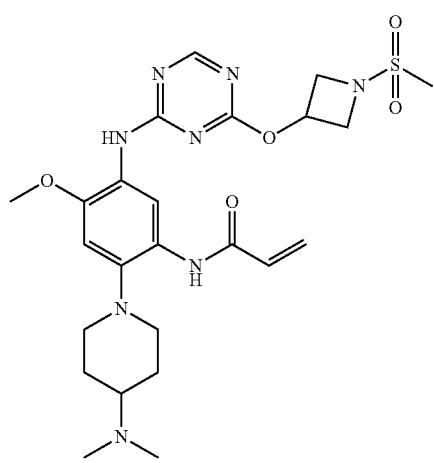
168
-continued
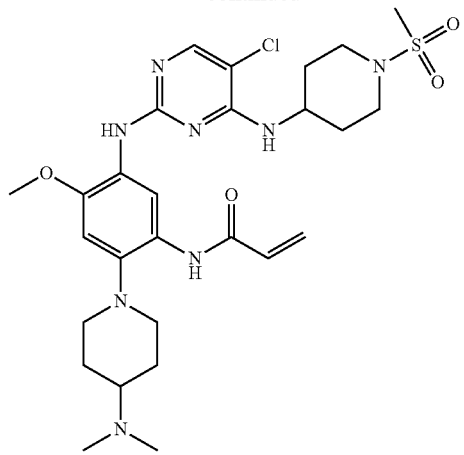
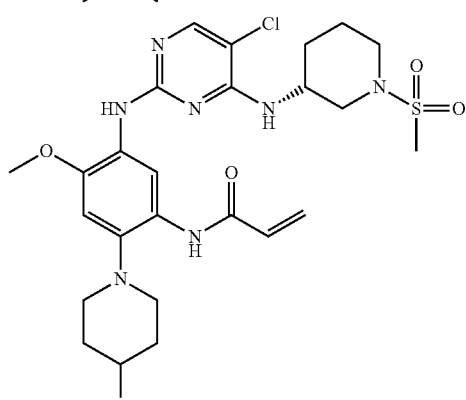
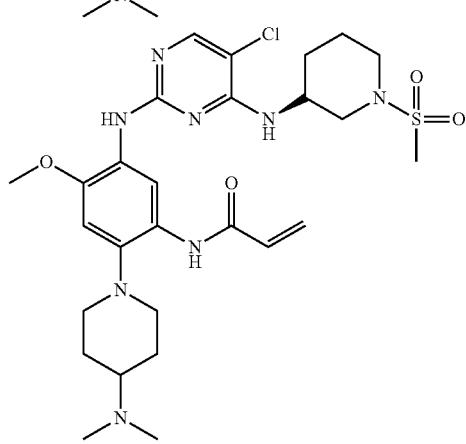
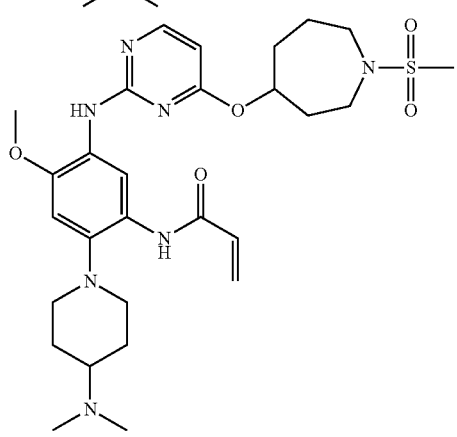

169
-continued
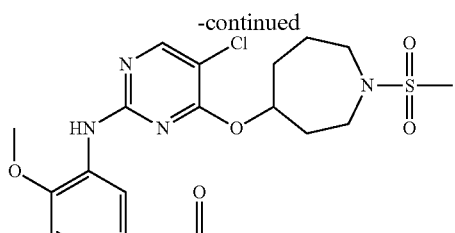
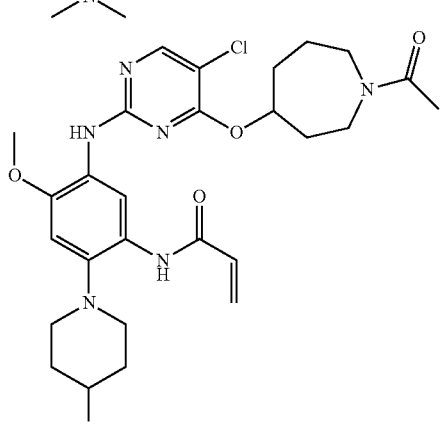
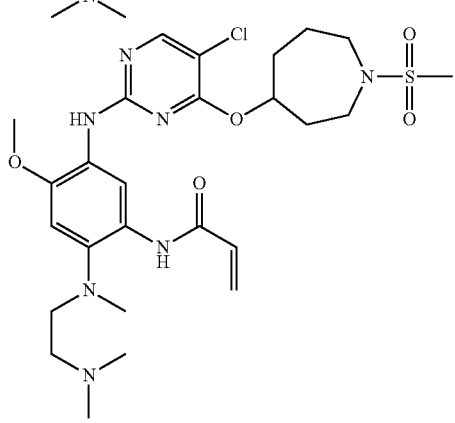
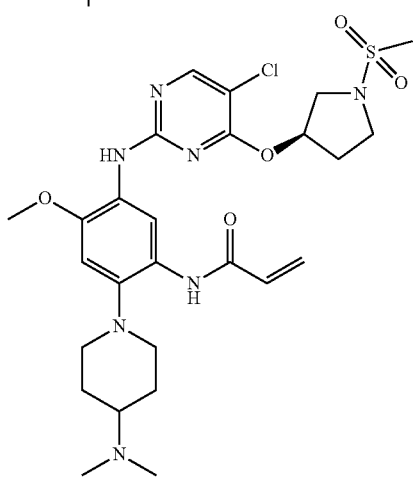
170
-continued
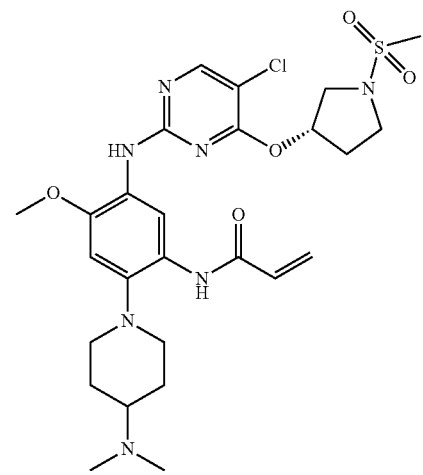
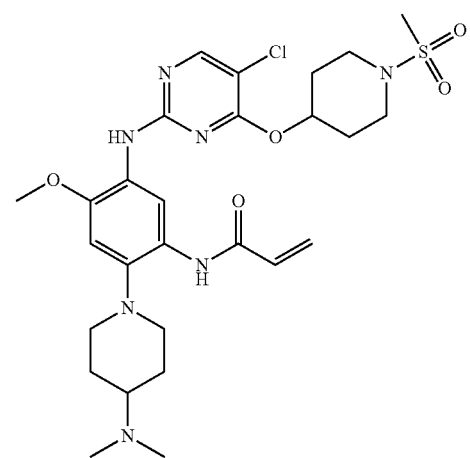 [SMILES: C=CC(=O)Nc1cc(Nc2ncc(Cl)c(OC3CCN(S(C)(=O)=O)CC3)n2)c(OC)cc1N1CCC(N(C)C)CC1]
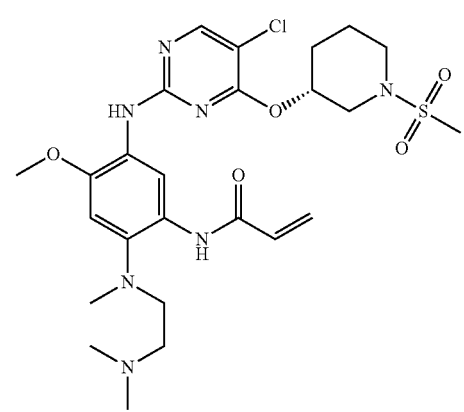

-continued

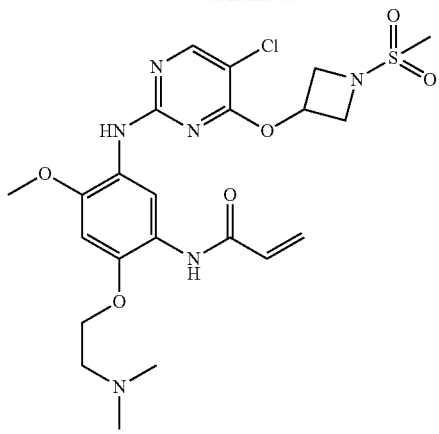

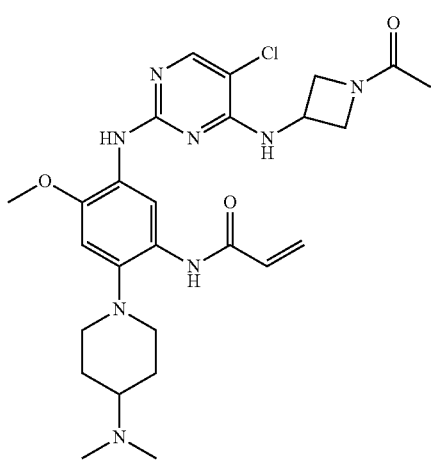

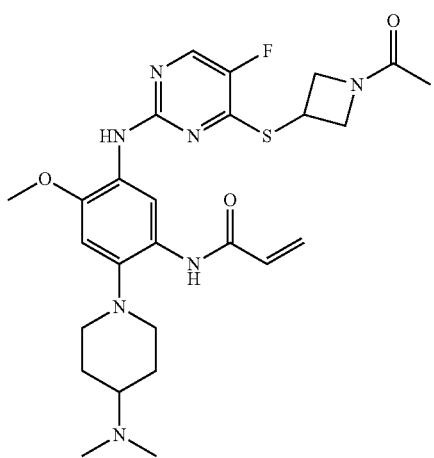 [SMILES: C=CC(=O)Nc1cc(Nc2ncc(Cl)c(OC3CN(C(C)=O)C3)n2)c(OC)cc1N1CCC(N(C)C)CC1]

-continued

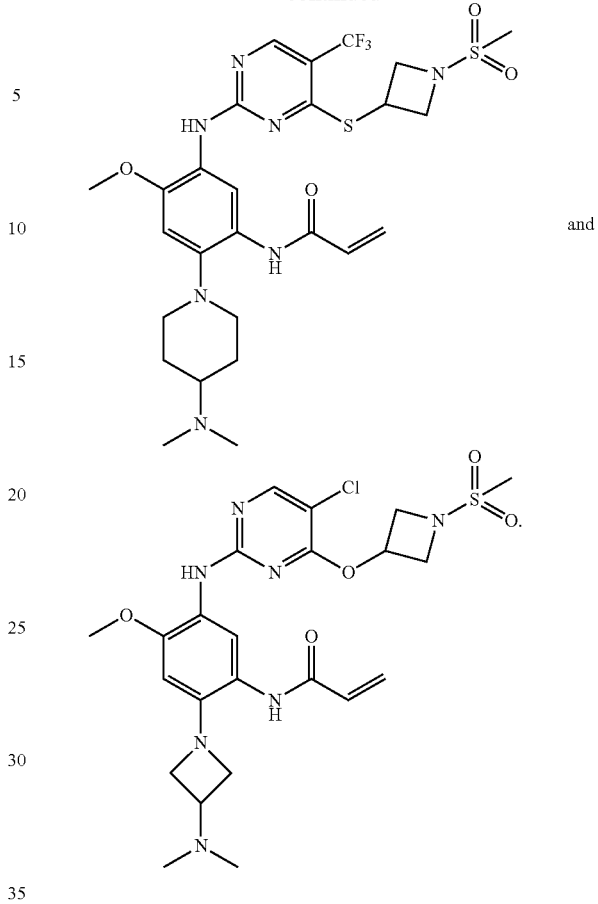

3. A pharmaceutical composition comprising a compound of claim 1, or a pharmaceutically acceptable salt, a solvate, a stereoisomer or a prodrug thereof; and a pharmaceutically acceptable carrier.

4. The compound of claim 1, wherein $R_0$ is a hydrogen, $C_{1-3}$ alkyl, —$COC_{1-3}$ alkyl, —CO-phenyl, —$SO_2C_{1-3}$ alkyl, —$SO_2$-phenyl, or t-butyloxycarbonyl; wherein each of alkyl and phenyl is unsubstituted or substituted with 1-3 substituents selected from the group consisting of fluorine, chlorine, methyl.

5. The compound of claim 1, wherein $R_0$ is $C_{1-3}$ alkyl, —$COC_{1-3}$ alkyl, or —$SO_2C_{1-3}$ alkyl; wherein, the alkyl is unsubstituted or substituted with 1 substituent selected from the group consisting of fluorine and chlorine.

6. The compound of claim 1, wherein $R_0$ is $C_{1-3}$ alkyl substituted by one fluorine, —$COC_{1-3}$ alkyl or —$SO_2C_{1-3}$ alkyl.

7. The compound of claim 1, wherein $n_3$ is 1, 2 or 3; $n_4$ is 1 or 2.

8. The compound of claim 1, wherein $n_3$ is 1; $n_4$ is 1.

9. The compound of claim 1, wherein in the compound of formula (VI), (i) $Z_2$ is $CR_{10}$, $R_{10}$ is trifluoromethyl, fluorine or chlorine; $m_3$ is 0; $n_3$ is 1; $n_4$ is 1;
X is NH, O or S;
$R_0$ is a hydrogen, $C_{1-3}$ alkyl, —$COC_{1-3}$ alkyl, —CO-phenyl, —$SO_2C_{1-3}$ alkyl, —$SO_2$-phenyl, or t-butyloxycarbonyl; wherein each of alkyl and phenyl is unsubstituted or substituted with 1-3 substituents selected from the group consisting of fluorine, chlorine and methyl;

$R_1$ is a hydrogen; $R_2$ is methoxy; each of $R_3$, $R_5$, $R_6$ and $R_7$ is independently a hydrogen;

$R_4$ is or

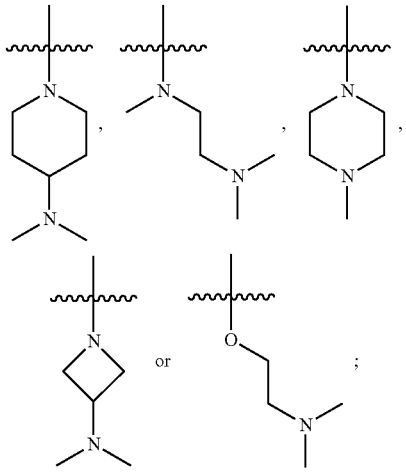

(ii) $Z_2$ is $CR_{10}$, $R_{10}$ is trifluoromethyl, fluorine or chlorine;

$m_3$ is 0; $n_3$ is 3; $n_4$ is 2;

X is O;

$R_0$ is a hydrogen, $C_{1-3}$ alkyl, —$COC_{1-3}$ alkyl, —CO-phenyl, —$SO_2C_{1-3}$ alkyl, —$SO_2$-phenyl, and t-butyloxycarbonyl; wherein each of alkyl and phenyl is unsubstituted or substituted with 1-3 substituents selected from the group consisting of fluorine, chlorine and methyl;

$R_1$ is a hydrogen; $R_2$ is methoxy; each of $R_3$, $R_5$, $R_6$ and $R_7$ is independently a hydrogen;

$R_4$ is

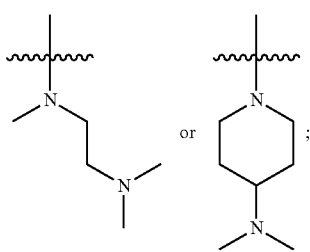

or (iii) $Z_2$ is $CR_{10}$, $R_{10}$ is trifluoromethyl, fluorine or chlorine;

$m_3$ is 0; $n_3$ is 2; $n_4$ is 2;

X is NH or O;

$R_0$ is a hydrogen, $C_{1-3}$ alkyl, —$COC_{1-3}$ alkyl, —CO-phenyl, —$SO_2C_{1-3}$ alkyl, —$SO_2$-phenyl, or t-butyloxycarbonyl; wherein each of alkyl and phenyl is unsubstituted or substituted with 1-3 substituents selected from the group consisting of fluorine, chlorine and methyl;

$R_1$ is a hydrogen; $R_2$ is methoxy; each of $R_3$, $R_5$, $R_6$ and $R_7$ is independently a hydrogen;

$R_4$ is or

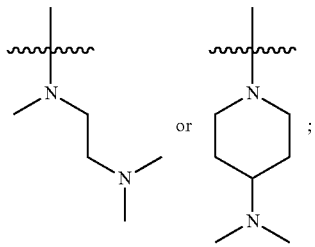

(iv) $Z_2$ is $CR_{10}$, $R_{10}$ is trifluoromethyl, fluorine or chlorine;

$m_3$ is 0; $n_3$ is 1; $n_4$ is 2;

X is O;

$R_0$ is a hydrogen, $C_{1-3}$ alkyl, —$COC_{1-3}$ alkyl, —CO-phenyl, —$SO_2C_{1-3}$ alkyl, —$SO_2$-phenyl, or t-butyloxycarbonyl; wherein each of alkyl and phenyl is unsubstituted or substituted with 1-3 substituents selected from the group consisting of fluorine, chlorine and methyl;

$R_1$ is a hydrogen; $R_2$ is methoxy; each of $R_3$, $R_5$, $R_6$ and $R_7$ is independently a hydrogen;

$R_4$ is

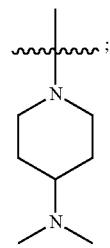

or (v) $Z_2$ is $CR_{10}$, $R_{10}$ is trifluoromethyl, fluorine or chlorine;

$m_3$ is 0; $n_3$ is 3; $n_4$ is 1;

X is NH or O;

$R_0$ is a hydrogen, $C_{1-3}$ alkyl, —$COC_{1-3}$ alkyl, —CO-phenyl, —$SO_2C_{1-3}$ alkyl, —$SO_2$-phenyl, or t-butyloxycarbonyl; wherein each of alkyl and phenyl is unsubstituted or substituted with 1-3 substituents selected from the group consisting of fluorine, chlorine and methyl;

$R_1$ is a hydrogen; $R_2$ is methoxy; each of $R_3$, $R_5$, $R_6$ and $R_7$ is independently a hydrogen;

$R_4$ is

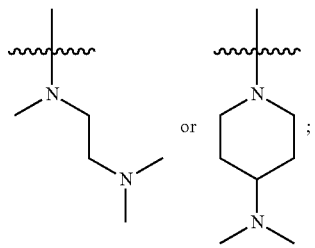

or (vi) $Z_2$ is $CR_{10}$, $R_{10}$ is trifluoromethyl, fluorine or chlorine;

$m_3$ is 1; $n_3$ is 1; $n_4$ is 1;

X is O;

$R_0$ is a hydrogen, $C_{1-3}$ alkyl, —$COC_{1-3}$ alkyl, —CO-phenyl, —$SO_2C_{1-3}$ alkyl, —$SO_2$-phenyl, or t-butyloxy-carbonyl; wherein each of alkyl and phenyl is unsubstituted or substituted with 1-3 substituents selected from the group consisting of fluorine, chlorine and methyl;

$R_1$ is a hydrogen; $R_2$ is methoxy; each of $R_3$, $R_5$, $R_6$ and $R_7$ is independently a hydrogen;

$R_4$ is

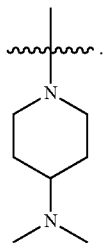 [SMILES: *N1CCC(N(C)C)CC1]

10. The compound of claim 1, wherein in the compound of formula (VI), (i) X is NH, $m_3$ is 0; $n_3$ is 1; $n_4$ is 1;
$Z_2$ is $CR_{10}$, $R_{10}$ is fluorine, chlorine or trifluoromethyl;
$R_0$ is —$COC_{1-3}$ alkyl or —$SO_2C_{1-3}$ alkyl;
$R_1$ is a hydrogen; $R_2$ is methoxy; each of $R_3$, $R_5$, $R_6$ and $R_7$ is independently a hydrogen;
$R_4$ is:

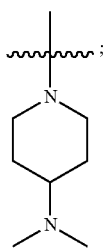

or (ii) X is O, $m_3$ is 0 or 1; $n_3$ is 1, 2 or 3; $n_4$ is 1 or 2;
$Z_2$ is $CR_{10}$, $R_{10}$ is fluorine, chlorine or trifluoromethyl;
$R_1$ is a hydrogen; $R_2$ is methoxy; each of $R_3$, $R_5$, $R_6$ and $R_7$ is independently a hydrogen;

$R_0$ is —$COC_{1-3}$ alkyl, —$SO_2C_{1-3}$ alkyl or $C_{1-3}$ alkyl substituted by one fluorine;

$R_4$ is selected from the group consisting of

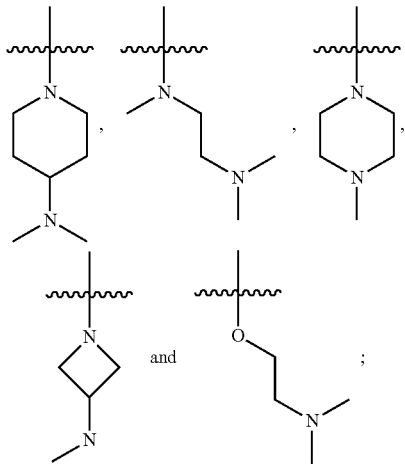

or (iii) X is S, $m_3$ is 0; $n_3$ is 1; $n_4$ is 1;
$Z_2$ is $CR_{10}$, $R_{10}$ is fluorine, chlorine or trifluoromethyl;
$R_1$ is a hydrogen; $R_2$ is methoxy; each of $R_3$, $R_5$, $R_6$ and $R_7$ is independently a hydrogen;
$R_0$ is —$COC_{1-3}$ alkyl, or —$SO_2C_{1-3}$ alkyl;
$R_4$ is

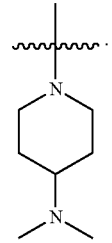 [SMILES: *N1CCC(N(C)C)CC1]

* * * * *